United States Patent
Chu et al.

(10) Patent No.: US 9,506,089 B2
(45) Date of Patent: *Nov. 29, 2016

(54) MICROORGANISM HAVING NOVEL ACRYLIC ACID SYNTHESIS PATHWAY AND METHOD OF PRODUCING ACRYLIC ACID BY USING THE MICROORGANISM

(71) Applicant: Samsung Electronics Co., Ltd., Suwon-si, Gyeonggi-do (KR)

(72) Inventors: Hunsu Chu, Seoul (KR); Jinho Ahn, Yongin-si (KR); Taewook Nam, Seoul (KR); Jiae Yun, Hwaseong-si (KR); Insuk Choi, Seongnam-si (KR); Yeoju Song, Incheon (KR); Jinsuk Lee, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/620,049

(22) Filed: Feb. 11, 2015

(65) Prior Publication Data
US 2015/0329881 A1 Nov. 19, 2015

(30) Foreign Application Priority Data
May 14, 2014 (KR) .................. 10-2014-0057954

(51) Int. Cl.
| C12P 7/40 | (2006.01) |
|---|---|
| C12N 1/20 | (2006.01) |
| C12N 15/52 | (2006.01) |
| C12N 9/10 | (2006.01) |
| C12N 9/16 | (2006.01) |
| C12N 9/00 | (2006.01) |
| C12N 9/88 | (2006.01) |

(52) U.S. Cl.
CPC . *C12P 7/40* (2013.01); *C12N 9/13* (2013.01); *C12N 9/16* (2013.01); *C12N 9/88* (2013.01); *C12N 9/93* (2013.01); *C12Y 208/03008* (2013.01); *C12Y 301/02* (2013.01); *C12Y 402/01* (2013.01); *C12Y 602/01007* (2013.01); *Y02P 20/52* (2015.11)

(58) Field of Classification Search
None
See application file for complete search history.

(56) References Cited

U.S. PATENT DOCUMENTS

| 7,186,541 B2 | 3/2007 | Gokarn et al. |
|---|---|---|
| 7,393,676 B2 | 7/2008 | Gokarn et al. |
| 8,076,120 B2 | 12/2011 | Gokarn et al. |
| 8,198,066 B2 | 6/2012 | Gokarn et al. |
| 2004/0076982 A1 | 4/2004 | Gokarn et al. |
| 2007/0184524 A1 | 8/2007 | Gokarn et al. |
| 2009/0053783 A1 | 2/2009 | Gokarn et al. |
| 2009/0325248 A1 | 12/2009 | Marx et al. |
| 2010/0009419 A1* | 1/2010 | Burk .................. C12P 7/46 435/135 |
| 2011/0105791 A1 | 5/2011 | Kuppinger et al. |
| 2012/0041232 A1 | 2/2012 | Lynch |
| 2012/0077236 A1 | 3/2012 | Gokarn et al. |
| 2012/0244586 A1 | 9/2012 | Gokarn et al. |
| 2014/0099676 A1* | 4/2014 | Xu ..................... C12P 13/02 435/92 |
| 2015/0267226 A1* | 9/2015 | Jung .................. C12P 7/20 435/159 |

FOREIGN PATENT DOCUMENTS

| EP | 1343874 A2 | 11/2005 |
|---|---|---|
| KR | 2015/0110144 | 10/2015 |
| WO | WO 2013/044076 A1 * | 3/2013 |
| WO | 2013/192453 | 12/2013 |

OTHER PUBLICATIONS

Kwak et al., Bioresource Technol. 135:432-439, 2013.*
Han et al., J. Biosci. Bioengineer. 108:517-523, 2009.*
Selmer et al., Eur. J. Biochem. 269:372-380, 2002.*
Danner et al, "Biotechnical Production of Acrylic Acid from Biomass", *Institute for Agrobiotechnology Tulln Department for Environmental Biotechnology*, 70-72: 887-894 (1998).
Straathof et al, "Feasibility of acrylic acid production by fermentation", *Appl. Microbiol. Biotechnol.*, 67: 727-734 (2005).
Van Maris et al., "Microbial export of lactic and 3-hydroxypropanoic acid: implications for industrial fermentation processes", *Metabolic Engineering*, 6:245-255 (2004).

* cited by examiner

*Primary Examiner* — David J Steadman
(74) *Attorney, Agent, or Firm* — Leydig, Voit & Mayer, Ltd.

(57) ABSTRACT

A microorganism capable of producing an acrylic acid (AA), wherein activities of a pathway producing AA through conversions of 3-HP to 3-HP-CoA and 3-HP-CoA to AA-CoA in the microorganisms are increased; as well as a method of producing the microorganism and a method of producing an acrylic acid by using the same.

13 Claims, 2 Drawing Sheets

MICROORGANISM HAVING NOVEL ACRYLIC ACID SYNTHESIS PATHWAY AND METHOD OF PRODUCING ACRYLIC ACID BY USING THE MICROORGANISM

RELATED APPLICATION

This application claims the benefit of Korean Patent Application No. 10-2014-0057954, filed on May 14, 2014, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 510,691 bytes ASCII (Text) file named "719112_ST25.TXT" created Feb. 3, 2015.

BACKGROUND

1. Field

The present disclosure relates to microorganisms having a novel acrylic acid synthesis pathway and a method of producing an acrylic acid by using the microorganisms.

2. Description of the Related Art

Recently, due to the rapid increase in the price of petroleum and as pressure to decrease carbon emissions has become a global issue, efforts to produce fuel or chemicals through a carbon-neutral biological process instead of a conventional chemical process using petroleum as a raw material have continued.

An acrylic acid is a bulk chemical that has a market value of about 10 trillion Korean Won (KRW). The recent demand for an environment-friendly production method has increased the need for a method of producing an acrylic acid through a pathway other than a petroleum-based pathway.

An example of a non-petroleum-based acrylic acid production pathway may be a method including producing 3-hydroxypropionic acid (3-HP) from glycerol or glucose; and chemically isolating and purifying the 3-HP. However, this method includes isolating the produced 3-HP from a culture, purifying the 3-HP, and chemically converting the 3-HP by using a catalyst. Therefore, the cost of the isolation, purification, and conversion is added to the 3-HP production cost, and thus the method may not be competitive with respect to a method of producing an acrylic acid derived from a petroleum-based compound.

Even in the conventional method, alternative microorganisms capable of producing acrylic acid and a method of producing an acrylic acid by using the microorganisms are needed.

SUMMARY

Provided is a genetically engineered microorganism that produces acrylate, wherein the genetically engineered microorganism comprises a genetic modification that increases activities of a CoA transferase catalyzing conversion of 3-hydroxypropionic acid (3-HP) to 3-hydroxypropionyl-CoA (3-HP-CoA), a 3-HP-CoA dehydratase catalyzing conversion of the 3-HP-CoA to acrylyl-CoA, and an enzyme catalyzing the acrylyl-CoA to an acrylate in the microorganisms are increased, compared to cells that are not genetically engineered. Also provided is a method of preparing the engineered microorganism by introducing into a microorganism an exogenous polynucleotide encoding the CoA transferase, an exogenous polynucleotide encoding 3-HP-CoA dehydratase, and an exogenous polynucleotide encoding an enzyme catalyzing conversion of acrylyl-CoA to acrylate.

Further provided is a method of producing an acrylate, wherein the method includes culturing the engineered microorganism in a culture medium. The acrylate produced by the microorganism can be recovered from the culture.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
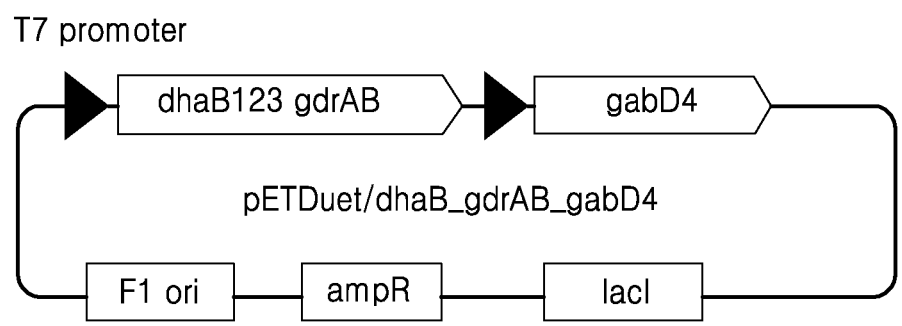
FIG. 1 is a cleavage map of a pETDuet/dhaB_gdrAB_gabD4 vector.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

As used herein, the wording "increase in activity" or "increased activity" and the like in reference to a cell, an enzyme, a polypeptide, or a protein may refer to any detectable increase in activity sufficient to show that the activity level of the cell, enzyme, polypeptide, or protein is higher than that of a comparable cell, enzyme, polypeptide, or protein (e.g., a cell, polypeptide, protein or enzyme of the same type that is not genetically engineered). For instance, the activity of a cell, an enzyme, a polypeptide, or protein may be increased by about 5% or more, about 10% or more, about 15% or more, about 20% or more, about 30% or more, about 50% or more, about 60% or more, about 70% or more, about 100%, about 200%, or about 300%, compared to the same biochemical activity of an unmanipulated polypeptide, protein, or enzyme, or the polypeptide, protein, or enzyme of an unmanipulated (non-genetically engineered) cell. Increased activity may be identified by using a method known in the art.

The increased activity of a polypeptide, protein, or enzyme may occur, for example, due to increased gene expression or increased specific activity of an enzyme, polypeptide or protein (hereinafter referred to collectively as "polypeptide"). The increased expression may occur by introducing a polynucleotide encoding a polypeptide into a cell, increasing a copy number of the polynucleotide in the cell, or mutating a regulatory region of the polynucleotide.

A polynucleotide that is introduced or present in an increased copy number may be an endogenous gene or an exogenous gene. The endogenous gene refers to a gene that exists in a genetic material included in a microorganism prior to genetic manipulation of the microorganism. The exogenous gene refers to a gene that is introduced into a host cell, such as a gene that is integrated into a host cell genome, wherein the introduced gene may be homologous or heterologous with respect to the host cell genome.

The expression "increased copy number" may include an increase in copy number by an introduction of an exogenous gene, or amplification of an endogenous gene. The expression "increased copy number" may also include a copy number increase by genetically manipulating a cell that did not previously have a gene so as to have the gene in the cell. The introduction of the gene may occur by using a vehicle such as a vector. The introduction may be a transient introduction, in which the gene is not integrated into the genome, or an integration into the genome. The introduction may, for example, occur by introducing a vector inserted with a polynucleotide encoding a desired polypeptide into the cell and then replicating the vector in the cell or integrating the polynucleotide into the genome of the cell and then replicating the polynucleotide together with the replication of the genome.

As used herein, the term "genetic modification" may refer to introduction of a polynucleotide encoding a polypeptide (i.e., an increase in copy number of the gene), or substitution, addition, insertion, or deletion of at least one nucleotide with a genetic material of a parent cell, or chemical mutation of a genetic material of a parent cell. In other words, genetic modification may include cases associated with a coding region of a polypeptide or a functional fragment thereof of a polypeptide that is heterologous, homologous, or both heterologous and homologous with a referenced species. Genetic modification may also refer to modification in non-coding regulatory regions that are capable of modifying expression of a gene or an operon, wherein the non-coding regulatory regions include a 5'-non coding sequence and/or a 3'-non coding sequence.

The term "gene" as used herein refers to a nucleic acid fragment expressing a specific protein and may include a regulatory sequence such as a 5'-non-coding sequence and a 3'-non-coding sequence in addition to a coding region. The regulatory region may include a promoter, an enhancer, an operator, a ribosome binding site, a poly(A) binding sequence, and a terminator region.

The term "endogenous" refers to a referenced molecule (e.g., nucleic acid) or activity already present in the host cell prior to a particular genetic modification (e.g., a genetic composition, trait, or biosynthetic activity of a "wild-type" cell or a parent cell).

The term "heterologous" refers to molecule (e.g., nucleic acid) or activity derived from a source other than referenced species; and the term "homologous" refers to a molecule (e.g., nucleic acid) or activity derived from a host parent cell. Accordingly, an exogenous molecule or activity (e.g., expression of an exogenous coding nucleic acid) may be heterologous (e.g., a coding nucleic acid from a different species) or homologous (e.g., an additional copy of a coding nucleic acid from the same species) or both.

The term "secretion" as used herein refers to a movement of a material from a cell interior to a periplasmic space or an extracellular environment.

The terms "cell", "strain", or "microorganism" as used herein may be interchangeably used and may include bacteria, yeast, fungi, or the like.

The term "acrylic acid" as used herein may refer to an acrylic acid, an acrylate, or its salt. An acrylic acid may be produced by fermentation or enzyme reaction of microorganisms.

The expression "decreased activity", "decrease in activity" or "reduced activity" of a cell or polypeptide (including an enzyme or protein) refers to an activity level at which a cell or polypeptide shows no activity or the activity level that is lower than that of a comparable cell of the same type (e.g., a cell that is not genetically engineered) or the original polypeptide. For instance, the activity of a cell or polypeptide may be decreased by about 20% or more, about 30% or more, about 40% or more, about 50% or more, about 55% or more, about 60% or more, about 70% or more, about 75% or more, about 80% or more, about 85% or more, about 90% or more, about 95% or more, or about 100%, compared to the same biochemical activity of an unmanipulated polypeptide or unmanipulated (i.e., not genetically engineered) cells. The decreased activity includes the case in which the enzyme is inactive or has reduced activity even when the enzyme is expressed and the case in which the gene encoding the enzyme is not expressed or has reduced expression in comparison to the unmanipulated gene or the unmanipulated cells, even when the enzyme is expressed.

The reduced activity of enzyme polypeptide (including an enzyme or protein) may be due to deletion or disruption of the gene encoding the polypeptide. The "deletion" or the "disruption" of the gene refers to mutation, substitution, or deletion of a part or entirety of the genes, or a promoter or a terminator region thereof, or an insertion of at least one base to the gene, such that the gene may not be expressed, have reduced expression, or show no activity or reduced activity of the polypeptide, even when the gene is expressed. The deletion or the disruption of the gene may be achieved by genetic manipulation such as homologous recombination, mutagenesis, or molecular evolution. When a cell includes a plurality of the same genes or two or more different paralogs, one or more genes may be removed or disrupted.

A sequence identity of nucleic acid or polypeptide according to an embodiment of the present disclosure refers to the extent of identity between bases or amino acid residues of sequences after aligning the sequences such that they maximally match in certain comparative regions. The sequence identity is a value calculated by optimally aligning two sequences at certain comparative regions, wherein portions of the sequences at the certain comparative regions may be added or deleted, compared to reference sequences. A percentage of sequence identity may be calculated by, for example, comparing two optimally aligned sequences in the entire comparative region, determining the number of locations in which the same amino acids or nucleic acids appear at corresponding positions in each aligned sequence (i.e. matched locations), dividing the number of matched locations by the total number of locations in the comparative region (that is, the size of the range), and multiplying by 100 to calculate the percentage of the sequence identity. The percentage of the sequence identity may be calculated by using a known sequence comparison program, and examples of such program include BLASTN (NCBI), CLC Main Workbench (CLC bio), and MegAlign™ (DNASTAR Inc).

Various levels of sequence identity may be used to identify various types of polypeptides or polynucleotides having the same or similar functions. For example, a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100% may be used.

91% or more, 92% or more, 93% or more, 94% or more, 95% or more, 96% or more, 97% or more, 98% or more, 99% or more, or 100% to at least one amino acid sequence of SEQ ID NOS: 1 to 10. The polynucleotide encoding the CoA transferase may have a sequence identity of 95% or more to at least one nucleotide sequence of SEQ ID NOS: 11 to 20. The CoA transferase may be at least one selected from enzymes shown in Table 1. All the enzymes of Table 1 may be E1-type.

TABLE 1

| No. | EC | Category | Source strain | Gene name | Place of strain purchase | Sequence* |
|---|---|---|---|---|---|---|
| 1 | 2.8.3.8 | Acetate CoA-transferase | *Clostridium propionicum* | pct | KCTC5582 | 1/11 |
| 2 | 2.8.3.8 | Acetate CoA-transferase | *Escherichia coli* (strain K12) | ydiF b1694 JW1684 | In-house | 2/12 |
| 3 | 2.8.3.8 | Acetate CoA-transferase | *Cupriavidus necator* | pct | KCTC22469 | 3/13 |
| 4 | 6.2.1.17 | CoA transferase | *Halomonas smyrnensis* | acuN | DSM21644 | 4/14 |
| 5 | 6.2.1.17 | CoA transferase | *Ruegeria pomeroyi* DSS-3 | SPO2934 | DSM15171 | 5/15 |
| 6 | 2.8.3.8 | Acetate CoA-transferase | *Desulfosporosinus youngiae* DSM 17734 | DesyoDRAFT_3698 | DSM17734 | 6/16 |
| 7 | 3.1.2.— | Thioesterase | *Peptoniphilus indolicus* ATCC 29427 | HMPREF9129_0351 | KCTC15023 | 7/17 |
| 8 | 2.8.3.8 | Acetate CoA-transferase | *Desulfosporosinus meridiei* (strain ATCC BAA-275/DSM 13257/NCIMB 13706/S10) | Desmer_1798 | DSM13257 | 8/18 |
| 9 | 2.8.3.8 | Acetate CoA-transferase | *Desulfosporosinus orientis* (strain ATCC 19365/DSM 765/NCIMB 8382/VKM B-1628) (*Desulfotomaculum orientis*) | Desor_3090 | DSM765 | 9/19 |
| 10 | 2.8.3.8 | Acetate CoA-transferase | *Peptostreptococcus anaerobius* CAG: 621 | BN738_00826 | KCTC5182 | 10/20 |

*Sequence denotes SEQ ID NO. of an amino acid/SEQ ID NO. of a nucleotide.

According to an aspect of the present disclosure, provided is a microorganism capable of producing acrylate, wherein activities of a coenzyme A (CoA) transferase catalyzing conversion of 3-hydroxypropionic acid (3-HP) to 3-hydroxypropionyl-CoA (3-HP-CoA), a 3-HP-CoA dehydratase catalyzing conversion of the 3-HP-CoA to acrylyl-CoA, and an enzyme catalyzing the acrylyl-CoA to an acrylate in the microorganisms are increased, compared to unengineered cells (i.e., cells that are not genetically engineered).

The CoA transferase may belong to EC 2.8.3.8, EC 3.1.2.-, or EC 6.2.1.17. The CoA transferase may have an activity catalyzing conversion of 3-HP to 3-HP-CoA, wherein the activity is higher than an activity catalyzing a reversed reaction of the conversion. The CoA transferase may include an amino acid sequence having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to at least one amino acid sequence of SEQ ID NOS: 1 to 10. The polynucleotide encoding the CoA transferase may have a nucleotide sequence encoding an amino acid sequence having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to at least one amino acid sequence of SEQ ID NOS: 1 to 10. The polynucleotide encoding the CoA transferase may have a sequence identity of 95% or more to at least one nucleotide sequence of SEQ ID NOS: 11 to 20. The CoA transferase may be at least one selected from enzymes shown in Table 1. All the enzymes of Table 1 may be E1-type.

The 3-HP-CoA dehydratase may belong to EC 4.2.1.- including EC 4.2.1.17, EC 4.2.1.55, and EC 4.2.1.166. The 3-HP-CoA dehydratase may have an activity catalyzing conversion of 3-HP-CoA to acrylyl-CoA, wherein the activity is higher than an activity catalyzing a reversed reaction of the conversion. The 3-HP-CoA dehydratase may include amino acid sequences having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to at least one amino acid sequence of SEQ ID NOS: 21 to 98 and 401. The polynucleotide encoding 3-HP-CoA dehydratase may encode amino acid sequences having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to at least one amino acid sequence of SEQ ID NOS: 21 to 98 and 401. The polynucleotide encoding 3-HP-CoA dehydratase may have a sequence identity of about 95% or more to one or more nucleotide sequence of SEQ ID NOS: 99 to 176 and 402. The 3-HP-CoA dehydratase may be at least one selected from enzymes shown in Tables 2 to 5. The enzymes shown in Tables 2 to 5 may be E2-type. The term "sequence*" as used herein denotes SEQ ID NO. of an amino acid/SEQ ID NO. of a nucleotide.

TABLE 2

| No. | EC | Category | Source strain | Gene | Place of purchase | Sequence* |
|---|---|---|---|---|---|---|
| 1 | 4.2.1.— | 3-hydroxybutyryl-CoA dehydratase(Crotonase) | *Dictyostelium discoideum* (Slime mold) | Q869N6 | DSM947 | 21/99 |
| 2 | 4.2.1.55 | 3-hydroxybutyryl-CoA dehydratase(Crotonase) | *Clostridium acetobutylicum* | crt CA_C2712 | KCTC1790 | 22/100 |
| 3 | 4.2.1.55 | 3-hydroxybutyryl-CoA dehydratase(Crotonase) | *Clostridium difficile* | crt ech | KCTC5009 | 23/101 |
| 4 | 4.2.1.55 | 3-hydroxybutyryl-CoA dehydratase(Crotonase) | *Clostridium pasteurianum* | F502_09038 | KCTC1674 | 24/102 |
| 5 | 4.2.1.55 | 3-hydroxybutyryl-CoA dehydratase(Crotonase) | *Clostridium pasteurianum* | F502_06297 | KCTC1674 | 25/103 |
| 6 | 4.2.1.55 | 3-hydroxybutyryl-CoA dehydratase(Crotonase) | *Megasphaera elsdenii* | MELS_1449 | KCTC5187 | 26/104 |
| 7 | 4.2.1.116 | 3-hydroxybutyryl-CoA dehydratase(Crotonase) | *Metallosphaera sedula* | Msed_2001 | DSM5348 | 27/105 |
| 8 | 4.2.1.55 | 3-hydroxybutyryl-CoA dehydratase(Crotonase) | *Clostridicum kluyvery* | crt1 | DSM555 | 28/106 |
| 9 | 4.2.1.— | 4-hydroxybutyryl-CoA dehydratase | *Sulfolobus tokodaii* | STK_16590 | DSM16993 | 29/107 |
| 10 | 4.2.1.— | 4-hydroxybutyryl-CoA dehydratase | *Geobacter metallireducens* | Gmet_2215 | DSM7210 | 30/108 |
| 11 | 4.2.1.— | 4-hydroxybutyryl-CoA dehydratase | *Sulfolobus solfataricus* | abfD-1 | DSM1617 | 31/109 |
| 12 | 4.2.1.— | 4-hydroxybutyryl-CoA dehydratase | *Syntrophobacter fumaroxidans* | Sfum_3141 | DSM10017 | 32/110 |
| 13 | 4.2.1.— | 4-hydroxybutyryl-CoA dehydratase | *Porphyromonas gingivalis* | PGN_0727 | DSM20709 | 33/111 |
| 14 | 4.2.1.— | 4-hydroxybutyryl-CoA dehydratase | *Polynucleobacter necessarius* subsp. *Asymbioticus* | Pnuc_0370 | DSM18221 | 34/112 |
| 15 | 4.2.1.116 | 3-hydroxypropionyl-CoA dehydratase | *Sulfolobus tokodaii* | STK_15160 | DSM16993 | 35/113 |
| 16 | 4.2.1.— | 3-hydroxypropionyl-CoA dehydratase | *Gordonia terrae* C-6 | GTC6_11571 | KCTC9807 | 36/114 |
| 17 | 4.2.1.— | 3-hydroxypropionyl-CoA dehydratase | *Halalkalicoccus jeotgali* | HacjB3_17558 C497_07209 | DSM18796 | 37/115 |
| 18 | 4.2.1.— | 3-hydroxypropionyl-CoA dehydratase | *Carboxydothermus hydrogenoformans* | CHY_1739 | DSM6008 | 38/116 |
| 19 | 4.2.1.55 | 3-hydroxypropionyl-CoA dehydratase | *Thermomicrobium roseum* | trd_0041 | DSM5159 | 39/117 |
| 20 | 4.2.1.17 | 3-hydroxypropionyl-CoA dehydratase | *Methylobacterium extorquens* | croA METDI5699 | DSM1337 | 40/118 |

TABLE 3

| No. | EC | Category | Source strain | Gene | Place of purchase | Sequence* |
|---|---|---|---|---|---|---|
| 21 | 4.2.1.— | R-phenyllactate dehydratase | *Clostridium sporogenes* | fldB | KCTC5654 | 41/119 |
| 22 | 4.2.1.— | R-phenyllactate dehydratase | | fldC | KCTC5654 | 42/120 |
| 23 | 4.2.1.— | R-phenyllactate dehydratase | | fldI | KCTC5654 | 43/121 |
| 24 | 4.2.1.— | R-phenyllactate dehydratase | | fldA | KCTC5654 | 44/122 |
| 25 | 4.2.1.— | R-phenyllactate dehydratase | *Lachnoanaerobaculum saburreum* | fldC HMPREF0381_2734 | DSM3986 | 45/123 |
| 26 | 4.2.1.— | R-phenyllactate dehydratase | | fldB HMPREF0381_2735 | DSM3986 | 46/124 |
| 27 | 4.2.1.— | R-phenyllactate dehydratase | | fldI2 HMPREF0381_2736 | DSM3986 | 47/125 |
| 28 | 4.2.1.— | R-phenyllactate dehydratase | *Peptostreptococcus stomatis* | fldI HMPREF0634_1391 | DSM17678 | 48/126 |
| 29 | 4.2.1.— | R-phenyllactate dehydratase | | HMPREF0634_1028 | DSM17678 | 49/127 |
| 30 | 4.2.1.— | R-phenyllactate dehydratase | | fldB HMPREF0634_1029 | DSM17678 | 50/128 |
| 31 | 4.2.1.— | 2-hydroxyisocaproyl-CoA dehydratase | *Clostridium difficile* | hadB | KCTC5009 | 51/129 |
| 32 | 4.2.1.— | 2-hydroxyisocaproyl-CoA dehydratase | | hadC | KCTC5009 | 52/130 |

TABLE 3-continued

| No. | EC | Category | Source strain | Gene | Place of purchase | Sequence* |
|---|---|---|---|---|---|---|
| 33 | 4.2.1.— | 2-hydroxyisocaproyl-CoA dehydratase | | hadI | KCTC5009 | 53/131 |
| 34 | 4.2.1.— | 2-hydroxyisocaproyl-CoA dehydratase | | hadA | KCTC5009 | 54/132 |
| 35 | 4.2.1.17 | Enoyl-CoA hydratase | *Escherichia coli* (strain K12) | paaF | In-house | 55/133 |
| 36 | 4.2.1.17 | Enoyl-CoA hydratase | *Rhodobacter capsulatus* | fadB1 | KCTC2583 | 56/134 |
| 37 | 4.2.1.— | Enoyl-CoA hydratase | *Pseudomonas stutzeri* | PSTAA_0117 | DSM4166 | 57/135 |
| 38 | 4.2.1.— | Enoyl-CoA hydratase | *Haliangium ochraceum* | Hoch_4602 | DSM14365 | 58/136 |
| 39 | 4.2.1.— | Enoyl-CoA hydratase | *Anoxybacillus flavithermus* | Aflv_0566 | DSM21510 | 59/137 |
| 40 | 4.2.1.— | Enoyl-CoA hydratase | *Streptomyces avermitilis* | echA3 SAV_717 | DSM46492 | 60/138 |
| 41 | 4.2.1.— | Enoyl-CoA hydratase | *Advenella kashmirensis* | TKWG_10020 | DSM17095 | 61/139 |

TABLE 4

| No. | EC | Category | Source strain | Gene | Place of purchase | Sequence* |
|---|---|---|---|---|---|---|
| 42 | 4.2.1.— | Enoyl-CoA hydratase | *Oligotropha carboxidovorans* | OCA5_c12950 OCAR_6780 | DSM1227 | 62/140 |
| 43 | 4.2.1.— | Enoyl-CoA hydratase | *Riemerella anatipestifer* | Riean_1526 RA0C_1812 | DSM15868 | 63/141 |
| 44 | 4.2.1.— | Enoyl-CoA hydratase | *Fusobacterium necrophorum* subsp. *funduliforme* Fnf 1007 | HMPREF1127_1435 | DSM19678 | 64/142 |
| 45 | 4.2.1.— | Enoyl-CoA hydratase | | HMPREF1127_1434 | DSM19678 | 65/143 |
| 46 | 4.2.1.— | Enoyl-CoA hydratase | | HMPREF1127_1436 | DSM19678 | 66/144 |
| 47 | 4.2.1.— | Enoyl-CoA hydratase | *Desulfosporosinus youngiae* DSM 17734 | DesyoDRAFT_3696 | DSM17734 | 67/145 |
| 48 | 4.2.1.— | Enoyl-CoA hydratase | | DesyoDRAFT_3695 | DSM17734 | 68/146 |
| 49 | 4.2.1.— | Enoyl-CoA hydratase | | DesyoDRAFT_3697 | DSM17734 | 69/147 |
| 50 | 4.2.1.— | Enoyl-CoA hydratase | *Peptoniphilus indolicus* ATCC 29427 | fldB HMPREF9129_0353 | KCTC15023 | 70/148 |
| 51 | 4.2.1.— | Enoyl-CoA hydratase | | HMPREF9129_0354 | KCTC15023 | 71/149 |
| 52 | 4.2.1.— | Enoyl-CoA hydratase | | HMPREF9129_0352 | KCTC15023 | 72/150 |
| 53 | 4.2.1.— | Enoyl-CoA hydratase | *Desulfosporosinus meridiei* (strain ATCC BAA-275/ DSM 13257/ NCIMB 13706/ S10) | Desmer_1800 | DSM13257 | 73/151 |
| 54 | 4.2.1.— | Enoyl-CoA hydratase | | Desmer_1801 | DSM13257 | 74/152 |
| 55 | 4.2.1.— | Enoyl-CoA hydratase | | Desmer_1799 | DSM13257 | 75/153 |
| 56 | 4.2.1.— | 2-hydroxyglutaryl-CoA dehydratase | *Acidaminococcus fermentans* | hgdA Acfer_1815 | DSM20731 | 76/154 |
| 57 | 4.2.1.— | 2-hydroxyglutaryl-CoA dehydratase | | hgdB Acfer_1815 | DSM20731 | 77/155 |
| 58 | 4.2.1.— | 2-hydroxyglutaryl-CoA dehydratase | | hgdC Acfer_1815 | DSM20731 | 78/156 |
| 59 | 4.2.1.— | 2-hydroxyglutaryl-CoA dehydratase | *Carboxydothermus hydrogenoformans* | hgdB CHY_0846 | DSM6008 | 79/157 |
| 60 | 4.2.1.— | 2-hydroxyglutaryl-CoA dehydratase | | hgdA CHY_0847 | DSM6008 | 80/158 |
| 61 | 4.2.1.— | 2-hydroxyglutaryl-CoA dehydratase | | hgdC CHY_0848 | DSM6008 | 81/159 |
| 62 | 4.2.1.— | 2-hydroxyglutaryl-CoA dehydratase | *Oscillibacter valericigenes* | hgdC OBV_10870 | DSM18026 | 82/160 |
| 63 | 4.2.1.— | 2-hydroxyglutaryl-CoA dehydratase | | hgdA OBV_10880 | DSM18026 | 83/161 |
| 64 | 4.2.1.— | 2-hydroxyglutaryl-CoA dehydratase | | hgdB OBV_10890 | DSM18026 | 84/162 |

TABLE 5

| No. | EC | Category | Source strain | Gene | Place of purchase | Sequence* |
|---|---|---|---|---|---|---|
| 65 | 4.2.1.— | 2-hydroxyglutaryl-CoA dehydratase | Desulfosporosinus orientis (strain ATCC 19365/DSM 765/NCIMB 8382/VKM B-1628) (Desulfotomaculum orientis) | Desor_3092 | DSM765 | 85/163 |
| 66 | 4.2.1.— | 2-hydroxyglutaryl-CoA dehydratase | | Desor_3093 | DSM765 | 86/164 |
| 67 | 4.2.1.— | 2-hydroxyglutaryl-CoA dehydratase | | Desor_3091 | DSM765 | 87/165 |
| 68 | 4.2.1.— | 2-hydroxyglutaryl-CoA dehydratase | Peptostreptococcus anaerobius CAG: 621 | BN738_00824 | KCTC5182 | 88/166 |
| 69 | 4.2.1.— | 2-hydroxyglutaryl-CoA dehydratase | | BN738_00823 | KCTC5182 | 89/167 |
| 70 | 4.2.1.— | 2-hydroxyglutaryl-CoA dehydratase | | BN738_00825 | KCTC5182 | 90/168 |
| 71 | 4.2.1.— | 2-hydroxyglutaryl-CoA dehydratase | Chloroflexus aggregans (strain MD-66/DSM 9485) | Cagg_1174 | DSM9485 | 91/169 |
| 72 | 4.2.1.17 | 2-hydroxyglutaryl-CoA dehydratase | Marivirga tractuosa (strain ATCC 23168/DSM 4126/NBRC 15989/NCIMB 1408/VKM B-1430/H-43) (Microscilla tractuosa) (Flexibacter tractuosus) | Ftrac_3721 | KCTC2958 | 92/170 |
| 73 | 4.2.1.— | 2-hydroxyglutaryl-CoA dehydratase | Marinithermus hydrothermalis (strain DSM 14884/JCM 11576/T1) | Marky_1278 | DSM14884 | 93/171 |
| 74 | 4.2.1.— | 2-hydroxyglutaryl-CoA dehydratase | Chitinophaga pinensis (strain ATCC 43595/DSM 2588/NCIB 11800/UQM 2034) | Cpin_6304 | KCTC3412 | 94/172 |
| 75 | 4.2.1.— | 2-hydroxyglutaryl-CoA dehydratase | Megasphaera elsdenii DSM 20460 | MELS_0744 | KCTC5187 | 95/173 |
| 76 | 4.2.1.— | 2-hydroxyglutaryl-CoA dehydratase | Megasphaera elsdenii DSM 20460 | MELS_0745 | KCTC5187 | 96/174 |
| 77 | 4.2.1.— | 2-hydroxyglutaryl-CoA dehydratase | Megasphaera elsdenii DSM 20460 | MELS_0746 | KCTC5187 | 97/175 |
| 78 | 4.2.1.— | 2-hydroxyglutaryl-CoA dehydratase | Chloroflexus aurantiacus (strain ATCC 29364/DSM 637/Y-400-fl) | Chy400_0108 | DSM635 | 98/176 |
| 79 | 4.2.1.— | enoyl-CoA hydrastase | Ruegeria pomeroyi DSS-3 | SP00147 | DSM15171 | 401/402 |

The enzyme catalyzing conversion of acrylyl-CoA to acrylate may belong to EC 3.1.2- including EC 3.1.2.4. The enzyme catalyzing conversion of acrylyl-CoA to acrylate may be 3-HP-CoA hydrolase or 3-hydroxyisobutyryl-CoA hydrolase. The enzyme catalyzing conversion of acrylyl-CoA to acrylate may have activity of catalyzing conversion of acrylyl-CoA to acrylate higher than activity of catalyzing the reversed reaction. The enzyme catalyzing the conversion of acrylyl-CoA to acrylate may include amino acid sequences having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to at least one amino acid sequence of SEQ ID NOS: 177 to 182. The polynucleotide encoding the enzyme catalyzing conversion of acrylyl-CoA to acrylate may encode amino acid sequences having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to at least one amino acid sequence of SEQ ID NOS: 177 to 182. The polynucleotide encoding the enzyme catalyzing conversion of acrylyl-CoA to acrylate may have a sequence identity of about 95% or more to nucleotide sequences of SEQ ID NOS: 405 to 410. The enzyme catalyzing conversion of acrylyl-CoA to acrylate may be at least one selected from enzymes shown in Table 6. The enzymes shown in Table 6 may be E3-type. The term "sequence*" as used in herein denotes SEQ ID NO. of an amino acid/SEQ ID NO. of a nucleotide.

TABLE 6

| No. | EC | Category | Source strain | Gene name | Place of purchase | Sequence* |
|---|---|---|---|---|---|---|
| 1 | 3.1.2.— | Acyl-CoA thioester hydrolase | E. coli | yciA | In-house | 177/405 |
| 2 | 3.1.2.— | Acyl-CoA thioester hydrolase | Klebsiella oxytoca 10-5245 | HMPREF9689_01673 | KCTC1686 | 178/406 |

TABLE 6-continued

| No. | EC | Category | Source strain | Gene name | Place of purchase | Sequence* |
|---|---|---|---|---|---|---|
| 3 | 3.1.2.— | Acyl-CoA thioester hydrolase | Cronobacter turicensis | yciA | In-house | 179/407 |
| 4 | 3.1.2.— | Acyl-CoA thioester hydrolase | Citrobacter freundii | D186_20262 | In-house | 180/408 |
| 5 | 3.1.2.— | Acyl-CoA thioester hydrolase | Salmonella enterica | Sel_A1458 | DSM5569 | 181/409 |
| 6 | 3.1.2.— | Acyl-CoA thioester hydrolase | Shigella flexneri 1235-66 | SF123566_2028 | In-house | 182/410 |

The microorganism may be microorganisms that are genetically engineered so that expression of the three types of enzyme genes (CoA transferase, 3-HP-CoA dehydratase, and enzyme catalyzing conversion of acrylyl-CoA to acrylate) may increase compared to that of cells that are not genetically engineered. When the activities of the three enzymes were already present in the parent cells, expression of the three enzymes may further increased by genetically engineering the microorganism. Also, when the activities of the three enzymes were not present in the parent (e.g., not genetically engineered) cells, genes that encode the three enzymes may be introduced to parent cells by genetic engineering and express or overexpress the genes. The genetically unengineered cells denote a wild microorganism or parent cells, from which the microorganism is derived.

The expression or overexpression of the three enzymes may be achieved by using various methods known to one of ordinary skill in the art. For example, the expression may be increased by increasing the number of gene copies, or by using a control material such as an inducer or a repressor. The number of gene copies may be increased by introduction or amplification of the gene. That is, the increasing of the number of gene copies may be achieved by introducing a vector or an expression cassette including a regulation element and the three enzyme genes that are operably linked to one another into a host cell.

Also, the increase in the activities of the three genes may be caused by modification of an expression regulatory sequence of the gene. The regulatory sequence may be e.g., a promoter sequence or a transcription terminator sequence for the gene expression. The regulatory sequence may be a sequence that encodes a motif which may influence the gene expression. The motif may be, for example, a secondary structure-stabilizing motif, an RNA destabilizing motif, a splice-activating motif, a polyadenylation motif, an adenine-rich sequence, or an endonuclease recognition site.

The microorganism may be selected from the group consisting of bacteria, yeast, and fungi. The microorganism may be selected from the group consisting of Escherichia, Corynebacterium genus, and Brevibacterium genus. The cells may be Corynebacterium genus. The microorganism may be a microorganism selected from the group consisting of E. coli, Corynebacterium glutamicum, Corynebacterium thermoaminogenes, Brevibacterium flavum, and Brevibacterium lactofermentum.

The microorganism may naturally produce the acrylic acid or may be genetically engineered to produce the acrylic acid by using a recombinant method. In this case, the microorganism may be a microorganism capable of producing acrylic acid from monosaccharides such as glucose, or a glycerol. Also, the microorganism may have the capability to produce 3-HP, for example from monosaccharides such as glucose, or a glycerol. The microorganism may have a biochemical pathway forming glycerol from monosaccharides such as glucose. The biochemical pathway may include glycolytic pathway converting monosaccharides such as glucose to dihydroxyacetone phosphate (DHAP), and a pathway converting DHAP to glycerol such as dihydroxyacetone phosphate phosphatase (DHAPP) that catalyzes the conversion of dihydroxyacetone phosphate (DHAP) into dihydroxyacetone (DHA); and glycerol dehydrogenase (GLDH) that catalyzes the conversion of DHA into glycerol. The microorganism may include a polynucleotide encoding dihydroxyacetone phosphate phosphatase (DHAPP) that catalyzes the conversion of dihydroxyacetone phosphate (DHAP) into dihydroxyacetone (DHA); and a polynucleotide encoding glycerol dehydrogenase (GLDH) that catalyzes the conversion of DHA into glycerol. 3-HP produced by the microorganism may be converted to acrylate by the increased CoA transferase activity, 3-HP-CoA dehydratase activity and activity of an enzyme that catalyzes conversion of acrylyl-CoA to acrylate of the claimed microorganism. When the microorganism does not naturally produce 3-HP, the microorganism may be genetically engineered to produce 3-HP. When a gene that encodes an enzyme catalyzing conversion of glycerol to 3-HPA and a gene that encodes an enzyme catalyzing conversion of 3-HPA to 3-HP are introduced to the microorganism, the microorganism may have a 3-HP productivity from glycerol. In this case, the microorganism may be a microorganism capable of producing a glycerol. The microorganism may be, for example, a microorganism of Escherichia genus including E. coli. The enzyme catalyzing conversion of glycerol to 3-HPA may be a glycerol dehydratase (GDH). The enzyme catalyzing conversion of 3-HPA to 3-HP may be an aldehyde dehydrogenase (ALD).

The GDH may include any enzyme catalyzing conversion of glycerol to 3-HPA. The GDH may belong to EC 4.2.1.30 or diol dehydratase (EC 4.2.1.28). The GDH and a nucleotide encoding the GDH may be derived from Ilyobacter polytropus, Klebsiella pneumoniae, Citrobacter freundii, Clostritidium pasteurianum, Salmonella typhimurium, or Klebsiella oxytoca. In each case, the GDH may be composed of three subunits. The subunits may be a large or "α" subunit, a medium or "β" subunit, and a small or "γ" subunit. The gene encoding the large or "α" subunit of the GDH may include dhaB1, gldA, and ghaB. The gene encoding the medium or "β" subunit of the GDH may include dhaB2, gldB, and dhaC. The gene encoding the small or "γ" subunit of the GDH may include dhaB3, gldC, and dhaE. The gene encoding the large or "α" subunit of the diol dehydratase may include pduC and pddA. The gene encoding the medium or "β" subunit of the diol dehydratase may include pduD and pddB. The gene encoding the small or "γ" subunit of the diol dehydratase may include pduE and pddC. Tables 7 and 8 show Gene names and GenBank references with respect to GDH and functions linked to GDH. The GDH may include dhaB1, dhaB2, and dhaB3 that are derived from

*Ilyobacter polytropus*. The *Ilyobacter polytropus*-derived dhaB1, dhaB2, and dhaB3 may each have amino acid sequences of SEQ ID NOS: 183, 184, and 185, respectively. The dhaB1 gene, dhaB2 gene, and dhaB3 gene may each encode amino acid sequences of SEQ ID NOS: 183, 184, and 185, respectively. The *Ilyobacter polytropus*-derived dhaB1 gene, dhaB2 gene, and dhaB3 gene may each have nucleotide sequences of SEQ ID NOS: 186, 187, and 188, respectively.

*coli*. For example, a gene encoding the SSADH may be polynucleotides encoding amino acid sequences of SEQ ID NOS: 189, 190, and 191. The SSADH may be gabD (a nucleotide sequence of SEQ ID NO: 192 and an amino acid sequence of SEQ ID NO: 193) derived from *Cupriavidus necator*. The gene encoding the SSADH may be, for example, a polynucleotide encoding amino acid sequences of SEQ ID NOS: 189, 190, 191, and 193. The gene encoding the SSADH may have, for example, nucleotide sequences of

TABLE 7

| Organism (GenBank reference number) | Gene function | | | | | | | |
|---|---|---|---|---|---|---|---|---|
| | Control | | Unknown | | Reactivation | | Unknown | |
| | Gene | Base pair | Gene | Base pair | Gene | Base pair | Gene | Base pair |
| *K. pneumoniae* (U30903) | | | orf2c | 7116-7646 | orf2b | 6762-7115 | orf2a | 5125-5556 |
| *K. pneumoniae* (U60992) | | | | | GdrB | | | |
| *C. freundii* (U09771) | dhaR | 3746-5671 | orfW | 5649-6179 | orfX | 6180-6533 | orfY | 7736-8164 |
| *C. pasteurianum* (AF051373) | | | | | | | | |
| *C. pasteurianum* (AF026270) | | | orfW | 210-731 | orfX | 1-196 | orfY | 746-1177 |
| *S. typhimurium* (AF026270) | | | | | pduH | 8274-8645 | | |
| *K. oxytoca* (AF017781) | | | | | DdrB | 2063-2440 | | |
| *K. oxytoca* (AF051373) | | | | | | | | |

TABLE 8

| Organism (GenBank reference number) | Gene function | | | | | | | |
|---|---|---|---|---|---|---|---|---|
| | dehydrase, α | | dehydrase, α | | dehydrase, α | | Reactivation | |
| | Gene | Base pair | Gene | Base pair | Gene | Base pair | Gene | Base pair |
| *K. pneumoniae* (U30903) | dhaB1 | 3047-4714 | dhaB2 | 2450-2890 | dhaB3 | 2022-2447 | orf2a | 186-2009 |
| *K. pneumoniae* (U60992) | gldA | 121-1788 | gldB | 1801-2382 | gldB | 2388-2813 | gdrA | |
| *C. freundii* (U09771) | dhaB | 8556-10223 | dhaC | 10235-10819 | dhaC | 10822-11250 | orfY | 11261-13072 |
| *C. pasteurianum* (AF051373) | dhaB | 84-1748 | dhaC | 1779-2318 | dhaC | 2333-2773 | | 2790-4598 |
| *C. pasteurianum* (AF026270) | | | | | | | orfY | |
| *S. typhimurium* (AF026270) | pduC | 3557-5221 | pduD | 5232-5906 | pduD | 5921-6442 | | 6452-8284 |
| *K. oxytoca* (AF017781) | | | | | | | | 241-2073 |
| *K. oxytoca* (AF051373) | pddA | 121-1785 | pddB | 1796-2470 | pddB | 2485-3006 | | |

The GDH may include an amino acid sequence having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to each sequence of dhaB1, dhaB2, and dhaB3 genes derived from *Ilyobacter polytropus*.

The ALD may include any protein that may catalyze conversion of 3-HPA to 3-HP. The ALD may use a redox cofactor such as NAD, NADP, FAD, or PQQ. The ALD may be EC 1.2.1.3 (NAD-dependent), EC 1.2.1.4 (NADP-dependent), EC 1.2.99.3 (PQQ-dependent), or EC 1.2.99.7 (FAD-dependent). An example of the NADP-dependent ALD may be AldB, which is encoded by an *E. coli* gene, aldB. An example of the NAD-dependent ALD may be AldA, which is encoded by an *E. coli* gene, aldA, or AldH, which is encoded by an *E. coli* gene, aldH. The ALD may be a succinate semialdehyde dehydrogenase (SSADH). The SSADH may belong to EC 1.2.1.24 or EC 1.2.1.16. The SSADH may be dependent upon NAD$^+$, NADP$^+$, or both. The SSADH may be CoA independent. For example, the SSADH may be derived from *Corynebacterium* genus, *Rhodococcus* genus, *Gordonia* genus, *Mycobacterium* genus, *Enterobacter* genus, and *Escherichia* genus. The SSADH may be gabD1, gabD2, or gabD3 derived from *E.*

SEQ ID NOS: 194, 195, 196, and 192. The SSADH may include amino acid sequences having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to amino acid sequences of SEQ ID NOS: 189, 190, 191, and 193.

The microorganism may further include a polynucleotide encoding a glycerol dehydratase reactivase (GDR). The glycerol and diol dehydratase may be subject to mechanism-based suicide inactivation by glycerol and other substrates (Daniel et al., FEMS Microbiol. Rev. 22, 553(1999)). The term "glycerol dehydratase reactivase (GDR)" refers to a protein that reactivates activity of the dehydratase. The term "dehydratase reactivating activity" refers to a phenomenon of converting a dehydratase not capable of catalysis of a substrate to one capable of catalysis of a substrate or to the phenomenon of inhibiting the inactivation of a dehydratase or the phenomenon of extending the useful half-life of the dehydratase enzyme in vivo. The GDR may be at least one of dhaB, gdrA, pduG, and ddrA. Also, the GDR may be at least one of orfX, orf2b, gdrB, pduH, and ddrB.

The GDR may be gdrA and gdrB derived from *K. pneumoniae* (U60992), each of which may have amino acid sequences of SEQ ID NOS: 197 and 198. Also, the GDR may be gdrA and gdrB derived from *Ilyobacter polytropus*, each of which may have amino acid sequences of SEQ ID NOS: 199 and 200. The GDR may include amino acid sequences having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to amino acid sequences of SEQ ID NOS: 197, 198, 199, and 200. Each of the Genes encoding GdrA and GdrB may have sequences encoding amino acid sequences of SEQ ID NOS: 197, 198, 199, and 200 or, for example, nucleotide sequences of SEQ ID NOS: 201, 202, 203, and 204.

In the microorganism, at least one of the polynucleotide encoding GDH, the polynucleotide encoding ALD, and the polynucleotide encoding GDR may be expressed at a level higher than that of an unengineered or parent microorganism. The expression level may be expression of mRNA or protein level. The expression of protein level may be based on an amount or activity of the expressed protein. The expression level may be about 5% or more, about 10% or more, about 15% or more, about 20% or more, about 30% or more, about 50% or more, about 60% or more, about 70% or more, about 100% or more, 200% or more, or 300% or more increased than that of an unengineered microorganism.

The microorganism may have a 3-HP productivity. In the microorganism, the increase in the expression of at least one of the polynucleotide encoding GDH, the polynucleotide encoding ALD, and the polynucleotide encoding GDR may allow the 3-HP to be produced at a higher level than in an unengineered microorganism. The 3-HP production may be performed by using a method of in-cell production, a method of secretion to outside the cell after producing inside the cell, or a combination thereof. The 3-HP produced inside the cell may be converted from another metabolic product such as an acrylic acid. The 3-HP production may be about 5% or more, about 10% or more, about 15% or more, about 20% or more, about 30% or more, about 50% or more, about 60% or more, about 70% or more, about 100% or more, about 200% or more, or about 300% or more increased than that of an unengineered microorganism.

The increased expression of at least one of the polynucleotide encoding GDH, the polynucleotide encoding ALD, and the polynucleotide encoding GDR may occur by introducing a polynucleotide encoding a polypeptide into a cell, increasing a copy number of the polynucleotide in the cell, or mutating a regulatory region of the polynucleotide. A polynucleotide that is introduced or present in an increased copy number may be an endogenous gene or an exogenous gene. The endogenous gene refers to a gene that exists in a genetic material included in a microorganism. The exogenous gene refers to a gene that is introduced into a host cell, such as a gene that is integrated into a host cell genome, wherein the introduced gene may be homologous or heterologous with respect to the host cell genome.

The microorganism may have reduced activity of one or more enzymes involved in a pathway of decomposition or conversion of an acrylate to another product. In the microorganism, a gene encoding one or more enzymes involved in a pathway of decomposition or conversion of an acrylate to another product may be deleted or disrupted.

Also, the microorganism may further include a pathway of conversion of an acrylate to the other product. In the microorganism, production of an acrylate may be performed by using a method of in-cell production or a method of secretion after producing in the cell. Thus, the microorganism may further include the pathway involved in production of acrylate in a cell and conversion to the other product, for example, an enzyme gene and its expressed product. The other product may be an acrylate ester.

The microorganism may have an inactivated or reduced pathway of synthesizing lactate from pyruvate. In the microorganism, activity of lactate dehydrogenase (LDH) may be deleted or reduced. The LDH may have activity of catalyzing conversion of pyruvate to lactate. The LDH may be an enzyme that is classified under EC.1.1.1.27. For example, the LDH may include amino acid sequences having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to an amino acid sequence of SEQ ID NO: 205. In the microorganism, a gene encoding lactate dehydrogenase may be disrupted or deleted. The LDH gene may encode amino acid sequences having a sequence identity of 65% or more, for example, 70% or more, 80% or more, 85% or more, 90% or more, 91% or more, 92% or more, 93% or more, 94% or more, 95% or more, 96% or more, 97% or more, 98% or more, 99% or more, or 100% to an amino acid sequence of SEQ ID NO: 205.

According to another aspect of the present disclosure, provided is a method of producing acrylate, the method including culturing the microorganism described above in a culture medium.

The culturing of the microorganism may be performed in a suitable medium under suitable culturing conditions known in the art. One of ordinary skill in the art may suitably change a culture medium and culturing conditions according to the microorganism selected. A culturing method may be batch culturing, continuous culturing, fed-batch culturing, or a combination thereof. The microorganism may secrete acrylate to outside the cell.

The culture medium may include various carbon sources, nitrogen sources, and trace elements.

The carbon source may be, for example, carbohydrate such as glucose, sucrose, lactose, fructose, maltose, starch, or cellulose; fat such as soybean oil, sunflower oil, castor oil, or coconut oil; fatty acid such as palmitic acid, stearic acid, linoleic acid; alcohol such as glycerol or ethanol; organic acid such as acetic acid, or a combination thereof. The culturing may be performed by having glucose as the carbon source. The nitrogen source may be an organic nitrogen source such as peptone, yeast extract, beef stock, malt extract, corn steep liquor (CSL), or soybean flour, or an inorganic nitrogen source such as urea, ammonium sulfate, ammonium chloride, ammonium phosphate, ammonium carbonate, and ammonium nitrate, or a combination thereof. The culture medium is a supply source of phosphorus and may include, for example, potassium dihydrogen phosphate, dipotassium phosphate, and corresponding sodium-containing salt thereof, and a metal salt such as magnesium sulfate or iron sulfate. Also, amino acid, vitamin, a suitable precursor, or the like may be included in the culture medium. The culture medium or individual component may be added to a culture medium solution in a batch, fed-batch, or continuous manner.

Also, pH of the culture medium solution may not be adjusted or may be adjusted by adding a compound such as ammonium hydroxide, potassium hydroxide, ammonia, phosphoric acid, and sulfuric acid to the culture medium solution by using a suitable method during the culturing process. Also, an antifoaming agent such as fatty acid polyglycol ester may be used during the culturing process to inhibit the generation of bubbles.

The culturing process may be performed in a microaerobic condition. As used herein, the term "microaerobic conditions" when used in reference to a culture or growth condition is intended to mean that the dissolved oxygen concentration in the medium remains between 0 and about 10% of saturation for dissolved oxygen in liquid media. Microaerobic conditions also include growing or resting cells in liquid medium or on solid agar inside a sealed chamber maintained with an atmosphere of less than 1% oxygen. The percent of oxygen can be maintained by, for example, sparging the culture with an N2/CO2 mixture or other suitable non-oxygen gas or gases. The oxygen conditions for the acrylic acid production may include maintaining a dissolved oxygen (DO) concentration of 1 to 10%, 1 to 8%, 1 to 6%, 1 to 4%, or 1 to 2%, 2 to 10%, 2 to 8%, 2 to 6%, 2 to 4%, 3 to 10%, 3 to 8%, 3 to 6%, 4 to 10%, 4 to 8%, or 4 to 6% of saturation for dissolved oxygen in liquid media.

The method may further include recovering acrylate from the culture (e.g., from the culture medium). The collecting may include isolating acrylate from the cells, from the culture solution (i.e. medium) except the cells, or from both the cells and the culture solution. The isolation of acrylate from the culture may be performed by a separation and purification method known in the art. The collecting may be performed by centrifugation, chromatography, extraction, filtration, precipitation, or a combination thereof.

In the method, the microorganism further includes a pathway of converting acrylate to the other product, and thus the method may further include converting the produced acrylate to the other product. The other product may be an acrylate ester including a polyacrylate.

According to an aspect of the present disclosure, a microorganism has an increased productivity of 3-acrylic acid.

According to another aspect of the present disclosure, an acrylic acid may be efficiently produced.

Hereinafter, the present disclosure is described in greater detail with reference to embodiments. However, the embodiments are for illustrative purposes only and do not limit the scope of the present invention.

Example 1

Confirmation of Enzyme Activities of Converting 3-HP to 3-HP-CoA, AA-CoA, and AA In this example, each of the enzyme activities of converting 3-HP to 3-HP-CoA, AA-CoA, and AA was confirmed. That is, the activities of an enzyme catalyzing conversion of 3-HP to 3-HP-CoA, an enzyme catalyzing conversion of 3-HP-CoA to AA-CoA, and an enzyme catalyzing conversion of AA-CoA to AA were confirmed in vitro. As a result, enzymes catalyzing the forward reaction to occur more dominantly than the reverse reaction thereof were isolated.

(1) Confirmation of Enzyme Catalyzing Conversion of 3-HP to 3-HP-CoA

First, CoA-transferase genes catalyzing conversion of 3-HP to 3-HP-CoA listed in Table 1 were amplified by PCR using genomic DNAs of microorganisms shown in Table 1 as a template and primer sets each including a HindIII restriction site or a BamHI restriction site. 30 cycles of the PCR were performed 30 seconds at 95° C., 30 seconds at 50° C., and 1 minute at 72° C. Table 9 shows the primers used in the PCR.

TABLE 9

| No. | Forward/Reverse primer (SEQ ID NO:) |
|---|---|
| 1 | 206/207 |
| 2 | 208/209 |
| 3 | 210/211 |
| 4 | 212/213 |
| 5 | 214/215 |
| 6 | 216/217 |
| 7 | 218/219 |
| 8 | 220/221 |
| 9 | 222/223 |
| 10 | 224/225 |

The amplified products thus obtained were digested with HindIII and BamHI, and the resultants were connected to HindIII and BamHI sites of a pETDuet™-1 vector (Novagen, cat. no. 71146-3) to prepare a CoA-transferase gene expression vector (hereinafter, also referred to as a pETDuet™-1(CT) vector). Each of the enzymes in the expression vector was operably linked with a His-Tag encoding sequence in the vector so that the expression product was expressed in a His-Tag fused form.

The pETDuet™-1(CT) vector obtained therefrom was transformed and then introduced to Escherichia coli BL21 (DE3). The transformed E. coli was inoculated in an LB medium and incubated in a 100 mL flask at 37° C. During the incubation, when optical density at 600 nanometers ($OD_{600}$) was 0.6 to 0.8, 1 mM IPTG was added to induce the expression of an introduced CoA transferase gene. After 24 hours of expression induction, only cells were separated by performing centrifugation, were put into Solution 1 (50 mM $NaH_2PO_4$, 0.5 M NaCl, and pH7.4) with ice, and then sonicated to disrupt the cells. Then, the protein was separated using a Ni Sepharose™ High Performance HIS Trap™ HP (GE Healthcare Bio-Sciences AB) kit. Briefly, after cell disruption, only the supernatant was separated from the cell debris by performing centrifugation, the supernatant was mixed with Ni Sepharose resin to bind the protein to the resin, the resin was washed with the solution 1, and then, after packing the resin in chromatography column, the protein was eluted from the resin using 200 mM of imidazole as elution buffer as indicated by the manufacturer to obtain an enzyme solution including each of the enzymes at a high purity in a 200 mL imidazole aqueous solution.

Activity of each CoA-transferase was analyzed as follows: In particular, after adding 100 mM Tris-HCl (pH 8.4), 2 mM $MgCl_2$, 3 mM ATP, and 15 mM CoA-containing aqueous solution, the enzyme solution (at an amount equivalent to 10 mg CoA transferase), and 10 mM 3-HP as a medium were mixed and reacted for about 2 minutes to about 10 minutes. The expected reaction scheme was as follows:

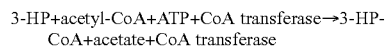

3-HP+acetyl-CoA+ATP+CoA transferase→3-HP-CoA+acetate+CoA transferase

Next, each of the reactants from the reaction was analyzed to confirm peaks and the amounts of the reactant, acetyl-CoA, and the product, 3-HP-CoA, by performing an HPLC analysis. The HPLC analysis was performed by using an Aminex HPX-87H (300 mm×7.8 mm) column and 0.5 mM of a sulfuric acid solution containing 9% of acetonitrile as a mobile phase. A flow rate was 0.4 ml/min, a temperature of the column was 35° C., and the RI detector and UV/VIS (210 nm) dual-mode were used.

Also, each of the reactants from the reaction was reacted with a citrate synthase to convert the remaining acetyl-CoA to CoA, 0.5 mM of DTNB (5,5'-Dithiobis-(2-Nitrobenzoic Acid) or an Ellman's reagent) was added thereto, and then an absorbance was measured at 412 nm. DTNB may be used to measure the amount of thiol in a material by measuring the absorbance thereof. DTNB easily forms a disulfide mixed by thiol and releases chromophore 5-merapto-2-nitrobenzoic acid (having a maximum absorbance at 410 nm). Only thiol among materials that may approach this water-soluble sample may be modified. As a result, activity of each of the enzymes was confirmed by comparing the amount of the remaining acetyl-CoA with its initial amount.

Table 10 shows the amounts of consumed acetyl-CoA, compared with their initial amounts.

TABLE 10

| No. | Gene name | Consumed acetyl-CoA (mol %) |
|---|---|---|
| 1 | Pct* | 62 ± 4.0 |
| 2 | ydiF b1694 JW1684 | 66 ± 4.0 |
| 3 | Pct** | 53 ± 3.0 |
| 4 | acuN | 17 ± 4.4 |
| 5 | SPO2934 | 32 ± 2.7 |
| 6 | DesyoDRAFT_3698 | 37 ± 2.4 |
| 7 | HMPREF9129 0351 | 33 ± 3.8 |
| 8 | Desmer_1798 | 28 ± 4.9 |
| 9 | Desor_3090 | 27 ± 3.6 |
| 10 | BN738_00826 | 35 ± 3.2 |

*Pct is derived from Clostridium propionicum
**Pct is derived from Cupriavidus necator As shown in Table 10, when the amount of acetyl-CoA decreased, it was considered that the amount of 3-HP-CoA increased, and, as a result, it was confirmed that 10 of the enzymes catalyzed the conversion of 3-HP to 3-HP-CoA.

(2) Confirmation of Enzyme Catalyzing Conversion of 3-HP-CoA to AA-CoA

First, the dehydratase genes listed in Tables 2 to 5 that catalyze conversion of 3-HP-CoA to AA-CoA were amplified by PCR using genomic DNAs of microorganisms shown in Tables 2 to 5 as a template and primer sets each including a HindIII restriction site or a BamHI restriction site. Then, a dehydratase enzyme was produced and purified in the same manner as in the process (1), except that a pACYCDuet™-1 vector (Novagen, cat. no. 71147-3) was used instead of a pETDuet™-1 vector (Novagen, cat. no. 71146-3). Table 11 shows information about the primer sets used in the PCR. In Table 11, numbers denote serial numbers of the enzymes or the genes in Tables 2 to 5.

TABLE 11

| No. | SEQ ID NO: forward/reverse |
|---|---|
| 1 | 226/227 |
| 2 | 228/229 |
| 3 | 230/231 |
| 4 | 232/233 |
| 5 | 234/235 |
| 6 | 236/237 |
| 7 | 238/239 |
| 8 | 240/241 |
| 9 | 242/243 |
| 10 | 244/245 |
| 11 | 246/247 |
| 12 | 248/249 |
| 13 | 250/251 |
| 14 | 252/253 |
| 15 | 254/255 |
| 16 | 256/257 |
| 17 | 258/259 |
| 18 | 260/261 |
| 19 | 262/263 |

TABLE 11-continued

| No. | SEQ ID NO: forward/reverse |
|---|---|
| 20 | 264/265 |
| 21 | 266/267 |
| 22 | 268/269 |
| 23 | 270/271 |
| 24 | 272/273 |
| 25 | 274/275 |
| 26 | 276/277 |
| 27 | 278/279 |
| 28 | 280/281 |
| 29 | 282/283 |
| 30 | 284/285 |
| 31 | 286/287 |
| 32 | 288/289 |
| 33 | 290/291 |
| 34 | 292/293 |
| 35 | 294/295 |
| 36 | 296/297 |
| 37 | 298/299 |
| 38 | 300/301 |
| 39 | 302/303 |
| 40 | 304/305 |
| 41 | 306/307 |
| 42 | 308/309 |
| 43 | 310/311 |
| 44 | 312/313 |
| 45 | 314/315 |
| 46 | 316/317 |
| 47 | 318/319 |
| 48 | 320/321 |
| 49 | 322/323 |
| 50 | 324/325 |
| 51 | 326/327 |
| 52 | 328/329 |
| 53 | 330/331 |
| 54 | 332/333 |
| 55 | 334/335 |
| 56 | 336/337 |
| 57 | 338/339 |
| 58 | 340/341 |
| 59 | 342/343 |
| 60 | 344/345 |
| 61 | 346/347 |
| 62 | 348/349 |
| 63 | 350/351 |
| 64 | 352/353 |
| 65 | 354/355 |
| 66 | 356/357 |
| 67 | 358/359 |
| 68 | 360/361 |
| 69 | 362/363 |
| 70 | 364/365 |
| 71 | 366/367 |
| 72 | 368/369 |
| 73 | 370/371 |
| 74 | 372/373 |
| 75 | 374/375 |
| 76 | 376/377 |
| 77 | 378/379 |
| 78 | 380/381 |
| 79 | 403/404 |

Activity of each of the purified dehydratases was analyzed as follows: For example, in the reaction that is catalyzed by a dehydratase such as a 3-HP-CoA/lactoyl-CoA dehydratase, an acrylyl-CoA reductase was added to the reactant to produce propionyl-CoA, and then the amount of consumed NAD(P)H was measured instead of directly measuring the amount of the reactant or the product of the reaction. In particular, 0.05 to 0.2 units of CoA transferase (which is derived from E. coli shown in No. 2 in Table 1) was added to 100 mM of MOPS (3-(N-morpholino)propanesulfonic acid)-KOH (pH 7.0), 10 mM $MgCl_2$, 3 mM ATP, 0.1 mM CoA, and 0.5 ml of 20 mM 3-HP-containing aqueous solution, and the mixture was pre-incubated for about 3 minutes. Then, each of the purified dehydratases (10 mM) was added to the pre-incubated mixture and then allowed to react for about 5 minutes at a temperature of 35° C. The expected reaction scheme was as follows:

3-HP+acetyl-CoA+ATP+CoA transferase→3-HP-CoA+acetate+dehydratase→AA-CoA+NAD(P)H+Acrylyl-CoA reductase(YhdH)→propionyl-CoA+NAD(P)

Next, as the result of the reaction, a decrease in the amount of NAD(P)H according to the addition of 5 mM NAD(P)H/AcuI was confirmed. AcuI is an acrylyl-CoA reductase which was added with a YhdH resemblant. The final NAD(P)H measurement was performed by measuring an absorbance at 340 nm.

Table 12 shows the remaining amounts of NAD(P)H, compared to their initial amounts (i.e., a degree of enzyme activity), as the results of the analysis.

TABLE 12

| No. | Consumed NAD(P)H (mol %) |
|---|---|
| 1 | 0.2 |
| 2 | 10.3 |
| 3 | 0.2 |
| 4 | 12.1 |
| 5 | 12.1 |
| 6 | 13.4 |
| 7 | 2.3 |
| 8 | 0.2 |
| 9 | 0.2 |
| 10 | 0.2 |
| 11 | 0.2 |
| 12 | 0.2 |
| 13 | 0.2 |
| 14 | 0.2 |
| 15 | 0.2 |
| 16 | 0.2 |
| 17 | 0.2 |
| 18 | 0.2 |
| 19 | 0.2 |
| 20 | 0.2 |
| 21 | 0.2 |
| 22 | 0.2 |
| 23 | 0.2 |
| 24 | 0.2 |
| 25 | 0.2 |
| 26 | 0.2 |
| 27 | 0.2 |
| 28 | 0.2 |
| 29 | 0.2 |
| 30 | 0.2 |
| 31 | 0.2 |
| 32 | 0.2 |
| 33 | 0.2 |
| 34 | 0.2 |
| 35 | 0.2 |
| 36 | 0.2 |
| 37 | 0.2 |
| 38 | 1.65 |
| 39 | 14.6 |
| 40 | 0.2 |
| 41 | 0.2 |
| 42 | 0.2 |
| 43 | 0.2 |
| 44 | 0.2 |
| 45 | 0.2 |
| 46 | 0.2 |
| 47 | 0.2 |
| 48 | 0.2 |
| 49 | 0.2 |
| 50 | 0.2 |
| 51 | 0.2 |
| 52 | 0.2 |
| 53 | 0.2 |
| 54 | 0.2 |

TABLE 12-continued

| No. | Consumed NAD(P)H (mol %) |
|---|---|
| 55 | 0.2 |
| 56 | 0.2 |
| 57 | 0.2 |
| 58 | 0.2 |
| 59 | 0.2 |
| 60 | 0.2 |
| 61 | 0.2 |
| 62 | 0.2 |
| 63 | 0.2 |
| 64 | 0.2 |
| 65 | 0.2 |
| 66 | 0.2 |
| 67 | 0.2 |
| 68 | 0.2 |
| 69 | 0.2 |
| 70 | 0.2 |
| 71 | 0.2 |
| 72 | 0.2 |
| 73 | 0.2 |
| 74 | 0.2 |
| 75 | 13.4 |
| 76 | 13.4 |
| 77 | 13.4 |
| 78 | 0.2 |
| 79 | 10.95 |

As shown in Table 12, it was confirmed that 79 of the enzymes catalyzed the conversion of 3-HP-CoA to AA-CoA.

Next, with respect to each of the reactants from the reaction, peaks and amounts of the reactant and the product were confirmed in the same manner as in the process (1). As the result of the HPLC analysis, it was confirmed that 79 of the enzymes listed in Tables 2 to 5 produced AA-CoA and thus were confirmed as having activity of catalyzing conversion of 3-HP-CoA to AA-CoA.

(3) Confirmation of Enzyme Catalyzing Conversion of AA-CoA to AA

First, a vector was prepared in the same manner as in the process (1), the vector was introduced to *E. coli*, and an enzyme was produced and purified, except that the CoA hydrolase genes catalyzing conversion of AA-CoA to AA, the genes listed in Table 6, were amplified by PCR using genomic DNAs of microorganisms shown in Table 6 as a template and primer sets each including a HindIII restriction site or a BamHI restriction site. Then, Table 13 shows information about the primer sets used in the PCR. In Table 13, numbers denote serial numbers of the enzymes or the genes in Table 6.

TABLE 13

| No. | SEQ ID NO::forward/reverse |
|---|---|
| 1 | 382/383 |
| 2 | 384/385 |
| 3 | 386/387 |
| 4 | 388/389 |
| 5 | 390/391 |
| 6 | 392/393 |

Activity of each of the purified CoA hydrolases was analyzed as follows: In particular, 100 mM Tris-HCl (pH 8.4), 2 mM MgCl$_2$, 3 mM ATP, 15 mM AA-CoA-containing aqueous solution and the enzyme solution (at an amount equivalent to 10 mg CoA hydrolase) were mixed and reacted for about 2 minutes to about 10 minutes. The expected reaction scheme was as follows:

AA-CoA+CoA hydrolase→AA+free CoA

Next, with respect to each of the reactants from the reaction, peaks and amounts of the reactant and the product (e.g., AA) were confirmed in the same manner as in the process (1) by performing an HPLC analysis. As a result of the HPLC analysis, it was confirmed that 6 of the enzymes listed in Table 6 produced the final product AA.

Also, with respect to each of the reactants from the reaction, the amount of the free CoA was confirmed by measuring an absorbance at 410 nm in the same manner as in the process (1). As the result, it was confirmed that 6 of the enzymes in Table 6 had activity of catalyzing the conversion of AA-CoA to AA. Table 14 shows the measurement results of the produced free CoA.

TABLE 14

| No. | Amount of produced CoA* |
|-----|-------------------------|
| 1   | 0.7                     |
| 2   | 0.2                     |
| 3   | 0.06                    |
| 4   | 0.06                    |
| 5   | 0.1                     |
| 6   | 0.2                     |

*an absorbance value at 410 nm, and a control group experiment was conducted by conducting a reaction as described in paragraph [0095], except that the enzyme solution was replaced with the same volume of the buffer used in the enzyme solution, where the absorbance value of the control group at 410 nm was 0.

As shown in Table 14, it was confirmed that 6 of the enzymes listed in Table 6 had activity of catalyzing the conversion of AA-CoA to AA.

Example 2

Preparation of Microorganisms Introduced with CoA Transferase, Dehydratase, and CoA Hydrolase Gene and Production of AA by Using the Microorganisms In this example, E. coli-derived CoA transferase (ydiF) genes, M. elsdenii-derived dehydratase MELS_1449 genes, and E. coli-derived CoA hydrolase yciA genes, which were confirmed as having the highest activity among CoA transferase genes, dehydratase genes, and CoA hydrolase genes in Example 1, were introduced to E. coli having 3-HP productivity, and the production of AA in the E. coli was confirmed.

(1) Preparation of E. coli Having 3-HP Productivity (1.1) Manufacture of ET_BAB_Dc5 Vector In order to prepare a microorganism producing 3-hydroxypropionic acid from glycerol, an ET_BAB_Dc5 vector was manufactured.

Genes (dhaB1, dhaB2, and dhaB3)(SEQ ID NOS: 186, 187, and 188) encoding a glycerol dehydratase (GDH) from a genomic DNA of Ilyobacter polytropus and genes (gdrA and gdrB)(SEQ ID NOS: 201 and 202) encoding a glycerol dehydratase reactivase (GDR) were secured. As an amplification product, dhaB123 was obtained by performing PCR amplification on the dhaB1, dhaB2, and dhaB3 genes using genomic DNAs of Ilyobacter polytropus as a template and primer sets of dhaB123_F (SEQ ID NO: 394) and dhaB123_R (SEQ ID NO: 395). As an amplification product, gdrAB was obtained by performing PCR amplification on the gdrA and gdrB genes using genomic DNA of Ilyobacter polytropus as a template and primer sets of gdrAB_F (SEQ ID NO: 396) and gdrAB_R (SEQ ID NO: 397). The PCR products thus obtained were treated with BamHI and SacI restrictive enzymes and then cloned to a pETDuet™-1 vector (Novagen).

Also, a gene (gabD, SEQ ID NO: 398) encoding a succinate semialdehyde dehydrogenase (SSADH) was obtained by PCR amplification using a genomic DNA of Cupriavidus necator as a template and primer sets of gabD_F (SEQ ID NO: 399) and gabD_R (SEQ ID NO: 400). The PCR product thus obtained was treated with NdeI and KpnI restrictive enzymes and cloned to the vector. As the result, a pETDuet-1/dhaB_gdrAB_gabD4 vector was obtained.

FIG. 1 is a cleavage map of a pETDuet/dhaB_gdrAB_gabD4 vector.

(1.2) Evaluation of 3-HP Productivity

A vector, pETDuet/dhaB_gdrAB_gabD4, produced in the process (1) was transformed and then introduced to Escherichia coli K(DE3).

The culture was performed by culturing the cells in a 50 ml culture medium (including (1.4 g/L of $MgSO_4H_2O$, 17.4 g/L of $K_2HPO_4$, 3 g/L of $KH_2PO_4$, 4 g/L of $(NH_4)_2HPO_4$, 1.7 g/L of citric acid, 0.014 g/L of $ZnCl_2$, 0.041 g/L of $FeCl_2H_2O$, 0.015 g/L of $MnCl_2$, 0.0015 g/L of $CuCl_2$, 0.003 g/L of $H_3BO_3$, 0.0025 g/L of $Na_2MoO_4$, 200 mg/L of nitriloacetic acid, 30 µg/L of sodium selenate, and 40 g/L of glycerol) in a 250 ml flask at a temperature of 33° C. and at a rate of 250 rpm. Initially, when an absorbance (OD) at 600 nm was 0.8, expression was induced by using 0.05 mM of IPTG, and then 50 µM of vitamin B12 was added.

After culturing for 24 hours, a part of the culture solution was extracted, an absorbance and pH of the culture solution were measured, and then production of 3-HP was confirmed by using an HPLC (Waters). The pH was adjusted to pH 7.0 by using 4 N of NaOH every 24 hours. The HPLC analysis was performed by using an Aminex HPX-87H (300 mm×7.8 mm) column and 0.5 mM of a sulfuric acid solution containing 9% of acetonitrile as a mobile phase. A flow rate was 0.4 ml/min, a temperature of the column was 35° C., and the RI detector and UV/VIS (210 nm) dual-mode were used. The 3-HP was detected at 17.5 minutes during the total analysis time of 30 minutes.

As a result, a strain obtained by transforming a vector, pETDuet/dhaB_gdrAB_gabD4, to E. coli K(DE3) was cultured in a 100 ml flask for 24 hours under the same conditions described above, and an amount of the 3-HP product was 13.2 g/L.

(2) Preparation of AA Production Strain

First, in the same manner as in the process (1), (2), and (3) of Example 1, ydiF gene, MELS_1449 gene, and yciA gene were amplified, and each of the genes were digested by using a restriction enzyme. Then, the genes were sequentially connected to a pETDuet™-1 vector, which was digested by the same enzyme, and a vector (pETDuet™-1/MELS_1449_yciA_YdiF) for expressing the three genes was prepared. Here, primers (SEQ ID NOS: 208/209, 236/237, and 382/383) used in amplification of ydiF gene, MELS_1449 gene, and yciA gene have restriction sites BamHI and HindIII, NdeI and BglII, and BglII and XhoI, respectively. When connected to the vector, the genes were digested by using the enzymes. In the vector for expression, each of the enzymes was operably linked with a His-Tag encoding sequence in the vector, and thus the expression product was expressed in the form that is fused with a His-tag.

Figure 2:
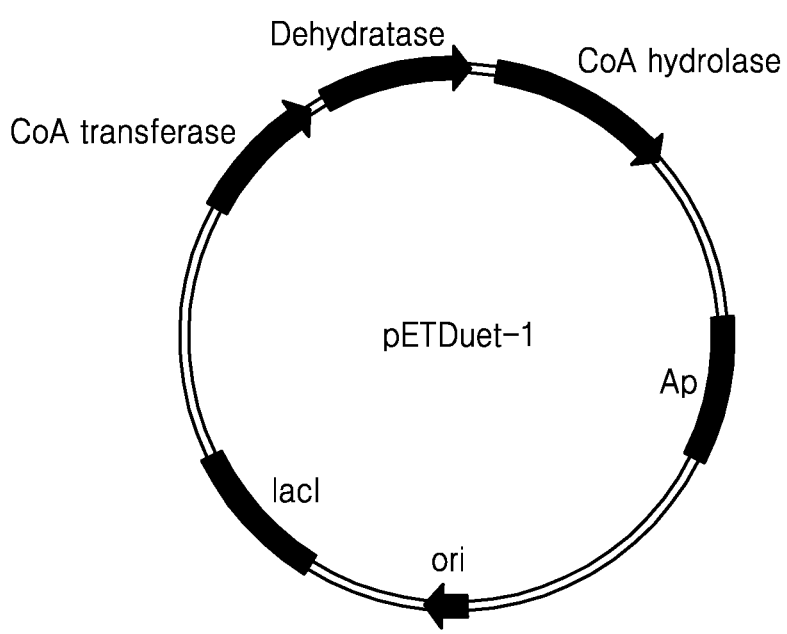
FIG. 2 is a map of pETDuet™-1/MELS_1449_yciA_YdiF.
Figure 3:
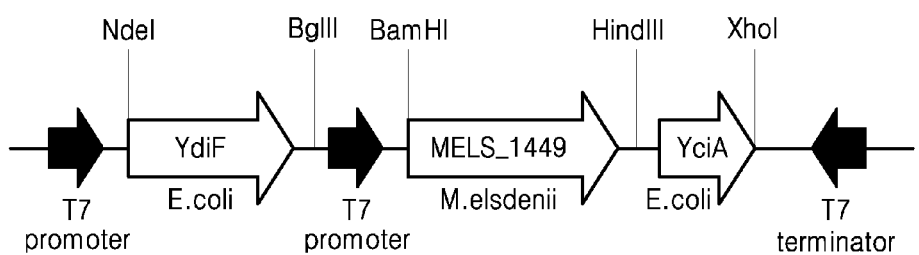
FIG. 3 is a magnified view of a part of the map of the pETDuet™-1/MELS_1449_yciA_YdiF vector.

FIGS. 2 and 3 are a map of pETDuet™-1/ MELS_1449_yciA_YdiF and a magnified view of a part of the map. FIG. 3 is a magnified view of a part including "CoA transferase-Dehdyratase-CoA hydrolase" of the map in FIG. 2.

Next, the pETDuet™-1/MELS_1449_yciA_YdiF vector was transformed to *E. coli* K(DE3) (pETDuet_dhaB_gdrAB_gabD4), which was a strain having 3-HP productivity. *E. coli*, to which the pETDuet™-1/MELS_1449_yciA_YdiF thus obtained was introduced, was inoculated into 100 mL of a M9 minimum culture medium (including 1.4 g/L of $MgSO_4H_2O$, 17.4 g/L of $K_2HPO_4$, 3 g/L of $KH_2PO_4$, 4 g/L of $(NH_4)_2HPO_4$, 1.7 g/L of citric acid, 0.014 g/L of $ZnCl_2$, 0.041 g/L of $FeCl_2H_2O$, 0.015 g/L of $MnCl_2$, 0.0015 g/L of $CuCl_2$, 0.003 g/L of $H_3BO_3$, 0.0025 g/L of $Na_2MoO_4$, 200 mg/L of nitriloacetic acid, 30 µg/L of sodium selenate, and 40 g/L of glycerol) so that $OD_{600}$ was 0.1 and cultured at a temperature of 30° C. until $OD_{600}$ was 0.6. Then, 0.02 mM of IPTG was added thereto and cultured at temperature of 33° C. for 24 hours. The culture was performed by shake culturing in a 250 mL flask for 24 hours.

Then, the expressed MELS_1449, YdiF, and YciA were separated and purified in the same manner as in the process (1), (2), and (3) of Example 1, an in vitro enzyme reaction was performed on a combination of the three purified enzymes, and the reaction product was analyzed by using a mass spectrometry. As a result, 0.5 g/L of AA was produced.

Thereafter, a concentration of acrylic acid in the culture was measured by using an HPLC. In particular, when the culture was terminated, a part of the culture solution was obtained to measure an absorbance, and then AA production in the culture without cells was confirmed by using HPLC (Waters). The HPLC analysis was performed by using an Aminex HPX-87H (300 mm×7.8 mm) column and 0.5 mM of a sulfuric acid solution containing 9% of acetonitrile as a mobile phase. A flow rate was 0.4 ml/min, a temperature of the column was 35° C., and the RI detector and UV/VIS (210 nm) dual-mode were used. As the result of the HPLC analysis, it was confirmed that the recombinant *E. coli* strain produced 0.50 g/L of acrylic acid (AA) after 24 hours of culture.

Figure 4:
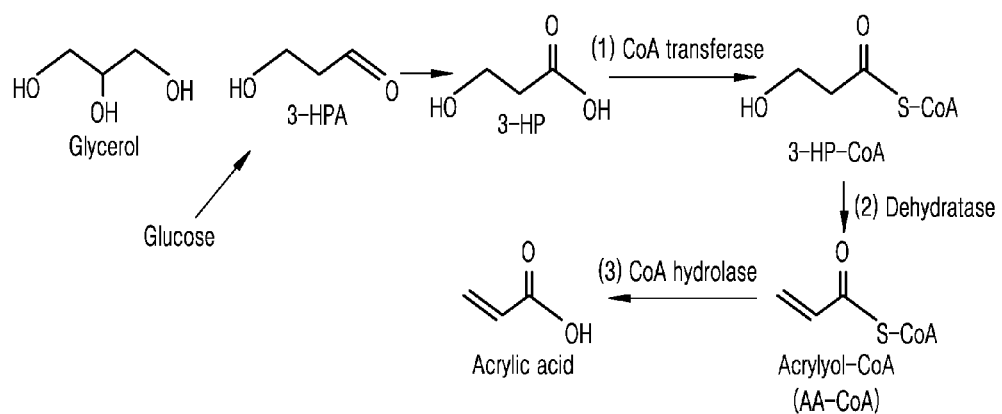
FIG. 4 illustrates a prospective pathway of an acrylic acid production from glucose or glycerol in *Escherichia coli*.

FIG. 4 illustrates a prospective pathway of an acrylic acid production from glucose or glycerol in *E. coli*, according to an embodiment of the present disclosure. In the current embodiment, the acrylic acid is expected to be produced along the pathway shown in FIG. 4, but the claimed invention is not particularly limited to the mechanism.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically engineered microorganism that produces acrylate, wherein the genetically engineered microorganism comprises:
   an exogenous polynucleotide encoding a coenzyme A (CoA) transferase catalyzing conversion of 3-hydroxypropionic acid (3-HP) to 3-hydroxypropionyl-CoA (3-HP-CoA) and belonging to EC 2.8.3.8, EC 3.1.2-, or EC 6.2.1.7,
   an exogenous polynucleotide encoding a 3-HP-CoA dehydratase catalyzing conversion of 3-HP-CoA to acrylyl-CoA and belonging to EC 4.2.1,
   an exogenous polynucleotide encoding a 3-HP-CoA hydrolase or a 3-hydroxyisobutyryl-CoA hydrolase belonging to EC 3.1.2,
   a polynucleotide encoding an enzyme catalyzing the conversion of glycerol to 3-propionic aldehyde (3-HPA), and
   a polynucleotide encoding an enzyme catalyzing the conversion of 3-HPA to 3-HP, and
   wherein the genetically engineered microorganism has increased expression of the exogenous polynucleotides as compared to a microorganism of the same type that does not comprise the exogenous polynucleotides,
   wherein the genetically engineered microorganism is an *Escherichia*, and
   wherein the *Escherichia* produces 3-HP.

2. The microorganism of claim 1, wherein the CoA transferase comprises an amino acid sequence selected from the group consisting of SEQ ID NOS: 1 to 10.

3. The microorganism of claim 1, wherein the 3-HP-CoA dehydratase comprises an amino acid sequence selected from the group consisting of SEQ ID NOS: 21 to 98 and 401.

4. The microorganism of claim 1, wherein the enzyme catalyzing conversion of acrylyl-CoA to acrylate comprises an amino acid sequence selected from the group consisting of SEQ ID NOs: 177 to 182.

5. The microorganism of claim 1, wherein a gene that encodes at least one enzyme involved in a pathway of decomposing acrylate or converting acrylate to another product is deleted or disrupted in the microorganism.

6. The microorganism of claim 1, wherein the genetically engineered microorganism is an *Escherichia coli*.

7. The microorganism of claim 6, wherein the enzyme catalyzing conversion of glycerol to 3-HPA is glycerol dehydratase (dhaB) and the enzyme catalyzing conversion of 3-HPA to 3-HP is aldehyde dehydrogenase (AldH) or succinate semialdehyde dehydrogenase (gabD).

8. A method of producing acrylate, the method comprising culturing the microorganism of claim 1 in a culture medium to thereby produce acrylate.

9. The method of claim 8, further comprising recovering the acrylate from the culture.

10. The microorganism of claim 1, further comprising polynucleotides encoding a glycerol dehydratase reactivase (GDR).

11. A method of producing the genetically engineered microorganism according to claim 1, the method comprising transforming an *Escherichia* microorganism with the exogenous polynucleotide encoding CoA transferase, the exogenous polynucleotide encoding 3-HP-CoA dehydratase, and the exogenous polynucleotide encoding the 3-HP-CoA hydrolase or the 3-hydroxyisobutyryl-CoA hydrolase, wherein the *Escherichia* microorganism comprises a polynucleotide encoding an enzyme catalyzing the conversion of glycerol to 3-propionic aldehyde (3-HPA), and a polynucleotide encoding an enzyme catalyzing the conversion of 3-HPA to 3-HP, and wherein the *Escherichia* produces 3-HP.

12. An expression vector comprising:
   a polynucleotide encoding a coenzyme A (CoA) transferase catalyzing conversion of 3-hydroxypropionic acid (3-HP) to 3-hydroxypropionyl-CoA (3-HP-CoA) and belonging to EC 2.8.3.8, EC 3.1.2-, or EC 6.2.1.7,
   a polynucleotide encoding a 3-HP-CoA dehydratase catalyzing conversion of 3-HP-CoA to acrylyl-CoA and belonging to EC 4.2.1,
   a polynucleotide encoding a 3-HP-CoA hydrolase or a 3-hydroxyisobutyryl-CoA hydrolase belonging to EC 3.1.2, and
   a polynucleotide that is heterologous to the polynucleotide encoding the CoA transferase, the polynucleotide encoding the 3-HP-CoA dehydratase, the polynucleotide encoding the 3-HP-CoA hydrolase, or the 3-hydroxyisobutyryl-CoA hydrolase.

13. The microorganism of claim 1, wherein
   the CoA transferase comprises an amino acid sequence selected from the group consisting of SEQ ID NOS: 1 to 10,
   the 3-HP-CoA dehydratase comprises an amino acid sequence selected from the group consisting of SEQ ID NOS: 21 to 98 or 401, and
   the 3 HP-CoA hydrolase or the 3-hydroxyisobutyryl-CoA hydrolase comprises an amino acid sequence selected from the group consisting of SEQ ID NOS: 177 to 182.

\* \* \* \* \*

SEQUENCE LISTING

<160> NUMBER OF SEQ ID NOS: 410

<210> SEQ ID NO 1
<211> LENGTH: 524
<212> TYPE: PRT
<213> ORGANISM: Clostridium propionicum

<400> SEQUENCE: 1

Met Arg Lys Val Pro Ile Ile Thr Ala Asp Glu Ala Ala Lys Leu Ile
 1               5                  10                  15

```
Lys Asp Gly Asp Thr Val Thr Thr Ser Gly Phe Val Gly Asn Ala Ile
                20                  25                  30

Pro Glu Ala Leu Asp Arg Ala Val Glu Lys Arg Phe Leu Glu Thr Gly
            35                  40                  45

Glu Pro Lys Asn Ile Thr Tyr Val Tyr Cys Gly Ser Gln Gly Asn Arg
        50                  55                  60

Asp Gly Arg Gly Ala Glu His Phe Ala His Glu Gly Leu Leu Lys Arg
65                  70                  75                  80

Tyr Ile Ala Gly His Trp Ala Thr Val Pro Ala Leu Gly Lys Met Ala
                85                  90                  95

Met Glu Asn Lys Met Glu Ala Tyr Asn Val Ser Gln Gly Ala Leu Cys
            100                 105                 110

His Leu Phe Arg Asp Ile Ala Ser His Lys Pro Gly Val Phe Thr Lys
        115                 120                 125

Val Gly Ile Gly Thr Phe Ile Asp Pro Arg Asn Gly Gly Lys Val
130                 135                 140

Asn Asp Ile Thr Lys Glu Asp Ile Val Glu Leu Val Glu Ile Lys Gly
145                 150                 155                 160

Gln Glu Tyr Leu Phe Tyr Pro Ala Phe Pro Ile His Val Ala Leu Ile
                165                 170                 175

Arg Gly Thr Tyr Ala Asp Glu Ser Gly Asn Ile Thr Phe Glu Lys Glu
            180                 185                 190

Val Ala Pro Leu Glu Gly Thr Ser Val Cys Gln Ala Val Lys Asn Ser
        195                 200                 205

Gly Gly Ile Val Val Val Gln Val Glu Arg Val Val Lys Ala Gly Thr
210                 215                 220

Leu Asp Pro Arg His Val Lys Val Pro Gly Ile Tyr Val Asp Tyr Val
225                 230                 235                 240

Val Val Ala Asp Pro Glu Asp His Gln Gln Ser Leu Asp Cys Glu Tyr
                245                 250                 255

Asp Pro Ala Leu Ser Gly Glu His Arg Arg Pro Glu Val Val Gly Glu
            260                 265                 270

Pro Leu Pro Leu Ser Ala Lys Lys Val Ile Gly Arg Arg Gly Ala Ile
        275                 280                 285

Glu Leu Glu Lys Asp Val Ala Val Asn Leu Gly Val Gly Ala Pro Glu
290                 295                 300

Tyr Val Ala Ser Val Ala Asp Glu Glu Gly Ile Val Asp Phe Met Thr
305                 310                 315                 320

Leu Thr Ala Glu Ser Gly Ala Ile Gly Gly Val Pro Ala Gly Gly Val
                325                 330                 335

Arg Phe Gly Ala Ser Tyr Asn Ala Asp Ala Leu Ile Asp Gln Gly Tyr
            340                 345                 350

Gln Phe Asp Tyr Tyr Asp Gly Gly Leu Asp Leu Cys Tyr Leu Gly
        355                 360                 365

Leu Ala Glu Cys Asp Glu Lys Gly Asn Ile Asn Val Ser Arg Phe Gly
370                 375                 380

Pro Arg Ile Ala Gly Cys Gly Gly Phe Ile Asn Ile Thr Gln Asn Thr
385                 390                 395                 400

Pro Lys Val Phe Phe Cys Gly Thr Phe Thr Ala Gly Gly Leu Lys Val
                405                 410                 415

Lys Ile Glu Asp Gly Lys Val Ile Ile Val Gln Glu Gly Lys Gln Lys
            420                 425                 430
```

```
Lys Phe Leu Lys Ala Val Glu Gln Ile Thr Phe Asn Gly Asp Val Ala
            435                 440                 445

Leu Ala Asn Lys Gln Gln Val Thr Tyr Ile Thr Glu Arg Cys Val Phe
        450                 455                 460

Leu Leu Lys Glu Asp Gly Leu His Leu Ser Glu Ile Ala Pro Gly Ile
465                 470                 475                 480

Asp Leu Gln Thr Gln Ile Leu Asp Val Met Asp Phe Ala Pro Ile Ile
                485                 490                 495

Asp Arg Asp Ala Asn Gly Gln Ile Lys Leu Met Asp Ala Ala Leu Phe
                500                 505                 510

Ala Glu Gly Leu Met Gly Leu Lys Glu Met Lys Ser
            515                 520

<210> SEQ ID NO 2
<211> LENGTH: 531
<212> TYPE: PRT
<213> ORGANISM: Escherichia coli
<220> FEATURE:
<221> NAME/KEY: MISC_FEATURE
<222> LOCATION: (1)..(531)
<223> OTHER INFORMATION: strain K12

<400> SEQUENCE: 2

Met Lys Pro Val Lys Pro Arg Ile Asn Gly Arg Val Pro Val Leu
 1               5                  10                  15

Ser Ala Gln Glu Ala Val Asn Tyr Ile Pro Asp Glu Ala Thr Leu Cys
                20                  25                  30

Val Leu Gly Ala Gly Gly Gly Ile Leu Glu Ala Thr Thr Leu Ile Thr
            35                  40                  45

Ala Leu Ala Asp Lys Tyr Lys Gln Thr Gln Thr Pro Arg Asn Leu Ser
        50                  55                  60

Ile Ile Ser Pro Thr Gly Leu Gly Asp Arg Ala Asp Arg Gly Ile Ser
 65                 70                  75                  80

Pro Leu Ala Gln Glu Gly Leu Val Lys Trp Ala Leu Cys Gly His Trp
                85                  90                  95

Gly Gln Ser Pro Arg Ile Ser Glu Leu Ala Glu Gln Asn Lys Ile Ile
                100                 105                 110

Ala Tyr Asn Tyr Pro Gln Gly Val Leu Thr Gln Thr Leu Arg Ala Ala
            115                 120                 125

Ala His Gln Pro Gly Ile Ile Ser Asp Ile Gly Ile Gly Thr Phe
        130                 135                 140

Val Asp Pro Arg Gln Gln Gly Gly Lys Leu Asn Glu Val Thr Lys Glu
145                 150                 155                 160

Asp Leu Ile Lys Leu Val Glu Phe Asp Asn Lys Glu Tyr Leu Tyr Tyr
                165                 170                 175

Lys Ala Ile Ala Pro Asp Ile Ala Phe Ile Arg Ala Thr Thr Cys Asp
            180                 185                 190

Ser Glu Gly Tyr Ala Thr Phe Glu Asp Glu Val Met Tyr Leu Asp Ala
        195                 200                 205

Leu Val Ile Ala Gln Ala Val His Asn Asn Gly Gly Ile Val Met Met
    210                 215                 220

Gln Val Gln Lys Met Val Lys Lys Ala Thr Leu His Pro Lys Ser Val
225                 230                 235                 240

Arg Ile Pro Gly Tyr Leu Val Asp Ile Val Val Asp Pro Asp Gln
                245                 250                 255

Thr Gln Leu Tyr Gly Gly Ala Pro Val Asn Arg Phe Ile Ser Gly Asp
```

```
                    260                 265                 270
Phe Thr Leu Asp Asp Ser Thr Lys Leu Ser Leu Pro Leu Asn Gln Arg
            275                 280                 285

Lys Leu Val Ala Arg Ala Leu Phe Glu Met Arg Lys Gly Ala Val
        290                 295                 300

Gly Asn Val Gly Val Gly Ile Ala Asp Gly Ile Gly Leu Val Ala Arg
305                 310                 315                 320

Glu Glu Gly Cys Ala Asp Asp Phe Ile Leu Thr Val Glu Thr Gly Pro
                325                 330                 335

Ile Gly Gly Ile Thr Ser Gln Gly Ile Ala Phe Gly Ala Asn Val Asn
            340                 345                 350

Thr Arg Ala Ile Leu Asp Met Thr Ser Gln Phe Asp Phe Tyr His Gly
        355                 360                 365

Gly Gly Leu Asp Val Cys Tyr Leu Ser Phe Ala Glu Val Asp Gln His
    370                 375                 380

Gly Asn Val Gly Val His Lys Phe Asn Gly Lys Ile Met Gly Thr Gly
385                 390                 395                 400

Gly Phe Ile Asp Ile Ser Ala Thr Ser Lys Lys Ile Phe Cys Gly
                405                 410                 415

Thr Leu Thr Ala Gly Ser Leu Lys Thr Glu Ile Thr Asp Gly Lys Leu
            420                 425                 430

Asn Ile Val Gln Glu Gly Arg Val Lys Lys Phe Ile Arg Glu Leu Pro
        435                 440                 445

Glu Ile Thr Phe Ser Gly Lys Ile Ala Leu Glu Arg Gly Leu Asp Val
    450                 455                 460

Arg Tyr Ile Thr Glu Arg Ala Val Phe Thr Leu Lys Glu Asp Gly Leu
465                 470                 475                 480

His Leu Ile Glu Ile Ala Pro Gly Val Asp Leu Gln Lys Asp Ile Leu
                485                 490                 495

Asp Lys Met Asp Phe Thr Pro Val Ile Ser Pro Glu Leu Lys Leu Met
            500                 505                 510

Asp Glu Arg Leu Phe Ile Asp Ala Ala Met Gly Phe Val Leu Pro Glu
        515                 520                 525

Ala Ala His
    530

<210> SEQ ID NO 3
<211> LENGTH: 542
<212> TYPE: PRT
<213> ORGANISM: Cupriavidus necator

<400> SEQUENCE: 3

Met Lys Val Ile Thr Ala Arg Glu Ala Ala Leu Val Gln Asp Gly
1               5                   10                  15

Trp Thr Val Ala Ser Ala Gly Phe Val Gly Ala Gly His Ala Glu Ala
            20                  25                  30

Val Thr Glu Ala Leu Glu Gln Arg Phe Leu Gln Ser Gly Leu Pro Arg
        35                  40                  45

Asp Leu Thr Leu Val Tyr Ser Ala Gly Gln Gly Asp Arg Gly Ala Arg
    50                  55                  60

Gly Val Asn His Phe Gly Asn Ala Gly Met Thr Ala Ser Ile Val Gly
65                  70                  75                  80

Gly His Trp Arg Ser Ala Thr Arg Leu Ala Thr Leu Ala Met Ala Glu
                85                  90                  95
```

```
Gln Cys Glu Gly Tyr Asn Leu Pro Gln Gly Val Leu Thr His Leu Tyr
                100                 105                 110

Arg Ala Ile Ala Gly Lys Pro Gly Val Met Thr Lys Ile Gly Leu
            115                 120                 125

His Thr Phe Val Asp Pro Arg Thr Ala Gln Asp Ala Arg Tyr His Gly
    130                 135                 140

Gly Ala Val Asn Glu Arg Ala Arg Gln Ala Ile Ala Gly Gly Lys Ala
145                 150                 155                 160

Cys Trp Val Asp Ala Val Asp Phe Arg Gly Glu Glu Tyr Leu Phe Tyr
                165                 170                 175

Pro Ser Phe Pro Ile His Cys Ala Leu Ile Arg Cys Thr Ala Ala Asp
            180                 185                 190

Thr Arg Gly Asn Leu Ser Thr His Arg Glu Ala Phe His His Glu Leu
        195                 200                 205

Leu Ala Met Ala Gln Ala Ala His Asn Ser Gly Gly Ile Val Ile Ala
210                 215                 220

Gln Val Glu Ser Leu Val Asp His His Glu Ile Leu Gln Ala Ile His
225                 230                 235                 240

Val Pro Gly Ile Leu Val Asp Tyr Val Val Cys Asp Asn Pro Ala
                245                 250                 255

Asn His Gln Met Thr Phe Ala Glu Ser Tyr Asn Pro Ala Tyr Val Thr
            260                 265                 270

Pro Trp Gln Gly Glu Ala Ala Val Glu Ala Glu Ala Thr Pro Val
                275                 280                 285

Ala Ala Gly Pro Leu Asp Ala Arg Thr Ile Val Gln Arg Arg Ala Val
290                 295                 300

Met Glu Leu Ala Arg Arg Ala Pro Arg Val Val Asn Leu Gly Val Gly
305                 310                 315                 320

Met Pro Ala Ala Val Gly Met Leu Ala His Gln Ala Gly Leu Asp Gly
                325                 330                 335

Phe Thr Leu Thr Val Glu Ala Gly Pro Ile Gly Gly Thr Pro Ala Asp
            340                 345                 350

Gly Leu Ser Phe Gly Ala Ser Ala Tyr Pro Glu Ala Val Val Asp Gln
        355                 360                 365

Pro Ala Gln Phe Asp Phe Tyr Glu Gly Gly Ile Asp Leu Ala Ile
370                 375                 380

Leu Gly Leu Ala Glu Leu Asp Gly His Gly Asn Val Asn Val Ser Lys
385                 390                 395                 400

Phe Gly Glu Gly Glu Gly Ala Ser Ile Ala Gly Val Gly Gly Phe Ile
                405                 410                 415

Asn Ile Thr Gln Ser Ala Arg Ala Val Val Phe Met Gly Thr Leu Thr
            420                 425                 430

Ala Gly Gly Leu Glu Val Arg Ala Gly Glu Gly Arg Leu Gln Ile Val
        435                 440                 445

Arg Glu Gly Arg Val Lys Lys Ile Val Pro Glu Val Ser His Leu Ser
    450                 455                 460

Phe Asn Gly Pro Tyr Val Ala Ser Leu Gly Ile Pro Val Leu Tyr Ile
465                 470                 475                 480

Thr Glu Arg Ala Val Phe Glu Met Arg Ala Gly Ala Gly Gly Glu Ala
                485                 490                 495

Arg Leu Thr Leu Val Glu Ile Ala Pro Gly Val Asp Leu Gln Arg Asp
            500                 505                 510

Val Leu Asp Gln Cys Ala Thr Pro Val Ala Val Ala Pro Asp Leu Arg
```

```
            515                 520                 525
Glu Met Asp Ala Arg Leu Phe Gln Ala Gly Pro Leu His Leu
        530                 535                 540

<210> SEQ ID NO 4
<211> LENGTH: 473
<212> TYPE: PRT
<213> ORGANISM: Halomonas smyrnensis

<400> SEQUENCE: 4

Met Thr Thr Ser Thr Gln Thr Glu Leu Lys Lys Gly Pro Leu Asn Gly
 1               5                  10                  15

Ile Thr Val Leu Asp Phe Ser Arg Val Leu Ala Gly Pro Tyr Cys Thr
            20                  25                  30

Met Val Leu Ala Asp Leu Gly Ala Arg Val Ile Lys Ile Glu Lys Ile
        35                  40                  45

Gly Thr Gly Asp Asp Thr Arg Glu Phe Gly Pro Phe Val Glu Gly Glu
    50                  55                  60

Ser Ala Tyr Phe Ser Cys Phe Asn Arg Asn Lys Glu Ser Ile Val Leu
 65                  70                  75                  80

Asp Ile Lys Ser Pro Arg Asp Arg Glu Leu Leu Glu Arg Leu Leu Asp
                85                  90                  95

Glu Ser Asp Val Leu Val Glu Asn Phe Arg Pro Gly Val Met Asp Arg
            100                 105                 110

Leu Gly Tyr Gly Pro Glu Arg Leu Ala Met Thr His Pro His Leu Ile
        115                 120                 125

Tyr Ser Ser Ile Ser Gly Phe Gly His Thr Gly Pro Phe Ser Glu Leu
    130                 135                 140

Pro Gly Tyr Asp Met Val Val Gln Ala Met Gly Gly Ile Met Ser Leu
145                 150                 155                 160

Thr Gly Trp Pro Asp Gly Glu Pro Ala Arg Val Gly Thr Ser Phe Gly
                165                 170                 175

Asp Leu Ser Ala Ala Leu Phe Ala Ala Ile Gly Ile Ile Ala Ser Leu
            180                 185                 190

Tyr Ser Arg Thr Lys Asp Ala Gln Gly Thr Arg Val Asp Ile Gly Met
        195                 200                 205

Leu Asp Cys Gln Ala Ala Leu Met Glu Thr Ala Leu Ala Arg Tyr Asp
    210                 215                 220

Ile Glu Gly Lys Val Pro Asn Arg Thr Gly Asp Cys His Pro Ser Leu
225                 230                 235                 240

Ala Pro Phe Glu Ser Phe Asn Ala Lys Asp Gly Lys Leu Val Ile Ala
                245                 250                 255

Ala Gly Asn Asp Thr Leu Phe Leu Met Ala Asp Ala Ile Gly Ala
            260                 265                 270

Ala Arg Leu Ala Phe Asp Pro Arg Phe Ile Ser Asn Asp Leu Arg Cys
        275                 280                 285

His Asn Arg Pro Glu Leu Val Ala Glu Met Glu Lys Ile Leu Leu Glu
    290                 295                 300

Gln Pro Val Gln His Trp Val Asp Leu Leu Asn Glu Glu Gly Val Pro
305                 310                 315                 320

Cys Ser Pro Ile Asn Thr Ile Asp Lys Leu Phe Asp His Pro Gln Leu
                325                 330                 335

Lys Ala Arg Asn Met Ile Val Gln Val Gln Gly Lys Ala Gly Lys Pro
            340                 345                 350
```

```
Phe Lys Thr Ala Gly Asn Pro Ile Lys Leu Thr Gly Arg Glu Asp Phe
            355                 360                 365

Asp Ser Gly Val Pro Met Ser Ala Pro Gly Leu Gly Gln His Arg Glu
370                 375                 380

Ala Ile Leu Thr Glu Leu Met Ala Arg His Gly Ser Tyr His Leu Pro
385                 390                 395                 400

Thr Gln Pro Asp Ile Gln Gly Ser Leu Pro Glu Ser Gly Thr Asp Thr
                405                 410                 415

Pro Trp Ala Phe Arg Pro Val Ala Ser Gly Asp Ser Gly Ala Ala Leu
            420                 425                 430

Ser Arg Asn Glu Pro Lys Ser Lys Asn Ala Gln Val Ala Ser Glu Asn
            435                 440                 445

Glu Arg Gly Arg Ser Ser Asn Ser Glu Pro Gln Pro Lys Ser Thr Ala
450                 455                 460

Lys Ser Lys Ser Glu Met Glu Asn Gly
465                 470
```

<210> SEQ ID NO 5
<211> LENGTH: 629
<212> TYPE: PRT
<213> ORGANISM: Ruegeria pomeroyi
<220> FEATURE:
<221> NAME/KEY: MISC_FEATURE
<222> LOCATION: (1)..(629)
<223> OTHER INFORMATION: DSS-3

<400> SEQUENCE: 5

```
Met Ala Tyr Gln Asp Val Tyr Glu Ser Trp Lys Ser Asp Pro Glu Ala
1               5                   10                  15

Phe Trp Met Glu Ala Ala Lys Ser Ile Asp Trp Val Glu Ala Pro Ser
            20                  25                  30

Arg Ala Leu Asp Asp Ser Asn Ala Pro Leu Tyr Glu Trp Phe Thr Asp
            35                  40                  45

Ala Lys Val Asn Thr Cys Trp Asn Ala Val Asp Arg His Val Glu Ala
        50                  55                  60

Gly Arg Gly Glu Gln Thr Ala Ile Ile Tyr Asp Ser Pro Ile Thr His
65                  70                  75                  80

Thr Lys Arg Gln Ile Ser Tyr Val Glu Leu Arg Asn Arg Val Ala Met
                85                  90                  95

Leu Ala Gly Ala Leu Arg Ala Lys Gly Val Glu Lys Gly Asp Arg Val
            100                 105                 110

Ile Ile Tyr Met Pro Met Ile Pro Glu Ala Leu Glu Ala Met Leu Ala
        115                 120                 125

Cys Ala Arg Leu Gly Ala Val His Ser Val Val Phe Gly Gly Phe Ala
130                 135                 140

Ala Asn Glu Leu Ala Val Arg Ile Asp Asp Ala Gln Pro Lys Ala Ile
145                 150                 155                 160

Ile Ala Ala Ser Cys Gly Leu Glu Pro Gly Arg Val Val His Tyr Lys
                165                 170                 175

Pro Leu Leu Asp Gly Ala Ile Asp Met Ala Lys His Lys Pro Glu Phe
            180                 185                 190

Cys Val Ile Phe Gln Arg Glu Gln Glu Val Ala His Leu Glu Glu Gly
        195                 200                 205

Arg Asp Tyr Asn Trp His Gly Phe Gln Tyr Gly Val Glu Pro Ala Glu
210                 215                 220

Cys Val Pro Val Glu Gly Asn His Pro Ala Tyr Ile Leu Tyr Thr Ser
```

```
                225                 230                 235                 240
Gly Thr Thr Gly Ala Pro Lys Gly Val Leu Arg Pro Thr Ala Gly His
                245                 250                 255
Leu Val Ala Leu Asn Trp Thr Met Lys Asn Ile Tyr Asn Val Asp Pro
                260                 265                 270
Gly Asp Val Phe Trp Ala Ala Ser Asp Val Gly Trp Val Gly His
                275                 280                 285
Ser Tyr Ile Cys Tyr Gly Pro Leu Ile His Gly Asn Thr Thr Ile Val
                290                 295                 300
Phe Glu Gly Lys Pro Val Gly Thr Pro Asp Ala Gly Thr Phe Trp Arg
305                 310                 315                 320
Val Ile Ser Glu His Lys Val Lys Ser Phe Phe Thr Ala Pro Thr Ala
                325                 330                 335
Ile Arg Ala Val Lys Arg Glu Asp Pro Lys Gly Glu Met Leu Ala Lys
                340                 345                 350
Tyr Asp Leu Ser His Leu Lys Ala Leu Tyr Leu Ala Gly Glu Arg Ala
                355                 360                 365
Asp Pro Asp Thr Ile Ile Trp Ala Gln Lys Ala Leu Ser Val Pro Val
                370                 375                 380
Ile Asp His Trp Trp Gln Thr Glu Thr Gly Trp Thr Ile Ala Gly Asn
385                 390                 395                 400
Pro Leu Gly Ile Glu Glu Leu Pro Thr Lys Leu Gly Ser Pro Ala Lys
                405                 410                 415
Ala Met Pro Gly Tyr Asp Val Gln Ile Leu Asp Glu Gly His Gln
                420                 425                 430
Met Lys Pro Gly Glu Leu Gly Ala Ile Ala Val Lys Leu Pro Leu Pro
                435                 440                 445
Pro Gly Thr Leu Pro Gly Leu Trp Asn Ala Glu Ala Arg Phe Arg Lys
                450                 455                 460
Ser Tyr Leu Glu His Phe Pro Gly Tyr Tyr Glu Thr Gly Asp Ala Gly
465                 470                 475                 480
Met Ile Asp Glu Asp Gly Tyr Leu Tyr Ile Met Ala Arg Thr Asp Asp
                485                 490                 495
Val Ile Asn Val Ala Gly His Arg Leu Ser Thr Gly Gly Met Glu Glu
                500                 505                 510
Val Leu Ala Gly His Glu Asp Val Ala Glu Cys Ala Val Ile Gly Val
                515                 520                 525
Ser Asp Asp Leu Lys Gly Gln Met Pro Leu Gly Phe Leu Cys Leu Asn
530                 535                 540
Asn Gly Cys Asn Arg Asp His Gly Asp Val Val Lys Glu Val Val Lys
545                 550                 555                 560
Leu Val Arg Asp Lys Ile Gly Pro Val Ala Ala Phe Lys Leu Ala Val
                565                 570                 575
Val Val Asp Arg Leu Pro Lys Thr Arg Ser Gly Lys Ile Leu Arg Gly
                580                 585                 590
Thr Met Val Ser Ile Ala Asp Gly Lys Glu Tyr Lys Met Pro Ala Thr
                595                 600                 605
Ile Asp Asp Pro Ala Ile Leu Asp Glu Ile Lys Val Ala Leu Gln Ser
                610                 615                 620
Leu Gly Tyr Ala Lys
625

<210> SEQ ID NO 6
```

```
<211> LENGTH: 518
<212> TYPE: PRT
<213> ORGANISM: Desulfosporosinus youngiae
<220> FEATURE:
<221> NAME/KEY: MISC_FEATURE
<222> LOCATION: (1)..(518)
<223> OTHER INFORMATION: DSM 17734

<400> SEQUENCE: 6
```

| | | | | | | | | | | | | | | |
|---|---|---|---|---|---|---|---|---|---|---|---|---|---|---|
| Met | Lys | Lys | Val | Ile | Val | Leu | Thr | Ala | Glu | Glu | Ala | Val | Asp | Leu | Val |
| 1 | | | | 5 | | | | | 10 | | | | | 15 | |
| Lys | Asp | Gly | Asp | Thr | Leu | Cys | Thr | Ser | Gly | Phe | Val | Gly | Asn | Ser | Leu |
| | | | 20 | | | | | 25 | | | | | 30 | | |
| Pro | Glu | Ala | Leu | Phe | Lys | Ala | Ile | Glu | Lys | Lys | Phe | Leu | Gly | Thr | Gly |
| | | 35 | | | | | 40 | | | | | 45 | | | |
| Tyr | Pro | Gln | Asn | Ile | Thr | Leu | Phe | Tyr | Pro | Ala | Ser | Gln | Gly | Ser | Arg |
| | 50 | | | | | 55 | | | | | 60 | | | | |
| Asn | Gly | Thr | Gly | Gly | Asp | His | Phe | Ala | His | Glu | Gly | Leu | Val | Lys | Arg |
| 65 | | | | | 70 | | | | | 75 | | | | | 80 |
| Val | Ile | Ala | Gly | His | Leu | Asn | Thr | Ala | Pro | Lys | Leu | Gly | Glu | Leu | Cys |
| | | | | 85 | | | | | 90 | | | | | 95 | |
| Leu | Ala | Asn | Lys | Cys | Glu | Gly | Tyr | Asn | Leu | Pro | Gln | Gly | Ala | Leu | Glu |
| | | | 100 | | | | | 105 | | | | | 110 | | |
| Tyr | Val | Ile | Arg | Asp | Ala | Ala | Gly | His | Arg | Pro | Gly | Thr | Ile | Thr | His |
| | | 115 | | | | | 120 | | | | | 125 | | | |
| Val | Gly | Leu | Gly | Thr | Phe | Val | Asp | Pro | Arg | Asn | Gly | Gly | Lys | Ile |
| | 130 | | | | | 135 | | | | | 140 | | | | |
| Asn | Ala | Arg | Thr | Thr | Glu | Asp | Leu | Val | Glu | Val | Ile | Lys | Ile | Gly | Asn |
| 145 | | | | | 150 | | | | | 155 | | | | | 160 |
| Glu | Glu | Lys | Leu | Phe | Tyr | Lys | Ala | Phe | Pro | Ile | Asp | Ile | Ala | Phe | Leu |
| | | | | 165 | | | | | 170 | | | | | 175 | |
| Arg | Gly | Thr | Tyr | Ala | Asp | Glu | Tyr | Gly | Asn | Val | Thr | Leu | Glu | Lys | Glu |
| | | | 180 | | | | | 185 | | | | | 190 | | |
| Val | Ala | Thr | Ile | Glu | Val | Thr | Ser | Ile | Ala | Gln | Ala | Val | Ile | Asn | Asn |
| | | 195 | | | | | 200 | | | | | 205 | | | |
| Gly | Gly | Lys | Val | Ile | Val | Gln | Val | Glu | Lys | Val | Lys | Gly | Gly | Thr |
| | 210 | | | | | 215 | | | | | 220 | | | | |
| Leu | Asp | Pro | Arg | Leu | Val | Gln | Ile | Pro | Gly | Ile | Tyr | Val | His | Ala | Val |
| 225 | | | | | 230 | | | | | 235 | | | | | 240 |
| Val | Glu | Val | Ala | Asp | Met | Lys | Asp | His | Glu | Gln | Ser | Val | Gly | His | Glu |
| | | | | 245 | | | | | 250 | | | | | 255 | |
| Tyr | Asn | Pro | Ala | Leu | Cys | Gly | Glu | Ala | Arg | Ala | Pro | Glu | Gly | Val |
| | | | 260 | | | | | 265 | | | | | 270 | | |
| Glu | Thr | Thr | Pro | Leu | Ser | Ile | Lys | Lys | Val | Ile | Gly | Arg | Arg | Ala | Ala |
| | | 275 | | | | | 280 | | | | | 285 | | | |
| Met | Glu | Leu | Val | Glu | Asn | Thr | Val | Val | Asn | Leu | Gly | Val | Gly | Thr | Pro |
| | 290 | | | | | 295 | | | | | 300 | | | | |
| Glu | Tyr | Val | Ala | Gln | Val | Ala | Ser | Glu | Glu | Gly | Ile | Ala | Ser | Tyr | Met |
| 305 | | | | | 310 | | | | | 315 | | | | | 320 |
| Thr | Leu | Thr | Val | Glu | Ser | Gly | Ala | Ile | Gly | Gly | Ser | Pro | Gln | Gly | Gly |
| | | | | 325 | | | | | 330 | | | | | 335 | |
| Ala | Arg | Phe | Gly | Ala | Thr | Leu | Asn | Pro | Asp | Ala | Ile | Ile | Asp | Gln | Asn |
| | | | 340 | | | | | 345 | | | | | 350 | | |
| Ser | Gln | Phe | Asp | Phe | Tyr | Asp | Gly | Gly | Gly | Leu | Asp | Met | Ala | Phe | Leu |
| | | 355 | | | | | 360 | | | | | 365 | | | |

```
Gly Leu Ala Glu Cys Asp Lys Gln Gly Asn Ile Asn Val Ser Lys Phe
        370                 375                 380

Gly Pro Lys Ile Pro Gly Cys Gly Gly Phe Ile Asn Ile Thr Gln Asn
385                 390                 395                 400

Ala Lys Lys Val Phe Phe Cys Gly Thr Phe Thr Ala Gly Gly Leu Lys
            405                 410                 415

Glu Arg Ile Glu Asp Gly Lys Leu Ile Val Glu Gln Glu Gly Arg Gln
        420                 425                 430

Arg Lys Phe Ile Lys Glu Val Glu Gln Val Thr Phe Ser Gly Asn Tyr
    435                 440                 445

Ala Val Lys Thr Lys Gln Pro Val Leu Tyr Ile Thr Glu Arg Ala Val
450                 455                 460

Phe Glu Leu Lys Glu Asp Gly Leu Asn Leu Ile Glu Val Ala Pro Gly
465                 470                 475                 480

Ile Asp Ile Gln Thr Gln Ile Ile Asp Leu Met Asp Phe Ala Pro Lys
            485                 490                 495

Ile Asp Ser Gly Leu Lys Leu Met Asp Ala Arg Leu Phe Ser Glu Glu
        500                 505                 510

Leu Met Asn Leu Lys Lys
        515

<210> SEQ ID NO 7
<211> LENGTH: 123
<212> TYPE: PRT
<213> ORGANISM: Peptoniphilus indolicus
<220> FEATURE:
<221> NAME/KEY: MISC_FEATURE
<222> LOCATION: (1)..(123)
<223> OTHER INFORMATION: ATCC 29427

<400> SEQUENCE: 7

Met Leu Glu Lys Gly Ser Thr Gln Glu Leu Thr Glu Ile Val Thr Lys
  1               5                  10                  15

Glu Asn Thr Ala Asp Ala Val Gly Asn Lys Ser Val Phe Val Tyr Ala
            20                  25                  30

Thr Pro Phe Leu Val Ala Leu Met Glu Arg Thr Cys Ile Lys Leu Met
        35                  40                  45

Glu Glu Asp Leu Asp Ser Gly Glu Val Ser Val Gly Thr Asn Ile Asn
    50                  55                  60

Leu Asp His Leu Ala Pro Thr Pro Ile Gly Asn Lys Ile Leu Cys Arg
65                  70                  75                  80

Ala Glu Leu Leu Glu Gln Ser Gly Lys Lys Tyr Val Phe Asp Val Lys
                85                  90                  95

Ala Phe Asp Asn Asp Lys Leu Ile Gly Lys Ala Ile His Thr Arg Tyr
            100                 105                 110

Lys Val Asn Leu Asp Lys Phe Leu Asn Asn Ile
        115                 120

<210> SEQ ID NO 8
<211> LENGTH: 518
<212> TYPE: PRT
<213> ORGANISM: Desulfosporosinus meridiei
<220> FEATURE:
<221> NAME/KEY: MISC_FEATURE
<222> LOCATION: (1)..(518)
<223> OTHER INFORMATION: strain ATCC BAA-275 / DSM 13257 / NCIMB
      13706 / S10

<400> SEQUENCE: 8
```

```
Met Lys Lys Val Asn Ile Leu Thr Ala Glu Ala Val Asp Leu Val
 1               5                  10                  15
Lys Asp Gly Asp Thr Leu Cys Thr Ser Gly Phe Val Gly Asn Ser Leu
             20                  25                  30
Pro Glu Ala Leu Phe Lys Ala Ile Glu Lys Lys Phe Leu Glu Thr Gly
         35                  40                  45
Tyr Pro Gln Asn Ile Thr Leu Phe Tyr Pro Ala Ser Gln Gly Ser Arg
     50                  55                  60
Asn Gly Thr Gly Gly Asp His Phe Ala His Glu Gly Leu Val Lys Arg
 65                  70                  75                  80
Val Ile Ala Gly His Leu Asn Thr Ala Pro Lys Leu Gly Glu Leu Cys
                 85                  90                  95
Leu Ala Asn Lys Cys Glu Gly Tyr Asn Leu Pro Gln Gly Ala Leu Glu
             100                 105                 110
Tyr Val Ile Arg Asp Ala Ala Gly His Arg Pro Gly Thr Ile Thr His
         115                 120                 125
Val Gly Leu Gly Thr Phe Val Asp Pro Arg Asn Gly Gly Gly Lys Ile
     130                 135                 140
Asn Ala Arg Thr Thr Glu Asp Leu Val Glu Val Ile Lys Ile Gly Asn
145                 150                 155                 160
Glu Glu Lys Leu Phe Tyr Lys Ala Phe Pro Ile Asp Ile Ala Phe Leu
                 165                 170                 175
Arg Gly Thr Tyr Ala Asp Glu Tyr Gly Asn Val Thr Leu Glu Lys Glu
             180                 185                 190
Val Ala Thr Ile Glu Val Thr Ser Ile Ala Gln Ala Val Ile Asn Asn
         195                 200                 205
Gly Gly Lys Val Ile Val Gln Val Glu Lys Val Val Lys Gly Gly Thr
     210                 215                 220
Leu Asp Pro Arg Leu Val Gln Ile Pro Gly Ile Tyr Val His Gly Val
225                 230                 235                 240
Val Glu Val Val Asp Met Lys Asp His Glu Gln Ser Val Gly His Glu
                 245                 250                 255
Tyr Asn Pro Ala Leu Cys Gly Ala Val Arg Ala Pro Glu Gly Asn Val
             260                 265                 270
Glu Lys Thr Pro Leu Ser Ile Lys Lys Val Ile Gly Arg Arg Ala Ala
         275                 280                 285
Met Glu Leu Val Lys Asp Thr Val Val Asn Leu Gly Val Gly Thr Pro
     290                 295                 300
Glu Tyr Val Ala Gln Val Ala Ser Glu Glu Ile Ala Ser Tyr Met
305                 310                 315                 320
Thr Leu Thr Val Glu Ser Gly Ala Ile Gly Gly Ser Pro Gln Gly Gly
                 325                 330                 335
Ala Arg Phe Gly Ala Thr Leu Asn Pro Asp Ala Ile Ile Asp Gln Asn
             340                 345                 350
Ser Gln Phe Asp Phe Tyr Asp Gly Gly Leu Asp Met Ala Phe Leu
         355                 360                 365
Gly Leu Ala Glu Cys Asp Glu Gln Gly Asn Ile Asn Val Ser Arg Phe
     370                 375                 380
Gly Pro Lys Ile Pro Gly Cys Gly Gly Phe Ile Asn Ile Thr Gln Asn
385                 390                 395                 400
Ala Lys Lys Val Phe Phe Cys Gly Thr Phe Thr Ala Arg Gly Leu Lys
                 405                 410                 415
Gln Lys Ile Glu Asp Gly Lys Leu Ile Ile Glu Gln Glu Gly Thr Gln
```

-continued

```
                420                 425                 430
Arg Lys Phe Ile Lys Gln Val Glu Gln Val Thr Phe Ser Gly Lys Tyr
            435                 440                 445

Ala Ile Lys Thr Lys Gln Pro Val Leu Tyr Ile Thr Glu Arg Ala Val
        450                 455                 460

Phe Glu Leu Lys Glu Glu Gly Leu Asn Leu Ile Glu Val Ala Pro Gly
465                 470                 475                 480

Ile Asp Ile Gln Thr Gln Ile Ile Asp Leu Met Asp Phe Val Pro Thr
                485                 490                 495

Val Asp Lys Asn Ile Lys Ile Met Asp Ser Arg Leu Phe Ser Glu Glu
            500                 505                 510

Leu Met Asn Leu Lys Lys
        515

<210> SEQ ID NO 9
<211> LENGTH: 521
<212> TYPE: PRT
<213> ORGANISM: Desulfosporosinus orientis
<220> FEATURE:
<221> NAME/KEY: MISC_FEATURE
<222> LOCATION: (1)..(521)
<223> OTHER INFORMATION: strain ATCC 19365/DSM 765/NCIMB 8382/VKM B-1628

<400> SEQUENCE: 9

Met Arg Lys Val Lys Ile Met Thr Ala Glu Glu Ala Val Asp Leu Val
1               5                   10                  15

Lys Asp Gly Val Thr Leu Cys Thr Ser Gly Phe Val Gly Asn Ser Leu
            20                  25                  30

Pro Glu Ala Leu Tyr Lys Ala Ile Glu Lys Lys Phe Leu Glu Thr Gly
        35                  40                  45

Tyr Pro Gln Ser Ile Thr Leu Phe Tyr Pro Ala Ser Gln Gly Ser Arg
    50                  55                  60

Asn Gly Thr Gly Gly Asp His Phe Ala His Glu Gly Leu Val Lys Arg
65                  70                  75                  80

Val Ile Ala Gly His Leu Asn Thr Ala Pro Lys Leu Gly Glu Leu Cys
            85                  90                  95

Leu Ala Asn Lys Cys Glu Gly Tyr Asn Leu Pro Gln Gly Thr Leu Glu
            100                 105                 110

Tyr Val Ile Arg Asp Ala Ala Gly His Arg Pro Gly Thr Ile Thr His
        115                 120                 125

Val Gly Leu Gly Thr Phe Val Asp Pro Arg Asn Gly Gly Lys Ile
    130                 135                 140

Asn Ala Arg Thr Thr Glu Asn Leu Val Glu Val Val Lys Ile Gly Asn
145                 150                 155                 160

Glu Glu Lys Leu Phe Tyr Lys Ala Phe Pro Ile Asp Ile Ala Phe Leu
            165                 170                 175

Arg Gly Thr Tyr Ala Asp Glu Tyr Gly Asn Val Thr Leu Glu Lys Glu
        180                 185                 190

Val Ala Thr Ile Glu Val Thr Ser Ile Ala Gln Ala Val Ile Asn Asn
        195                 200                 205

Gly Gly Lys Val Ile Val Gln Val Glu Lys Val Lys Gly Gly Thr
    210                 215                 220

Leu Asp Pro Arg Leu Val Gln Ile Pro Gly Ile Tyr Val His Ala Val
225                 230                 235                 240

Val Glu Ala Asp Leu Lys Asp His Glu Gln Ser Val Gly His Glu Tyr
            245                 250                 255
```

```
Asn Pro Ala Leu Cys Gly Glu Ala Arg Ala Pro Gly Asn Val Glu
            260                 265                 270

Ile Thr Pro Leu Ser Ile Lys Lys Val Ile Gly Arg Ala Ala Met
275                 280                 285

Glu Leu Val Glu Asp Thr Val Val Asn Leu Gly Val Gly Thr Pro Glu
            290                 295                 300

Tyr Val Ala Gln Val Ala Ser Glu Gly Ile Ala Asn Tyr Met Thr
305                 310                 315                 320

Leu Thr Val Glu Ser Gly Ala Ile Gly Gly Ser Pro Gln Gly Gly Ala
            325                 330                 335

Arg Phe Gly Ala Thr Leu Asn Pro Asp Ala Ile Ile Asp Gln Asn Ser
            340                 345                 350

Gln Phe Asp Phe Tyr Asp Gly Gly Leu Asp Met Ala Phe Leu Gly
            355                 360                 365

Leu Ala Glu Cys Asp Glu Gln Gly Asn Ile Asn Val Ser Arg Phe Gly
    370                 375                 380

Pro Lys Ile Pro Gly Cys Gly Gly Phe Ile Asn Ile Thr Gln Asn Ala
385                 390                 395                 400

Lys Lys Val Phe Phe Cys Gly Thr Phe Thr Ala Gly Gly Leu Lys Glu
                405                 410                 415

Arg Ile Glu Asp Gly Met Leu Ile Ile Asp Gln Glu Gly Lys Gln Arg
            420                 425                 430

Lys Phe Ile Lys Glu Val Glu Gln Val Thr Phe Ser Gly Arg Tyr Ala
            435                 440                 445

Ile Lys Thr Glu Gln Pro Val Leu Tyr Ile Thr Glu Arg Ala Val Phe
            450                 455                 460

Glu Leu Lys Glu Glu Gly Leu Asn Leu Ile Glu Ile Ala Pro Gly Val
465                 470                 475                 480

Asp Ile Gln Thr Gln Ile Ile Asp Leu Met Asp Phe Val Pro Thr Ile
                485                 490                 495

Asp Lys Asn Leu Lys Leu Met Asp Pro Arg Leu Phe Ser Glu Glu Lys
                500                 505                 510

Met Asn Leu Lys Asn Asn Glu Gly Glu
            515                 520

<210> SEQ ID NO 10
<211> LENGTH: 412
<212> TYPE: PRT
<213> ORGANISM: Peptostreptococcus anaerobius CAG:621
<220> FEATURE:
<221> NAME/KEY: MISC_FEATURE
<222> LOCATION: (1)..(412)
<223> OTHER INFORMATION: CAG:621

<400> SEQUENCE: 10

Met Ser Thr Arg Lys Arg Pro Leu Glu Gly Val Lys Val Ile Glu Leu
1               5                   10                  15

Ala Asn Phe Ile Ala Ala Ala Thr Thr Gly Arg Phe Leu Ala Asp Leu
                20                  25                  30

Gly Ala Asp Val Ile Lys Ile Glu Ser Ala Lys Gly Asp Pro Leu Arg
            35                  40                  45

Tyr Thr Ala Pro Thr Glu Gly Arg Pro Leu Asp Met His Glu Asn Thr
    50                  55                  60

Thr Trp Glu Leu Glu Asn Ala Asn Lys Arg Cys Ile Ser Leu Asn Met
65                  70                  75                  80
```

Lys Asp Pro Lys Gly Lys Glu Ala Phe Phe Lys Leu Leu Asp Asp Ala
                    85                  90                  95

Asp Ile Leu Ile Thr Asn Trp Arg Val Gln Ala Leu Gln Arg Ala Gly
            100                 105                 110

Leu Asp Tyr Glu Thr Leu Lys Val Lys Tyr Pro Ser Leu Val Tyr Ala
        115                 120                 125

Ile Cys Thr Gly Tyr Gly Glu Tyr Gly Pro Asp Lys Asp Leu Pro Gly
    130                 135                 140

Phe Asp Phe Thr Ala Phe Ala Arg Gly Tyr Leu Glu Asn Leu
145                 150                 155                 160

Arg Gln Lys Ser Asp Val Pro Met Asn Val Pro Gly Leu Gly Asp
                165                 170                 175

His Asn Val Gly Ile Asn Leu Ala Ala Gly Val Leu Ala Ala Leu Tyr
            180                 185                 190

His Ala Lys Leu Thr Gly Glu Gly Glu Lys Val Glu Thr Ser Leu Phe
        195                 200                 205

Glu Ser Ala Ile Phe Asn Met Gly Met Met Val Gln Ala Ala Gln Tyr
    210                 215                 220

Pro Asp Tyr Gly Thr Pro Tyr Pro Ile Asn Ile Arg Glu Ala Asn Asn
225                 230                 235                 240

Pro Phe Asn Ala Cys Trp Met Thr Lys Asp Gly Arg Tyr Val Gln Thr
                245                 250                 255

Cys Met Pro Asp Tyr Asn Thr Tyr Phe Lys Lys Phe Leu Thr Ala Leu
            260                 265                 270

Glu Leu Met Asp Ile Val Glu Asp Arg Phe Phe Pro Val Gln Asn
        275                 280                 285

Leu His Ala Asn Asp Leu Gly Thr Thr Val Tyr Asp Arg Val Met Ala
290                 295                 300

Arg Phe Gly Glu Arg Asp Phe Ser Glu Trp Ser Gln Val Leu Thr Asp
305                 310                 315                 320

Ala Asp Ile Pro Phe Ala Leu Ala Lys Asn Trp Glu Glu Leu Leu Glu
                325                 330                 335

Asp Glu Gln Ala Trp Ala Asn Asp Cys Phe Tyr Lys Met Lys Tyr Pro
            340                 345                 350

Ser Gly Glu Arg Ile Leu Cys Lys His Pro Val Lys Tyr His Glu Met
        355                 360                 365

Gly Pro Thr Pro Tyr Asn Arg Gly Pro Tyr Ile Gly Glu His Gly Val
    370                 375                 380

Glu Val Met Lys Glu Leu Gly Tyr Ser Asp Glu Asp Ile Lys Gln Met
385                 390                 395                 400

Leu Glu Asp Lys Thr Leu Tyr Val Trp Glu Asp Lys
                405                 410

<210> SEQ ID NO 11
<211> LENGTH: 1575
<212> TYPE: DNA
<213> ORGANISM: Clostridium propionicum

<400> SEQUENCE: 11
atgagaaagg ttcccattat taccgcagat gaggctgcaa agcttattaa agacggtgat      60
acagttacaa caagtggttt cgttggaaat gcaatccctg aggctcttga tagagctgta     120
gaaaaaagat tcttagaaac aggcgaaccc aaaaacatta catatgttta ttgtggttct     180
caaggtaaca gagacggaag aggtgctgag cactttgctc atgaaggcct tttaaaacgt     240

```
tacatcgctg gtcactgggc tacagttcct gctttgggta aaatggctat ggaaaataaa        300
atggaagcat ataatgtatc tcagggtgca ttgtgtcatt tgttccgtga tatagcttct        360
cataagccag gcgtatttac aaaggtaggt atcggtactt tcattgaccc cagaaatggc        420
ggcggtaaag taatgatat taccaaagaa gatattgttg aattggtaga gattaagggt         480
caggaatatt tattctaccc tgcttttcct attcatgtag ctcttattcg tggtacttac        540
gctgatgaaa gcggaaatat cacatttgag aaagaagttg ctcctctgga aggaacttca       600
gtatgccagg ctgttaaaaa cagtggcggt atcgttgtag ttcaggttga aagagtagta       660
aaagctggta ctcttgaccc tcgtcatgta aaagttccag gaatttatgt tgactatgtt       720
gttgttgctg acccagaaga tcatcagcaa tctttagatt gtgaatatga tcctgcatta       780
tcaggcgagc atagaagacc tgaagttgtt ggagaaccac ttcctttgag tgcaaagaaa       840
gttattggtc gtcgtggtgc cattgaatta gaaaaagatg ttgctgtaaa tttaggtgtt        900
ggtgcgcctg aatatgtagc aagtgttgct gatgaagaag gtatcgttga ttttatgact       960
ttaactgctg aaagtggtgc tattggtggt gttcctgctg gtggcgttcg ctttggtgct       1020
tcttataatg cggatgcatt gatcgatcaa ggttatcaat tcgattacta tgatggcggc       1080
ggcttagacc tttgctattt aggcttagct gaatgcgatg aaaaaggcaa tatcaacgtt        1140
tcaagatttg gccctcgtat cgctggttgt ggtggtttca tcaacattac acagaataca      1200
cctaaggtat tcttctgtgg tactttcaca gcaggtggct taaaggttaa aattgaagat        1260
ggcaaggtta ttattgttca agaaggcaag cagaaaaaat tcttgaaagc tgttgagcag        1320
attacattca atggtgacgt tgcacttgct aataagcaac aagtaactta tattacagaa       1380
agatgcgtat tccttttgaa ggaagatggt ttgcacttat ctgaaattgc acctggtatt        1440
gatttgcaga cacagattct tgacgttatg gattttgcac ctattattga cagagatgca       1500
aacggccaaa tcaaattgat ggacgctgct ttgtttgcag aaggcttaat gggtctgaag       1560
gaaatgaagt cctga                                                         1575
```

<210> SEQ ID NO 12
<211> LENGTH: 1596
<212> TYPE: DNA
<213> ORGANISM: Escherichia coli
<220> FEATURE:
<221> NAME/KEY: MISC_FEATURE
<222> LOCATION: (1)..(1596)
<223> OTHER INFORMATION: strain K12

<400> SEQUENCE: 12

```
atgaaacctg taaaccacc tcgtattaat ggacgagtgc cggtcctgtc ggcacaggaa         60
gcggtgaatt atattcccga cgaagcaaca ctttgtgtgt taggcgctgg cggcggtatt       120
ctggaagcca ccacgttaat tactgctctt gctgataaat ataaacagac tcaaacacca       180
cgtaatttat cgattattag tccaacaggg cttggcgatc gcgccgaccg tggtattagt       240
cctctggcgc aagaaggtct ggtgaaatgg gcattatgtg gtcactgggg acaatcgccg       300
cgtatttctg aactcgcaga acaaaataaa attattgctt ataactaccc acaaggtgta       360
cttacacaaa ccttacgcgc cgccgcagcc caccagcctg gtattattag tgatattggc       420
atcgggacat ttgtcgatcc acgccagcaa ggcggcaaac tgaatgaagt cactaaagaa       480
gacctgatta aactggtcga gtttgataac aaagaatatc tctattacaa agcgattgcg       540
ccagatattg ccttcattcg cgctaccacc tgcgacagtg aaggctacgc cacttttgaa       600
gatgaggtga tgtatctcga cgcattggtt attgcccagg cggtgcacaa taacggcggt       660
```

```
attgtgatga tgcaggtgca gaaaatggtt aagaaagcca cgctgcatcc taaatctgtc      720
cgtattccgg gttatctggt ggatattgtg gtggtcgatc cggatcaaac ccaactgtat      780
ggcggtgcac cggttaaccg ctttatttct ggtgacttca cccttgatga cagtaccaaa      840
cttagcctgc ccctaaacca acgtaaatta gttgcgcggc gcgcattatt cgaaatgcgt      900
aaaggcgcgg tggggaatgt cggcgtcggt attgctgacg gcattggcct ggtcgcccga      960
gaagaaggtt gtgctgatga ctttattctg acggtagaaa caggtccgat ggcggaatt     1020 acttcacagg ggatcgcctt tggcgcgaac gtgaataccc gtgccattct ggatatgacg     1080
tcccagtttg atttttatca cggtggcggt ctggatgttt gttatttgag ttttgctgaa     1140
gtcgaccagc acggtaacgt cggcgtgcat aaattcaatg gtaaaatcat gggcaccggt     1200
ggatttattg atatcagtgc cacttcgaag aaaatcattt tctgcggcac attaactgcg     1260
ggcagtttaa aaacagaaat taccgacggc aaattaaata tcgtccagga aggacgggtg     1320
aagaaattta ttcgggaact accggaaatt actttcagcg gaaaaatcgc tctcgagcga     1380
gggctggatg ttcgttatat cactgagcgc gcagtattca cgctgaaaga agacggcctg     1440
catttaatcg aaatcgcccc tggcgtcgat ttacaaaaag atattctcga caaaatggat     1500
ttcaccccag tgatttcgcc agaactcaaa ctgatggacg aaagattatt tatcgatgcg     1560
gcgatgggtt ttgtcctgcc tgaagcggct cattaa                              1596

<210> SEQ ID NO 13
<211> LENGTH: 1629
<212> TYPE: DNA
<213> ORGANISM: Cupriavidus necator

<400> SEQUENCE: 13
atgaaggtga tcaccgcacg cgaagcggcg gcactggtgc aggacggctg gaccgtggcc       60
agcgcgggct ttgtcggcgc cggccatgcc gaggccgtga ccgaggcgct ggagcagcgc      120
ttcctgcaga gcgggctgcc gcgcgacctg acgctggtgt actcggccgg gcagggcgac      180
cgcggcgcgc gcggcgtgaa ccacttcggc aatgccggca tgaccgccag catcgtcggc      240
ggccactggc gctcggccac gcggctggcc acgctggcca tggccgagca gtgcgagggc      300
tacaacctgc gcagggcgt gctgacgcac ctataccgcg ccatcgccgg cggcaagccc      360
ggcgtgatga ccaagatcgg cctgcacacc ttcgtcgacc gcgcaccgc gcaggatgcg      420 cgctaccacg gcggcgccgt caacgagcgc gcgcgccagg ccattgccga gggcaaggca      480
tgctgggtca tgcggtcga cttccgcggc gacgaatacc tgttctaccc gagcttcccg      540
atccactgcg cgctgatccg ctgcaccgcg gccgacgccc gcggcaacct cagcacccat      600
cgcgaagcct tccaccatga gctgctggcg atggcgcagg cggcccacaa ctcgggcggc      660
atcgtgatcg cgcaggtgga aagcctggtc gaccaccacg agatcctgca ggccatccac      720
gtgcccggca tcctggtcga ctacgtggtg gtctgcgaca accccgccaa ccaccagatg      780
acgtttgccg agtcctacaa cccggcctac gtgacgccat ggcaaggcga ggcagcggtg      840
gccgaagcgg aagcggcgcc ggtggctgcc ggcccgctcg acgcgcgcac catcgtgcag      900 cgccgtgcg tgatggaact ggcgcgccgt gcgccgcgcg tggtcaacct gggcgtgggc      960
atgccggcag cggtcggcat gctggcgcac caggccgggc tggacggctt cacgctgacc     1020
gtcgaggccg gccccatcgg cggcacgccc gcggatggcc tcagcttcgg tgcctcggcc     1080
tacccggagg cggtggtgga tcagcccgcg cagttcgatt tctacgaggg cggcggcatc     1140
```

| | |
|---|---|
| gacctggcca tcctcggcct ggccgagctg gatggccacg gcaacgtcaa tgtcagcaag | 1200 |
| ttcggcgaag gcgagggcgc atcgattgcc ggcgtcggcg gctttatcaa catcacgcag | 1260 |
| agcgcgcgcg cggtggtgtt catgggcacg ctgacggcgg gcgggctgga agtccgcgcc | 1320 |
| ggcgacggcg gcctgcagat cgtgcgcgaa ggcgcgtga agaagatcgt gcctgaggtg | 1380 |
| tcgcacctga gcttcaacgg gccctatgtg gcgtcgctcg gcatcccggt gctgtacatc | 1440 |
| accgagcgcg cggtgttcga gatgcgcgct ggcgcagacg gcgaagcccg cctcacgctg | 1500 |
| gtcgagatcg ccccggcgt ggacctgcag cgcgacgtgc tcgaccagtg ctcgacgccc | 1560 |
| atcgccgttg cgcaggacct gcgcgaaatg gatgcgcggc tgttccaggc cgggcccctg | 1620 |
| cacctgtaa | 1629 |

<210> SEQ ID NO 14
<211> LENGTH: 1421
<212> TYPE: DNA
<213> ORGANISM: Halomonas smyrnensis

<400> SEQUENCE: 14

| | |
|---|---|
| atgaccacct caacgcaaac ggaacttaag aagggccctc tcaacgggat taccgtgctt | 60 |
| gattttctc gggtactcgc cgggccctat tgcaccatgg tgctggccga tttaggcgcc | 120 |
| cgtgtcatta agattgaaaa gatcggaacc ggcgatgaca cgcgggagtt tggaccgttc | 180 |
| gtcgagggcg agagcgcgta tttcagctgc ttcaacagga acaaggaaag cattgtcctg | 240 |
| gatattaagt cgccgcgcga ccgcgagctg ctggaacgat tactggacga gtctgatgtg | 300 |
| ctagtcgaaa actttcggcc tggagtgatg gaccgtctgg ggtatggccc ggaacgcttg | 360 |
| gccatgacgc accctcactt aatctactca tcgatctctg gcttcggtca taccggcccc | 420 |
| ttcagtgagt taccoggcta cgacatggtg gtgcaggcca tgggggaat tatgagcctg | 480 |
| acggggtggc ccgatggtga gccggctcgc gtgggaacca gcttcggtga cctgagtgcg | 540 |
| gcactgttcg cggcgatcgg tatcatcgca tcgctctata gccgaaccaa ggatgctcag | 600 |
| ggaacccgtg tcgatatcgg catgctcgac tgccaggcgg cactgatgga aaccgcattg | 660 |
| gctcgctatg acatcgaggg gaaagtgccg aaccgaaccg gcgattgcca ccoctcactg | 720 |
| gcgcccttcg aaagcttcaa tgccaaggac ggcaagctcg tcatcgccgc tggcaacgat | 780 |
| acccttttcc tattaatggc cgatgccatc ggtgcggcaa ggctcgcctt cgatcctcgg | 840 |
| tttatcagta acgacttgcg ttgtcacaac cggcccgagt tggtcgctga aatggaaaag | 900 |
| atcctactgg agcagcccgt gcagcactgg gtggatctgc tgaacgagga gggggtgcct | 960 |
| tgttcgccga tcaacaccat cgacaagcta ttcgatcatc cgcagctgaa agctcgaaat | 1020 |
| atgatcgttc aggttcaggg taaggccggt aagcctttca aaacagcggg taatccgatc | 1080 |
| aagctgaccg ggcgcgagga ctttgatagt ggcgtcccaa tgagtgcgcc gggtcttggg | 1140 |
| caacatcgag aagccatctt gacggagttg atggctcgtc atggttccta tcatttgcca | 1200 |
| acacagccgg acattcaggg ctcgttaccg gaatctggaa cggacactcc atgggcgttt | 1260 |
| cgccctgtcg catccggtga ttcaggggcc gctctttcga gaaacgagcc gaagagtaag | 1320 |
| aacgcccaag tagcgtctga aaacgagcgg ggccgatcgt caaactctga gccacaaccc | 1380 |
| aagtcgaccg ccaaaagtaa atcggagatg gaaaatggat a | 1421 |

<210> SEQ ID NO 15
<211> LENGTH: 1889
<212> TYPE: DNA
<213> ORGANISM: Ruegeria pomeroyi

```
<220> FEATURE:
<221> NAME/KEY: MISC_FEATURE
<222> LOCATION: (1)..(1889)
<223> OTHER INFORMATION: DSS-3

<400> SEQUENCE: 15
atggcatatc aggacgtata cgagagctgg aagagcgatc ccgaagcctt ctggatggag      60
gccgccaaaa gcatcgactg ggttgaagcg cccagccgcg cgctggatga cagcaacgcg     120
ccgctttacg aatggttcac cgatgccaag gtcaacacct gctggaacgc cgttgaccgc     180
catgtcgagg cgggtcgggg cgagcagacc gcgatcatct atgacagccc gatcacccat     240
accaagcggc agatctctta cgtcgagctg cgcaaccggg tggccatgct ggccggcgcg     300
ctgcgcgcca aggtgtgga aaagggcgat cgcgtcatca tctatatgcc gatgatcccc      360
gaggcgctgg aggcgatgct ggcctgtgcc cgtctgggcg ccgtgcattc ggtggtcttc     420
ggcgggtttg ccgccaacga actggccgta cgcatcgacg acgcccaacc caaggcgatc     480
atcgcggcat cctgcgggtt ggaaccgggc gcgtggtgc attacaagcc cctcctcgac      540
ggcgccatcg acatggcgaa acacaagccc gaattctgtg tgatcttcca gcgcgaacag     600
gaagtggcgc atctcgaaga gggccgcgat tacaattggc acgggttcca gtatggcgtc     660
gaaccggccg aatgcgtccc cgtagagggc aaccacccgg cctatatcct ctatacctcc     720
ggcaccactg gcgcgcccaa gggggtgctg cgtccgaccg cgggtcatct ggtggcgctg     780
aactggacga tgaagaacat ctataacgtc gatccgggcg atgtgttctg gcggcatcc      840 gatgtgggct gggtcgtcgg ccacagctat atctgctatg cccactgat ccacggcaac      900 accaccatcg tattcgaggg caagcccgtc ggcaccccg atgcgggcac cttctggcgg      960
gtgatctccg agcacaaggt caagagcttc ttcaccgccc ccaccgccat ccgcgccgtg    1020
aaacgcgagg atcccaaggg cgagatgctg gcgaaatacg acctgagcca tctcaaggcg    1080
ctctatctgg cgggcgaacg ggccgatccc gacaccatca tctgggcgca aaaggcgctg    1140
agtgtgcctg tgatcgacca ttggtggcag accgaaaccg gctggaccat cgcgggcaac    1200
ccgctgggga tagaggagct gccgacaaaa ctgggctcgc ccgccaaggc aatgcccggc    1260
tatgacgtac agatcctcga cgagggcggc caccagatga aaccgggcga gctgggcgcc    1320
atcgcggtga aactgccgct gccgccgggc accctgcccg gctgtggaa cgccgaggcg    1380 cggttcagga aatcctatct ggagcatttc cccggctact atgagaccgg cgacgccggc    1440
atgatcgacg aggacgggta cctctatatc atggcgcgca ccgatgacgt catcaacgtt    1500
gcgggccacc gcctgtccac cggcggcatg gaagaggttc tggccgggca cgaggatgtg    1560
gccgaatgcg cggtgatcgg cgtcagcgac gacctcaagg gtcagatgcc gctgggcttc    1620
ctgtgcctaa caacgggtg caaccgcgac cacggggatg tggtgaaaga ggtagtcaag    1680
ctggtgcgcg acaagatcgg cccagtcgcg gccttcaagc tggccgtggt ggtcgaccgc    1740
ctgcccaaga cccgctcggg caagatcctg cgcggcacca tggtctcgat cgctgacggc    1800
aaggagtaca gatgcccgc caccatcgac gatccggcca tcctggacga gatcaaggtc    1860
gcactgcaat cgctgggcta cgccaagta                                      1889

<210> SEQ ID NO 16
<211> LENGTH: 1557
<212> TYPE: DNA
<213> ORGANISM: Desulfosporosinus youngiae
<220> FEATURE:
<221> NAME/KEY: MISC_FEATURE
<222> LOCATION: (1)..(1557)
```

<223> OTHER INFORMATION: DSM 17734

<400> SEQUENCE: 16

```
atgaagaagg ttatcgttct gacagcagaa gaggctgtag atttagttaa agatgggggac    60
actctttgta caagtggatt tgttggaaat agtcttccgg aagcactttt taaggctata   120
gaaagaaat ttttagggac cggctatcct caaaatataa cgttgtttta tccggcatca   180
caaggcagca ggaacggcac aggcggtgat cattttgctc acgaaggttt ggttaaaaga   240
gtcatagcag gtcatttaaa tactgctccg aagttaggcg aactgtgtct ggctaataag   300
tgtgaaggtt ataacttacc acaaggtgct ttggaatatg ttatcagaga tgctgcgggt   360
cataggcccg gcacaattac ccatgttggg ttaggtacgt ttgttgatcc gagaaatggc   420
ggaggtaaaa taaacgccag gacgacagaa gatttagtag aagttataaa aattggcaat   480
gaagaaaagc ttttctacaa agcatttcct atagatatcg ctttcctgag aggtacttat   540
gcggatgagt atggcaatgt aaccctggaa aagaagtag ctactattga ggttacatct   600
atagcacagg cagttatcaa taatggcgga aaagtcattg ttcaggtgga aaaggttgta   660
aaaggcggta ctttagaccc cagactggtt caaatacctg gcatttatgt tcatgctgtt   720
gtagaagtag ctgatatgaa agatcacgaa caaagcgttg acatgaata taacccggca   780
ctttgcgggg aagcaagagc acctgaaggt ggcgttgaaa cgaccccatt aagtattaaa   840
aaggttattg gcagagagc agctatgaaa ttggtagaga ataccgttgt taatttaggt   900
gtaggaacac ctgagtatgt tgctcaagtt gccagtgaag aaggaatagc aagttatatg   960
accttaacag ttgaatcagg ggcaataggga ggcagtcctc aaggcggagc cagatttggt  1020
gctactttaa atcctgacgc tattattgat caaaatagtc agtttgattt ttatgatggc  1080
ggcggtctgg acatggcatt tttaggctta gctgaatgtg ataaacaggg caacattaat  1140
gtcagcaaat ttggccccaa ataccaggt tgcggtggtt tcatcaatat cacccaaaat  1200
gccaaaaaag tattcttctg cggcacattt acagccgggg gcttaaaaga agaattgaa   1260
gatggcaagc taatagtcga gcaagaaggc aggcaaagga aatttattaa agaagttgaa  1320
caagttacat ttagtggaaa ttatgccgtt aaaacgaaac aaccggtttt atatattaca  1380
gaaagagctg tatttgaatt aaaagaagat ggacttaact taatagaagt tgctcctgga  1440
attgatatcc aaacccaaat tatcgattta atggattttg cccctaagat tgacagcgga  1500
cttaagctca tggacgcaag acttttttagt gaagaactaa tgaacttgaa aaaataa    1557
```

<210> SEQ ID NO 17
<211> LENGTH: 372
<212> TYPE: DNA
<213> ORGANISM: Peptoniphilus indolicus
<220> FEATURE:
<221> NAME/KEY: MISC_FEATURE
<222> LOCATION: (1)..(372)
<223> OTHER INFORMATION: ATCC 29427

<400> SEQUENCE: 17

```
atgctggaaa aggtagtac acaagaactt accgaaattg ttacaaaaga aaatacagct    60
gatgctgtag gaaataaatc agtatttgtt tatgcaactc cattttttagt agcattaatg   120
gagcgaactt gtataaaatt gatggaagaa gatttagaca gtggagaagt ttcagttgga   180
actaatataa atttagatca tcttgctcca acaccaattg gaaataaaat tttatgcaga   240
gcagaactgc ttgaacaaag tggtaaaaaa tatgtatttg atgtaaaagc ttttgataat   300
gacaaactta ttggaaaggc aatacataca agatacaaag ttaacttaga taaatttta   360
```
aataacattt aa 372

<210> SEQ ID NO 18
<211> LENGTH: 1557
<212> TYPE: DNA
<213> ORGANISM: Desulfosporosinus meridiei
<220> FEATURE:
<221> NAME/KEY: MISC_FEATURE
<222> LOCATION: (1)..(1557)
<223> OTHER INFORMATION: strain ATCC BAA-275 / DSM 13257 / NCIMB 13706 / S10

<400> SEQUENCE: 18

| | | | | | |
|---|---|---|---|---|---|
| atgaagaagg | ttaatattct | cacagcagaa | gaggctgttg | atttagtcaa | agatggggac | 60 |
| actctttgta | ccagtggatt | tgttggcaat | agtcttccgg | aagcactttt | taaagctata | 120 |
| gaaaagaaat | ttttagagac | tggctatcct | caaaatataa | ctttgtttta | tccagcatca | 180 |
| caaggcagca | gaaacggcac | gggcggtgat | cattttgctc | acgaaggttt | ggttaaaagg | 240 |
| gtcatagcag | gtcatttaaa | tactgctccg | aagttaggcg | aactgtgtct | agctaataaa | 300 |
| tgcgaaggtt | ataacttacc | acaaggtgct | ttggaatatg | ttattagaga | tgctgcgggt | 360 |
| cataggcccg | gtacaattac | ccatgttgga | ttaggtactt | ttgttgatcc | aagaaatggc | 420 |
| ggaggtaaaa | taaacgctag | gacgacagaa | gatttagtag | aagttataaa | aatcggcaat | 480 |
| gaagaaaagc | ttttctacaa | agcttttcct | atagatatcg | ccttccttag | aggtacttat | 540 |
| gcggatgagt | atggtaatgt | aaccctagaa | aaagaagtag | ctactattga | ggttacatct | 600 |
| atagcacagg | cagttataaa | taatggtgga | aaagtaattg | ttcaagtgga | aaaggttgta | 660 |
| aaaggtggta | ctttagaccc | cagactggta | caaataccag | gcatttatgt | tcatggtgtt | 720 |
| gtagaagtag | ttgatatgaa | agatcatgaa | caaagtgttg | gacatgaata | taatccagca | 780 |
| ctttgcgggg | cagtaagagc | acctgaaggt | aatgttgaaa | aaccccatt | gagtattaaa | 840 |
| aaagttattg | gcagaagagc | agctatgaaa | ttggtaaagg | atacagttgt | taatttaggt | 900 |
| gttggaacac | ctgagtatgt | tgctcaagtt | gcaagtgaag | aagagatagc | tagttatatg | 960 |
| actttaactg | ttgaatcagg | agcaatagga | ggcagtcctc | aaggtggagc | cagatttggt | 1020 |
| gctactttaa | atcctgacgc | tattattgac | caaaatagtc | agtttgattt | ttatgatggc | 1080 |
| ggcggtctgg | atatggcatt | tttaggttta | gctgaatgtg | atgaacaggg | caacattaat | 1140 |
| gtcagcagat | tcggtcccaa | aataccggga | tgtggtggtt | tcatcaatat | cacccaaaat | 1200 |
| gcaaaaaaag | tattcttctg | cggtacattt | acagcaagag | gcttaaaaca | aaaaattgaa | 1260 |
| gatggcaagt | taataattga | acaagaagga | acgcaaagga | aatttattaa | acaagttgaa | 1320 |
| caggtaacat | ttagtggaaa | atatgcaatt | aaaactaaac | aacctgtttt | atatataaca | 1380 |
| gaaagagctg | tatttgaatt | aaaagaagag | ggacttaact | taattgaagt | tgctcccgga | 1440 |
| attgatattc | aaacacaaat | tatagattta | atggattttg | tccctacagt | tgacaaaaat | 1500 |
| attaaaatta | tggactcaag | acttttagt | gaagaactaa | tgaacttgaa | gaaataa | 1557 |

<210> SEQ ID NO 19
<211> LENGTH: 1566
<212> TYPE: DNA
<213> ORGANISM: Desulfosporosinus orientis
<220> FEATURE:
<221> NAME/KEY: MISC_FEATURE
<222> LOCATION: (1)..(1566)
<223> OTHER INFORMATION: strain ATCC 19365 / DSM 765 / NCIMB 8382 / VKM B-1628

<400> SEQUENCE: 19

```
atgaggaagg ttaagattat gacagcagaa gaggctgttg atttagttaa agatggggtg      60
actctctgta caagtggatt tgttggaaat agtcttccgg aagcacttta taaggctatc     120
gaaaagaaat ttttagagac cggctatcct caaagtatca ctttatttta tccggcctca     180
caaggcagca gaaatggcac cggcggtgat cattttgctc acgaaggttt ggttaaaaga     240
gtcatagccg tcatttaaa tactgctccc aagttaggcg agctgtgtct ggctaataaa      300
tgtgaaggtt ataacttacc ccaaggtact ttggaatatg ttatcagaga tgctgcgggt     360
cataggcccg gtaccatcac ccatgtaggc ttaggtactt tgttgatcc cagaaatggc      420
ggaggtaaaa taaacgccag gacgacagaa aatttagtgg aagttgtaaa aatcggcaat     480
gaagaaaagc ttttctacaa agcatttcct atagatatcg ctttcttgag aggtacttat     540
gcggatgagt atggtaatgt aaccctggaa aaagaagtag ctactattga ggttacttcc     600
atagcacagg cagttatcaa taatggcggc aaagtaattg ttcaagtgga aaaggttgta     660
aaaggcggga ctttagaccc cagactggtg caaatacctg gcatttatgt tcatgctgtt     720
gtcgaagctg atctgaaaga tcatgaacaa agtgtcgggc atgaatataa cccggcactg     780
tgcggggaag caagggcacc tgaaggcaat gttgaaataa ctcccttaag tattaaaaaa     840
gttattggca aagagccgc tatggaattg gtagaggata ccgttgtcaa tttaggtgtt      900
ggaacacctg agtatgttgc tcaagttgcc agtgaagaag aatcgccaa ttatatgacc      960
ttaaccgtag aatccggtgc catcggcggc agtcctcaag ggggagcccg atttggtgct    1020
actttaaatc ctgacgctat tattgatcaa aatagtcagt ttgacttta cgatggcggc    1080
ggtctggaca tggcattttt aggcttagct gaatgtgatg aacagggcaa cattaacgtc    1140
agccgctttg gtcccaaaat acccggttgc ggcggtttca tcaatatcac ccagaatgcc    1200
aaaaagtat tcttctgcgg tacatttact gcaggaggct aaaagaaag aattgaagac     1260
ggcatgctaa tcatagatca agagggaaaa cagcggaaat ttatcaaaga agttgaacag    1320
gttaccttta gcggaagata tgccattaaa accgaacagc ccgttttata tattacggaa    1380
agagctgtct ttgaattaaa agaagagggg ctgaacttaa tcgaaatcgc tcccggcgtt    1440
gatatccaaa cccaaattat tgatttaatg gattttgtcc ctaccattga caaaaacctc    1500
aagcttatgg acccaagact tttcagtgag gaaaaaatga acttgaaaaa caacgaggga    1560
gaataa                                                               1566
```

<210> SEQ ID NO 20
<211> LENGTH: 1239
<212> TYPE: DNA
<213> ORGANISM: Peptostreptococcus anaerobius CAG:621
<220> FEATURE:
<221> NAME/KEY: MISC_FEATURE
<222> LOCATION: (1)..(1239)
<223> OTHER INFORMATION: CAG:621

<400> SEQUENCE: 20

```
atgagcacaa gaaagagacc attagaagga gtaaaggtaa tagaacttgc aaactttata      60
gcagctgcaa ctacaggaag attttttagct gacttaggtg cagatgtaat aaagattgaa    120
agtgcaaagg gagacccact aagatatacg gctccaactg aaggtagacc gcttgatatg     180
cacgaaaata caacttggga attagaaaat gctaataaga gatgtatatc tctaaatatg     240
aaggatccta agggtaaaga agctttcttt aagctacttg atgatgcaga tatacttata     300
acaaactgga gagtacaggc actacagaga gctggacttg actatgaaac actaaaggtt     360
```

-continued

```
aagtatccaa gccttgtata cgctatttgt acaggttatg gtgaatacgg tcctgataag      420
gatcttccag gattcgactt tacagctttc tttgctagag gtggatatct tgaaaacctt      480
agacagaaat ctgatgttcc aatgaacgtt gttccaggac ttggtgacca caatgttggt      540
atcaacctag ctgcaggtgt acttgctgca ttatatcacg ctaaattaac aggcgaaggt      600
gaaaaggttg aaacaagttt attcgaatca gcaatattca atatgggtat gatggttcag      660
gctgctcagt atcctgacta cggtactcca tatccaataa atataagaga agctaacaat      720
ccatttaacg cttgttggat gactaaggac ggaagatatg ttcagacttg tatgcctgac      780
tacaatactt acttcaaaaa gttcttaaca gcattagagc ttatggatat agtagaagat      840
gaaagattct tcccagtgca gaacttacat gcaaacgacc taggaactac agtatatgat      900
agagtaatgg ctaggtttgg agaaagagac tttagcgaat ggtcacaggt acttacagat      960
gctgacatcc catttgctct agctaagaat tgggaagaac tattagaaga tgaacaggca     1020
tgggcaaatg actgcttcta caagatgaag tatccaagtg gtgaaagaat actttgtaag     1080
cacccagtta agtaccatga atgggacct actccataca acagaggacc atacatcggt     1140
gaacatggtg ttgaagtaat gaaggagtta ggatactctg atgaagacat caagcagatg     1200
ttagaagaca agactctata tgtttgggaa gacaaatag                            1239
```

<210> SEQ ID NO 21
<211> LENGTH: 299
<212> TYPE: PRT
<213> ORGANISM: Dictyostelium discoideum
<220> FEATURE:
<221> NAME/KEY: MISC_FEATURE
<222> LOCATION: (1)..(299)
<223> OTHER INFORMATION: Slime mold

<400> SEQUENCE: 21

```
Met Ile Asn Arg Leu Phe Ser Ile Asn Asn Ile Lys Asn Gly Ser Lys
  1               5                  10                  15

Phe Phe Ser Ser Ser Thr Thr Val Glu Thr Lys Gln Pro Leu Val Leu
                 20                  25                  30

Leu Glu Lys His Leu Val Asn Gly Lys Tyr Thr Gly Ile Gln Ile Val
             35                  40                  45

Lys Leu Asn Lys Pro Lys Gln Leu Asn Ala Leu Thr Phe Glu Met Gly
         50                  55                  60

Val Asp Tyr Lys Lys Val Val Asp Thr Leu Ala Glu Asp Lys Asp Leu
 65                  70                  75                  80

Lys Cys Val Val Leu Thr Gly Glu Gly Lys Ala Phe Ser Ala Gly Gly
                 85                  90                  95

Asp Leu Asp Phe Leu Ile Glu Arg Thr Lys Asp Thr Pro Glu Asn Asn
                100                 105                 110

Gln Arg Ile Met Glu Arg Phe Tyr Arg Thr Phe Leu Tyr Ile Arg Ser
            115                 120                 125

Leu Pro Val Pro Ile Ile Ser Ala Ile Asn Gly Ala Ala Ile Gly Ala
        130                 135                 140

Gly Phe Cys Leu Ala Leu Ala Thr Asp Ile Arg Val Val Ser Asn Lys
145                 150                 155                 160

Ala Pro Val Gly Leu Thr Phe Thr Lys Leu Gly Ile His Pro Gly Met
                165                 170                 175

Gly Val Thr His Ser Ile Thr Asn Ile Val Gly Gln Asp Val Ala Ser
            180                 185                 190
```

```
Tyr Met Leu Leu Ser Ser Asp Ile Ile Lys Gly Asp Glu Ala Gln Arg
            195                 200                 205

Leu Gly Leu Val Leu Lys Ser Val Glu Ser Asp Gln Val Leu Pro Thr
        210                 215                 220

Ala Leu Asn Leu Ala Glu Thr Ile Ser Lys Asn Ser Thr Ile Ala Val
225                 230                 235                 240

Asn Ser Thr Thr Lys Thr Leu Arg Asn Lys Tyr Asn Ser Asp Leu Asp
                245                 250                 255

Lys Ser Leu Thr Arg Glu Ala Asp Gln Ser Gln Cys Trp Ala Ser
            260                 265                 270

Lys Asp Ile Val Glu Gly Ile Leu Ala Ile Arg Glu Ser Arg Asp Pro
        275                 280                 285

Lys His Asn Tyr Leu Leu Phe Asp Asp Gln Lys
        290                 295

<210> SEQ ID NO 22
<211> LENGTH: 261
<212> TYPE: PRT
<213> ORGANISM: Clostridium acetobutylicum

<400> SEQUENCE: 22

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260
```

<210> SEQ ID NO 23
<211> LENGTH: 155
<212> TYPE: PRT
<213> ORGANISM: Clostridium difficile

<400> SEQUENCE: 23

```
Asn Ser Lys Lys Val Val Ile Ala Ala Val Asn Gly Phe Ala Leu Gly
  1               5                  10                  15

Gly Cys Glu Leu Ala Met Ala Cys Asp Ile Arg Ile Ala Ser Ala Lys
             20                  25                  30

Ala Lys Phe Gly Gln Pro Glu Val Thr Leu Gly Ile Thr Pro Gly Tyr
         35                  40                  45

Gly Gly Thr Gln Arg Leu Thr Arg Leu Val Gly Met Ala Lys Ala Lys
     50                  55                  60

Glu Leu Ile Phe Thr Gly Gln Val Ile Lys Ala Asp Glu Ala Glu Lys
 65                  70                  75                  80

Ile Gly Leu Val Asn Arg Val Val Glu Pro Asp Ile Leu Ile Glu Glu
                 85                  90                  95

Val Glu Lys Leu Ala Lys Ile Ile Ala Lys Asn Ala Gln Leu Ala Val
            100                 105                 110

Arg Tyr Ser Lys Glu Ala Ile Gln Leu Gly Ala Gln Thr Asp Ile Asn
        115                 120                 125

Thr Gly Ile Asp Ile Glu Ser Asn Leu Phe Gly Leu Cys Phe Ser Thr
    130                 135                 140

Lys Asp Gln Lys Glu Gly Ile Val Ser Phe Arg
145                 150                 155
```

<210> SEQ ID NO 24
<211> LENGTH: 258
<212> TYPE: PRT
<213> ORGANISM: Clostridium pasteurianum

<400> SEQUENCE: 24

```
Met Gly Asn Ile Ile Phe Glu Glu Asp Gly Ile Glu Lys Val Thr
  1               5                  10                  15

Ile Asn Arg Pro Lys Ala Leu Asn Ala Leu Asn Ser Glu Thr Leu Lys
             20                  25                  30

Glu Leu Gly Thr Val Ile Asn Asp Ile Ser Val Asn Asp Gly Ile Lys
         35                  40                  45

Ala Val Ile Ile Thr Gly Ser Gly Ser Lys Ala Phe Val Ala Gly Ala
     50                  55                  60

Asp Ile Ala Glu Met Ser Thr Leu Asn Ser Ile Glu Ala Thr Asn Phe
 65                  70                  75                  80

Ser Arg Leu Ala Gln Asn Val Phe Ser Gln Ile Glu Asn Leu Pro Lys
                 85                  90                  95

Leu Val Val Ala Ala Val Asn Gly Phe Ala Leu Gly Gly Gly Cys Glu
            100                 105                 110

Leu Ala Met Ala Cys Asp Val Arg Phe Ala Ser Lys Lys Ala Lys Phe
        115                 120                 125

Gly Gln Pro Glu Val Asn Leu Gly Ile Leu Pro Ser Phe Gly Gly Thr
    130                 135                 140

Gln Arg Leu Pro Lys Leu Val Gly Lys Gly Ile Ala Lys Glu Leu Ile
145                 150                 155                 160

Phe Ser Thr Asp Met Ile Thr Ala Asp Glu Ala Tyr Arg Ile Gly Leu
                165                 170                 175
```

```
Ala Asn Lys Val Tyr Glu Pro Glu Leu Leu Val Lys Ser Gln Glu
            180                 185                 190

Phe Ala Glu Lys Val Met Thr Lys Ser Pro Trp Gly Val Lys Leu Ala
            195                 200                 205

Lys Ala Cys Ile Asn Asn Gly Leu Asp Val Asp Leu Glu Ala Gly Leu
210                 215                 220

Lys Tyr Glu Ala Asn Ser Phe Gly Leu Cys Phe Ser Thr Glu Asp Gln
225                 230                 235                 240

Lys Glu Gly Met Lys Ala Phe Leu Glu Lys Arg Lys Ala Asp Phe Lys
            245                 250                 255

Gly Leu

<210> SEQ ID NO 25
<211> LENGTH: 262
<212> TYPE: PRT
<213> ORGANISM: Clostridium pasteurianum

<400> SEQUENCE: 25

Met Asp Phe Asn Asn Ile Ile Leu Glu Lys Glu Glu Lys Ile Ala Val
1               5                   10                  15

Val Thr Ile Asn Arg Pro Lys Ala Leu Asn Ala Leu Asn Ser Glu Thr
            20                  25                  30

Leu Thr Glu Leu Asp Ser Val Ile Asp Glu Ile Asp Lys Asp Asn Glu
        35                  40                  45

Ile Leu Ala Val Val Leu Thr Gly Ala Gly Lys Ser Phe Val Ala Gly
    50                  55                  60

Ala Asp Ile Ser Glu Met Lys Asp Met Asn Val Val Glu Gly Arg Lys
65                  70                  75                  80

Phe Gly Ile Leu Gly Asn Lys Val Phe Arg Lys Leu Glu Asn Leu Glu
                85                  90                  95

Lys Pro Val Ile Ala Ala Leu Asn Gly Phe Thr Leu Gly Gly Gly Cys
            100                 105                 110

Glu Ile Ala Met Ser Cys Asp Ile Arg Ile Ala Ser Thr Lys Ala Lys
        115                 120                 125

Phe Gly Gln Pro Glu Val Gln Leu Gly Ile Thr Pro Gly Phe Gly Gly
    130                 135                 140

Thr Gln Arg Leu Ala Arg Leu Ile Gly Pro Gly Ala Ala Lys Glu Leu
145                 150                 155                 160

Ile Tyr Thr Gly Lys Ile Ile Asn Ala Glu Glu Ala Tyr Arg Leu Gly
                165                 170                 175

Leu Val Asn Arg Val Ile Glu Pro Glu Thr Leu Leu Asp Glu Ala Lys
            180                 185                 190

Gln Leu Ala Asn Thr Ile Ala Ala Asn Ala Pro Ile Ala Val Lys Leu
        195                 200                 205

Ala Lys Ser Ala Ile Asn Arg Gly Ile Gln Thr Asp Ile Asp Thr Gly
    210                 215                 220

Val Ser Ile Glu Ser Glu Val Phe Gly Ala Cys Phe Ser Thr Glu Asp
225                 230                 235                 240

Gln Lys Glu Gly Met Asn Thr Phe Leu Asn Asp Lys Lys Tyr Leu Thr
                245                 250                 255

Gly Asn Phe Lys Asn Lys
            260

<210> SEQ ID NO 26
```

```
<211> LENGTH: 260
<212> TYPE: PRT
<213> ORGANISM: Megasphaera elsdenii

<400> SEQUENCE: 26

Met Asp Tyr Gln Asn Ile Ile Phe Ala Val Glu Asp Gly Ile Ala Thr
 1               5                  10                  15

Ile Thr Ile Asn Arg Pro Lys Ala Leu Asn Ala Leu Asn Gln Ala Thr
            20                  25                  30

Val Ser Glu Leu Lys Asp Val Glu Lys Ile Ala Ala Asp Lys Ala
        35                  40                  45

Ile Lys Val Val Ile Ile Thr Gly Ala Gly Ala Lys Ser Phe Val Ala
    50                  55                  60

Gly Ala Asp Ile Lys Glu Met Ala Ser Lys Asn Ala Ala Glu Gly Arg
 65                 70                  75                  80

Glu Trp Gly Gln Phe Gly Gln Asn Val Phe Thr Glu Ile Glu Asn Leu
                85                  90                  95

Pro Gln Pro Val Ile Ala Ala Ile Asn Gly Phe Ala Leu Gly Gly Gly
            100                 105                 110

Cys Glu Leu Ser Cys Ala Cys Asp Ile Arg Tyr Ala Ala Glu Asn Ala
        115                 120                 125

Lys Phe Gly Gln Pro Glu Val Gly Leu Gly Ile Thr Pro Gly Phe Gly
    130                 135                 140

Gly Thr Gln Arg Leu Thr Arg Val Val Gly Arg Gly His Ala Lys Glu
145                 150                 155                 160

Leu Ile Tyr Thr Gly Gly Met Ile Asp Ala Glu Lys Ala Lys Ala Ile
                165                 170                 175

Gly Leu Val Asn Glu Val Phe Pro Gln Glu Leu Met Pro Ala Ala
            180                 185                 190

Val Lys Leu Ala Lys Lys Ile Ala Lys Asn Ala Pro Ile Ala Val Gln
        195                 200                 205

Leu Ser Lys Ala Ala Ile Asn Arg Gly Ile Asn Cys Asp Val Val Thr
    210                 215                 220

Gly Ile Ala Tyr Glu Ala Glu Val Phe Gly Leu Cys Phe Ser Thr Ala
225                 230                 235                 240

Asp Gln Lys Glu Gly Met Ala Ala Phe Cys Glu Lys Arg Lys Ala Thr
                245                 250                 255

Phe Glu Gly Lys
            260

<210> SEQ ID NO 27
<211> LENGTH: 259
<212> TYPE: PRT
<213> ORGANISM: Metallosphaera sedula

<400> SEQUENCE: 27

Met Glu Phe Glu Thr Ile Glu Thr Lys Lys Glu Gly Asn Leu Phe Trp
 1               5                  10                  15

Ile Thr Leu Asn Arg Pro Asp Lys Leu Asn Ala Leu Asn Ala Lys Leu
            20                  25                  30

Leu Glu Glu Leu Asp Arg Ala Val Ser Gln Ala Glu Ser Asp Pro Glu
        35                  40                  45

Ile Arg Val Ile Ile Thr Gly Lys Gly Lys Ala Phe Cys Ala Gly
    50                  55                  60

Ala Asp Ile Thr Gln Phe Asn Gln Leu Thr Pro Ala Glu Ala Trp Lys
 65                 70                  75                  80
```

```
Phe Ser Lys Lys Gly Arg Glu Ile Met Asp Lys Ile Glu Ala Leu Ser
                85                  90                  95

Lys Pro Thr Ile Ala Met Ile Asn Gly Tyr Ala Leu Gly Gly Gly Leu
            100                 105                 110

Glu Leu Ala Leu Ala Cys Asp Ile Arg Ile Ala Glu Glu Ala Gln
        115                 120                 125

Leu Gly Leu Pro Glu Ile Asn Leu Gly Ile Tyr Pro Gly Tyr Gly Gly
130                 135                 140

Thr Gln Arg Leu Thr Arg Val Ile Gly Lys Gly Arg Ala Leu Glu Met
145                 150                 155                 160

Met Met Thr Gly Asp Arg Ile Pro Gly Lys Asp Ala Glu Lys Tyr Gly
                165                 170                 175

Leu Val Asn Arg Val Val Pro Leu Ala Asn Leu Glu Gln Glu Thr Arg
            180                 185                 190

Lys Leu Ala Glu Lys Ile Ala Lys Lys Ser Pro Ile Ser Leu Ala Leu
        195                 200                 205

Ile Lys Glu Val Val Asn Arg Gly Leu Asp Ser Pro Leu Leu Ser Gly
210                 215                 220

Leu Ala Leu Glu Ser Val Gly Trp Gly Val Val Phe Ser Thr Glu Asp
225                 230                 235                 240

Lys Lys Glu Gly Val Ser Ala Phe Leu Glu Lys Arg Glu Pro Thr Phe
                245                 250                 255

Lys Gly Lys

<210> SEQ ID NO 28
<211>   LENGTH: 259
<212> TYPE: PRT
<213> ORGANISM: Clostridicum kluyvery

<400> SEQUENCE: 28

Met Glu Phe Lys Asn Ile Ile Leu Glu Lys Asp Gly Asn Val Ala Ser
1               5                   10                  15

Ile Thr Leu Asn Arg Pro Lys Ala Leu Asn Ala Leu Asn Ala Ala Thr
            20                  25                  30

Leu Lys Glu Ile Asp Ala Ala Ile Asn Asp Ile Ala Glu Asp Asp Asn
        35                  40                  45

Val Tyr Ala Val Ile Ile Thr Gly Ser Gly Lys Ala Phe Val Ala Gly
    50                  55                  60

Ala Asp Ile Ala Glu Met Lys Asp Leu Thr Ala Val Glu Gly Arg Lys
65                  70                  75                  80

Phe Ser Val Leu Gly Asn Lys Ile Phe Arg Lys Leu Glu Asn Leu Glu
                85                  90                  95

Lys Pro Val Ile Ala Ala Ile Asn Gly Phe Ala Leu Gly Gly Gly Cys
            100                 105                 110

Glu Leu Ser Leu Ser Cys Asp Ile Arg Ile Ala Ser Ser Lys Ala Lys
        115                 120                 125

Phe Gly Gln Pro Glu Val Gly Leu Gly Ile Thr Pro Gly Phe Gly Gly
130                 135                 140

Thr Gln Arg Leu Ala Arg Ala Ile Gly Val Gly Met Ala Lys Glu Leu
145                 150                 155                 160

Ile Tyr Thr Gly Lys Val Ile Asn Ala Glu Glu Ala Leu Arg Ile Gly
                165                 170                 175

Leu Val Asn Lys Val Val Glu Pro Asp Lys Leu Leu Glu Glu Ala Lys
            180                 185                 190
```

```
Ala Leu Val Asp Ala Ile Ile Val Asn Ala Pro Ile Ala Val Arg Met
            195                 200                 205

Cys Lys Ala Ala Ile Asn Gln Gly Leu Gln Cys Ile Asp Thr Gly
        210                 215                 220

Val Ala Tyr Glu Ala Glu Val Phe Gly Glu Cys Phe Ala Thr Glu Asp
225                 230                 235                 240

Arg Val Glu Gly Met Thr Ala Phe Val Glu Lys Arg Asp Lys Ala Phe
                245                 250                 255

Lys Asn Lys

<210> SEQ ID NO 29
<211> LENGTH: 502
<212> TYPE: PRT
<213> ORGANISM: Sulfolobus tokodaii

<400> SEQUENCE: 29

Met Ala Ile Arg Thr Gly Glu Gln Tyr Leu Asp Ser Ile Lys Ile Arg
 1               5                  10                  15

Asn Lys Ala Glu Ile Tyr Val Met Gly Lys Glu Val Lys Asp Val Thr
            20                  25                  30

Thr His Pro Phe Leu Lys Pro Ser Val Met Ala Phe Lys Ala Thr Phe
        35                  40                  45

Asp Ala Ala Trp Glu Glu Asp Thr Lys Glu Leu Ala Arg Ala Trp Ser
    50                  55                  60

Pro Phe Ile Asn Glu Glu Val Asn Arg Phe Asn His Ile His Arg Ser
65                  70                  75                  80

Pro Glu Asp Leu Ala Ala Lys Val Lys Leu Leu Arg Lys Leu Ser His
                85                  90                  95

Lys Thr Gly Ala Cys Phe Gln Arg Cys Val Gly Trp Asp Ala Leu Asn
            100                 105                 110

Thr Leu Trp Ile Met Thr Asn Ile Met Ala Gln Lys Gly Lys Lys Glu
        115                 120                 125

Tyr Lys Asp Arg Phe Val Glu Tyr Leu Ser Tyr Val Gln Lys Lys Asp
    130                 135                 140

Leu Ala Leu Ala Gly Ala Met Thr Asp Ala Lys Gly Val Arg Thr Leu
145                 150                 155                 160

Lys Pro His Gln Gln Pro Asn Lys Asn Ala Tyr Val Arg Ile Glu Glu
                165                 170                 175

Val Thr Lys Asp Gly Ile Tyr Val Ser Gly Ala Lys Ala Asn Ile Thr
            180                 185                 190

Gly Val Ala Ala Thr Glu Glu Ile Val Val Leu Pro Thr Arg Ala Met
        195                 200                 205

Gly Pro Glu Asp Lys Asp Tyr Ala Val Ala Phe Ser Ile Pro Thr Asp
    210                 215                 220

Thr Glu Gly Ile Lys Ile Ile Val Gly Arg Gln Leu Asn Asp Ala Arg
225                 230                 235                 240

Arg Leu Glu Gly Gly Asp Ile Asp Ala Leu Pro Tyr Phe Tyr Asn His
                245                 250                 255

Glu Gly Leu Val Ile Phe Asp His Val Phe Val Pro Met Asp Arg Val
            260                 265                 270

Phe Leu Met Gly Glu Tyr Glu Phe Thr Ser Gln Leu Val Glu Val Phe
        275                 280                 285

Ser Ala Tyr His Arg Gln Gly Tyr Gly Gly Cys Lys Ala Gly Leu Gly
    290                 295                 300
```

```
Asp Val Ile Ile Gly Ala Ser Met Asn Leu Ala Lys Gln Leu Gly Val
305                 310                 315                 320

Glu Lys Ala Ser His Val Gln Glu Lys Leu Thr Glu Met Ile Phe Leu
            325                 330                 335

Thr Glu Thr Met Tyr Ser Ala Gly Ile Ala Ala Ser Leu Asn Ala Val
            340                 345                 350

Lys Val Cys Asp Asn Cys Trp Trp Val Asn Pro Met His Ala Asn Val
            355                 360                 365

Thr Lys His Leu Val Ala Arg Phe Pro Ala Gln Ile Ser Gln Leu Ser
370                 375                 380

Ile Asp Ile Ala Gly Gly Ile Ile Gly Thr Ala Pro Ser Glu Trp Asp
385                 390                 395                 400

Leu Lys Asn Pro Lys Leu Arg Glu Tyr Ile Ala Lys Tyr Leu Gln Gly
                405                 410                 415

Val Glu Gly Tyr Thr Ala Glu Asp Arg Leu Arg Met Val Arg Leu Leu
            420                 425                 430

Glu Asn Val Ser Leu Gly Val Ala Phe Gln Ile Glu Ser Val His Gly
            435                 440                 445

Ala Gly Ser Pro Ala Ala Gln Arg Ile Met Phe Ser Arg Leu Tyr Asp
450                 455                 460

Leu Asn Tyr Ala Glu Glu Val Ala Lys Arg Leu Ala Gly Lys Lys Thr
465                 470                 475                 480

Asp Leu Gln Trp Lys Pro Lys Ala Glu Pro Trp Arg Glu Ser Glu Thr
                485                 490                 495

Glu Lys Leu Val Lys Ser
            500

<210> SEQ ID NO 30
<211> LENGTH: 483
<212> TYPE: PRT
<213> ORGANISM: Geobacter metallireducens

<400> SEQUENCE: 30

Met Ala Leu Arg Asp Gly Asn Ser Tyr Arg Glu Ser Leu Arg Ala Leu
1               5                   10                  15

Asn Ile Lys Val Tyr Ala Phe Gly Glu Lys Ile Asp Ser Ile Val Asp
            20                  25                  30

His Pro Leu Phe Gln Pro His Ile Asn Ala Ala Ala Leu Thr Phe Asp
            35                  40                  45

Leu Ala His Asp Pro Thr Thr Glu Ala Leu Val Thr Ala Thr Ser His
        50                  55                  60

Leu Thr Gly Ser Lys Ile Ser Arg Phe Thr His Ile His Gln Ser Thr
65                  70                  75                  80

Asp Asp Leu Ile Lys Lys Val Lys Met Leu Arg Leu Ile Ala Gly Lys
                85                  90                  95

Thr Gly Ser Cys Tyr Gln Arg Cys Val Gly Trp Asp Ala Leu Asn Ala
            100                 105                 110

Asn Tyr Thr Val Thr Tyr Glu Met Asp Gln Glu Leu Gly Thr Asp Tyr
            115                 120                 125

His Gln Arg Phe Arg Arg Tyr Leu Glu Tyr Ile Gln Asp Asn Asp Leu
        130                 135                 140

Met Val Ala Gly Ala Met Thr Asp Pro Lys Gly Asp Arg Gly Leu Pro
145                 150                 155                 160

Pro Ala Lys Gln Lys Asp Pro Asp Met Phe Val His Val Val Ala Lys
```

```
                165                 170                 175
Asn Asp Lys Gly Ile Val Ile Arg Gly Ala Lys Val His Gln Thr Gly
            180                 185                 190

Ile Val Asn Ser His Glu Met Leu Ile Met Pro Thr Met Ala Met Gly
        195                 200                 205

Glu Glu Asp Gly Asp Tyr Ala Val Ala Cys Ala Leu Pro Thr Asp Ser
    210                 215                 220

Pro Gly Val Ile His Ile Phe Gly Arg Gln Thr Asn Asp Thr Arg Arg
225                 230                 235                 240

Leu Glu Lys Gly Asp Leu Asp Gln Gly Asn Ala Glu Tyr Gly Thr Val
            245                 250                 255

Gly Gly Glu Ala Leu Thr Ile Leu Glu Asp Val Phe Val Pro Trp Glu
        260                 265                 270

Arg Val Phe Met Cys Gly Glu Tyr Lys Tyr Ala Gly Leu Leu Val Glu
    275                 280                 285

Arg Phe Ala Ser Tyr His Arg Gln Asn Tyr Gly Gly Cys Lys Ala Gly
290                 295                 300

Val Ser Asp Val Ile Ile Gly Ala Thr Thr Ala Met Ala Glu Tyr Asn
305                 310                 315                 320

Gly Ala Ala Lys Ala Ser His Val Arg Asp Lys Ile Val Glu Met Val
            325                 330                 335

His Leu Thr Glu Thr Leu Tyr Cys Gly Ser Ile Ala Cys Ser Cys Glu
        340                 345                 350

Gly Ala Pro Thr Pro Ser Gly Ala Tyr Phe Val Asn Pro Leu Leu Ala
    355                 360                 365

Asn Thr Val Lys Gln Asn Val Thr Arg Phe Ile Tyr Glu Ile Ala Arg
370                 375                 380

Leu Ser His Asp Ile Ser Gly Gly Cys Met Ala Thr Met Pro Ser Glu
385                 390                 395                 400

Lys Asp Leu His His Asp Glu Ile Gly Lys Tyr Val Glu Lys Tyr Phe
            405                 410                 415

Arg Gly Val Asp Glu Ala Pro Thr Glu Glu Arg Met Arg Met Ala Arg
        420                 425                 430

Leu Val Glu Asn Met Thr Gly Gly Thr Ala Leu Val Glu Ser Met His
    435                 440                 445

Gly Ala Gly Ser Pro Gln Ala Gln Arg Val Met Ile Leu Arg Gln Ala
450                 455                 460

Asn Leu Gly His Lys Val Lys Leu Ala Lys Lys Leu Ala Gly Ile Lys
465                 470                 475                 480

Glu Glu Lys

<210> SEQ ID NO 31
<211> LENGTH: 463
<212> TYPE: PRT
<213> ORGANISM: Sulfolobus solfataricus

<400> SEQUENCE: 31

Met Arg Ser Lys Glu Asp Phe Leu Lys Ser Leu Lys Asp Gly Arg Asn
  1               5                  10                  15

Leu Tyr Tyr Arg Gly Lys Leu Val Glu Asp Ile Thr Thr His Gln Ile
             20                  25                  30

Leu Lys Thr Ala Ala Leu His Ala Ala Lys Leu Tyr Glu Tyr Ala Asp
         35                  40                  45

Arg Val Tyr Glu Asp Asn Lys Met Gly Lys Met Ser Lys Phe Phe Lys
```

```
            50                  55                  60
Val Pro Trp Thr Ser Gln Asp Leu Leu Asp Arg His Lys Leu Ile Tyr
 65                  70                  75                  80

Asp Leu Thr Met Tyr Cys Asn Gly Val Phe Asn Ile Ser Gln Ala Ile
                 85                  90                  95

Gly Ser Asp Ala Ile Phe Ala Leu Met Ile Thr Ala Lys Gln Val Asp
                100                 105                 110

Arg Lys Tyr Gly Thr Asp Tyr Ser Lys Arg Val Glu Lys Tyr Phe Glu
                115                 120                 125

Arg Val Ala Lys Glu Asp Leu Thr Leu Ala Thr Ala Gln Thr Asp Val
                130                 135                 140

Lys Gly Asp Arg Ser Lys Arg Pro Ser Glu Gln Val Asp Pro Asp Met
145                 150                 155                 160

Tyr Val Arg Val Val Asp Val Lys Ser Asp Gly Ile Val Val Arg Gly
                165                 170                 175

Ala Lys Ala His Thr Thr Gln Ser Ala Val Ser Asp Glu Ile Ile Val
                180                 185                 190

Ile Pro Thr Arg Val Met Arg Asp Ser Asp Lys Asp Tyr Ala Val Ala
                195                 200                 205

Phe Ala Val Pro Ala Asn Thr Lys Gly Leu Lys Met Tyr Ile Arg Pro
210                 215                 220

Ile Asp Glu Ile Glu Gly Asn Ser Ser Ser Val Leu Ser Arg Lys Asp
225                 230                 235                 240

Tyr Glu Leu Glu Thr Leu Thr Val Phe Asn Asp Val Phe Val Pro Trp
                245                 250                 255

Asp Arg Val Phe Leu Phe Lys Glu Tyr Asp Tyr Ala Gly Thr Leu Ala
                260                 265                 270

Met Leu Phe Ala Thr Phe His Arg Phe Thr Ala Leu Ser Tyr Arg Ser
                275                 280                 285

Ala Thr Met Asn Leu Tyr Leu Gly Ala Ser Lys Val Ala Ser Gln Val
                290                 295                 300

Asn Gly Ile Glu Asn Glu Lys His Val Arg Asp Asp Ile Val Asp Ile
305                 310                 315                 320

Ile Leu Tyr Lys Glu Ile Met Arg Ser Ser Ala Ile Ala Ala Ala Val
                325                 330                 335

Tyr Pro Val Asn Met Glu Gly Ile Ala Val Pro Asn Pro Leu Phe Thr
                340                 345                 350

Asn Val Gly Lys Leu Tyr Ser Asn Met His Phe His Asp Val Val Arg
                355                 360                 365

Asp Leu Ile Asp Ile Ala Gly Gly Ile Ile Ala Thr Met Pro Ser Gln
                370                 375                 380

Glu Asp Leu Glu Ser Asp Glu Gly Lys Asn Ile Val Lys Tyr Leu Arg
385                 390                 395                 400

Gly Ser Val Asp Gly Glu Glu Arg Ala Lys Val Leu Lys Leu Ala Lys
                405                 410                 415

Glu Leu Gly Ala Ser Thr Phe Thr Gly Tyr Leu Leu Thr Gly Met Ile
                420                 425                 430

His Ala Glu Gly Ser Met Glu Ala Ser Lys Ile Glu Leu Phe Arg Ser
                435                 440                 445

Tyr Asn Phe Lys Glu Ala Glu Asn Leu Val Lys Arg Val Leu Ser
                450                 455                 460

<210> SEQ ID NO 32
```

<211> LENGTH: 479
<212> TYPE: PRT
<213> ORGANISM: Syntrophobacter fumaroxidans

<400> SEQUENCE: 32

```
Met Gly Leu Lys Thr Lys Ala Glu Tyr Ile Glu Ser Leu Arg Gly Met
1               5                   10                  15

Lys Pro Thr Val Tyr Met Phe Gly Glu Lys Ile Glu Ser Val Val Asp
            20                  25                  30

Asn Pro Arg Leu Arg Ala Gly Ile Glu Ala Thr Gly Ala Thr Tyr Glu
        35                  40                  45

Leu Ala Glu Thr Glu Glu Tyr Arg Pro Leu Ile Val Thr Glu Ser Pro
    50                  55                  60

Leu Ile His Glu Pro Val Asn Arg Tyr Thr Leu Pro Pro Ser Ser Ile
65                  70                  75                  80

Ala Asp Leu Val Ala Arg Val Lys Ile Asn Arg Leu Met Gly Thr Arg
                85                  90                  95

Val Gly Thr Cys Phe Gln Arg Cys Thr Gly Leu Asp Cys Leu Ser Ala
            100                 105                 110

Leu Ser Ile Val Thr Tyr Asp Ile Asp Ala Lys His Ser Thr Pro Tyr
        115                 120                 125

Phe Lys Arg Phe Ile Glu Phe Leu Lys His Val Gln Lys Asn Asp Leu
    130                 135                 140

Thr Cys Asn Ala Gly Val Thr Asp Val Lys Gly Asp Arg Ser Leu Ala
145                 150                 155                 160

Pro His Glu Gln Glu Asp Lys Asp Met Tyr Val Arg Val Val Glu Arg
                165                 170                 175

Asn Ala Asp Gly Ile Val Val Arg Gly Ala Lys Ala His Gln Thr Gly
            180                 185                 190

Ser Leu Ser Ser His Glu Ile Ile Val Leu Pro Thr Arg Ala Leu Arg
        195                 200                 205

Lys Gly Asp Glu Asp Tyr Ala Leu Ala Phe Ala Ile Pro Asn Asp Thr
    210                 215                 220

Pro Gly Leu Ile His Val Val Gly Arg Ser Ser Leu Asp Thr Arg Gln
225                 230                 235                 240

Leu Asp Gly Cys Asp Leu Gly Asn Leu His Tyr Ser Lys Tyr Cys Pro
                245                 250                 255

Thr Val Ile Phe Lys Asp Val Phe Val Pro Trp Glu Arg Val Phe Met
            260                 265                 270

Cys Gly Glu Val Glu Phe Ala Val Glu Met Val Asn Arg Phe Ser Ala
        275                 280                 285

Tyr His Arg Gln Ser His Gly Gly Cys Lys Ser Gly Lys Ile Asp Cys
    290                 295                 300

Met Val Gly Ala Ala Leu Thr Met Met Asp Tyr Asn Gly Thr Glu Lys
305                 310                 315                 320

Ala Gly His Leu Lys Gln Lys Ala Ile Glu Met Val His Arg Ala Glu
                325                 330                 335

Thr Leu Tyr Gly Cys Ser Leu Ala Ala Ser Tyr Glu Gly Lys Lys Glu
            340                 345                 350

Pro Ser Gly Thr Tyr Phe Ile Asp Thr Val Leu Ala Asn Ala Ser Lys
        355                 360                 365

Ile His Glu Gly Lys Glu Met Ser Glu Ala Gly Arg Leu Leu Val Asp
    370                 375                 380

Ile Ala Gly Gly Phe Val Ala Asp Leu Pro Ser Asp Arg Asp Leu Ala
```

```
                385                 390                 395                 400
Ile Pro Glu Val Gly Glu Leu Leu Lys Lys Tyr Leu Lys Gly Val Ala
                    405                 410                 415

Ser Val Pro Val Glu Asp Arg Val Lys Met Tyr Arg Leu Ile Glu Lys
                    420                 425                 430

Leu Val Met Glu Ser Ala Asp Thr Ile Ser Asp Ile His Gly Gly Gly
                435                 440                 445

Ser Pro Glu Ala His Arg Ile Thr Ile Leu Arg Glu Ser Asn Leu Lys
450                 455                 460

Ala Lys Lys Asp Ala Ala Lys Arg Leu Ala Gly Ile Glu Ser Lys
465                 470                 475

<210> SEQ ID NO 33
<211> LENGTH: 486
<212> TYPE: PRT
<213> ORGANISM: Porphyromonas gingivalis

<400> SEQUENCE: 33

Met Met Thr Ser Glu Gln Tyr Val Glu Ser Leu Arg Lys Leu Asn Leu
1               5                   10                  15

Lys Val Tyr Phe Met Gly Glu Arg Ile Glu Asn Pro Val Asp His Pro
                20                  25                  30

Met Ile Arg Pro Ser Met Asn Ser Val Ala Met Thr Tyr Lys Leu Ala
            35                  40                  45

Glu Met Asp Glu Tyr Lys His Leu Met Thr Ala Thr Ser Asn Leu Thr
        50                  55                  60

Gly Lys Gln Val Asn Arg Phe Cys His Leu His Gln Ser Thr Glu Asp
65                  70                  75                  80

Leu Lys Asp Lys Val Lys Met Gln Arg Leu Met Gly Gln Lys Thr Ala
                85                  90                  95

Ser Cys Phe Gln Arg Cys Val Gly Met Asp Ala Phe Asn Ala Ile Tyr
            100                 105                 110

Ser Thr Thr Tyr Glu Met Asp Gln Ala Leu Gly Thr Thr Tyr His Lys
        115                 120                 125

Arg Phe Ile Glu Tyr Met Lys Tyr Val Gln Asp Asn Asp Leu Val Val
    130                 135                 140

Asp Gly Ala Met Thr Asp Pro Lys Gly Asp Arg Gly Leu Ser Pro Ser
145                 150                 155                 160

Glu Gln Ala Asp Pro Asp Leu Tyr Leu His Ile Val Glu Val Arg Glu
                165                 170                 175

Asp Gly Ile Val Val Ser Gly Ala Lys Ala His Gln Thr Gly Ala Val
            180                 185                 190

Asn Ser His Glu His Leu Ile Met Pro Thr Ile Ala Met Arg Glu Ala
        195                 200                 205

Asp Ala Asp Tyr Ala Val Ser Phe Ala Val Pro Ser Asp Ala Glu Gly
    210                 215                 220

Val Ile Met Ile Tyr Gly Arg Gln Ser Cys Asp Thr Arg Lys Met Glu
225                 230                 235                 240

Glu Gly Ala Asp Ile Asp Leu Gly Asn Ser Glu Phe Gly His Glu
                245                 250                 255

Ala Leu Val Val Phe Asp Arg Val Phe Val Pro Asn Asp Arg Val Phe
            260                 265                 270

Met Cys Lys Glu Tyr Gln Phe Ala Gly Met Met Val Glu Arg Phe Ala
        275                 280                 285
```

```
Gly Tyr His Arg Gln Ser Tyr Gly Gly Cys Lys Val Gly Val Gly Asp
    290                 295                 300

Val Leu Ile Gly Ala Ala Ala Leu Ala Ala Asp Tyr Asn Gly Val Pro
305                 310                 315                 320

Lys Ala Ser His Ile Lys Asp Lys Leu Ile Glu Met Ile His Leu Asn
                325                 330                 335

Glu Thr Leu Tyr Ala Cys Gly Ile Ala Cys Ser Ser Glu Gly Thr Gln
                340                 345                 350

Met Lys Ala Gly Asn Tyr Met Ile Asp Leu Leu Leu Ala Asn Val Cys
            355                 360                 365

Lys Gln Asn Ile Thr Arg Leu Pro Tyr Glu Ile Ala Arg Leu Ala Glu
    370                 375                 380

Asp Ile Ala Gly Gly Leu Met Val Thr Met Pro Ser Gln Gln Asp Phe
385                 390                 395                 400

Arg His Pro Glu Ile Gly Pro Ile Val Lys Lys Tyr Leu Ala Gly Ala
                405                 410                 415

Thr Gly Lys Ser Thr Glu Asn Arg Met Arg Val Leu Arg Leu Ile Glu
                420                 425                 430

Asn Ile Thr Leu Gly Thr Ala Ala Val Gly Tyr Arg Thr Glu Ser Met
            435                 440                 445

His Gly Ala Gly Ser Pro Gln Ala Gln Arg Ile Met Ile Ala Arg Gln
    450                 455                 460

Gly Asp Leu Glu Gly Lys Lys Lys Leu Ala Arg Ala Ile Ala His Ile
465                 470                 475                 480

Asp Glu Ser Leu Asp Lys
                485

<210> SEQ ID NO 34
<211> LENGTH: 529
<212> TYPE: PRT
<213> ORGANISM: Polynucleobacter necessarius
<220> FEATURE:
<221> NAME/KEY: MISC_FEATURE
<222> LOCATION: (1)..(529)
<223> OTHER INFORMATION: subsp. Asymbioticus

<400> SEQUENCE: 34

Met Ser Gln Ser Thr Ser Gln Phe Met Asn Ser Lys Asp Tyr Gln Glu
1               5                   10                  15

Ser Leu Arg Ser Leu Lys Pro Thr Val Tyr Val Asp Gly Arg Leu Ile
            20                  25                  30

Glu Ser Val Ala Asp Glu Pro Ser Leu Arg Pro Gly Val Gln Ala Leu
        35                  40                  45

Gly Val Thr Tyr Asp Met Val His Asp Pro Ala Leu Ala Pro Leu Met
    50                  55                  60

Leu Ala Asp Ser Asn Gly Thr Pro Val Pro Arg Met Leu His Ile Asn
65                  70                  75                  80

Gln Ser Ser Gly Asp Leu Leu Asn Lys Leu Glu Ala Val Arg Val Leu
                85                  90                  95

Cys Gln Glu Thr Gly Cys Ala Gln Arg Tyr Leu Ala His Asp Ala Leu
            100                 105                 110

Asn Ala Ile Ala Gln Val Ser Ala Arg Ile Asp Asp Ala Lys Gly Ser
        115                 120                 125

Asn Glu His Ser Ala Lys Phe Ser Glu Tyr Leu Ser His Val Gln Thr
    130                 135                 140

Lys Asp Leu Ala Leu Gly Ile Ala Met Thr Asp Ala Lys Gly Asp Arg
```

```
            145                 150                 155                 160
        Ser Arg Arg Pro His Glu Gln Glu Asn Pro Asp Thr Tyr Val His Ile
                        165                 170                 175
        Val Ser Gln Asp Ala Lys Gly Val Val Ile Ser Gly Thr Lys Ala Ile
                        180                 185                 190
        Val Thr Gly Ala Pro Tyr Met His Glu Phe Leu Val Met Pro Gly Arg
                        195                 200                 205
        Asn Met Thr Lys Glu Asp Ala Ala Phe Ala Ile Cys Cys Ala Val Pro
                        210                 215                 220
        Val Asp Ala Lys Gly Ile Thr Ile Val Ala Arg Pro Ala Gly Arg Pro
        225                 230                 235                 240
        Gly Asp Lys Val Glu His Gly Lys Pro Ile Phe Ser Ser Lys Tyr Gly
                        245                 250                 255
        Gln Ser Thr Gly Val Val Ile Phe Asp Lys Val Phe Val Pro Trp Asp
                        260                 265                 270
        Arg Val Phe Tyr Ala Gly Glu Trp Glu His Ser Ser Val Leu Thr Tyr
                        275                 280                 285
        Asn Tyr Ala Thr His His Arg His Ser Cys Ile Ala Ala Arg Ala Gly
                        290                 295                 300
        Phe Gly Asp Leu Leu Ile Gly Ala Gly Ala Leu Met Cys Glu Ala Asn
        305                 310                 315                 320
        Gly Leu Asp Pro Ala Thr Lys Ser Asn Leu Arg Asp Pro Met Val Glu
                        325                 330                 335
        Leu Ile Lys Ile Thr Glu Gly Phe Tyr Ala Cys Gly Val Ala Ala Ser
                        340                 345                 350
        Val Tyr Gly Thr Gln Asp Pro Tyr Ser Lys Ser Phe Met Pro Glu Pro
                        355                 360                 365
        Val Phe Ser Asn Ile Gly Lys Leu Leu Leu Ala Thr Gln Ile Tyr Asp
                        370                 375                 380
        Met His Arg Leu Ala His Glu Val Ser Gly Gly Leu Ile Val Ala Leu
        385                 390                 395                 400
        Pro Gly Pro Asp Glu Asp His Asn Pro Ala Thr Ala Ala Thr Leu Ala
                        405                 410                 415
        Glu Val Leu Arg Ala Asn Pro Ala Val Pro Tyr Asp Lys Arg Ile Glu
                        420                 425                 430
        Val Ala Arg Phe Ile Glu Asp Leu Thr Ala Ser Tyr Gln Gly Gly Trp
                        435                 440                 445
        Tyr Ser Val Ile Ser Leu His Gly Gly Ser Pro Ala Ala Met Lys
        450                 455                 460
        Gln Glu Ile Tyr Arg Gln Tyr Pro Ile Gly Asn Lys Val Glu Leu Val
        465                 470                 475                 480
        Glu Arg Leu Leu Asp Arg Gly Val Leu Thr Ser Ser Glu Glu Arg Ala
                        485                 490                 495
        Ile Thr Lys Asn Lys Gln Pro Gly Arg Cys Cys Asp Gln Gly Cys Ser
                        500                 505                 510
        Ala Pro Gly Gln Ala Val Met Val Pro Leu Pro Glu Pro Gly Arg Arg
                        515                 520                 525
        Thr

<210> SEQ ID NO 35
<211> LENGTH: 257
<212> TYPE: PRT
<213> ORGANISM: Sulfolobus tokodaii
```

<400> SEQUENCE: 35

```
Met Glu Thr Ile Val Ile Lys Lys Glu Thr Pro Ile Gly Trp Ile Tyr
  1               5                  10                  15

Leu Asn Arg Pro Asp Arg Leu Asn Ala Ile Asn Gln Gln Met Ile Lys
             20                  25                  30

Glu Leu Arg Gln Gly Ile Asp Glu Met Val Tyr Asp Ser Asp Ile Lys
         35                  40                  45

Val Ile Ile Ile Thr Gly Asn Gly Lys Ala Phe Ser Ala Gly Ala Asp
     50                  55                  60

Ile Ser Arg Phe Lys Glu Leu Asn Gly Tyr Thr Ala Trp Gln Phe Ala
 65                  70                  75                  80

Lys Ser Gly Arg Glu Leu Met Asp Tyr Ile Glu Asn Ile Ser Lys Pro
                 85                  90                  95

Thr Ile Ala Met Val Asn Gly Tyr Ala Leu Gly Gly Gly Leu Glu Leu
            100                 105                 110

Ala Met Ala Cys Asp Ile Arg Ile Ala Ala Glu Glu Ala Gln Leu Gly
        115                 120                 125

Leu Pro Glu Ile Asn Leu Gly Ile Tyr Pro Gly Phe Gly Gly Thr Gln
    130                 135                 140

Arg Leu Val Arg Leu Ile Gly Lys Gly Lys Ala Leu Glu Leu Met Leu
145                 150                 155                 160

Thr Gly Asp Arg Ile Ser Ala Lys Glu Ala Lys Ile Gly Leu Val
                165                 170                 175

Asn Lys Val Val Pro Leu Ser Asn Leu Glu Gln Glu Thr Arg Asn Phe
            180                 185                 190

Ala Leu Lys Leu Ala Glu Lys Pro Pro Ile Ser Ile Ala Leu Ile Lys
        195                 200                 205

Leu Leu Val Asn Gln Gly Ile Asp Leu Pro Ile Leu Ala Gly Leu Asn
    210                 215                 220

Met Glu Ser Leu Gly Trp Gly Val Val Phe Ser Thr Glu Asp Glu Lys
225                 230                 235                 240

Glu Gly Val Ser Ala Phe Leu Glu Lys Arg Lys Ala Gln Phe Lys Gly
                245                 250                 255

Lys
```

```
<210> SEQ ID NO 36
<211> LENGTH: 258
<212> TYPE: PRT
<213> ORGANISM: Gordonia terrae
<220> FEATURE:
<221> NAME/KEY: MISC_FEATURE
<222> LOCATION: (1)..(258)
<223> OTHER INFORMATION: C-6
```

<400> SEQUENCE: 36

```
Met Thr Glu His Gln Thr Ile Val Val Glu Thr Ser Gly Arg Val Gly
  1               5                  10                  15

Ile Ile Thr Leu Asn Arg Pro Lys Ala Leu Asn Ala Leu Asn Thr Glu
             20                  25                  30

Leu Met Asn Glu Val Val Gly Ala Val Lys Glu Phe Asp Val Asp Gln
         35                  40                  45

Gly Ile Gly Ala Ile Val Ile Thr Gly Ser Gly Glu Lys Ala Phe Ala Ala
     50                  55                  60

Gly Ala Asp Ile Lys Glu Met Ser Ser Lys Ser Tyr Ala Asp Val Val
 65                  70                  75                  80
```

```
Asn Glu Gln Phe Phe Gly Ala Trp Asp Glu Leu Ser Arg Ala Arg Thr
                 85                  90                  95

Pro Ile Ile Ala Ala Val Thr Gly Tyr Ala Leu Gly Gly Gly Cys Glu
            100                 105                 110

Leu Ala Met Leu Cys Asp Thr Ile Ile Ala Gly Asp Asn Ala Val Phe
            115                 120                 125

Gly Gln Pro Glu Ile Asn Leu Gly Val Ile Pro Gly Ile Gly Gly Ser
            130                 135                 140

Gln Arg Leu Thr Arg Ala Val Gly Lys Ala Lys Ala Met Asp Met Val
145                 150                 155                 160

Leu Thr Gly Arg Gln Met Lys Val Asp Glu Ala Glu Arg Leu Gly Leu
                165                 170                 175

Val Ser Arg Val Val Pro Lys Glu Asp Cys Arg Ala Ala Ala Ile Glu
            180                 185                 190

Val Ala Glu Ile Ile Ala Ser Lys Ser Leu Ile Ala Ala Ala Ala Ala
            195                 200                 205

Lys Asp Ala Val Asn Arg Ala Phe Glu Ser Ser Leu Val Glu Gly Val
            210                 215                 220

Arg Ala Glu Arg Ala Leu Phe Tyr Ser Thr Phe Ala Thr Asp Asp Gln
225                 230                 235                 240

Thr Glu Gly Met Ala Ala Phe Val Glu Lys Arg Asp Pro Asn Phe Thr
                245                 250                 255

His Arg

<210> SEQ ID NO 37
<211> LENGTH: 258
<212> TYPE: PRT
<213> ORGANISM: Halalkalicoccus jeotgali

<400> SEQUENCE: 37

Met Ala Asp Arg Val Leu Ile Glu Arg Glu Asn Asp Ile Ala Thr Ile
  1               5                  10                  15

Ile Val Asn Arg Pro Glu Lys Arg Asn Ala Met Asp Ile Pro Thr Arg
                 20                  25                  30

Lys Ala Leu Tyr Ala Ala Phe Glu Glu Val Ser Glu Asp Asp Asp Val
             35                  40                  45

Arg Ala Ile Val Leu Arg Gly Ala Gly Asp Gly Ser Phe Ile Ala Gly
         50                  55                  60

Gly Asp Ile Asp Ser Phe Ala Asp Phe Asp His Met Asp Gly Met Glu
 65                  70                  75                  80

Tyr Ser Glu Lys Tyr Ala Gln Gly Leu Tyr Asn Tyr Val Ala Asp Arg
                 85                  90                  95

His Lys Pro Thr Ile Ala Ala Val Asp Gly Tyr Ala Leu Gly Gly Gly
            100                 105                 110

Thr Glu Ile Ala Leu Ala Cys Asp Ile Arg Leu Ala Thr Asp Asp Ala
            115                 120                 125

Lys Phe Gly Leu Pro Glu Val Gly Ile Gly Val Ile Pro Ala Gly Gly
            130                 135                 140

Gly Thr Gln Arg Leu Val Gln Val Val Gly Ala Gly Leu Ala Ser Glu
145                 150                 155                 160

Leu Ile Leu Thr Gly Arg Ile Ile Ser Ala Asp Glu Ala Lys Arg Ile
                165                 170                 175

Gly Leu Ala Asn His Val Tyr Ala Ala Glu Glu Phe Asp Asn Glu Val
            180                 185                 190
```

Arg Ala Met Ala Glu Asp Leu Ala Ser Lys Ala Pro Val Ala Gln Arg
            195                 200                 205

Leu Ala Lys Glu Ser Ile Arg Arg Ser Leu Asp Ile Asp Ala Gly Leu
        210                 215                 220

Glu Tyr Glu Arg Leu Ala Gly Ala Phe Leu Phe Gly Thr Asp Asp Gln
225                 230                 235                 240

Lys Glu Gly Ala Asn Ala Phe Leu Glu Asp Arg Glu Pro Lys Tyr Arg
                245                 250                 255

Asn Arg

<210> SEQ ID NO 38
<211> LENGTH: 257
<212> TYPE: PRT
<213> ORGANISM: Carboxydothermus hydrogenoformans

<400> SEQUENCE: 38

Met Glu Phe Glu Lys Ile Lys Phe Glu Val Thr Asp Gly Tyr Ala Val
1               5                   10                  15

Ile Tyr Leu Asn Asn Pro Pro Val Asn Ala Leu Gly Gln Lys Val Leu
            20                  25                  30

Lys Asp Leu Gln Lys Ala Leu Gln Glu Ile Glu Lys Asn Pro Glu Ile
        35                  40                  45

Arg Ala Val Ile Ile Ser Gly Glu Gly Ser Lys Val Phe Cys Ala Gly
    50                  55                  60

Ala Asp Ile Thr Glu Phe Ala Asp Arg Ala Lys Gly Ile Leu Pro Glu
65                  70                  75                  80

Val Glu Gly Ser Val Leu Phe Arg Gln Ile Glu Leu Phe Pro Lys Pro
                85                  90                  95

Val Ile Ala Ala Leu Asn Gly Ser Ser Tyr Gly Gly Gly Thr Glu Leu
            100                 105                 110

Ala Ile Ser Cys His Leu Arg Ile Leu Ala Asp Asp Ala Ser Met Ala
        115                 120                 125

Leu Pro Glu Val Lys Leu Gly Ile Ile Pro Gly Trp Gly Gly Thr Gln
    130                 135                 140

Arg Leu Pro Arg Leu Ile Gly Lys Thr Arg Ala Leu Glu Ala Met Leu
145                 150                 155                 160

Thr Gly Glu Pro Ile Thr Ala Glu Glu Ala Leu Ser Tyr Gly Leu Val
                165                 170                 175

Asn Lys Val Val Pro Lys Asp Gln Val Leu Thr Glu Ala Arg Ala Leu
            180                 185                 190

Ala Ala Lys Leu Ala Lys Gly Ala Pro Ile Ala Met Arg Glu Ile Leu
        195                 200                 205

Lys Ala Val Thr Leu Gly Leu Asp Thr Ser Ile Glu Glu Gly Leu Lys
    210                 215                 220

Ile Glu Lys Glu Gly Ser Lys Val Ala Phe Ser Ser Glu Asp Ala Val
225                 230                 235                 240

Glu Gly Arg Thr Ala Phe Phe Glu Lys Arg Pro Pro Asn Phe Lys Gly
                245                 250                 255

Arg

<210> SEQ ID NO 39
<211> LENGTH: 257
<212> TYPE: PRT
<213> ORGANISM: Thermomicrobium roseum

<400> SEQUENCE: 39

-continued

```
Met Ser Val Arg Val Glu Arg Gly Ala Ile Thr Leu Val Thr Val
1               5                  10                  15

Glu Arg Pro Glu Arg Leu Asn Ala Leu Asp Thr Ala Thr Leu Arg Ala
                20                  25                  30

Leu Leu Ala Ala Val Gln Glu Leu Ala Thr Glu Ala Ile Ala Val
        35                  40                  45

Val Val Leu Thr Gly Ala Gly Asp Arg Ala Phe Ile Ala Gly Ala Asp
    50                  55                  60

Ile Ser Glu Met Val Glu Lys Ser Pro Ala Glu Ala Leu Ala Phe Ala
65                  70                  75                  80

Glu Leu Gly His Ala Val Cys Arg Ala Ile Glu Glu Ala Pro Gln Pro
                85                  90                  95

Tyr Ile Ala Ala Val Asn Gly Tyr Ala Leu Gly Gly Gly Cys Glu Ile
                100                 105                 110

Ala Leu Ala Cys Asp Ile Arg Leu Ala Ser Glu Arg Ala Val Phe Ala
            115                 120                 125

Gln Pro Glu Val Thr Leu Gly Ile Pro Pro Gly Trp Gly Gly Ser Gln
        130                 135                 140

Arg Leu Pro Arg Val Val Pro Pro Gly Ile Ala Arg Glu Leu Leu Tyr
145                 150                 155                 160

Thr Gly Arg Arg Val Asp Ala Gln Glu Ala Leu Arg Ile Gly Leu Val
                165                 170                 175

Asn Ala Val Tyr Pro Ala Asp Gln Leu Leu Glu Arg Ala Arg Glu Leu
                180                 185                 190

Ala Asn Arg Ile Ala Ala Asn Gly Pro Leu Ala Val Arg Leu Thr Lys
            195                 200                 205

Ala Ala Val Arg Phe Gly Leu Glu Gln Gly Leu Glu Ala Gly Leu Thr
        210                 215                 220

Tyr Glu Arg Gln Val Phe Ala Tyr Ala Phe Thr Thr Glu Asp Gln Arg
225                 230                 235                 240

Glu Gly Met Arg Ala Phe Leu Glu Lys Arg Arg Pro Ala Phe Arg Gly
                245                 250                 255

Arg
```

<210> SEQ ID NO 40
<211> LENGTH: 274
<212> TYPE: PRT
<213> ORGANISM: Methylobacterium extorquens

<400> SEQUENCE: 40

```
Met Asn Ala Asp Ala Glu Thr Ala Ser Thr Asp Glu Leu Leu Phe Ala
1               5                   10                  15

Val Asp Ala Ala Gly Ile Ala Arg Ile Thr Leu Asn Arg Pro Lys Ala
                20                  25                  30

Arg Asn Ala Leu Thr Phe Ala Met Tyr Arg Gly Leu Val Glu Leu Cys
            35                  40                  45

Glu Arg Ile Glu Ala Asp His Ala Ile Lys Ala Val Ile Ile Thr Gly
    50                  55                  60

Ala Gly Asp Lys Ala Phe Ala Gly Thr Asp Ile Ala Gln Phe Arg
65                  70                  75                  80

Ser Phe Ser Lys Pro Glu Asp Ala Ile Gly Tyr Glu Arg Phe Met Asp
                85                  90                  95

Arg Val Leu Gly Gly Leu Glu Arg Leu Arg Val Pro Thr Ile Ala Ala
                100                 105                 110
```

```
Val Ala Gly Ala Cys Thr Gly Gly Gly Ala Ala Ile Ala Ala Ala Cys
        115                 120                 125

Asp Met Arg Ile Ala Ser Arg Asp Ala Arg Phe Gly Ile Pro Ile Ala
    130                 135                 140

Arg Thr Leu Gly Asn Cys Leu Ser Gln Asn Thr Leu Arg Arg Leu Ala
145                 150                 155                 160

Asn Leu Ile Gly Ala Pro Arg Val Lys Asp Ile Leu Phe Thr Ala Arg
                165                 170                 175

Leu Val Glu Ala Gln Glu Ala Leu Ala Ile Gly Leu Val Asn Glu Val
            180                 185                 190

Val Glu Asp Ala Ala Ala Val Ala Ala Arg Ala Asp Ala Leu Ala Thr
        195                 200                 205

Leu Leu Ala Ser His Ala Pro Leu Thr Leu Gln Ala Thr Lys Glu Gly
    210                 215                 220

Leu Arg Arg Ile Gly Glu Glu Gly Ala Ala Glu Ala Ala Glu Gly Glu
225                 230                 235                 240

Arg Pro Gly Asp Asp Leu Ile Val Met Thr Tyr Met Ser Ala Asp Phe
                245                 250                 255

Arg Glu Gly Met Glu Ala Phe Leu Gly Lys Arg Pro Pro Asn Phe Lys
            260                 265                 270

Gly Arg

<210> SEQ ID NO 41
<211> LENGTH: 407
<212> TYPE: PRT
<213> ORGANISM: Clostridium sporogenes

<400> SEQUENCE: 41

Met Ser Asp Arg Asn Lys Glu Val Lys Glu Lys Lys Ala Lys His Tyr
  1               5                  10                  15

Leu Arg Glu Ile Thr Ala Lys His Tyr Lys Glu Ala Leu Glu Ala Lys
             20                  25                  30

Glu Arg Gly Glu Lys Val Gly Trp Cys Ala Ser Asn Phe Pro Gln Glu
         35                  40                  45

Ile Ala Thr Thr Leu Gly Val Lys Val Val Tyr Pro Glu Asn His Ala
     50                  55                  60

Ala Ala Val Ala Ala Arg Gly Asn Gly Gln Asn Met Cys Glu His Ala
 65                  70                  75                  80

Glu Ala Met Gly Phe Ser Asn Asp Val Cys Gly Tyr Ala Arg Val Asn
                 85                  90                  95

Leu Ala Val Met Asp Ile Gly His Ser Glu Asp Gln Pro Ile Pro Met
            100                 105                 110

Pro Asp Phe Val Leu Cys Cys Asn Asn Ile Cys Asn Gln Met Ile Lys
        115                 120                 125

Trp Tyr Glu His Ile Ala Lys Thr Leu Asp Ile Pro Met Ile Leu Ile
    130                 135                 140

Asp Ile Pro Tyr Asn Thr Glu Asn Thr Val Ser Gln Asp Arg Ile Lys
145                 150                 155                 160

Tyr Ile Arg Ala Gln Phe Asp Asp Ala Ile Lys Gln Leu Glu Glu Ile
                165                 170                 175

Thr Gly Lys Lys Trp Asp Glu Asn Lys Phe Glu Glu Val Met Lys Ile
            180                 185                 190

Ser Gln Glu Ser Ala Lys Gln Trp Leu Arg Ala Ala Ser Tyr Ala Lys
        195                 200                 205
```

Tyr Lys Pro Ser Pro Phe Ser Gly Phe Asp Leu Phe Asn His Met Ala
              210                 215                 220

Val Ala Val Cys Ala Arg Gly Thr Gln Glu Ala Ala Asp Ala Phe Lys
225                 230                 235                 240

Met Leu Ala Asp Glu Tyr Glu Asn Val Lys Thr Gly Lys Ser Thr
                245                 250                 255

Tyr Arg Gly Glu Glu Lys Gln Arg Ile Leu Phe Glu Gly Ile Ala Cys
                260                 265                 270

Trp Pro Tyr Leu Arg His Lys Leu Thr Lys Leu Ser Glu Tyr Gly Met
                275                 280                 285

Asn Val Thr Ala Thr Val Tyr Ala Glu Ala Phe Gly Val Ile Tyr Glu
                290                 295                 300

Asn Met Asp Glu Leu Met Ala Ala Tyr Asn Lys Val Pro Asn Ser Ile
305                 310                 315                 320

Ser Phe Glu Asn Ala Leu Lys Met Arg Leu Asn Ala Val Thr Ser Thr
                325                 330                 335

Asn Thr Glu Gly Ala Val Ile His Ile Asn Arg Ser Cys Lys Leu Trp
                340                 345                 350

Ser Gly Phe Leu Tyr Glu Leu Ala Arg Arg Leu Glu Lys Glu Thr Gly
                355                 360                 365

Ile Pro Val Val Ser Phe Asp Gly Asp Gln Ala Asp Pro Arg Asn Phe
370                 375                 380

Ser Glu Ala Gln Tyr Asp Thr Arg Ile Gln Gly Leu Asn Glu Val Met
385                 390                 395                 400

Val Ala Lys Lys Glu Ala Glu
                405

<210> SEQ ID NO 42
<211> LENGTH: 374
<212> TYPE: PRT
<213> ORGANISM: Clostridium sporogenes

<400> SEQUENCE: 42

Met Ser Asn Ser Asp Lys Phe Phe Asn Asp Phe Lys Asp Ile Val Glu
1               5                   10                  15

Asn Pro Lys Lys Tyr Ile Met Lys His Met Glu Gln Thr Gly Gln Lys
                20                  25                  30

Ala Ile Gly Cys Met Pro Leu Tyr Thr Pro Glu Glu Leu Val Leu Ala
                35                  40                  45

Ala Gly Met Phe Pro Val Gly Val Trp Gly Ser Asn Thr Glu Leu Ser
            50                  55                  60

Lys Ala Lys Thr Tyr Phe Pro Ala Phe Ile Cys Ser Ile Leu Gln Thr
65                  70                  75                  80

Thr Leu Glu Asn Ala Leu Asn Gly Glu Tyr Asp Met Leu Ser Gly Met
                85                  90                  95

Met Ile Thr Asn Tyr Cys Asp Ser Leu Lys Cys Met Gly Gln Asn Phe
                100                 105                 110

Lys Leu Thr Val Glu Asn Ile Glu Phe Ile Pro Val Thr Val Pro Gln
                115                 120                 125

Asn Arg Lys Met Glu Ala Gly Lys Glu Phe Leu Lys Ser Gln Tyr Lys
                130                 135                 140

Met Asn Ile Glu Gln Leu Glu Lys Ile Ser Gly Asn Lys Ile Thr Asp
145                 150                 155                 160

Glu Ser Leu Glu Lys Ala Ile Glu Ile Tyr Asp Glu His Arg Lys Val

```
                165                 170                 175
Met Asn Asp Phe Ser Met Leu Ala Ser Lys Tyr Pro Gly Ile Ile Thr
            180                 185                 190

Pro Thr Lys Arg Asn Tyr Val Met Lys Ser Ala Tyr Tyr Met Asp Lys
        195                 200                 205

Lys Glu His Thr Glu Lys Val Arg Gln Leu Met Asp Glu Ile Lys Ala
    210                 215                 220

Ile Glu Pro Lys Pro Phe Glu Gly Lys Arg Val Ile Thr Thr Gly Ile
225                 230                 235                 240

Ile Ala Asp Ser Glu Asp Leu Leu Lys Ile Leu Glu Glu Asn Asn Ile
                245                 250                 255

Ala Ile Val Gly Asp Asp Ile Ala His Glu Ser Arg Gln Tyr Arg Thr
            260                 265                 270

Leu Thr Pro Glu Ala Asn Thr Pro Met Asp Arg Leu Ala Glu Gln Phe
        275                 280                 285

Ala Asn Arg Glu Cys Ser Thr Leu Tyr Asp Pro Glu Lys Lys Arg Gly
    290                 295                 300

Gln Tyr Ile Val Glu Met Ala Lys Glu Arg Lys Ala Asp Gly Ile Ile
305                 310                 315                 320

Phe Phe Met Thr Lys Phe Cys Asp Pro Glu Glu Tyr Asp Tyr Pro Gln
                325                 330                 335

Met Lys Lys Asp Phe Glu Glu Ala Gly Ile Pro His Val Leu Ile Glu
            340                 345                 350

Thr Asp Met Gln Met Lys Asn Tyr Glu Gln Ala Arg Thr Ala Ile Gln
        355                 360                 365

Ala Phe Ser Glu Thr Leu
    370
```

<210> SEQ ID NO 43
<211> LENGTH: 264
<212> TYPE: PRT
<213> ORGANISM: Clostridium sporogenes

<400> SEQUENCE: 43

```
Met Ala Asp Ile Tyr Thr Met Gly Val Asp Ile Gly Ser Thr Ala Ser
  1               5                  10                  15

Lys Thr Val Val Leu Lys Asn Gly Lys Glu Ile Val Ser Gln Ala Val
             20                  25                  30

Ile Ser Val Gly Ala Gly Thr Ser Gly Pro Lys Arg Ala Ile Asp Ser
         35                  40                  45

Val Leu Lys Asp Ala Lys Leu Ser Ile Glu Asp Leu Asp Tyr Ile Val
     50                  55                  60

Ser Thr Gly Tyr Gly Arg Asn Ser Phe Asp Phe Ala Asn Lys Gln Ile
 65                  70                  75                  80

Ser Glu Leu Ser Cys His Ala Lys Gly Val Tyr Phe Asp Asn Asn Lys
                 85                  90                  95

Ala Arg Thr Val Ile Asp Ile Gly Gly Gln Asp Ile Lys Val Leu Lys
            100                 105                 110

Leu Ala Asp Ser Gly Arg Leu Leu Asn Phe Ile Met Asn Asp Lys Cys
        115                 120                 125

Ala Ala Gly Thr Gly Arg Phe Leu Asp Val Met Ser Arg Val Ile Glu
    130                 135                 140

Val Pro Val Asp Glu Leu Gly Lys Lys Ala Leu Glu Ser Lys Asn Pro
145                 150                 155                 160
```

-continued

```
Cys Thr Ile Ser Ser Thr Cys Thr Val Phe Ala Glu Ser Glu Val Ile
                165                 170                 175

Ser Gln Leu Ala Arg Gly Val Lys Thr Glu Asp Leu Ile Ala Gly Ile
            180                 185                 190

Cys Lys Ser Val Ala Ser Arg Val Ala Ser Leu Ala Lys Arg Ser Gly
            195                 200                 205

Ile Glu Glu Leu Val Val Met Ser Gly Val Ala Lys Asn Ile Gly
210                 215                 220

Val Val Lys Ala Met Glu Ala Glu Leu Gly Arg Asp Ile Tyr Ile Ser
225                 230                 235                 240

Lys Asn Ser Gln Leu Asn Gly Ala Leu Gly Ala Ser Leu Tyr Ala Tyr
                245                 250                 255

Glu Ser Phe Gln Lys Glu Arg Ser
            260

<210> SEQ ID NO 44
<211> LENGTH: 412
<212> TYPE: PRT
<213> ORGANISM: Clostridium sporogenes

<400> SEQUENCE: 44

Met Glu Asn Asn Thr Asn Met Phe Ser Gly Val Lys Val Ile Glu Leu
  1               5                  10                  15

Ala Asn Phe Ile Ala Ala Pro Ala Ala Gly Arg Phe Phe Ala Asp Gly
             20                  25                  30

Gly Ala Glu Val Ile Lys Ile Glu Ser Pro Ala Gly Asp Pro Leu Arg
         35                  40                  45

Tyr Thr Ala Pro Ser Glu Gly Arg Pro Leu Ser Gln Glu Glu Asn Thr
     50                  55                  60

Thr Tyr Asp Leu Glu Asn Ala Asn Lys Lys Ala Ile Val Leu Asn Leu
 65                  70                  75                  80

Lys Ser Glu Lys Gly Lys Lys Ile Leu His Glu Met Leu Ala Glu Ala
                 85                  90                  95

Asp Ile Leu Leu Thr Asn Trp Arg Thr Lys Ala Leu Val Lys Gln Gly
            100                 105                 110

Leu Asp Tyr Glu Thr Leu Lys Glu Lys Tyr Pro Lys Leu Val Phe Ala
        115                 120                 125

Gln Ile Thr Gly Tyr Gly Glu Lys Gly Pro Asp Lys Asp Leu Pro Gly
    130                 135                 140

Phe Asp Tyr Thr Ala Phe Phe Ala Arg Gly Gly Val Ser Gly Thr Leu
145                 150                 155                 160

Tyr Glu Lys Gly Thr Val Pro Pro Asn Val Val Pro Gly Leu Gly Asp
                165                 170                 175

His Gln Ala Gly Met Phe Leu Ala Ala Gly Met Ala Gly Ala Leu Tyr
            180                 185                 190

Lys Ala Lys Thr Thr Gly Gln Gly Asp Lys Val Thr Val Ser Leu Met
        195                 200                 205

His Ser Ala Met Tyr Gly Leu Gly Ile Met Ile Gln Ala Ala Gln Tyr
    210                 215                 220

Lys Asp His Gly Leu Val Tyr Pro Ile Asn Arg Asn Glu Thr Pro Asn
225                 230                 235                 240

Pro Phe Ile Val Ser Tyr Lys Ser Lys Asp Asp Tyr Phe Val Gln Val
                245                 250                 255

Cys Met Pro Pro Tyr Asp Val Phe Tyr Asp Arg Phe Met Thr Ala Leu
            260                 265                 270
```

```
Gly Arg Glu Asp Leu Val Gly Asp Glu Arg Tyr Asn Lys Ile Glu Asn
            275                 280                 285

Leu Lys Asp Gly Arg Ala Lys Glu Val Tyr Ser Ile Ile Glu Gln Gln
        290                 295                 300

Met Val Thr Lys Thr Lys Asp Glu Trp Asp Asn Ile Phe Arg Asp Ala
305                 310                 315                 320

Asp Ile Pro Phe Ala Ile Ala Gln Thr Trp Glu Asp Leu Leu Glu Asp
                325                 330                 335

Glu Gln Ala Trp Ala Asn Asp Tyr Leu Tyr Lys Met Lys Tyr Pro Thr
            340                 345                 350

Gly Asn Glu Arg Ala Leu Val Arg Leu Pro Val Phe Phe Lys Glu Ala
        355                 360                 365

Gly Leu Pro Glu Tyr Asn Gln Ser Pro Gln Ile Ala Glu Asn Thr Val
    370                 375                 380

Glu Val Leu Lys Glu Met Gly Tyr Thr Glu Gln Glu Ile Glu Glu Leu
385                 390                 395                 400

Glu Lys Asp Lys Asp Ile Met Val Arg Lys Glu Lys
                405                 410

<210> SEQ ID NO 45
<211> LENGTH: 368
<212> TYPE: PRT
<213> ORGANISM: Lachnoanaerobaculum saburreum

<400> SEQUENCE: 45

Met Trp His Cys Leu Glu Thr Leu Lys Lys Ile Ser Ala Ser Pro Lys
  1               5                  10                  15

Glu Gln Leu Asn Lys Tyr Leu Glu Glu Gly Lys Lys Val Ile Ala Val
             20                  25                  30

Ala Pro Val Tyr Thr Pro Glu Ile Ile His Ala Phe Gly Phe Val
         35                  40                  45

Pro Met Gly Val Trp Gly Ala Asp Ile Glu Ile Asn Glu Ser Lys Lys
     50                  55                  60

Tyr Tyr Pro Ala Phe Ile Cys Ser Ile Met Gln Thr Val Leu Glu Leu
 65                  70                  75                  80

Gly Ile Lys Gly Asn Tyr Asn Gly Val Ser Ala Ile Val Pro Ser
                 85                  90                  95

Leu Cys Asp Ser Leu Lys Thr Leu Gly Gln Asn Trp Lys Tyr Ala Val
             100                 105                 110

Lys Asp Ile Pro Phe Ile Pro Met Thr Tyr Pro Gln Asn Arg Lys Ser
         115                 120                 125

Asp Tyr Ala Val Asp Phe Thr Leu Glu Met Tyr Lys Arg Val Ile Ser
    130                 135                 140

Asp Leu Glu Asn Ile Thr Gly Glu Lys Phe Asp Glu Gly Lys Leu Lys
145                 150                 155                 160

Asn Thr Tyr Glu Ile Tyr Asn Glu His Asn Arg Val Met Arg Glu Phe
                165                 170                 175

Thr Lys Val Ser Glu Glu Tyr Glu Val Ser Ala Thr Asp Arg Ser Ala
            180                 185                 190

Val Phe Lys Ser Ala Trp Phe Met Leu Lys Glu His Thr Glu Leu
        195                 200                 205

Val Arg Glu Leu Ile Glu Leu Ile Lys Lys Glu Gly Lys Ile Ser Lys
    210                 215                 220

Lys Leu Arg Ile Tyr Thr Thr Gly Ile Leu Ala Asp Ala Pro Asp Leu
```

-continued

```
                225                 230                 235                 240

Leu Asn Ile Phe Asp Ser Asn Asn Met Gln Ile Val Gly Asp Asp Ile
                245                 250                 255

Ala Tyr Glu Ser Arg Gln Tyr Arg Thr Asp Ile Pro Asp Gly Asn Gly
            260                 265                 270

Leu Tyr Ala Leu Ala Lys Lys Phe Ser Asn Met Asp Asn Cys Thr Leu
        275                 280                 285

Leu Tyr Asp Lys Asp Lys Arg Arg Val Asp Phe Ile Ile Glu Glu Ala
    290                 295                 300

Lys Lys Lys Arg Ala Asp Gly Ile Val Val Leu Met Thr Lys Phe Cys
305                 310                 315                 320

Asp Pro Glu Glu Phe Asp Tyr Val Pro Ile Lys Arg Ala Ala Asn Glu
                325                 330                 335

Ala Gly Ile Pro His Ile Asn Ile Glu Val Asp Arg Gln Met Lys Asn
            340                 345                 350

Tyr Gln Gln Ala Asn Thr Met Leu Gln Thr Phe Ala Asp Met Leu Val
        355                 360                 365

<210> SEQ ID NO 46
<211> LENGTH: 409
<212> TYPE: PRT
<213> ORGANISM: Lachnoanaerobaculum saburreum

<400> SEQUENCE: 46

Met Glu Glu Ala Lys Lys Gln Lys Pro Thr Val Asp Pro Asn Ser Ala
  1               5                  10                  15

Lys Ala Arg Leu Gly Arg Ile Ala Ala Lys Ala Tyr Ser Asp Cys Val
                20                  25                  30

Glu Ala Lys Lys Arg Gly Glu Leu Val Gly Trp Cys Ala Ser Asn Phe
            35                  40                  45

Pro Val Glu Ile Pro Glu Thr Leu Gly Leu Tyr Val Cys Tyr Pro Glu
        50                  55                  60

Asn Gln Ala Ala Gly Ile Ala Ala Arg Gly Gly Glu Arg Met Cys
 65                  70                  75                  80

Ser Glu Ser Glu Gly Asp Gly Tyr Ser Asn Asp Ile Cys Ala Tyr Ala
                85                  90                  95

Arg Ile Ser Leu Ala Tyr Met Lys Leu Lys Glu Ala Pro Glu Gln Asp
            100                 105                 110

Met Pro Gln Pro Asp Phe Val Leu Cys Cys Asn Asn Ile Cys Asn Cys
        115                 120                 125

Met Ile Lys Trp Tyr Glu Asn Ile Ala Lys Glu Leu Asn Ile Pro Met
    130                 135                 140

Ile Met Ile Asp Ile Pro Phe Asn Pro Asp Tyr Glu Val Ser Asp Ala
145                 150                 155                 160

Met Thr Ala Tyr Ile Arg Asn Gln Phe Trp Asp Ala Ile His Gln Leu
                165                 170                 175

Glu Glu Ile Thr Gly Lys Lys Trp Ser Asn Glu Arg Tyr Glu Glu Val
            180                 185                 190

Arg Lys Ile Ser Gly Arg Ser Ser Arg Ala Trp Leu Glu Ala Thr Ala
        195                 200                 205

Thr Ala Lys Tyr Ser Pro Ser Pro Phe Asn Gly Phe Asp Leu Leu Asn
    210                 215                 220

His Met Ala Val Met Val Thr Ala Arg Gly Lys Leu Glu Ala Ala Glu
225                 230                 235                 240
```

Ala Met Glu Thr Leu Leu Gln Glu Tyr Lys Asp Asn His Glu Lys Gly
            245                 250                 255

Glu Ser Thr Phe Lys Gly Glu Lys Tyr Arg Ile Met Phe Glu Gly
        260                 265                 270

Ile Ala Cys Trp Pro Trp Leu Arg Ala Thr Ala Thr Gly Leu Lys Ser
        275                 280                 285

Arg Gly Ile Asn Met Val Thr Thr Ile Tyr Ala Asp Ala Phe Gly Phe
    290                 295                 300

Ile Tyr Asp Asp Phe Asp Gly Met Cys Arg Ala Tyr Ala Asn Val Pro
305                 310                 315                 320

Asn Cys Met Asn Ile Glu His Ala Arg Asp Lys Arg Ile Lys Leu Cys
                325                 330                 335

Lys Asp Asn Ser Val Glu Gly Leu Leu Val His Thr Asn Arg Ser Cys
            340                 345                 350

Lys Leu Trp Ser Gly Phe Met Ser Glu Met Ser Arg Gln Ile Gly Glu
        355                 360                 365

Glu Cys Gly Ile Pro Val Val Ser Phe Asp Gly Asp Gln Ala Asp Pro
    370                 375                 380

Arg Asn Phe Ser Glu Ala Gln Tyr Asp Thr Arg Val Gln Gly Leu Thr
385                 390                 395                 400

Glu Ile Met Glu Ala Asn Lys Glu Ile
                405

<210> SEQ ID NO 47
<211> LENGTH: 256
<212> TYPE: PRT
<213> ORGANISM: Lachnoanaerobaculum saburreum

<400> SEQUENCE: 47

Met Tyr Thr Leu Gly Val Asp Ile Gly Ser Thr Thr Ser Lys Ala Val
1               5                   10                  15

Ile Leu Glu Asp Gly Glu Asn Ile Val Ala Ser Ser Ile Val Ile Ala
            20                  25                  30

Thr Val Gly Thr Ala Gly Val Glu Glu Ala Val Lys Asn Val Leu Asn
        35                  40                  45

Phe Ser Lys Leu Glu Leu Asn Asp Ile Lys Ala Val Val Ala Thr Gly
    50                  55                  60

Tyr Gly Arg Met Asn Tyr Asp Val Ala Asp Tyr Lys Val Ser Glu Leu
65                  70                  75                  80

Thr Cys His Ala Leu Gly Val His Lys Glu Phe Pro Asn Val Arg Thr
                85                  90                  95

Val Ile Asp Ile Gly Gly Gln Asp Ala Lys Val Ile Ser Leu Ala Ala
            100                 105                 110

Asn Gly Lys Met Thr Asn Phe Val Met Asn Asp Lys Cys Ala Ala Gly
        115                 120                 125

Thr Gly Arg Phe Leu Asp Val Met Ala Asn Ile Leu Asn Leu Asp Ile
    130                 135                 140

Gln Asp Leu Glu Val Glu Ala Leu Lys Ser Asp Asn Pro Ala Asn Ile
145                 150                 155                 160

Ser Ser Thr Cys Thr Val Phe Ala Glu Ser Glu Val Ile Ser Gln Leu
                165                 170                 175

Ala Thr Gly Arg Asn Ile Pro Asp Leu Val Ala Gly Ile Cys Lys Ser
            180                 185                 190

Val Ala Val Arg Val Ala Ala Leu Ala Lys Arg Val Gly Ile Val Glu
        195                 200                 205

```
Glu Val Cys Met Ser Gly Gly Val Ala Lys Asn Ser Gly Val Arg Asn
    210                 215                 220

Ala Met Ser Lys Glu Leu Gly Val Asp Ile Val Phe Ser Lys Asp Ala
225                 230                 235                 240

Gln Leu Met Gly Ala Leu Gly Ala Ala Ile Tyr Gly Phe Lys Lys Leu
                245                 250                 255

<210> SEQ ID NO 48
<211> LENGTH: 264
<212> TYPE: PRT
<213> ORGANISM: Peptostreptococcus stomatis

<400> SEQUENCE: 48

Met Ser Ser Val Tyr Thr Met Gly Ile Asp Ile Gly Ser Thr Ser Ser
  1               5                  10                  15

Lys Cys Val Ile Met Lys Asp Gly Lys Glu Ile Val Ser Glu Gly Val
                 20                  25                  30

Val Ser Leu Gly Ala Gly Thr Lys Gly Ser Asp Leu Val Ile Glu Glu
             35                  40                  45

Val Leu Gly Lys Ala Gly Met Thr Phe Asp Glu Ile Asp Leu Ile Val
         50                  55                  60

Ser Thr Gly Tyr Gly Arg Asn Ser Tyr Glu Arg Ala Ala Lys Thr Val
 65                  70                  75                  80

Ser Glu Leu Ser Cys His Ala Lys Gly Gly Tyr Ile Phe Gly Gly
                 85                  90                  95

Ala Gly Thr Ile Ile Asp Ile Gly Gly Gln Asp Ile Lys Val Leu Lys
                100                 105                 110

Leu Asn Asp Lys Gly Gly Leu Val Asn Phe Leu Met Asn Asp Lys Cys
            115                 120                 125

Ala Ala Gly Thr Gly Arg Phe Leu Glu Val Met Ser Gly Val Leu Asp
130                 135                 140

Val Lys Leu Asp Glu Leu Gly Glu Leu Asp Ala Lys Ala Thr Glu Val
145                 150                 155                 160

Thr Pro Ile Ser Ser Thr Cys Thr Val Phe Ala Glu Ser Glu Val Ile
                165                 170                 175

Ser Cys Met Ala Lys Lys Ile Pro Leu Glu Asn Ile Ile Arg Gly Ile
            180                 185                 190

His Ala Ser Val Ala Thr Arg Val Ala Ser Leu Ala Arg Arg Gly Gly
        195                 200                 205

Leu Lys Thr Pro Val Ala Met Thr Gly Gly Val Ser Leu Asn Lys Gly
    210                 215                 220

Ile Val Arg Ala Leu Lys Glu Glu Leu Glu Cys Asp Ile Leu Ile Ser
225                 230                 235                 240

Pro Asp Ser Gln Met Ala Gly Ala Ile Gly Ala Ala Leu Tyr Ala Tyr
                245                 250                 255

Asp Glu Tyr Gln Lys Gln Asn Ala
            260

<210> SEQ ID NO 49
<211> LENGTH: 372
<212> TYPE: PRT
<213> ORGANISM: Peptostreptococcus stomatis

<400> SEQUENCE: 49

Met Ser Asn Ile Asp Val Leu Leu Gly Lys Leu Asp Val Ser Leu Leu
  1               5                  10                  15
```

```
Gly Gln Val Asp Lys Tyr Val Ser Glu Gly Lys Lys Val Ile Gly Cys
            20                  25                  30

Ala Pro Val Tyr Thr Pro Glu Glu Leu Val Tyr Ala Ala Gly Met Val
            35                  40                  45

Pro Ile Gly Val Trp Gly Ala Glu Gly Glu Val Gly Leu Ser Lys Glu
50                  55                  60

Tyr Phe Pro Ala Phe Tyr Ala Ala Ile Ile Leu Arg Leu Met Asp Leu
65                  70                  75                  80

Gly Leu Glu Gly Lys Leu Asp Lys Met Ser Gly Met Ile Ile Pro Gly
            85                  90                  95

Leu Ser Asp Gly Leu Lys Gly Leu Ser Gln Asn Trp Lys Arg Ala Ile
            100                 105                 110

Lys Gln Val Pro Ala Leu Tyr Ile Gly Tyr Gly Gln Asn Arg Lys Ile
            115                 120                 125

Glu Ala Gly Ile Thr Tyr Asn Glu Lys Gln Tyr Ile Lys Leu Arg Gly
130                 135                 140

Gln Leu Glu Glu Ile Ala Gly Cys Lys Ile Glu Asp Ala Lys Val Glu
145                 150                 155                 160

Glu Ala Ile Val Leu Tyr Asn Lys His Arg Lys Ala Met Gln Glu Phe
            165                 170                 175

Ser Ser Leu Ala Ala Ser His Leu Asn Thr Ile Thr Pro Ile Leu Arg
            180                 185                 190

Ala Arg Val Met Thr Ser Ala Phe Leu Phe Asp Lys Ala Glu His Leu
            195                 200                 205

Ala Ile Leu Glu Glu Leu Asn Lys Glu Leu Lys Ala Leu Pro Glu Glu
            210                 215                 220

Lys Phe Ala Gly Lys Lys Val Val Thr Thr Gly Ile Leu Ala Asn Ser
225                 230                 235                 240

Pro Gly Met Leu Glu Ile Leu Asp Glu Tyr Lys Leu Gly Ile Val Asp
            245                 250                 255

Asp Asn Ile Asn His Glu Ser Gly Gln Phe Asp Tyr Leu Val Asp Glu
            260                 265                 270

Gly Thr Gly Asn Pro Val Arg Ala Leu Ser Lys Trp Ile Ser Asp Ile
            275                 280                 285

Glu Gly Ser Thr Leu Leu Tyr Asp Pro Glu Lys Leu Arg Gly Gln Ile
290                 295                 300

Ile Ile Asp Lys Val Lys Lys His Gln Ala Asp Gly Val Ile Tyr Leu
305                 310                 315                 320

Met Thr Lys Phe Ser Asp Ser Asp Glu Phe Asp Tyr Pro Ile Ile Arg
            325                 330                 335

Lys Glu Leu Glu Asn Ala Gly Ile Leu His Ile Leu Val Glu Val Asp
            340                 345                 350

Gln Gln Met Thr Asn Phe Glu Gln Ala Lys Thr Ala Leu Gln Thr Phe
            355                 360                 365

Ala Asp Met Ile
            370

<210> SEQ ID NO 50
<211> LENGTH: 411
<212> TYPE: PRT
<213> ORGANISM: Peptostreptococcus stomatis

<400> SEQUENCE: 50

Met Ser Asn Thr Gly Met Val Glu Glu Lys Pro Ala Lys Val Leu Leu
```

```
          1               5              10              15
        Gly Glu Ile Val Ala Lys His Tyr Lys Glu Ala Trp Glu Ala Lys Asn
                        20                  25                  30
        Asn Gly Glu Leu Val Gly Trp Cys Ala Ser Asn Phe Pro Gln Glu Ile
                        35                  40                  45
        Phe Glu Thr Met Asp Ile Lys Val Val Tyr Pro Glu Asn Gln Ala Ala
         50                  55                  60
        Ala Ile Ser Ala Lys Gly Gly Gln Arg Met Cys Glu Ile Ala Glu
         65                  70                  75                  80
        Asn Glu Gly Tyr Ser Asn Asp Ile Cys Ala Tyr Ala Arg Ile Ser Leu
                        85                  90                  95
        Ala Tyr Met Asp Val Lys Asp Ala Pro Glu Leu Asn Met Pro Gln Pro
                       100                 105                 110
        Asp Phe Val Ala Cys Cys Asn Asn Ile Cys Asn Cys Met Ile Lys Trp
                       115                 120                 125
        Tyr Glu Asn Ile Ala Lys Glu Leu Asn Ile Pro Leu Ile Leu Ile Asp
                       130                 135                 140
        Val Pro Tyr Asn Asn Asp Tyr Glu Ala Glu Asp Asp Arg Val Glu Tyr
        145                 150                 155                 160
        Leu Arg Gly Gln Phe Asp Tyr Ala Ile Lys Gln Leu Glu Glu Leu Thr
                       165                 170                 175
        Gly Lys Lys Trp Asp Glu Lys Phe Glu Glu Val Met Glu Val Ser
                       180                 185                 190
        Gln Arg Thr Gly Arg Ala Trp Leu Lys Ala Thr Gly Tyr Ala Lys Tyr
                       195                 200                 205
        Thr Pro Ser Pro Phe Ser Gly Phe Asp Val Phe Asn His Met Ala Val
        210                 215                 220
        Ala Val Cys Ala Arg Gly Lys Ile Glu Ser Ala Ile Ala Phe Glu Lys
        225                 230                 235                 240
        Leu Ala Glu Glu Phe Asp Glu Asn Val Arg Thr Gly Lys Ser Thr Phe
                       245                 250                 255
        Lys Gly Glu Glu Lys Phe Arg Val Leu Phe Glu Gly Ile Ala Cys Trp
                       260                 265                 270
        Pro His Leu Arg His Thr Phe Lys Gln Leu Lys Asp Ala Gly Val Asn
                       275                 280                 285
        Val Cys Gly Thr Val Tyr Ala Asp Ala Phe Gly Tyr Ile Tyr Asp Asn
                       290                 295                 300
        Thr Tyr Gln Leu Met Gln Ala Tyr Cys Gly Thr Pro Asn Ala Ile Ser
        305                 310                 315                 320
        Tyr Glu Arg Ala Thr Asp Met Arg Leu Lys Val Ile Glu Glu Asn Asn
                       325                 330                 335
        Ile Asp Gly Met Leu Ile His Ile Asn Arg Ser Cys Lys Gln Trp Ser
                       340                 345                 350
        Gly Ile Met Tyr Glu Met Glu Arg Asp Ile Arg Glu Lys Thr Gly Ile
                       355                 360                 365
        Pro Thr Ala Thr Phe Asp Gly Asp Gln Ala Asp Pro Arg Asn Phe Ser
        370                 375                 380
        Glu Ala Gln Tyr Asp Thr Arg Val Gln Gly Leu Ile Glu Leu Met Glu
        385                 390                 395                 400
        Ala Asn Lys Ala Ala Lys Met Lys Glu Ala His
                       405                 410

<210> SEQ ID NO 51
```

<211> LENGTH: 408
<212> TYPE: PRT
<213> ORGANISM: Clostridium difficile

<400> SEQUENCE: 51

```
Met Ser Glu Lys Lys Glu Ala Arg Val Val Ile Asn Asp Leu Leu Ala
  1               5                  10                  15

Glu Gln Tyr Ala Asn Ala Phe Lys Ala Lys Glu Glu Gly Arg Pro Val
             20                  25                  30

Gly Trp Ser Thr Ser Val Phe Pro Gln Glu Leu Ala Glu Val Phe Asp
         35                  40                  45

Leu Asn Val Leu Tyr Pro Glu Asn Gln Ala Ala Gly Val Ala Ala Lys
     50                  55                  60

Lys Gly Ser Leu Glu Leu Cys Glu Ile Ala Glu Ser Lys Gly Tyr Ser
 65                  70                  75                  80

Ile Asp Leu Cys Ala Tyr Ala Arg Thr Asn Phe Gly Leu Leu Glu Asn
                 85                  90                  95

Gly Gly Cys Glu Ala Leu Asp Met Pro Ala Pro Asp Phe Leu Leu Cys
            100                 105                 110

Cys Asn Asn Ile Cys Asn Gln Val Ile Lys Trp Tyr Glu Asn Ile Ser
        115                 120                 125

Arg Glu Leu Asp Ile Pro Leu Ile Met Ile Asp Thr Thr Phe Asn Asn
130                 135                 140

Glu Asp Glu Val Thr Gln Ser Arg Ile Asp Tyr Ile Lys Ala Gln Phe
145                 150                 155                 160

Glu Glu Ala Ile Lys Gln Leu Glu Ile Ile Ser Gly Lys Lys Phe Asp
                165                 170                 175

Pro Lys Lys Phe Glu Glu Val Met Lys Ile Ser Ala Glu Asn Gly Arg
            180                 185                 190

Leu Trp Lys Tyr Ser Met Ser Leu Pro Ala Asp Ser Ser Pro Ser Pro
        195                 200                 205

Met Asn Gly Phe Asp Leu Phe Thr Tyr Met Ala Val Ile Val Cys Ala
    210                 215                 220

Arg Gly Lys Lys Glu Thr Thr Glu Ala Phe Lys Leu Leu Ile Glu Glu
225                 230                 235                 240

Leu Glu Asp Asn Met Lys Thr Gly Lys Ser Ser Phe Arg Gly Glu Glu
                245                 250                 255

Lys Tyr Arg Ile Met Met Glu Gly Ile Pro Cys Trp Pro Tyr Ile Gly
            260                 265                 270

Tyr Lys Met Lys Thr Leu Ala Lys Phe Gly Val Asn Met Thr Gly Ser
        275                 280                 285

Val Tyr Pro His Ala Trp Ala Leu Gln Tyr Glu Val Asn Asp Leu Asp
    290                 295                 300

Gly Met Ala Val Ala Tyr Ser Thr Met Phe Asn Asn Val Asn Leu Asp
305                 310                 315                 320

Arg Met Thr Lys Tyr Arg Val Asp Ser Leu Val Glu Gly Lys Cys Asp
                325                 330                 335

Gly Ala Phe Tyr His Met Asn Arg Ser Cys Lys Leu Met Ser Leu Ile
            340                 345                 350

Gln Tyr Glu Met Gln Arg Arg Ala Ala Glu Glu Thr Gly Leu Pro Tyr
        355                 360                 365

Ala Gly Phe Asp Gly Asp Gln Ala Asp Pro Arg Ala Phe Thr Asn Ala
    370                 375                 380

Gln Phe Glu Thr Arg Ile Gln Gly Leu Val Glu Val Met Glu Glu Arg
```

```
385                 390                 395                 400

Lys Lys Leu Asn Arg Gly Glu Ile
                405

<210> SEQ ID NO 52
<211> LENGTH: 375
<212> TYPE: PRT
<213> ORGANISM: Clostridium difficile

<400> SEQUENCE: 52

Met Glu Ala Ile Leu Ser Lys Met Lys Glu Val Val Glu Asn Pro Asn
  1               5                  10                  15

Ala Ala Val Lys Lys Tyr Lys Ser Glu Thr Gly Lys Lys Ala Ile Gly
             20                  25                  30

Cys Phe Pro Val Tyr Cys Pro Glu Glu Ile Ile His Ala Ala Gly Met
         35                  40                  45

Leu Pro Val Gly Ile Trp Gly Gly Gln Thr Glu Leu Asp Leu Ala Lys
     50                  55                  60

Gln Tyr Phe Pro Ala Phe Ala Cys Ser Ile Met Gln Ser Cys Leu Glu
 65                  70                  75                  80

Tyr Gly Leu Lys Gly Ala Tyr Asp Glu Leu Ser Gly Val Ile Ile Pro
                 85                  90                  95

Gly Met Cys Asp Thr Leu Ile Cys Leu Gly Gln Asn Trp Lys Ser Ala
            100                 105                 110

Val Pro His Ile Lys Tyr Ile Ser Leu Val His Pro Gln Asn Arg Lys
        115                 120                 125

Leu Glu Ala Gly Val Lys Tyr Leu Ile Ser Glu Tyr Lys Gly Val Lys
    130                 135                 140

Arg Glu Leu Glu Glu Ile Cys Gly Tyr Glu Ile Glu Glu Ala Lys Ile
145                 150                 155                 160

His Glu Ser Ile Glu Val Tyr Asn Glu His Arg Lys Thr Met Arg Asp
                165                 170                 175

Phe Val Glu Val Ala Tyr Lys His Ser Asn Thr Ile Lys Pro Ser Ile
            180                 185                 190

Arg Ser Leu Val Ile Lys Ser Gly Phe Phe Met Arg Lys Glu Glu His
        195                 200                 205

Thr Glu Leu Val Lys Asp Leu Ile Ala Lys Leu Asn Ala Met Pro Glu
    210                 215                 220

Glu Val Cys Ser Gly Lys Lys Val Leu Leu Thr Gly Ile Leu Ala Asp
225                 230                 235                 240

Ser Lys Asp Ile Leu Asp Ile Leu Glu Asp Asn Asn Ile Ser Val Val
                245                 250                 255

Ala Asp Asp Leu Ala Gln Glu Thr Arg Gln Phe Arg Thr Asp Val Pro
            260                 265                 270

Ala Gly Asp Asp Ala Leu Glu Arg Leu Ala Arg Gln Trp Ser Asn Ile
        275                 280                 285

Glu Gly Cys Ser Leu Ala Tyr Asp Pro Lys Lys Lys Arg Gly Ser Leu
    290                 295                 300

Ile Val Asp Glu Val Lys Lys Lys Asp Ile Asp Gly Val Ile Phe Cys
305                 310                 315                 320

Met Met Lys Phe Cys Asp Pro Glu Glu Tyr Asp Tyr Pro Leu Val Arg
                325                 330                 335

Lys Asp Ile Glu Asp Ser Gly Ile Pro Thr Leu Tyr Val Glu Ile Asp
            340                 345                 350
```

Gln Gln Thr Gln Asn Asn Glu Gln Ala Arg Thr Arg Ile Gln Thr Phe
            355                 360                 365

Ala Glu Met Met Ser Leu Ala
        370             375

<210> SEQ ID NO 53
<211> LENGTH: 266
<212> TYPE: PRT
<213> ORGANISM: Clostridium difficile

<400> SEQUENCE: 53

Met Tyr Thr Met Gly Leu Asp Ile Gly Ser Thr Ala Ser Lys Gly Val
 1               5                  10                  15

Ile Leu Lys Asn Gly Glu Asp Ile Val Ala Ser Glu Thr Ile Ser Ser
             20                  25                  30

Gly Thr Gly Thr Thr Gly Pro Ser Arg Val Leu Glu Lys Leu Tyr Gly
         35                  40                  45

Lys Thr Gly Leu Ala Arg Glu Asp Ile Lys Lys Val Val Thr Gly
     50                  55                  60

Tyr Gly Arg Met Asn Tyr Ser Asp Ala Asp Lys Gln Ile Ser Glu Leu
 65                  70                  75                  80

Ser Cys His Ala Arg Gly Val Asn Phe Ile Ile Pro Glu Thr Arg Thr
                 85                  90                  95

Ile Ile Asp Ile Gly Gly Gln Asp Ala Lys Val Leu Lys Leu Asp Asn
            100                 105                 110

Asn Gly Arg Leu Leu Asn Phe Leu Met Asn Asp Lys Cys Ala Ala Gly
        115                 120                 125

Thr Gly Arg Phe Leu Asp Val Met Ala Lys Ile Ile Glu Val Asp Val
130                 135                 140

Ser Glu Leu Gly Ser Ile Ser Met Asn Ser Gln Asn Glu Val Ser Ile
145                 150                 155                 160

Ser Ser Thr Cys Thr Val Phe Ala Glu Ser Glu Val Ile Ser His Leu
                165                 170                 175

Ser Glu Asn Ala Lys Ile Glu Asp Ile Val Ala Gly Ile His Thr Ser
            180                 185                 190

Val Ala Lys Arg Val Ser Ser Leu Val Lys Arg Ile Gly Val Gln Arg
        195                 200                 205

Asn Val Val Met Val Gly Gly Val Ala Arg Asn Ser Gly Ile Val Arg
    210                 215                 220

Ala Met Ala Arg Glu Ile Asn Thr Glu Ile Ile Val Pro Asp Ile Pro
225                 230                 235                 240

Gln Leu Thr Gly Ala Leu Gly Ala Ala Leu Tyr Ala Phe Asp Glu Ala
                245                 250                 255

Lys Glu Ser Gln Lys Glu Val Lys Asn Ile
            260                 265

<210> SEQ ID NO 54
<211> LENGTH: 399
<212> TYPE: PRT
<213> ORGANISM: Clostridium difficile

<400> SEQUENCE: 54

Met Leu Leu Glu Gly Val Lys Val Val Glu Leu Ser Ser Phe Ile Ala
 1               5                  10                  15

Ala Pro Cys Cys Ala Lys Met Leu Gly Asp Trp Gly Ala Glu Val Ile
             20                  25                  30

```
Lys Ile Glu Pro Ile Glu Gly Asp Gly Ile Arg Val Met Gly Gly Thr
             35                  40                  45

Phe Lys Ser Pro Ala Ser Asp Asp Glu Asn Pro Met Phe Glu Leu Glu
 50                  55                  60

Asn Gly Asn Lys Lys Gly Val Ser Ile Asn Val Lys Ser Lys Glu Gly
 65                  70                  75                  80

Val Glu Ile Leu His Lys Leu Leu Ser Glu Ala Asp Ile Phe Val Thr
                 85                  90                  95

Asn Val Arg Val Gln Ala Leu Glu Lys Met Gly Ile Ala Tyr Asp Gln
                100                 105                 110

Ile Lys Asp Lys Tyr Pro Gly Leu Ile Phe Ser Gln Ile Leu Gly Tyr
            115                 120                 125

Gly Glu Lys Gly Pro Leu Lys Asp Lys Pro Gly Phe Asp Tyr Thr Ala
130                 135                 140

Tyr Phe Ala Arg Gly Gly Val Ser Gln Ser Val Met Glu Lys Gly Thr
145                 150                 155                 160

Ser Pro Ala Asn Thr Ala Ala Gly Phe Gly Asp His Tyr Ala Gly Leu
                165                 170                 175

Ala Leu Ala Ala Gly Ser Leu Ala Ala Leu His Lys Lys Ala Gln Thr
            180                 185                 190

Gly Lys Gly Glu Arg Val Thr Val Ser Leu Phe His Thr Ala Ile Tyr
        195                 200                 205

Gly Met Gly Thr Met Ile Thr Thr Ala Gln Tyr Gly Asn Glu Met Pro
210                 215                 220

Leu Ser Arg Glu Asn Pro Asn Ser Pro Leu Met Thr Thr Tyr Lys Cys
225                 230                 235                 240

Lys Asp Gly Arg Trp Ile Gln Leu Ala Leu Ile Gln Tyr Asn Lys Trp
                245                 250                 255

Leu Gly Lys Phe Cys Lys Val Ile Asn Arg Glu Tyr Ile Leu Glu Asp
            260                 265                 270

Asp Arg Tyr Asn Asn Ile Asp Ser Met Val Asn His Val Glu Asp Leu
        275                 280                 285

Val Lys Ile Val Gly Glu Ala Met Leu Glu Lys Thr Leu Asp Glu Trp
290                 295                 300

Ser Ala Leu Leu Glu Glu Ala Asp Leu Pro Phe Glu Lys Ile Gln Ser
305                 310                 315                 320

Cys Glu Asp Leu Leu Asp Asp Glu Gln Ala Trp Ala Asn Asp Phe Leu
                325                 330                 335

Phe Lys Lys Thr Tyr Asp Ser Gly Asn Thr Gly Val Leu Val Asn Thr
            340                 345                 350

Pro Val Met Phe Arg Asn Glu Gly Ile Lys Glu Tyr Thr Pro Ala Pro
        355                 360                 365

Lys Val Gly Gln His Thr Val Glu Val Leu Lys Ser Leu Gly Tyr Asp
370                 375                 380

Glu Glu Lys Ile Asn Asn Phe Lys Asp Ser Lys Val Val Arg Tyr
385                 390                 395

<210> SEQ ID NO 55
<211> LENGTH: 255
<212> TYPE: PRT
<213> ORGANISM: Escherichia coli
<220> FEATURE:
<221> NAME/KEY: MISC_FEATURE
<222> LOCATION: (1)..(255)
<223> OTHER INFORMATION: strain K12
```

```
<400> SEQUENCE: 55

Met Ser Glu Leu Ile Val Ser Arg Gln Gln Arg Val Leu Leu Leu Thr
  1               5                  10                  15

Leu Asn Arg Pro Ala Arg Asn Ala Leu Asn Asn Ala Leu Leu Thr
             20                  25                  30

Gln Leu Val Asn Glu Leu Glu Ala Ala Ile Asp Thr Ser Ile Ser
         35                  40                  45

Val Cys Val Ile Thr Gly Asn Ala Arg Phe Phe Ala Ala Gly Ala Asp
 50                  55                  60

Leu Asn Glu Met Ala Glu Lys Asp Leu Ala Ala Thr Leu Asn Asp Thr
 65                  70                  75                  80

Arg Pro Gln Leu Trp Ala Arg Leu Gln Ala Phe Asn Lys Pro Leu Ile
                 85                  90                  95

Ala Ala Val Asn Gly Tyr Ala Leu Gly Ala Gly Cys Glu Leu Ala Leu
                100                 105                 110

Leu Cys Asp Val Val Val Ala Gly Glu Asn Ala Arg Phe Gly Leu Pro
            115                 120                 125

Glu Ile Thr Leu Gly Ile Met Pro Gly Ala Gly Gly Thr Gln Arg Leu
130                 135                 140

Ile Arg Ser Val Gly Lys Ser Leu Ala Ser Lys Met Val Leu Ser Gly
145                 150                 155                 160

Glu Ser Ile Thr Ala Arg Gln Ala Gln Gln Ala Gly Leu Val Ser Asp
                165                 170                 175

Val Phe Pro Ser Asp Leu Thr Leu Glu Tyr Ala Leu Gln Leu Ala Ser
            180                 185                 190

Lys Met Ala Arg His Ser Pro Leu Ala Leu Gln Ala Ala Lys Gln Ala
        195                 200                 205

Leu Arg Gln Ser Gln Glu Val Ala Leu Gln Ala Gly Leu Ala Gln Glu
    210                 215                 220

Arg Gln Leu Phe Thr Leu Leu Ala Ala Thr Glu Asp Arg His Glu Gly
225                 230                 235                 240

Ile Ser Ala Phe Leu Gln Lys Arg Ser Pro Asp Phe Lys Gly Arg
                245                 250                 255

<210> SEQ ID NO 56
<211> LENGTH: 257
<212> TYPE: PRT
<213> ORGANISM: Rhodobacter capsulatus

<400> SEQUENCE: 56

Met Ser Tyr His Thr Ile Arg Tyr Glu Ile Ser Glu Gly Leu Ala Val
  1               5                  10                  15

Ile Thr Leu Asp Arg Pro Glu Val Met Asn Ala Leu Asn Ala Ala Met
             20                  25                  30

Arg His Glu Leu Thr Ala Ala Leu His Arg Ala Arg Gly Glu Ala Arg
         35                  40                  45

Ala Ile Val Leu Thr Gly Ser Gly Arg Ala Phe Cys Ser Gly Gln Asp
 50                  55                  60

Leu Gly Asp Gly Ala Ala Glu Gly Leu Asn Leu Glu Thr Val Leu Arg
 65                  70                  75                  80

Glu Glu Tyr Glu Pro Leu Leu Gln Ala Ile Tyr Ser Cys Pro Leu Pro
                 85                  90                  95

Val Leu Ala Ala Val Asn Gly Ala Ala Gly Ala Gly Ala Asn Leu
                100                 105                 110
```

```
Ala Leu Ala Ala Asp Val Val Ile Ala Ala Gln Ser Ala Ala Phe Met
            115                 120                 125

Gln Ala Phe Thr Arg Ile Gly Leu Met Pro Asp Ala Gly Gly Thr Trp
130                 135                 140

Trp Leu Pro Arg Gln Val Gly Met Ala Arg Ala Met Gly Met Ala Leu
145                 150                 155                 160

Phe Ala Glu Lys Ile Gly Ala Glu Ala Arg Met Gly Leu Ile
                165                 170                 175

Trp Glu Ala Val Pro Asp Val Asp Phe Glu His His Trp Arg Ala Arg
                180                 185                 190

Ala Ala His Leu Ala Arg Gly Pro Ser Ala Ala Phe Ala Ala Val Lys
            195                 200                 205

Lys Ala Phe His Ala Gly Leu Ser Asn Pro Leu Pro Ala Gln Leu Ala
            210                 215                 220

Leu Glu Ala Arg Leu Gln Gly Glu Leu Gly Gln Ser Ala Asp Phe Arg
225                 230                 235                 240

Glu Gly Val Gln Ala Phe Leu Glu Lys Arg Pro Pro His Phe Thr Gly
                245                 250                 255

Arg

<210> SEQ ID NO 57
<211> LENGTH: 701
<212> TYPE: PRT
<213> ORGANISM: Pseudomonas stutzeri

<400> SEQUENCE: 57

Met Thr Asp Val Ile Arg Leu Glu Arg Arg Gly Asp Ile Ala Leu Ile
1               5                   10                  15

Leu Val Asn Asn Pro Pro Val Asn Ala Leu Gly His Ala Val Arg Lys
                20                  25                  30

Gly Leu Leu Asp Ala Phe Gln Glu Ala Asp Glu Ala Pro Glu Val Thr
            35                  40                  45

Ala Val Val Leu Val Cys Glu Gly Pro Thr Phe Met Ala Gly Ala Asp
        50                  55                  60

Ile Lys Glu Phe Gly Lys Pro Pro Gln Ala Pro Ser Leu Pro Glu Val
65                  70                  75                  80

Ile Glu Val Ile Glu Gly Cys Arg Lys Pro Ser Val Ala Val Ile His
                85                  90                  95

Gly Thr Ala Leu Gly Gly Gly Leu Glu Val Ala Leu Gly Cys His Tyr
            100                 105                 110

Arg Ile Ala Arg Ser Asp Ala Lys Val Gly Leu Pro Glu Val Lys Leu
        115                 120                 125

Gly Leu Leu Pro Gly Ala Gly Gly Thr Gln Arg Leu Pro Arg Leu Ala
130                 135                 140

Gly Val Glu Lys Ala Leu Glu Met Ile Val Ser Gly Gln Pro Ile Gly
145                 150                 155                 160

Ala Ala Glu Ala Leu Glu His Tyr Ile Val Asp Glu Leu Phe Glu Gly
                165                 170                 175

Asp Leu Ile Glu Ala Gly Leu Thr Tyr Ala Arg Arg Leu Val Glu Glu
            180                 185                 190

Gly Arg Gly Pro Arg Arg Ser Gly Glu Gln Thr Arg Gly Leu Glu Gly
        195                 200                 205

Val Asp Asn Glu Ala Leu Ile Arg Ala Lys His Ala Glu Val Ala Lys
210                 215                 220
```

Arg Met Pro Gly Leu Phe Ser Pro Leu Arg Cys Ile Ala Ala Val Glu
225                 230                 235                 240

Ala Ala Thr Arg Leu Pro Leu Ala Glu Gly Leu Lys Arg Glu Arg Glu
            245                 250                 255

Leu Phe Thr Glu Cys Leu Asn Ser Pro Gln Arg Gly Ala Leu Ile His
        260                 265                 270

Ser Phe Phe Ala Glu Arg Gln Ala Gly Lys Ile Asp Asp Leu Pro Ser
    275                 280                 285

Asp Val Thr Pro Arg Pro Ile Arg Thr Ala Ala Val Ile Gly Gly Gly
290                 295                 300

Thr Met Gly Val Gly Ile Ala Leu Ser Phe Ala Asn Ala Gly Val Pro
305                 310                 315                 320

Val Lys Leu Leu Glu Ile Asn Asp Glu Ala Leu Gln Arg Gly Leu Gln
                325                 330                 335

Arg Ala Arg Glu Thr Tyr Ala Ala Ser Val Lys Arg Gly Ser Leu Thr
            340                 345                 350

Glu Asp Ala Met Glu Gln Arg Leu Ala Leu Ile Ala Gly Val Thr Asp
        355                 360                 365

Tyr Gly Ala Leu Ala Asp Ala Asp Val Val Glu Ala Val Phe Glu
    370                 375                 380

Glu Met Gly Val Lys Gln Gln Val Phe Glu Gln Leu Asp Ala Val Cys
385                 390                 395                 400

Lys Pro Gly Ala Ile Leu Ala Ser Asn Thr Ser Ser Leu Asp Leu Asn
                405                 410                 415

Ala Ile Ala Gly Phe Thr Arg Arg Pro Glu Asp Val Val Gly Met His
            420                 425                 430

Phe Phe Ser Pro Ala Asn Val Met Arg Leu Leu Glu Val Val Arg Gly
        435                 440                 445

Glu Arg Thr Ser Asp Glu Val Leu Ala Ala Met Ala Ile Gly Lys
    450                 455                 460

Gln Leu Lys Lys Val Ser Val Val Gly Val Cys Asp Gly Phe Val
465                 470                 475                 480

Gly Asn Arg Met Val Phe Gln Tyr Gly Arg Glu Ala Glu Phe Leu Leu
            485                 490                 495

Glu Glu Gly Ala Thr Pro Gln Gln Val Asp Ala Ala Leu Arg Asn Phe
        500                 505                 510

Gly Met Ala Met Gly Pro Phe Ala Met Arg Asp Leu Ser Gly Leu Asp
    515                 520                 525

Ile Gly Gln Ala Ile Arg Lys Arg Gln Arg Ala Thr Leu Pro Ala His
530                 535                 540

Leu Asp Phe Pro Thr Val Ser Asp Lys Leu Cys Ala Ala Gly Met Leu
545                 550                 555                 560

Gly Gln Lys Thr Gly Ala Gly Tyr Tyr Arg Tyr Glu Pro Gly Asn Arg
            565                 570                 575

Thr Pro Gln Glu Asn Pro Asp Leu Ala Pro Met Leu Glu Ala Ala Ser
        580                 585                 590

Arg Glu Lys Gly Ile Glu Arg Gln Ala Leu Asp Glu Gln Tyr Ile Val
    595                 600                 605

Glu Arg Cys Ile Phe Ala Leu Val Asn Glu Gly Ala Lys Ile Leu Glu
610                 615                 620

Glu Gly Ile Ala Gln Arg Ser Ser Asp Ile Asp Val Ile Tyr Leu Asn
625                 630                 635                 640

Gly Tyr Gly Phe Pro Ala Phe Arg Gly Gly Pro Met Tyr Tyr Ala Asp

-continued

```
                645                 650                 655
Ser Val Gly Leu Asp Lys Val Leu Ala Arg Val Lys Glu Leu His Ala
            660                 665                 670
Arg Cys Gly Asp Trp Trp Lys Pro Ala Pro Leu Leu Glu Lys Leu Ala
            675                 680                 685
Ala Glu Gly Arg Thr Phe Thr Glu Trp Gln Ala Gly Gln
690                 695                 700

<210> SEQ ID NO 58
<211> LENGTH: 655
<212> TYPE: PRT
<213> ORGANISM: Haliangium ochraceum

<400> SEQUENCE: 58

Met Ile Gly Val Ile Gly Ser Gly Ala Ile Gly Pro Asp Leu Ala
1               5                   10                  15
Tyr Gly Phe Ala Ser Ala Leu Ala Ser Val Pro Gly Ala Arg Val Tyr
                20                  25                  30
Leu His Asp Ile Lys Gln Glu Ala Leu Asp Ala Gly Met Gln Arg Ile
            35                  40                  45
Arg Gly Tyr Ile Ala Lys Gly Leu Ala Arg Gly Lys Ile Ser Glu Arg
        50                  55                  60
Val Ala Gly Ala Leu Glu Thr Val Leu Val Pro Thr Leu Ser Leu Ala
65                  70                  75                  80
Asp Leu Ala Pro Cys Ser Tyr Val Leu Glu Ala Ala Thr Glu Glu Leu
                85                  90                  95
Gly Val Lys Arg Ala Ile Leu Arg Ser Leu Glu Asp Thr Val Asp Ser
            100                 105                 110
Glu Cys Leu Ile Gly Phe Ala Thr Ser Gly Leu Pro Arg Ala Ile Ile
        115                 120                 125
Ala Ala Glu Val Lys His Pro Glu Arg Cys Phe Val Asn His Pro Phe
130                 135                 140
Tyr Pro Ala Trp Arg Ser Leu Pro Val Glu Val Val Leu Ser Gly Ser
145                 150                 155                 160
Pro Ala His Gly Gln Arg Met Leu Ala Thr Leu Glu Ala Leu Gly Lys
                165                 170                 175
Val Pro Val Ile Thr Ala Asp Ala Pro Cys Phe Ala Ala Asp Asp Ile
            180                 185                 190
Phe Cys Asn Tyr Cys Ser Glu Ala Ala Arg Ile Val Glu Glu Gly Ile
        195                 200                 205
Ala Asn Pro Ala Gln Val Asp Ala Ile Val His Gly Ala Ile Gly Gly
    210                 215                 220
Gly Gly Pro Leu Asn Val Leu Asp Ala Thr Arg Gly Asn Leu Leu Thr
225                 230                 235                 240
Val His Cys Gln Glu Leu Met Arg Asp Ala Asp Thr Gly Thr Pro Trp
                245                 250                 255
Phe Glu Pro Pro Ala Ile Leu Arg Glu Arg Gly Asp Ala Leu Trp His
            260                 265                 270
Asp Pro Lys Ala Pro His Asp Pro Ala Phe Asp Glu Ala Leu Arg Glu
        275                 280                 285
Arg Val Leu Asp Arg Ile Leu Ala Val Leu Leu Ala Arg Thr Val Phe
    290                 295                 300
Val Leu Asp His Gly Ile Cys Ala Ala Thr Glu Leu Asp Trp Met Thr
305                 310                 315                 320
```

Arg Thr Ala Leu Gly Phe Arg Thr Gly Leu Val Asp Leu Val Asp Glu
                325                 330                 335

Leu Gly Pro Glu Arg Val Ala Glu Leu Cys Gln Arg Tyr Ala Ala Glu
            340                 345                 350

His Pro Gly Phe Val Ile Pro Asp Ser Ile Arg Glu Gln His Lys Pro
        355                 360                 365

Arg Phe Tyr Gly Asn Leu Arg Val Thr Arg Gln Asp Glu Leu Ala Ile
    370                 375                 380

Val Arg Ile Phe Arg Pro Glu Val Lys Asn Ala Leu Asp Arg Arg Thr
385                 390                 395                 400

Leu Ser Glu Leu Asp His Leu Met Ala Ala Leu Ser Ala Asp Asp Ser
                405                 410                 415

Val Glu Gly Val Val Leu Ser Ser Ala Gly Ala Leu Ala Gly Ala
            420                 425                 430

Asp Ile Thr Glu Leu Ala Arg Val Arg Thr Thr Glu Glu Ala Val Ser
        435                 440                 445

Thr Cys Ala Phe Gly Gln Ala Val Leu Asn Arg Ile Ala Ala Met Asp
    450                 455                 460

Lys Pro Val Val Ala Val Asp Gly Pro Val Leu Gly Gly Ala
465                 470                 475                 480

Glu Leu Ser Met Ala Cys His Ala Arg Val Val Gly Pro Arg Leu Ser
                485                 490                 495

Met Gly Gln Pro Glu Val Asn Leu Gly Ile Ile Pro Gly Tyr Gly Gly
            500                 505                 510

Thr Gln Arg Leu Pro Arg Leu Ile Gly Val Glu Arg Ala Leu Ala Met
        515                 520                 525

Met Arg Thr Ala Gln Ser Ile Asp Ala Gln Thr Ala Cys Glu Trp Gly
    530                 535                 540

Trp Ala Ser Gly Thr Pro Met Val Asp Phe Val Gly Ala Ala Thr
545                 550                 555                 560

Leu Ile Arg Ser His Leu Ala Gly Glu Ala Glu Leu Ala Pro Leu Asp
                565                 570                 575

Pro Ala Pro Met Ser Val Pro Ala Ala Ala Pro Val Asp Ile Gly
            580                 585                 590

His Arg Ser Arg Val Ile Asp Glu Ile Leu Val Asp Val Val Gln Ser
        595                 600                 605

Gly Leu Arg Ala Pro Leu Ser Glu Gly Leu Ala Thr Glu Ala Ala Gly
    610                 615                 620

Phe Gly Arg Cys Val Leu Thr Val Asp Leu Asp Ile Gly Leu Lys Asn
625                 630                 635                 640

Phe Met Gln Asn Gly Pro Arg Val Pro Ala Leu Phe Leu His Glu
                645                 650                 655

<210> SEQ ID NO 59
<211> LENGTH: 255
<212> TYPE: PRT
<213> ORGANISM: Anoxybacillus flavithermus

<400> SEQUENCE: 59

Met Phe Ser Ile Gln Gln Glu Gly Tyr Val Ala Ile Leu Ala Leu His
1               5                   10                  15

Arg Pro Pro Ala Asn Ala Leu Ala Ser Ser Val Leu Lys Glu Leu Ser
            20                  25                  30

Glu Arg Leu Asp Ala Leu Lys Glu Asp Glu Gln Val Arg Val Ile Val
        35                  40                  45

-continued

```
Leu His Gly Glu Gly Arg Phe Phe Ser Ala Gly Ala Asp Ile Lys Glu
 50                  55                  60

Phe Thr Ala Ile Glu Ala Ser Glu Gln Ala Ala Glu Leu Ala Arg Ala
 65                  70                  75                  80

Gly Gln Gln Val Met Glu Lys Ile Glu Gln Phe Pro Lys Pro Ile Ile
                 85                  90                  95

Ala Ala Ile His Gly Ala Ala Leu Gly Gly Gly Leu Glu Leu Ala Met
                100                 105                 110

Ser Cys His Leu Arg Ile Val Ala Glu Asn Ala Lys Leu Gly Leu Pro
            115                 120                 125

Glu Leu Gln Leu Gly Ile Ile Pro Gly Phe Ala Gly Thr Gln Arg Leu
130                 135                 140

Leu Arg His Val Gly Met Ala Lys Ala Leu Glu Met Met Trp Thr Ser
145                 150                 155                 160

Glu Pro Ile Thr Gly Ala Glu Ala Val Gln Trp Gly Leu Ala Asn Lys
                165                 170                 175

Ala Val Pro Glu Glu Gln Leu Leu Asp Thr Ala Lys Gln Leu Ala Gln
            180                 185                 190

Lys Ile Ala Gln Lys Ser Pro Ile Ser Val Gln Ala Val Leu Lys Leu
        195                 200                 205

Val Asn Glu Ala Arg Thr Lys Thr Phe His Glu Cys Val Glu Lys Glu
210                 215                 220

Ala Gln Leu Phe Gly Gln Val Phe Val Thr Glu Asp Ala Lys Glu Gly
225                 230                 235                 240

Ile Ser Ala Phe Ile Glu Lys Arg Thr Pro Gln Phe Gln Gly Lys
                245                 250                 255

<210> SEQ ID NO 60
<211> LENGTH: 260
<212> TYPE: PRT
<213> ORGANISM: Streptomyces avermitilis

<400> SEQUENCE: 60

Met Ser Thr Ala Pro Glu Ala Ala Asp Leu Val Leu His Glu Arg His
  1               5                  10                  15

Gly Gly Val Leu Thr Ile Thr Ile Asn Arg Pro Ala Gln Lys Asn Ala
                 20                  25                  30

Val Asp His Glu Ala Ala Val Gln Leu Ala Ala Ala Val Asp Leu Leu
            35                  40                  45

Asp Ala Asp Pro Glu Leu Ser Val Gly Val Leu Thr Gly Ala Gly Gly
 50                  55                  60

Val Phe Ser Ala Gly Met Asp Leu Lys Ala Phe Ala Lys Gly Glu Leu
 65                  70                  75                  80

Pro Leu Leu Pro Ser Arg Gly Leu Gly Leu Thr Arg Ala Ser Val
                 85                  90                  95

Arg Lys Pro Leu Val Ala Ala Val Glu Gly Trp Ala Leu Gly Gly Gly
            100                 105                 110

Phe Glu Leu Val Leu Ala Cys Asp Leu Ile Val Ala Ala Glu Asp Ala
            115                 120                 125

Arg Phe Gly Phe Pro Glu Val Met Arg Gly Leu Val Ala Ala Glu Gly
130                 135                 140

Gly Leu Val Arg Leu Pro Arg Arg Leu Pro Tyr His Val Ala Ala Arg
145                 150                 155                 160

Val Leu Leu Thr Gly Glu Pro Leu Thr Ala Val Glu Ala Lys Glu Tyr
```

```
                        165                 170                 175
Gly Leu Val Asn Glu Leu Thr Pro Pro Gly Ala Ala Leu Asp Ala Ala
                180                 185                 190

Arg Glu Leu Ala Gly Arg Val Ala Arg Asn Ala Pro Leu Ala Leu Ala
            195                 200                 205

Ala Val Lys Glu Val Leu Arg Glu Thr Gln Gly Leu Lys Glu Ser Asp
        210                 215                 220

Ala Phe Arg Arg Gln Asp Glu Leu Thr Ser Gly Leu Ala Ala Ser Glu
225                 230                 235                 240

Asp Ala Arg Glu Gly Ala Gln Ala Phe Ala Glu Lys Arg Ala Pro Val
                245                 250                 255

Trp His Gly Arg
            260

<210> SEQ ID NO 61
<211> LENGTH: 560
<212> TYPE: PRT
<213> ORGANISM: Advenella kashmirensis

<400> SEQUENCE: 61

Met Asp Asn Gly Arg Lys Leu Ile Glu Arg Gly Trp His Leu Phe Asn
1               5                   10                  15

Arg Ile Glu Lys Leu Ala Phe Pro Thr Leu Ala Leu Met His Gly Pro
            20                  25                  30

Cys Leu Gly Gly Gly Leu Glu Leu Ala Leu Ala Cys Arg Tyr Arg Ile
        35                  40                  45

Ala Ile Asp Ser Pro Lys Pro Val Ile Gly Leu Pro Glu Val Lys Leu
    50                  55                  60

Gly Ile Phe Pro Ala Trp Gly Gly Leu Met Arg Leu Pro Arg Leu Ile
65                  70                  75                  80

Gly Pro Gln Thr Ala Leu Asn Met Met Leu Thr Gly Arg Thr Leu Asp
                85                  90                  95

Gly Arg Lys Ala Arg Ser Ala Gly Leu Val Asp Leu Leu Val Ala Pro
            100                 105                 110

Arg Val Ala Glu Lys Ser Ala Ile Asp Leu Val Thr Ser Gly Lys Pro
        115                 120                 125

Ala Arg Gln Ala Arg Gly Leu Ala Gly Leu Leu Asn Arg Ala Pro Phe
    130                 135                 140

Lys Ser Leu Val Ala Ala Gln Ala Arg Lys Ser Val Lys Gln Lys Asp
145                 150                 155                 160

Pro Tyr Gly His Tyr Pro Ala Thr Leu Thr Met Leu Asp Leu Trp Glu
                165                 170                 175

Lys His Asp Gly Asp Pro Leu Ala Asp Pro Gln Ala Leu Thr Arg Leu
            180                 185                 190

Leu Gln Ser Asp Val Thr Arg Asn Leu Ile Arg Val Phe His Leu Gln
        195                 200                 205

Glu Arg Leu Lys Ala Phe Gly Lys Lys Asp Asn Ala Thr Pro Val Asn
    210                 215                 220

His Val His Val Ile Gly Ala Gly Val Met Gly Gly Ile Ala Ala
225                 230                 235                 240

Trp Cys Ala Leu Gln Gly Ile Lys Thr Thr Leu Gln Asp Thr Asp Ala
                245                 250                 255

Gln Arg Ile Ala Gly Ala Phe Lys Asn Ala Val Ser Ile Tyr Ala Arg
            260                 265                 270
```

```
Lys Asp Arg Tyr Thr Ala Gln Ala Ala Arg Asp Arg Leu Ile Pro Asp
            275                 280                 285

Leu Ala Gly His Gly Ile Ala Thr Ala Asp Leu Val Ile Glu Ala Ile
        290                 295                 300

Ser Glu Asn Pro Gln Ala Lys Gln Ser Leu Tyr Gln Gln Ile Glu Pro
305                 310                 315                 320

Lys Met Lys Glu Gly Ala Ile Leu Ala Thr Asn Thr Ser Ser Leu Ser
                325                 330                 335

Ile Ala Gln Leu Arg Ser Val Leu Val His Pro Glu Arg Phe Val Gly
            340                 345                 350

Ile His Phe Phe Asn Pro Val Ser Arg Met Pro Leu Val Glu Val Val
        355                 360                 365

His Ala Asp Gly Ile Ala Gln Glu Thr Leu Asp Thr Ala Ala Ala Phe
    370                 375                 380

Val Gly Lys Ile Gly Lys Leu Pro Leu Pro Val Gln Asp Thr Pro Gly
385                 390                 395                 400

Phe Leu Val Asn Ala Val Leu Ala Pro Tyr Met Leu Gln Ala Met Arg
                405                 410                 415

Cys Ile Asp Glu Gly Met Asp Pro Glu Val Ile Asp Thr Ala Met Leu
            420                 425                 430

Glu Phe Gly Met Pro Met Gly Pro Ile Thr Leu Ala Asp Thr Val Gly
        435                 440                 445

Leu Asp Ile Ala Met Ala Ala Gly Lys Gln Leu Ser Glu Gly Gln Glu
    450                 455                 460

Pro Pro Arg Cys Leu Gln Glu Lys Ile Ala Gln Gly Lys Leu Gly Val
465                 470                 475                 480

Lys Ser Gly Glu Gly Phe Tyr Val Trp Lys Asp Arg Lys His Asp Gln
                485                 490                 495

Arg Ser Ser Lys Ala Ile Pro Gln Gly Leu Ala Gln Arg Leu Ile Lys
            500                 505                 510

Pro Leu Ile Glu Gln Thr Glu Lys Gln Leu Ala Asn Asn Ile Val Gln
        515                 520                 525

Asp Ala Asp Leu Ala Asp Ala Gly Val Ile Phe Gly Thr Gly Phe Ala
    530                 535                 540

Pro Phe Thr Gly Gly Pro Ile His Tyr Lys Gln Ser Lys Gly Gly Leu
545                 550                 555                 560

<210> SEQ ID NO 62
<211> LENGTH: 237
<212> TYPE: PRT
<213> ORGANISM: Oligotropha carboxidovorans

<400> SEQUENCE: 62

Met Ser Leu Ser Pro Leu Ala Asn Gly Val Arg Val Leu Thr Leu Asp
  1               5                  10                  15

Arg Pro Ser Lys Ala Asn Ala Leu Asn Ala Glu Val Val Asp Gln Leu
             20                  25                  30

Leu Ala Cys Val Ala Gln Ala Glu Ala Asp Cys Arg Val Leu Ile
         35                  40                  45

Leu Ala Ala Asn Gly Lys Ala Phe Cys Gly Gly Phe Asp Phe Gly Gly
     50                  55                  60

Tyr Glu Ser Met Ser Ala Gly Asp Leu Leu Arg Phe Val Arg Ile
 65                  70                  75                  80

Glu Glu Leu Leu Gln Arg Met Arg Gln Ser Ser Phe Val Ser Ile Ala
                 85                  90                  95
```

```
Leu Val His Gly Ala Ala Met Gly Ala Gly Ala Asp Ile Val Ala Ser
            100                 105                 110

Cys Thr Tyr Arg Ile Gly Thr Asp Ala Ser Arg Phe Arg Phe Pro Gly
            115                 120                 125

Phe Arg Phe Gly Val Ala Leu Gly Thr Arg His Leu Ala Gln Leu Val
130                 135                 140

Gly Pro Gln Arg Ala Arg Asp Ile Leu Leu Thr Asn Ala Thr Ile Asp
145                 150                 155                 160

Ala Leu Thr Ala Val Asp Ile Gly Leu Leu Thr His Leu Val Asp Ala
                165                 170                 175

Gly Ser Met Arg Gln Lys Ala Asp Glu Ile Ile Ala Gln Ile Gly Ser
            180                 185                 190

Leu Asp Arg Val Ala Arg Asn Arg Ile Leu His Leu Thr Ser Ala Gln
            195                 200                 205

Asn Asn Asp Gly Asp Met Ala Glu Leu Val Lys Ser Val Ser Ala Pro
210                 215                 220

Gly Leu His Glu Arg Ile Ala Gln Tyr Arg Ala Gly His
225                 230                 235

<210> SEQ ID NO 63
<211> LENGTH: 266
<212> TYPE: PRT
<213> ORGANISM: Riemerella anatipestifer

<400> SEQUENCE: 63

Met Tyr Lys Leu Ile Asp Val Asp Asn His Phe Glu Gly Lys Leu Gln
1               5                   10                  15

Ile Ala Tyr Ile Asn Gln Pro Glu Ser Phe Asn Ser Leu Asn Lys Val
            20                  25                  30

Val Leu Glu Glu Leu Leu His Phe Ile Lys Ala Cys Asp Ala Asp Ser
        35                  40                  45

Ser Val Arg Cys Ile Ala Ile Ser Gly Lys Gly Lys Ala Phe Cys Ser
    50                  55                  60

Gly Gln Asn Leu Lys Glu Ala Leu Asp Tyr Lys Ala Glu Ala Asn Glu
65                  70                  75                  80

Glu Arg Phe Ile Gln Arg Ile Val Ile Asp Tyr Tyr Asn Pro Leu Val
                85                  90                  95

Lys Ala Ile Val Tyr Ala Lys Lys Pro Val Ile Ala Leu Val Asn Gly
            100                 105                 110

Pro Ala Val Gly Ala Gly Ala Met Leu Ala Leu Ile Cys Asp Phe Ala
            115                 120                 125

Val Ala Ser Glu Ser Ala Tyr Phe Ser Leu Ala Phe Ser Asn Ile Gly
130                 135                 140

Leu Val Pro Asp Thr Ala Gly Thr Tyr Tyr Leu Pro Lys Leu Leu Gly
145                 150                 155                 160

Arg Ser Leu Ala Ser Tyr Leu Ala Phe Thr Gly Lys Lys Leu Ser Ala
                165                 170                 175

Lys Glu Ser Leu Glu Arg Gly Leu Val Val Asp Val Phe Ser Asp Ala
            180                 185                 190

Thr Phe Ser Glu Gln Ser Leu Gln Val Leu Glu His Ile Thr His Gln
        195                 200                 205

Pro Thr Val Ala Leu Gly Leu Thr Lys Lys Ala Phe Asn Lys Ser Tyr
    210                 215                 220

Gln Asn Ser Leu Ser Glu Gln Leu Asp Leu Glu Ser Ile Leu Gln Gln
```

```
            225                 230                 235                 240

Asp Ala Ala Glu Thr Trp Asp Phe Gln Glu Gly Ile Ala Ala Phe Leu
                245                 250                 255

Ala Lys Arg Lys Pro Gln Tyr Lys Gly Lys
                260                 265

<210> SEQ ID NO 64
<211> LENGTH: 422
<212> TYPE: PRT
<213> ORGANISM: Fusobacterium necrophorum
<220> FEATURE:
<221> NAME/KEY: MISC_FEATURE
<222> LOCATION: (1)..(422)
<223> OTHER INFORMATION: subsp. funduliforme Fnf 1007

<400> SEQUENCE: 64

Met Ser Glu Thr Ile Asn Leu Asp Glu Met Ser Ala Lys Gln Leu Leu
  1               5                  10                  15

Gly Tyr Tyr Gln Glu Lys Leu Asp Glu Glu Ala Arg Gln Ala Lys Arg
                 20                  25                  30

Glu Gly Lys Leu Val Cys Trp Ser Ala Ser Val Ala Pro Pro Glu Phe
             35                  40                  45

Cys Val Ala Met Asp Ile Ala Met Val Tyr Pro Glu Thr His Ala Ala
         50                  55                  60

Gly Ile Gly Ala Arg Lys Gly Ser Leu Asp Leu Leu Glu Val Ala Asp
 65                  70                  75                  80

Glu Lys Gly Tyr Ser Leu Asp Ile Cys Ser Tyr Ala Arg Val Asn Leu
                 85                  90                  95

Gly Tyr Met Glu Leu Leu Lys Gln Gln Ala Leu Thr Gly Glu Thr Pro
            100                 105                 110

Glu Lys Leu Ala Asn Ser Pro Ala Ala Lys Val Pro Leu Pro Asp Leu
        115                 120                 125

Val Ile Thr Cys Asn Asn Ile Cys Asn Thr Leu Leu Lys Trp Tyr Glu
    130                 135                 140

Asn Leu Ala Lys Glu Leu Asn Ile Pro Cys Ile Val Ile Asp Val Pro
145                 150                 155                 160

Phe Asn His Thr Met Pro Ile Thr Lys His Ser Lys Glu Tyr Ile Ala
                165                 170                 175

Asp Gln Phe Lys Tyr Ala Ile Gln Gln Leu Glu Glu Ile Thr Gly Lys
            180                 185                 190

Lys Phe Asp Tyr Asp Lys Phe Leu Glu Val Gln Glu Gln Thr Gln Arg
        195                 200                 205

Ser Val Tyr Gln Trp Asn Arg Leu Ala Ala Leu Ala His Tyr Lys Pro
    210                 215                 220

Ser Pro Leu Asn Gly Phe Asp Leu Phe Asn Phe Met Ala Leu Ile Val
225                 230                 235                 240

Cys Ala Arg Ser Arg Asp Tyr Ala Glu Ile Thr Phe Lys Lys Phe Ala
                245                 250                 255

Asp Glu Leu Glu Glu Asn Leu Lys Asn Glu Val Tyr Ala Phe Lys Gly
            260                 265                 270

Ala Glu Lys Asn Arg Val Thr Trp Glu Gly Ile Ala Val Trp Pro Tyr
        275                 280                 285

Leu Gly His Thr Phe Lys Ser Leu Lys Gly Met Gly Ser Ile Met Thr
    290                 295                 300

Gly Ser Ala Tyr Pro Gly Ile Trp Asn Leu Thr Tyr Pro Gly Asp
305                 310                 315                 320
```

Met Glu Ser Met Ala Glu Ala Tyr Thr Arg Val Tyr Ile Asn Thr Cys
            325                 330                 335

Leu Gln Asn Lys Ala Asp Val Leu Ser Lys Ile Val Thr Asp Gly Lys
            340                 345                 350

Cys Asp Gly Ile Leu Tyr His Leu Asn Arg Ser Cys Lys Leu Met Ser
            355                 360                 365

Phe Leu Asn Val Glu Thr Ala Glu Leu Val Glu Lys Ala Thr Gly Val
            370                 375                 380

Pro Tyr Val Ser Phe Asp Gly Asp Gln Thr Asp Pro Arg Asn Phe Ala
385                 390                 395                 400

Pro Ala Gln Phe Asp Thr Arg Val Gln Ala Leu Asn Glu Met Met Glu
            405                 410                 415

Val Asn Asn Glu Thr Lys
            420

<210> SEQ ID NO 65
<211> LENGTH: 277
<212> TYPE: PRT
<213> ORGANISM: Fusobacterium necrophorum
<220> FEATURE:
<221> NAME/KEY: MISC_FEATURE
<222> LOCATION: (1)..(277)
<223> OTHER INFORMATION: subsp. funduliforme Fnf 1007

<400> SEQUENCE: 65

Met Gln Asp Asp Arg Ser Phe Lys Lys Gly Lys Arg Arg Gly Met Tyr
1               5                   10                  15

Thr Val Gly Val Asp Ile Gly Ser Ser Ser Lys Val Val Ile Leu
            20                  25                  30

Lys Asp Gly Thr Glu Ile Val Ser Gln Ser Ala Ile Gln Ser Gly Ile
            35                  40                  45

Gly Ser Asn Arg Ala Ile Val Ala Leu Glu Asp Asn Leu Lys Lys Ala
        50                  55                  60

Asn Leu Thr Lys Glu Asp Ile Gly Phe Thr Val Val Thr Gly Tyr Gly
65                  70                  75                  80

Arg Phe Thr Phe Glu Gly Ala Asp Lys Gln Ile Ser Glu Ile Ser Cys
                85                  90                  95

His Ala Arg Gly Ile His Phe Leu Leu Pro Asn Val Arg Thr Ile Ile
            100                 105                 110

Asp Ile Gly Gly Gln Asp Ala Lys Ala Ile Ser Leu Asp Glu Lys Gly
            115                 120                 125

His Val Arg Gln Phe Phe Met Asn Asp Lys Cys Ala Ala Gly Thr Gly
            130                 135                 140

Arg Phe Leu Thr Val Met Ala Arg Val Leu Glu Ile Ser Leu Asp Glu
145                 150                 155                 160

Met Gly Thr Tyr Asp Ala Leu Ser Lys Asn Pro Cys Asn Ile Ser Ser
                165                 170                 175

Thr Cys Ala Val Phe Ala Glu Ser Glu Val Ile Ser Gln Leu Ala Lys
            180                 185                 190

Gly Asn Thr Lys Glu Asp Val Ile Ala Gly Val His Asn Ser Val Ala
            195                 200                 205

His Lys Ile Leu Gly Leu Val Tyr Arg Thr Ser Met Glu Glu Lys Phe
            210                 215                 220

Ala Ile Cys Gly Gly Val Ala Gln Asn Thr Gly Ala Leu Arg Ala Ile
225                 230                 235                 240

-continued

```
Arg Glu Ala Leu Lys Lys Glu Val Ile Val Ala Pro Asn Pro Gln Leu
                245                 250                 255

Thr Gly Ala Leu Gly Ala Ala Ile Phe Ala Tyr Asp Glu Leu Lys Lys
            260                 265                 270

Leu Arg Lys Gly Glu
        275

<210> SEQ ID NO 66
<211> LENGTH: 374
<212> TYPE: PRT
<213> ORGANISM: Fusobacterium necrophorum
<220> FEATURE:
<221> NAME/KEY: MISC_FEATURE
<222> LOCATION: (1)..(374)
<223> OTHER INFORMATION: subsp. funduliforme Fnf 1007

<400> SEQUENCE: 66

Met Lys Gly Arg Leu Glu Leu Ile His Ile Phe Glu Asp Val Ala
  1               5                  10                  15

Asn Asn Pro Lys Lys Met Val Ala Glu Tyr Lys Glu Val Gly Lys
             20                  25                  30

Glu Val Ile Gly Val Met Pro Val Tyr Ala Pro Glu Glu Ile Ile His
             35                  40                  45

Ala Ala Gly Cys Leu Pro Ile Gly Leu Trp Gly Gly Lys Lys Glu Val
         50                  55                  60

Ser Lys Ala Arg Ala Tyr Leu Pro Pro Phe Ala Cys Ser Ile Met Gln
 65                  70                  75                  80

Thr Val Met Glu Leu Gln Ile Gly Gly Thr Tyr Asp Ile Leu Asp Ala
                 85                  90                  95

Val Leu Phe Ser Val Pro Cys Asp Thr Leu Lys Cys Leu Ser Gln Lys
            100                 105                 110

Trp Lys Gly Lys Ser Pro Val Ile Val Phe Thr His Pro Gln Asn Arg
        115                 120                 125

Val Ile Glu Gly Ala Asn Ala Tyr Leu Val Lys Glu Tyr Gln Ala Val
    130                 135                 140

Lys Glu Lys Leu Glu Gly Ile Leu Gly Arg Thr Ile Pro Met Glu Ala
145                 150                 155                 160

Ile Glu Glu Ser Val Lys Val Tyr Asn Glu Asn Arg Arg Val Met Arg
                165                 170                 175

Glu Phe Val Glu Val Ala Ala Gln Tyr Pro Gln Ile Ile Asp Pro Ile
            180                 185                 190

Val Arg His Asn Val Met Lys Ser Arg Trp Phe Leu Arg Lys Glu Lys
        195                 200                 205

His Thr Glu Tyr Val Lys Glu Leu Ile Ala Glu Leu Lys Lys Glu Thr
    210                 215                 220

Ile Val Pro Trp Asp Gly Lys Lys Val Ile Leu Thr Gly Ile Met Thr
225                 230                 235                 240

Glu Pro Val Glu Leu Leu Gln Ile Phe Lys Asp Glu Lys Leu Ala Ile
                245                 250                 255

Val Ala Asp Asp Leu Ala His Glu Ser Arg Gln Phe Arg Gly Asp Val
            260                 265                 270

Pro Glu Gly Gly Asp Val Leu Tyr Arg Met Ala Lys Trp Trp Gln
        275                 280                 285

Asn Leu Glu Gly Cys Ser Leu Ala Thr Asp Thr Asn Lys Gly Arg Gly
    290                 295                 300

Gln Met Leu Met Asp Met Cys Lys Asp Thr Lys Ala Asp Ala Val Ile
```

```
                305                 310                 315                 320
Val Cys Met Met Lys Phe Cys Asp Pro Glu Glu Phe Asp Tyr Pro Val
                    325                 330                 335

Tyr Tyr Arg Glu Phe Thr Glu Ser Gly Ile Lys Asn Ile Thr Val Glu
                340                 345                 350

Val Asp Leu Glu Val Ser Ser Phe Glu Gln Ile Arg Thr Arg Ile Gln
                355                 360                 365

Thr Phe Lys Asp Ile Leu
        370

<210> SEQ ID NO 67
<211> LENGTH: 422
<212> TYPE: PRT
<213> ORGANISM: Desulfosporosinus youngiae
<220> FEATURE:
<221> NAME/KEY: MISC_FEATURE
<222> LOCATION: (1)..(422)
<223> OTHER INFORMATION: DSM 17734

<400> SEQUENCE: 67

Met Thr Asp Thr Thr Thr Met Ser Ala Lys Glu Leu Leu Gly Phe Tyr
 1               5                  10                  15

Gln Glu Glu Leu Tyr Glu Ala Arg Gln Ala Lys Lys Glu Gly Lys
                20                  25                  30

Leu Val Cys Trp Ser Ala Ser Val Ala Pro Ser Glu Phe Cys Val Ala
                35                  40                  45

Met Asp Val Ala Met Ile Tyr Pro Glu Thr His Ala Ala Gly Ile Gly
            50                  55                  60

Ala Arg Lys Gly Ala Leu Asp Val Leu Glu Val Ala Asp Glu Lys Gly
65                  70                  75                  80

Tyr Asn Leu Asp Thr Cys Ser Tyr Ala Arg Val Asn Met Gly Tyr Met
                85                  90                  95

Glu Leu Leu Lys Gln Glu Ala Leu Thr Gly Ile Thr Pro Glu Lys Leu
            100                 105                 110

Glu Lys Ser Pro Ala Ala Arg Ile Pro Leu Pro Asp Phe Val Ile Thr
        115                 120                 125

Cys Asn Asn Ile Cys Asn Thr Leu Leu Lys Trp Tyr Glu Asn Leu Ala
    130                 135                 140

Val Glu Leu Asn Ile Pro Cys Ile Ile Ile Asp Val Pro Phe Asn His
145                 150                 155                 160

Thr Met Pro Ile Pro Gln Tyr Ala Lys Asp Tyr Ile Ala Glu Gln Phe
                165                 170                 175

Lys Glu Ala Ile Thr Gln Leu Glu Glu Ile Cys Gly Arg Lys Phe Asp
            180                 185                 190

Tyr Asp Lys Phe Leu Lys Val Gln Glu Gln Thr Gln Arg Ser Val Ala
        195                 200                 205

Gln Trp Asn Arg Ile Ala Ala Leu Ser Gly His Lys Pro Ser Pro Leu
    210                 215                 220

Asn Gly Phe Asp Leu Phe Asn Tyr Met Ala Leu Ile Val Cys Ala Arg
225                 230                 235                 240

Ser Arg Asp Tyr Ala Glu Ile Thr Phe Lys Lys Phe Ala Asp Glu Leu
                245                 250                 255

Glu Glu Asn Leu Lys Asn Gly Ile Tyr Ala Phe Lys Gly Asn Glu Gln
            260                 265                 270

Lys Arg Val Thr Trp Glu Gly Ile Ala Val Trp Pro His Leu Gly His
        275                 280                 285
```

Thr Phe Lys Gly Leu Lys Asn Leu Gly Asn Ile Met Thr Gly Ser Ala
    290                 295                 300

Tyr Pro Gly Leu Trp Asn Leu Thr Tyr Thr Pro Gly Asp Met Ser Ser
305                 310                 315                 320

Met Ala Glu Ala Tyr Thr Arg Ile Tyr Ile Asn Thr Cys Leu Asp Asn
                325                 330                 335

Lys Val Lys Val Leu Ser Asp Val Ile Ser Gly Gly Lys Cys Asp Gly
            340                 345                 350

Val Ile Tyr His Gln Asn Arg Ser Cys Lys Leu Met Ser Leu Leu Asn
        355                 360                 365

Val Glu Thr Ala Asp Ile Leu Gln Lys Gln Asn His Leu Pro Tyr Val
370                 375                 380

Ser Phe Asp Gly Asp Gln Thr Asp Pro Arg Asn Phe Ala Pro Ala Gln
385                 390                 395                 400

Phe Asp Thr Arg Ile Gln Ala Leu Asp Glu Met Met Lys Gln Asn Lys
                405                 410                 415

Glu Gly Val Ser Asn Glu
            420

<210> SEQ ID NO 68
<211> LENGTH: 372
<212> TYPE: PRT
<213> ORGANISM: Desulfosporosinus youngiae
<220> FEATURE:
<221> NAME/KEY: MISC_FEATURE
<222> LOCATION: (1)..(372)
<223> OTHER INFORMATION: DSM 17734

<400> SEQUENCE: 68

Met Ser Arg Ile Glu Thr Ile Ile Ser Glu Leu Thr Ser Ile Ala Asn
1               5                   10                  15

Asn Pro Arg Gln Ala Met Glu Asp Tyr Lys Lys Glu Thr Gly Lys Gly
            20                  25                  30

Ser Val Gly Val Met Pro Tyr Tyr Ala Pro Glu Glu Ile Ile His Ala
        35                  40                  45

Ala Gly Tyr Leu Pro Val Gly Ile Trp Gly Gly Gln Lys Ser Ile Ser
    50                  55                  60

Lys Ala Arg Ala Tyr Leu Pro Pro Phe Ala Cys Ser Ile Met Gln Ser
65                  70                  75                  80

Val Val Glu Met Gln Leu Glu Gly Val Tyr Asp Asp Leu Glu Ala Val
                85                  90                  95

Leu Phe Pro Val Pro Cys Asp Thr Leu Lys Cys Leu Ser Gln Lys Trp
            100                 105                 110

Lys Gly Thr Ser Pro Val Ile Val Leu Thr His Pro Gln Asn Arg Lys
        115                 120                 125

Leu Glu Ala Ala Asn Lys Phe Leu Ala Glu Glu Tyr Arg Leu Val Arg
130                 135                 140

Glu Lys Leu Glu Lys Ile Leu Asn Val Lys Ile Thr Asp Glu Ala Leu
145                 150                 155                 160

Asn Gln Ser Ile Glu Ile Tyr Asn Glu Asn Arg Lys Val Met Arg Glu
                165                 170                 175

Phe Thr Glu Ile Ala Ala Asn Tyr Pro Asn Ile Ile Asp Pro Val Lys
            180                 185                 190

Arg His Ala Leu Ile Lys Ala Arg Phe Phe Met Glu Lys Ala Lys His
        195                 200                 205

```
Thr Ala Leu Val Lys Glu Leu Asn Ala Glu Leu Lys Ala Leu Pro Val
    210                 215                 220

Glu Ala Phe Thr Gly Lys Lys Val Val Leu Thr Gly Ile Met Ala Glu
225                 230                 235                 240

Pro Asn Glu Val Leu Asp Ile Leu Gln Asp Asn Gly Phe Ala Val Val
                245                 250                 255

Ala Asp Asp Leu Ala Gln Glu Ser Arg Leu Phe Arg Asn Asp Val Pro
            260                 265                 270

Ser Gly Thr Asp Pro Leu Tyr Arg Leu Ala Lys Trp Trp Gln Glu Phe
        275                 280                 285

Asp Gly Cys Ser Leu Ala Val Asp Ala Lys Lys Pro Arg Gly Pro Met
    290                 295                 300

Leu Met Asp Met Val Lys Ala Ser Lys Ala Asp Ala Val Val Val Cys
305                 310                 315                 320

Met Met Lys Phe Cys Asp Pro Glu Glu Phe Asp Tyr Pro Ile Tyr Tyr
                325                 330                 335

Arg Gln Phe Glu Glu Ala Gly Ile Lys Ser Leu Phe Ile Glu Ile Asp
            340                 345                 350

Leu Glu Pro Thr Ser Phe Glu Gln Thr Lys Thr Arg Val Gln Ser Phe
        355                 360                 365

Arg Glu Met Leu
    370

<210> SEQ ID NO 69
<211> LENGTH: 272
<212> TYPE: PRT
<213> ORGANISM: Desulfosporosinus youngiae
<220> FEATURE:
<221> NAME/KEY: MISC_FEATURE
<222> LOCATION: (1)..(272)
<223> OTHER INFORMATION: DSM 17734

<400> SEQUENCE: 69

Met Phe Thr Met Gly Ile Asp Ile Gly Ser Ser Ser Lys Val Val
 1               5                  10                  15

Ile Leu Glu Asp Gly Val Asn Ile Ile Ala Gly Glu Val Ile Gln Ile
                20                  25                  30

Gly Thr Gly Ser Thr Gly Pro Lys Arg Val Leu Asp Glu Ala Leu Ala
            35                  40                  45

Lys Ala Gly Leu Thr Leu Gln Asp Met Ala Lys Ile Ile Ala Thr Gly
        50                  55                  60

Tyr Gly Arg Ser Ser Val Glu Glu Ala His Lys Gln Ile Ser Glu Ile
65                  70                  75                  80

Ser Cys Gln Ala Lys Gly Val Phe Phe Leu Val Pro Ser Ala Lys Leu
                85                  90                  95

Ile Ile Asp Ile Gly Gly Gln Asp Val Lys Ala Ile Lys Leu Asp Ser
            100                 105                 110

Lys Gly Cys Val Lys Gln Phe Phe Met Asn Asp Lys Cys Ala Ala Gly
        115                 120                 125

Thr Gly Arg Phe Leu Asp Val Met Ser Arg Val Leu Glu Val Asn Leu
130                 135                 140

Asp Glu Met Ala Glu Tyr Asp Ala Arg Ala Thr Glu Pro Ala Thr Val
145                 150                 155                 160

Ser Ser Thr Cys Thr Val Phe Ala Glu Ser Glu Val Ile Ser Gln Leu
                165                 170                 175

Ala Asn Gly Val Ala Lys Glu Asn Ile Ile Ala Gly Val His Gln Ser
```

```
                    180                 185                 190
Val Ala Ser Lys Ala Cys Gly Leu Ala Tyr Arg Cys Gly Val Glu Glu
            195                 200                 205

Asp Ile Val Met Cys Gly Gly Val Ala Lys Asp Leu Gly Val Val Arg
        210                 215                 220

Ala Ile Ser Lys Glu Leu Lys Lys Pro Val Ile Val Ala Pro Asn Pro
225                 230                 235                 240

Gln Ile Thr Ala Ala Leu Gly Ala Ala Ile Phe Ala Phe Glu Glu Val
                245                 250                 255

Met Glu Thr Val Met Val Ala Phe Glu Glu Val Arg Gly Ala Asn Lys
            260                 265                 270
```

<210> SEQ ID NO 70
<211> LENGTH: 422
<212> TYPE: PRT
<213> ORGANISM: Peptoniphilus indolicus
<220> FEATURE:
<221> NAME/KEY: MISC_FEATURE
<222> LOCATION: (1)..(422)
<223> OTHER INFORMATION: ATCC 29427

<400> SEQUENCE: 70

```
Met Asn Thr Ile Asp Ile Ser Asn Met Lys Ala Lys Glu Met Leu Gly
1               5                   10                  15

Tyr Phe Gln Asn Lys Leu Asp Glu Glu Ala Arg Glu Ala Lys Lys Asn
            20                  25                  30

Gly Lys Leu Val Cys Trp Ser Ala Ser Val Ala Pro Ser Glu Phe Cys
        35                  40                  45

Val Thr Met Asp Ile Ala Leu Val Tyr Pro Glu Thr His Ala Ala Gly
    50                  55                  60

Ile Gly Ala Arg Lys Gly Ser Leu Ala Met Leu Asp Val Ala Asp Arg
65                  70                  75                  80

Lys Gly Tyr Asn Thr Asp Ile Cys Ser Tyr Ala Arg Val Asn Leu Gly
                85                  90                  95

Tyr Met Glu Leu Leu Lys Glu Tyr Ala Lys Thr Gly Val Lys Pro Lys
            100                 105                 110

Glu Leu Glu Glu Ser Pro Ala Ala Asp Val Pro Leu Pro Asp Leu Val
        115                 120                 125

Ile Thr Cys Asn Asn Ile Cys Asn Thr Leu Leu Lys Trp Tyr Glu Asn
    130                 135                 140

Leu Ala Ala Glu Leu Asn Ile Pro Cys Ile Val Ile Asp Val Pro Phe
145                 150                 155                 160

Asn His Thr Met Pro Ile Pro Lys Tyr Ser Lys Glu Tyr Ile Ala Asp
                165                 170                 175

Gln Phe Lys Glu Ala Ile Arg Gln Leu Glu Glu Ile Thr Gly Lys Asp
            180                 185                 190

Phe Asp Tyr Asp Lys Phe Leu Glu Val Gln Glu Gln Thr Gln Arg Ser
        195                 200                 205

Val Ala Gln Trp Asn Arg Leu Ala Ala Leu Ser Lys Tyr Glu Pro Ser
    210                 215                 220

Pro Leu Asn Gly Phe Asp Leu Phe Asn Tyr Met Ala Leu Ile Val Cys
225                 230                 235                 240

Ala Arg Ser Lys Asn Tyr Ala Glu Leu Thr Phe Lys Lys Phe Ala Asp
                245                 250                 255

Glu Leu Glu Glu Asn Met Gln Asn Gly Val Tyr Pro Tyr Lys Ala Gly
            260                 265                 270
```

```
Glu Gln Ser Arg Ile Thr Trp Glu Gly Ile Ala Ile Trp Pro Tyr Leu
            275                 280                 285

Gly His Thr Phe Lys Thr Leu Lys Gly Tyr Gly Ser Ile Met Thr Gly
            290                 295                 300

Ser Ala Tyr Pro Gly Leu Trp Asn Leu Glu Tyr Thr Pro Gly Asp Met
305                 310                 315                 320

Leu Ser Met Ala Glu Ala Tyr Thr Arg Ile Tyr Ile Asn Thr Cys Leu
                325                 330                 335

Asp Asn Lys Val Asp Val Leu Arg Lys Ile Ile Lys Asn Gly Lys Cys
                340                 345                 350

Asp Gly Val Ala Tyr His Leu Asn Arg Ser Cys Lys Leu Met Ser Leu
                355                 360                 365

Leu Asn Val Glu Thr Ala Glu Ile Leu Asn Lys Glu Asn Asn Leu Pro
            370                 375                 380

Tyr Val Ser Phe Asp Gly Asp Gln Thr Asp Pro Arg Asn Phe Ser Glu
385                 390                 395                 400

Ala Gln Tyr Asp Asn Arg Ile Gln Thr Leu Thr Glu Met Met Ser Ala
                405                 410                 415

Asn Lys Lys Met Arg Gly
            420

<210> SEQ ID NO 71
<211> LENGTH: 263
<212> TYPE: PRT
<213> ORGANISM: Peptoniphilus indolicus
<220> FEATURE:
<221> NAME/KEY: MISC_FEATURE
<222> LOCATION: (1)..(263)
<223> OTHER INFORMATION: ATCC 29427

<400> SEQUENCE: 71

Met Tyr Thr Met Gly Val Asp Ile Gly Ser Thr Ser Lys Ile Ile
1               5                   10                  15

Ile Leu Glu Asp Gly Ile Lys Ile Ile Gly Asn Ile Val Val Gln Ser
            20                  25                  30

Gly Thr Gly Thr Ser Gly Pro Thr Ile Ala Thr Ala Lys Ala Lys Ser
        35                  40                  45

Phe Leu Ser Asn Asn Asn Leu Thr Leu Asp Asp Ile Ser Lys Ile Val
    50                  55                  60

Val Thr Gly Tyr Gly Arg Phe Ser Phe Asp Ile Ala Asp Lys Gln Ile
65                  70                  75                  80

Ser Glu Ile Thr Cys His Thr Lys Gly Ile Asn Phe Leu Val Pro Glu
                85                  90                  95

Ala Arg Thr Ile Leu Asp Ile Gly Gly Gln Asp Thr Lys Ala Ile Ser
            100                 105                 110

Val Asn Asp Lys Gly Gln Val Leu Gln Phe Phe Met Asn Asp Lys Cys
        115                 120                 125

Ala Ala Gly Thr Gly Arg Phe Leu Glu Val Met Ala Lys Ile Leu Glu
    130                 135                 140

Ile Pro Leu Glu Lys Met Gly Glu Tyr Asp Arg Leu Ser Thr Asn Pro
145                 150                 155                 160

Val Ala Ile Ser Ser Thr Cys Thr Val Phe Ala Glu Ser Glu Val Ile
                165                 170                 175

Ser Gln Leu Ser Lys Gly Ile Ser Lys Glu Asn Ile Leu Ala Gly Val
            180                 185                 190
```

His Asn Ser Thr Ala Asn Lys Val Cys Gly Leu Leu Tyr Arg Thr Gly
            195                 200                 205

Ile Lys Glu Lys Ile Val Leu Cys Gly Gly Val Ala Gln Asn Gln Gly
    210                 215                 220

Val Val Arg Ala Leu Gln Glu Leu Lys Lys Glu Ile Thr Ile Ala
225                 230                 235                 240

Pro His Pro Gln Met Thr Gly Ala Ile Gly Ala Ala Leu Phe Ala Tyr
                245                 250                 255

Glu Glu Ala Asn Lys Asn Leu
            260

<210> SEQ ID NO 72
<211> LENGTH: 372
<212> TYPE: PRT
<213> ORGANISM: Peptoniphilus indolicus
<220> FEATURE:
<221> NAME/KEY: MISC_FEATURE
<222> LOCATION: (1)..(372)
<223> OTHER INFORMATION: ATCC 29427

<400> SEQUENCE: 72

Met Asn Lys Ile Asn Glu Ile Ile Asn Leu Leu Asp Glu Val Ser Lys
1               5                   10                  15

Asp Pro Lys Leu Thr Val Lys Lys Tyr Lys Glu Lys Thr Gly Lys Gly
            20                  25                  30

Val Val Gly Val Met Pro Leu Tyr Ala Pro Glu Glu Ile Ile His Ala
        35                  40                  45

Ala Gly Phe Leu Pro Met Gly Leu Trp Gly Ala Gln Lys Glu Val Ser
    50                  55                  60

Lys Ala Arg Ile Tyr Leu Pro Pro Phe Ala Cys Ser Ile Met Gln Thr
65                  70                  75                  80

Asn Met Glu Leu Gln Ile Gly Ala Tyr Asp Asp Leu Asp Ala Val
                85                  90                  95

Val Phe Ser Val Pro Cys Asp Thr Leu Lys Cys Met Ser Gln Lys Trp
            100                 105                 110

Lys Gly Lys Ser Pro Val Ile Val Phe Thr His Pro Gln Asn Arg Lys
        115                 120                 125

Leu Glu Ser Ala Asn Lys Phe Leu Val Thr Glu Tyr Glu Ile Leu Lys
    130                 135                 140

Asp Lys Leu Glu Lys Ile Leu Asn Val Lys Ile Ser Asp Glu Ser Ile
145                 150                 155                 160

Thr Asn Ser Ile Glu Ile Tyr Asn Glu Asn Arg Lys Val Met Arg Glu
                165                 170                 175

Phe Ser Asp Leu Ala Gly Gln Tyr Pro Asn Ile Ile Asp Pro Ile Gln
            180                 185                 190

Arg His Ile Val Phe Lys Ser Arg Trp Phe Met Glu Lys Ser Glu His
        195                 200                 205

Thr Lys Leu Val Lys Glu Leu Ile Ser Glu Ile Lys Lys Leu Pro Ile
    210                 215                 220

Glu Glu Trp Asp Gly Tyr Lys Val Ile Ala Thr Gly Ile Met Ile Glu
225                 230                 235                 240

Pro Glu Glu Ile Leu Gln Ile Phe Lys Asp Lys Lys Ile Ala Ile Val
                245                 250                 255

Ala Asp Asp Leu Ala Gln Glu Ser Arg Gln Phe Arg His Asp Val Pro
            260                 265                 270

Glu Gly Asp Gln Pro Leu Leu Arg Leu Ala Lys Trp Trp Gln Asn Leu

```
            275                 280                 285
Glu Gly Cys Ala Leu Ala Thr Asp Thr Lys Lys Leu Arg Gly Gln Met
            290                 295                 300

Leu Ile Asp Met Ala Lys Lys Tyr Asn Ala Asp Ala Val Leu Ile Cys
305                 310                 315                 320

Met Met Lys Phe Cys Asp Pro Glu Glu Phe Asp Tyr Pro Val Tyr Tyr
                    325                 330                 335

Arg Glu Phe Gln Glu Ala Gly Ile Lys Asn Leu Leu Ile Glu Ile Asp
                340                 345                 350

Leu Glu Met Thr Ala Phe Glu Gln Thr Asn Thr Arg Leu Gln Thr Leu
            355                 360                 365

Val Glu Thr Leu
370

<210> SEQ ID NO 73
<211> LENGTH: 422
<212> TYPE: PRT
<213> ORGANISM: Desulfosporosinus meridiei
<220> FEATURE:
<221> NAME/KEY: MISC_FEATURE
<222> LOCATION: (1)..(422)
<223> OTHER INFORMATION: strain ATCC BAA-275 / DSM 13257 / NCIMB 13706 /
      S10

<400> SEQUENCE: 73

Met Thr Asp Thr Thr Ala Met Ser Ala Lys Glu Leu Leu Gly Phe Tyr
1               5                   10                  15

Gln Glu Glu Leu Tyr Glu Ala Arg Arg Ala Lys Lys Glu Gly Lys
            20                  25                  30

Leu Val Cys Trp Ser Ala Ser Val Ala Pro Ser Glu Phe Cys Val Ala
            35                  40                  45

Met Asp Val Ala Met Ile Tyr Pro Glu Thr His Ala Ala Gly Ile Gly
        50                  55                  60

Ala Arg Lys Gly Ala Leu Asp Val Leu Glu Val Ala Asp Glu Lys Gly
65                  70                  75                  80

Tyr Asn Val Asp Thr Cys Ser Tyr Ala Arg Val Asn Leu Gly Tyr Met
                85                  90                  95

Glu Leu Leu Lys Gln Glu Ala Leu Thr Gly Ile Thr Pro Glu Lys Leu
            100                 105                 110

Glu Lys Ser Pro Ala Ala Arg Ile Pro Leu Pro Asp Phe Val Ile Thr
        115                 120                 125

Cys Asn Asn Ile Cys Asn Thr Leu Leu Lys Trp Tyr Glu Asn Leu Ala
130                 135                 140

Val Glu Leu Asn Ile Pro Cys Ile Ile Ile Asp Val Pro Phe Asn His
145                 150                 155                 160

Thr Met Pro Ile Pro Gln Tyr Ala Lys Asp Tyr Ile Ala Glu Gln Phe
                165                 170                 175

Lys Glu Ala Ile Thr Gln Leu Gly Glu Ile Cys Gly Lys Lys Phe Asp
            180                 185                 190

Tyr Asp Lys Phe Leu Lys Val Gln Glu Gln Thr Gln Arg Ser Val Ala
        195                 200                 205

Gln Trp Asn Arg Ile Ala Ala Leu Ser Ser His Lys Pro Ser Pro Leu
210                 215                 220

Asn Gly Phe Asp Leu Phe Asn Tyr Met Ala Leu Ile Val Cys Ala Arg
225                 230                 235                 240

Ser Lys Asp Tyr Ala Glu Ile Thr Phe Lys Lys Phe Ala Asp Glu Leu
```

```
                        245                 250                 255
Glu Glu Asn Leu Asn Lys Gly Ile Phe Ala Phe Lys Gly Asn Glu Gln
            260                 265                 270

Lys Arg Val Thr Trp Glu Gly Ile Ala Val Trp Pro His Leu Gly His
            275                 280                 285

Thr Phe Lys Gly Leu Lys Asn Leu Gly Asn Ile Met Thr Gly Ser Ala
            290                 295                 300

Tyr Pro Gly Leu Trp Asn Val Ser Tyr Thr Pro Gly Asp Met Ser Ser
305                 310                 315                 320

Met Ala Glu Ala Tyr Thr Arg Ile Tyr Ile Asn Thr Cys Leu Asp Asn
                325                 330                 335

Lys Val Lys Val Leu Ser Asp Val Ile Ser Gly Gly Lys Cys Asp Gly
            340                 345                 350

Val Ile Tyr His Gln Asn Arg Ser Cys Lys Leu Met Ser Phe Leu Asn
            355                 360                 365

Val Glu Thr Ala Asp Ile Leu Gln Lys Glu Asn Gly Leu Pro Tyr Val
            370                 375                 380

Ser Phe Asp Gly Asp Gln Thr Asp Pro Arg Asn Phe Ser Pro Ala Gln
385                 390                 395                 400

Phe Asp Thr Arg Ile Gln Ala Leu Asp Glu Met Met Lys Gln Asn Lys
                405                 410                 415

Glu Gly Val Ser Asn Glu
            420

<210> SEQ ID NO 74
<211> LENGTH: 372
<212> TYPE: PRT
<213> ORGANISM: Desulfosporosinus meridiei
<220> FEATURE:
<221> NAME/KEY: MISC_FEATURE
<222> LOCATION: (1)..(372)
<223> OTHER INFORMATION: strain ATCC BAA-275 / DSM 13257 / NCIMB 13706 /
      S10

<400> SEQUENCE: 74

Met Ser Arg Ile Glu Thr Ile Ile Ser Glu Leu Ser Ser Ile Ser Asn
1               5                   10                  15

Asn Pro Arg Lys Ala Met Glu Asp Tyr Lys Lys Glu Thr Gly Lys Gly
            20                  25                  30

Ser Val Gly Val Met Pro Tyr Tyr Ala Pro Glu Glu Ile Ile His Ala
            35                  40                  45

Ala Gly Phe Leu Pro Val Gly Ile Trp Gly Gly Gln Lys Ser Ile Ser
        50                  55                  60

Lys Ala Arg Ala Tyr Leu Pro Pro Phe Ala Cys Ser Ile Met Gln Ser
65                  70                  75                  80

Val Met Glu Met Gln Leu Glu Gly Val Tyr Asp Asp Leu Glu Ala Val
                85                  90                  95

Leu Phe Pro Val Pro Cys Asp Thr Leu Lys Cys Leu Ser Gln Lys Trp
            100                 105                 110

Lys Gly Thr Ser Pro Val Ile Val Phe Thr His Pro Gln Asn Arg Lys
            115                 120                 125

Leu Glu Ala Ala Asn Lys Phe Leu Ala Glu Glu Tyr Arg Leu Val Arg
        130                 135                 140

Glu Lys Leu Glu Thr Ile Leu Asn Val Lys Ile Thr Asp Glu Ala Leu
145                 150                 155                 160

Asn Gln Ser Ile Glu Thr Tyr Asn Glu Asn Arg Lys Val Met Arg Glu
```

```
                165                 170                 175
Phe Thr Asp Leu Ala Ala Asn Tyr Pro Gln Ile Ile Asp Pro Arg Ile
            180                 185                 190

Arg His Ala Ile Ile Lys Ala Arg Phe Phe Met Glu Lys Ser Lys His
        195                 200                 205

Thr Ala Met Val Lys Glu Leu Asn Ser Glu Leu Lys Ser Leu Pro Val
    210                 215                 220

Glu Ala Phe Thr Gly Lys Lys Val Val Leu Thr Gly Ile Met Ala Glu
225                 230                 235                 240

Pro Asn Glu Val Leu Asp Ile Leu Lys Asp Asn Gly Phe Ala Val Val
                245                 250                 255

Ala Asp Asp Leu Ala Gln Glu Ser Arg Leu Phe Arg Asn Asp Val Pro
            260                 265                 270

Ser Gly Thr Asp Pro Leu Tyr Arg Leu Ala Lys Trp Trp Gln Glu Phe
        275                 280                 285

Asp Gly Cys Ser Leu Ala Thr Asp Ala Lys Lys Ser Arg Gly Pro Met
    290                 295                 300

Leu Met Glu Met Val Lys Gly Ser Lys Ala Asp Ala Val Val Val Cys
305                 310                 315                 320

Met Met Lys Phe Cys Asp Pro Glu Glu Phe Asp Tyr Pro Ile Tyr Tyr
                325                 330                 335

Arg Gln Phe Glu Glu Ala Gly Ile Lys Ser Leu Phe Ile Glu Ile Asp
            340                 345                 350

Leu Glu Thr Thr Ser Phe Glu Gln Thr Lys Thr Arg Val Gln Ser Phe
        355                 360                 365

Ser Glu Met Leu
    370

<210> SEQ ID NO 75
<211> LENGTH: 261
<212> TYPE: PRT
<213> ORGANISM: Desulfosporosinus meridiei
<220> FEATURE:
<221> NAME/KEY: MISC_FEATURE
<222> LOCATION: (1)..(261)
<223> OTHER INFORMATION: strain ATCC BAA-275 / DSM 13257 / NCIMB 13706 /
      S10

<400> SEQUENCE: 75

Met Phe Thr Met Gly Ile Asp Ile Gly Ser Ser Ser Lys Val Val
1               5                   10                  15

Ile Leu Glu Asp Gly Val Asn Ile Ala Gly Glu Val Ile Gln Ile
            20                  25                  30

Gly Thr Gly Ser Thr Gly Pro Lys Arg Val Leu Asn Glu Ala Leu Ser
        35                  40                  45

Lys Ala Gly Leu Lys Leu Glu Asp Met Ala Lys Ile Ile Ala Thr Gly
    50                  55                  60

Tyr Gly Arg Ser Ser Val Glu Glu Ala His Lys Gln Ile Ser Glu Ile
65                  70                  75                  80

Ser Cys Gln Ala Lys Gly Val Phe Phe Leu Val Pro Ser Ala Lys Leu
                85                  90                  95

Ile Ile Asp Ile Gly Gly Gln Asp Val Lys Ala Ile Arg Leu Asp Ser
            100                 105                 110

Lys Gly Gly Val Lys Gln Phe Phe Met Asn Asp Lys Cys Ala Ala Gly
        115                 120                 125

Thr Gly Arg Phe Leu Asp Val Met Ser Arg Val Leu Glu Val Asn Leu
```

```
                130                 135                 140
Asp Glu Met Ala Glu Tyr Asp Ala Arg Ala Thr Glu Pro Ala Thr Val
145                 150                 155                 160

Ser Ser Thr Cys Thr Val Phe Ala Glu Ser Glu Val Ile Ser Gln Leu
                165                 170                 175

Ser Asn Gly Val Ala Lys Glu Asn Ile Ile Ala Gly Val His Gln Ser
                180                 185                 190

Val Ala Ser Lys Ala Cys Gly Leu Ala Tyr Arg Cys Gly Val Glu Glu
            195                 200                 205

Asp Ile Val Met Cys Gly Gly Val Ala Lys Asp Leu Gly Val Val Arg
210                 215                 220

Ala Ile Ser Lys Glu Leu Lys Lys Pro Val Ile Val Ala Pro Asn Pro
225                 230                 235                 240

Gln Ile Thr Ala Ala Leu Gly Ala Ala Ile Phe Ala Phe Glu Glu Val
                245                 250                 255

Arg Gly Ala Asn Lys
            260

<210> SEQ ID NO 76
<211> LENGTH: 477
<212> TYPE: PRT
<213> ORGANISM: Acidaminococcus fermentans

<400> SEQUENCE: 76

Met Pro Lys Thr Val Ser Pro Gly Val Gln Ala Leu Arg Asp Val Val
1               5                   10                  15

Glu Lys Val Tyr Arg Glu Leu Arg Glu Ala Lys Glu Arg Gly Glu Lys
                20                  25                  30

Val Gly Trp Ser Ser Ser Lys Phe Pro Cys Glu Leu Ala Glu Ser Phe
            35                  40                  45

Gly Leu His Val Gly Tyr Pro Glu Asn Gln Ala Ala Gly Ile Ala Ala
        50                  55                  60

Asn Arg Asp Gly Glu Val Met Cys Gln Ala Ala Glu Asp Ile Gly Tyr
65                  70                  75                  80

Asp Asn Asp Ile Cys Gly Tyr Ala Arg Ile Ser Leu Ala Tyr Ala Ala
                85                  90                  95

Gly Phe Arg Gly Ala Asn Lys Met Asp Lys Asp Gly Asn Tyr Val Ile
                100                 105                 110

Asn Pro His Ser Gly Lys Gln Met Lys Asp Ala Asn Gly Lys Lys Val
            115                 120                 125

Phe Asp Ala Asp Gly Lys Pro Val Ile Asp Pro Lys Thr Leu Lys Pro
130                 135                 140

Phe Ala Thr Thr Asp Asn Ile Tyr Glu Ile Ala Ala Leu Pro Glu Gly
145                 150                 155                 160

Glu Glu Lys Thr Arg Arg Gln Asn Ala Leu His Lys Tyr Arg Gln Met
                165                 170                 175

Thr Met Pro Met Pro Asp Phe Val Leu Cys Cys Asn Asn Ile Cys Asn
            180                 185                 190

Cys Met Thr Lys Trp Tyr Glu Asp Ile Ala Arg Arg His Asn Ile Pro
        195                 200                 205

Leu Ile Met Ile Asp Val Pro Tyr Asn Glu Phe Asp His Val Asn Glu
    210                 215                 220

Ala Asn Val Lys Tyr Ile Arg Ser Gln Leu Asp Thr Ala Ile Arg Gln
225                 230                 235                 240
```

Met Glu Glu Ile Thr Gly Lys Lys Phe Asp Glu Lys Phe Glu Gln
                        245                 250                 255

Cys Cys Gln Asn Ala Asn Arg Thr Ala Lys Ala Trp Leu Lys Val Cys
                260                 265                 270

Asp Tyr Leu Gln Tyr Lys Pro Ala Pro Phe Asn Gly Phe Asp Leu Phe
            275                 280                 285

Asn His Met Ala Asp Val Val Thr Ala Arg Gly Arg Val Glu Ala Ala
290                 295                 300

Glu Ala Phe Glu Leu Leu Ala Lys Glu Leu Gln His Val Lys Glu
305                 310                 315                 320

Gly Thr Thr Thr Ala Pro Phe Lys Glu Gln His Arg Ile Met Phe Glu
                325                 330                 335

Gly Ile Pro Cys Trp Pro Lys Leu Pro Asn Leu Phe Lys Pro Leu Lys
                340                 345                 350

Ala Asn Gly Leu Asn Ile Thr Gly Val Val Tyr Ala Pro Ala Phe Gly
            355                 360                 365

Phe Val Tyr Asn Asn Leu Asp Glu Leu Val Lys Ala Tyr Cys Lys Ala
        370                 375                 380

Pro Asn Ser Val Ser Ile Glu Gln Gly Val Ala Trp Arg Glu Gly Leu
385                 390                 395                 400

Ile Arg Asp Asn Lys Val Asp Gly Val Leu Val His Tyr Asn Arg Ser
                405                 410                 415

Cys Lys Pro Trp Ser Gly Tyr Met Pro Glu Met Gln Arg Arg Phe Thr
                420                 425                 430

Lys Asp Met Gly Ile Pro Thr Ala Gly Phe Asp Gly Asp Gln Ala Asp
            435                 440                 445

Pro Arg Asn Phe Asn Ala Ala Gln Tyr Glu Thr Arg Val Gln Gly Leu
        450                 455                 460

Val Glu Ala Met Glu Ala Asn Asp Glu Lys Lys Gly Lys
465                 470                 475

<210> SEQ ID NO 77
<211> LENGTH: 379
<212> TYPE: PRT
<213> ORGANISM: Acidaminococcus fermentans

<400> SEQUENCE: 77

Met Ala Ile Ser Ala Leu Ile Glu Glu Phe Gln Lys Val Ser Ala Ser
1               5                   10                  15

Pro Lys Thr Met Leu Ala Lys Tyr Lys Ala Gln Gly Lys Lys Ala Ile
            20                  25                  30

Gly Cys Leu Pro Tyr Tyr Val Pro Glu Glu Leu Val Tyr Ala Ala Gly
        35                  40                  45

Met Val Pro Met Gly Val Trp Gly Cys Asn Gly Lys Gln Glu Val Arg
    50                  55                  60

Ser Lys Glu Tyr Cys Ala Ser Phe Tyr Cys Thr Ile Ala Gln Gln Ser
65                  70                  75                  80

Leu Glu Met Leu Leu Asp Gly Thr Leu Asp Gly Leu Asp Gly Ile Ile
                85                  90                  95

Thr Pro Val Leu Cys Asp Thr Leu Arg Pro Met Ser Gln Asn Phe Lys
            100                 105                 110

Val Ala Met Lys Asp Lys Met Pro Val Ile Phe Leu Ala His Pro Gln
        115                 120                 125

Val Arg Gln Asn Ala Ala Gly Lys Gln Phe Thr Tyr Asp Ala Tyr Ser
    130                 135                 140

Glu Val Lys Gly His Leu Glu Ile Cys Gly His Glu Ile Thr Asn
145                 150                 155                 160

Asp Ala Ile Leu Asp Ala Ile Lys Val Tyr Asn Lys Ser Arg Ala Ala
            165                 170                 175

Arg Arg Glu Phe Cys Lys Leu Ala Asn Glu His Pro Asp Leu Ile Pro
            180                 185                 190

Ala Ser Val Arg Ala Thr Val Leu Arg Ala Ala Tyr Phe Met Leu Lys
        195                 200                 205

Asp Glu Tyr Thr Glu Lys Leu Glu Glu Leu Asn Lys Glu Leu Ala Ala
    210                 215                 220

Ala Pro Ala Gly Lys Phe Asp Gly His Lys Val Val Ser Gly Ile
225                 230                 235                 240

Ile Tyr Asn Met Pro Gly Ile Leu Lys Ala Met Asp Asp Asn Lys Leu
            245                 250                 255

Ala Ile Ala Ala Asp Asp Cys Ala Tyr Glu Ser Arg Ser Phe Ala Val
            260                 265                 270

Asp Ala Pro Glu Asp Leu Asp Asn Gly Leu Gln Ala Leu Ala Val Gln
        275                 280                 285

Phe Ser Lys Gln Lys Asn Asp Val Leu Leu Tyr Asp Pro Glu Phe Ala
    290                 295                 300

Lys Asn Thr Arg Ser Glu His Val Cys Asn Leu Val Lys Glu Ser Gly
305                 310                 315                 320

Ala Glu Gly Leu Ile Val Phe Met Met Gln Phe Cys Asp Pro Glu Glu
            325                 330                 335

Met Glu Tyr Pro Asp Leu Lys Lys Ala Leu Asp Ala His His Ile Pro
            340                 345                 350

His Val Lys Ile Gly Val Asp Gln Met Thr Arg Asp Phe Gly Gln Ala
        355                 360                 365

Gln Thr Ala Leu Glu Ala Phe Ala Glu Ser Leu
    370                 375

<210> SEQ ID NO 78
<211> LENGTH: 260
<212> TYPE: PRT
<213> ORGANISM: Acidaminococcus fermentans

<400> SEQUENCE: 78

Met Ser Ile Tyr Thr Leu Gly Ile Asp Val Gly Ser Thr Ala Ser Lys
1               5                   10                  15

Cys Ile Ile Leu Lys Asp Gly Lys Glu Ile Val Ala Lys Ser Leu Val
            20                  25                  30

Ala Val Gly Thr Gly Thr Ser Gly Pro Ala Arg Ser Ile Ser Glu Val
        35                  40                  45

Leu Glu Asn Ala His Met Lys Lys Glu Asp Met Ala Phe Thr Leu Ala
    50                  55                  60

Thr Gly Tyr Gly Arg Asn Ser Leu Glu Gly Ile Ala Asp Lys Gln Met
65                  70                  75                  80

Ser Glu Leu Ser Cys His Ala Met Gly Ala Ser Phe Ile Trp Pro Asn
            85                  90                  95

Val His Thr Val Ile Asp Ile Gly Gly Gln Asp Val Lys Val Ile His
            100                 105                 110

Val Glu Asn Gly Thr Met Thr Asn Phe Gln Met Asn Asp Lys Cys Ala
        115                 120                 125

Ala Gly Thr Gly Arg Phe Leu Asp Val Met Ala Asn Ile Leu Glu Val

```
                130                 135                 140
Lys Val Ser Asp Leu Ala Glu Leu Gly Ala Lys Ser Thr Lys Arg Val
145                 150                 155                 160

Ala Ile Ser Ser Thr Cys Thr Val Phe Ala Glu Ser Glu Val Ile Ser
                165                 170                 175

Gln Leu Ser Lys Gly Thr Asp Lys Ile Asp Ile Ile Ala Gly Ile His
                180                 185                 190

Arg Ser Val Ala Ser Arg Val Ile Gly Leu Ala Asn Arg Val Gly Ile
                195                 200                 205

Val Lys Asp Val Val Met Thr Gly Val Ala Gln Asn Tyr Gly Val
210                 215                 220

Arg Gly Ala Leu Glu Glu Gly Leu Gly Val Glu Ile Lys Thr Ser Pro
225                 230                 235                 240

Leu Ala Gln Tyr Asn Gly Ala Leu Gly Ala Ala Leu Tyr Ala Tyr Lys
                245                 250                 255

Lys Ala Ala Lys
                260

<210> SEQ ID NO 79
<211> LENGTH: 336
<212> TYPE: PRT
<213> ORGANISM: Carboxydothermus hydrogenoformans

<400> SEQUENCE: 79

Met Lys Leu Asn Tyr Phe Cys Ser Tyr Trp Pro Val Glu Ile Ser Glu
1               5                   10                  15

Gly Ala Gly Ile Ser Thr Val Arg Tyr Phe Pro Ser Asp Glu Ser Lys
                20                  25                  30

Ala Pro Val Arg Leu Pro Ala Tyr Cys Cys Ser Tyr Ala Arg Gly Ser
                35                  40                  45

Leu Ala Glu Ile Glu Glu Gly Asp Gly Asp Phe Trp Gly Phe Ala
        50                  55                  60

His Ser Cys Asp Thr Met Gln Ser Leu Tyr Gly Ile Thr Lys Ser Leu
65                  70                  75                  80

Leu Gly Asp Asp Arg Val Phe Leu Phe Val Pro Pro Asp Leu Thr
                85                  90                  95

Thr Ala Phe Ala Arg Glu Tyr Tyr Arg Glu Ala Leu Ile Tyr Leu Trp
                100                 105                 110

Arg Glu Leu Ser Gln Lys Ser Gly Val Asn Gly Glu Glu Lys Leu Lys
                115                 120                 125

Leu Thr Trp Glu Lys Leu Lys Glu Leu Arg Asn Lys Val Lys Ser Leu
                130                 135                 140

Glu Asn Leu Thr Ser Ile Ile Pro Ser Ser Gly Ile Phe Glu Leu Leu
145                 150                 155                 160

Lys Lys Leu Gln Thr Leu Pro Leu Asp Glu Ala Leu Asp Tyr Leu Glu
                165                 170                 175

Ala Lys Lys Ala Glu Phe Thr Ser Leu Ser Val Ala Gln Lys Ala Ile
                180                 185                 190

Gly Ile Ile Leu Thr Gly Ala Val Val Thr Asn Ser Lys Leu Tyr Leu
                195                 200                 205

Ala Leu Glu Gln Gln Gly Phe Arg Val Val Tyr Asp Asp Thr Cys Thr
        210                 215                 220

Gly Phe Arg His Phe Ala Gly Glu Ile Glu Asp Lys Asp Ile Leu
225                 230                 235                 240
```

```
Glu Ala Ile Val Ser Tyr Tyr Leu Ser Lys Pro Pro Cys Pro Cys Arg
                245                 250                 255

His Lys Gly Val Trp Ala Arg Ala Glu Tyr Leu Lys Asn Leu Tyr His
            260                 265                 270

Asn Lys Asn Ala Arg Ala Ile Val Leu Leu Gln Asn Lys Phe Cys Asp
        275                 280                 285

Pro Phe Ala Trp Asp Val Pro Tyr Leu Val Asp Tyr Phe Lys Lys Gln
    290                 295                 300

Gly Val Pro Val Leu Val Leu Glu Val Glu Gly Glu Ile Gly Glu
305                 310                 315                 320

Gln Asn Lys Thr Arg Leu Gln Ala Phe Arg Glu Ser Val Gly Val
            325                 330                 335

<210> SEQ ID NO 80
<211> LENGTH: 404
<212> TYPE: PRT
<213> ORGANISM: Carboxydothermus hydrogenoformans

<400> SEQUENCE: 80

Met Ala Lys Lys Ile Phe Lys Pro Leu Lys Ala Ser Glu Lys Ile Asn
1               5                   10                  15

Lys Ile Leu Lys Asn His Tyr Leu Lys Ala Lys Tyr Leu Pro Thr Leu
            20                  25                  30

Gly Lys Phe Phe Gly Tyr Lys Thr Ala Trp Ile Thr Ser Gly Ala Pro
        35                  40                  45

Val Glu Leu Leu Arg Ala Phe Gly Ile Glu Pro Val Tyr Pro Glu Asn
    50                  55                  60

Tyr Gly Ala Ile Cys Gly Ala Arg Lys Val Ser Pro Ser Leu Cys Gln
65                  70                  75                  80

Val Ala Glu Asn Arg Gly Tyr Ser Leu Asp Leu Cys Ser Tyr Ala Lys
                85                  90                  95

Ser Asn Leu Gly Ser Ile Trp Asn Pro Lys Glu Ser Pro Phe Asn Gly
            100                 105                 110

Leu Pro Arg Pro Asp Leu Leu Val Cys Asn Asn Ile Cys Gly Thr
        115                 120                 125

Val Leu Lys Trp Tyr Glu Thr Leu Ser Arg Glu Phe Asn Ile Pro Leu
    130                 135                 140

Phe Ile Ile Asp Thr Pro Phe Ile Thr Gly Gly Pro Gln Pro Trp Gln
145                 150                 155                 160

Ile Gln Tyr Val Ala Lys Gln Ile Glu Lys Leu Ala Ile Glu Leu Glu
                165                 170                 175

Lys Phe Phe Arg Lys Lys Leu Asp Leu Asn Arg Leu Glu Lys Val Ile
            180                 185                 190

Leu Leu Ala Asn Glu Thr Val Asp Leu Trp Lys Gly Ile Arg Asn Phe
        195                 200                 205

Ala Lys Asn Lys Pro Ser Pro Val Asn Val Thr Asp Leu Phe Ile Asn
    210                 215                 220

Leu Gly Pro Met Val Val Leu Arg Gly Thr Glu Val Ala Arg Asp Phe
225                 230                 235                 240

Tyr Glu Glu Val Tyr Arg Glu Val Glu Arg Tyr Lys Ala Gly Val
                245                 250                 255

Pro Ala Val Glu Gly Glu Lys Tyr Arg Leu Val Trp Asp Asn Ile Pro
            260                 265                 270

Ile Trp Tyr Gly Leu Tyr Arg Phe Tyr Gly Tyr Phe Ala Glu Arg Gly
        275                 280                 285
```

Ala Val Phe Val Thr Asp Ser Tyr Thr Gly Gly Trp Ala Val Asn Ile
290                 295                 300

Lys Lys Gly Pro Pro Phe Tyr Ala Leu Ala Glu Thr Tyr Ala Gly Val
305                 310                 315                 320

Phe Leu Asn Arg Asp Leu Glu Phe Arg Lys Asn Gln Leu Gln Ser Phe
                325                 330                 335

Ile Glu Glu Phe Ser Ala Asp Gly Phe Val Met His Ser Asn Arg Ser
                340                 345                 350

Cys Lys Ala Tyr Ser Phe Val Gln Glu Ile Arg Arg Gln Ile Met
                355                 360                 365

Arg Ser Leu Gly Val Pro Gly Leu Ile Val Asp Ala Asp Met Thr Asp
370                 375                 380

Ser Arg Leu Tyr Ser Glu Glu Thr Val Leu Asn Arg Val Gln Ala Phe
385                 390                 395                 400

Leu Glu Ser Leu

<210> SEQ ID NO 81
<211> LENGTH: 254
<212> TYPE: PRT
<213> ORGANISM: Carboxydothermus hydrogenoformans

<400> SEQUENCE: 81

Met Tyr Leu Gly Val Asp Ile Gly Ser Leu Thr Thr Lys Val Val Leu
1               5                   10                  15

Ile Asp Arg Gly Lys Asn Leu Ile Ala Tyr Arg Tyr Ser Lys Thr Gly
                20                  25                  30

Pro Ala Gly Lys Glu Thr Ala Glu Arg Leu Ile Gln Glu Val Leu Ile
            35                  40                  45

Lys Ala Asn Ile Ser Arg Asp Asp Ile Gln Gly Ile Val Ala Thr Gly
50                  55                  60

Tyr Gly Arg Val Leu Phe Ser Gly Lys Glu Phe Ser Glu Ile Thr Cys
65                  70                  75                  80

Gln Ala Arg Gly Ile Gly His Leu Tyr Pro Glu Ala Lys Thr Ile Ile
                85                  90                  95

Asp Ile Gly Gly Gln Asp Ser Lys Val Ile Ser Leu Gly Lys Asn Gly
            100                 105                 110

Lys Val Leu Asp Phe Ala Met Asn Asp Lys Cys Ala Ala Gly Thr Gly
        115                 120                 125

Arg Phe Leu Glu Val Met Ser Gln Ala Leu Glu Val Arg Leu Glu Glu
    130                 135                 140

Ile Gly Glu Leu Ala Glu Lys Ser Gln Glu Ala Ala Lys Ile Ser Ser
145                 150                 155                 160

Val Cys Thr Val Phe Ala Glu Ser Glu Val Ile Ser Asn Leu Ser Arg
                165                 170                 175

Gly Gln Ser Arg Glu Ala Val Ala Arg Gly Ile Cys Glu Ala Val Ala
            180                 185                 190

Ala Arg Thr Ala Ile Leu Ala Gln Lys Val Gly Val Val Glu Pro Val
        195                 200                 205

Val Phe Thr Gly Gly Val Ala Lys Asn Thr Gly Val Val Ala Ala Leu
    210                 215                 220

Glu Arg Lys Leu Gly Val Lys Leu Leu Ile Pro Glu Asp Ser Thr Ile
225                 230                 235                 240

Thr Ala Ala Leu Gly Ala Ala Leu Leu Ala Ala Glu Asn Ser
                245                 250

```
<210> SEQ ID NO 82
<211> LENGTH: 261
<212> TYPE: PRT
<213> ORGANISM: Oscillibacter valericigenes

<400> SEQUENCE: 82

Met Asn Asn Ile Tyr Thr Met Gly Ile Asp Val Gly Ser Thr Ala Ser
 1               5                  10                  15

Lys Cys Leu Ile Leu Lys Asp Gly Ser Glu Ile Val Ala Lys Ser Leu
                20                  25                  30

Val Asp Val Gly Ala Gly Thr Ser Gly Pro Thr Arg Ala Ile Ala Glu
            35                  40                  45

Val Leu Glu Ala Ala Gly Met Lys Lys Glu Asp Met Ala Phe Ile Leu
        50                  55                  60

Ala Thr Gly Tyr Gly Arg Asn Ser Leu Asp Asp Ile Ala Asp His Gln
 65                  70                  75                  80

Met Ser Glu Leu Ser Cys His Ala Lys Gly Ala Phe Phe Leu Phe Pro
                85                  90                  95

Asp Val His Thr Val Ile Asp Ile Gly Gly Gln Asp Val Lys Ile Leu
            100                 105                 110

Glu Ile Glu Asn Gly Val Met Val Asn Phe Ala Met Asn Asp Lys Cys
        115                 120                 125

Ala Ala Gly Thr Gly Arg Phe Leu Asp Val Met Ala Arg Val Leu Glu
    130                 135                 140

Val Lys Val Glu Asp Leu Ala Asp Leu Gly Ala Gln Ser Thr Lys Asn
145                 150                 155                 160

Val Glu Ile Ser Ser Thr Cys Thr Val Phe Ala Glu Ser Glu Val Ile
                165                 170                 175

Ser Gln Leu Ala Lys Gly Ser Asp Lys Arg Asp Ile Ile His Gly Ile
            180                 185                 190

His Lys Ser Val Ala Ser Arg Val Val Gly Leu Ala Asn Arg Ile Gly
        195                 200                 205

Val Arg Asp Ala Val Val Met Thr Gly Gly Val Ala Gln Asn Gly Gly
    210                 215                 220

Val Val Ser Ala Leu Gln Glu Ala Leu Gly His Pro Ile His Thr Ser
225                 230                 235                 240

Pro Leu Thr Gln Tyr Asn Gly Ala Leu Gly Ala Ala Leu Phe Ala Trp
                245                 250                 255

Gln Lys Ala Thr Lys
            260

<210> SEQ ID NO 83
<211> LENGTH: 427
<212> TYPE: PRT
<213> ORGANISM: Oscillibacter valericigenes

<400> SEQUENCE: 83

Met Ala Glu Asn Glu Lys Ala Thr Ala Ala Pro Glu Ala Pro
 1               5                  10                  15

Val Lys Lys Ala Pro Lys Pro Val Ser Pro Gly Thr Gln Ala Leu Arg
                20                  25                  30

Asp Val Val Thr Lys Val Tyr Ala Ala Ala Trp Asp Ala Lys Lys Ala
            35                  40                  45

Gly Arg Pro Val Gly Trp Ser Ser Ser Lys Phe Pro Cys Glu Ile Ala
        50                  55                  60
```

Glu Ala Leu Gly Leu Ala Val Val Tyr Pro Glu Asn Gln Ala Ala Gly
 65                  70                  75                  80

Ile Gly Ala Gln His Asp Gly Gln Arg Met Cys Glu Ser Ala Glu Ser
                 85                  90                  95

Leu Gly Phe Asp Pro Asp Ile Cys Gly Tyr Ala Arg Ile Ser Leu Ala
            100                 105                 110

Tyr Ser Ala Gly Val Glu Thr Thr Asn Glu Ser Arg Arg Val Pro Met
        115                 120                 125

Pro Asp Phe Val Leu Cys Cys Asn Asn Ile Cys Asn Cys Met Thr Lys
    130                 135                 140

Trp Tyr Glu Asn Ile Ala Arg Met His Asn Ile Pro Leu Ile Met Ile
145                 150                 155                 160

Asp Val Pro Tyr Asn Asn Glu Val Thr Val Ser Asp Ser Gln Val Ala
                165                 170                 175

Tyr Ile Arg Gly Gln Phe Asp Asp Ala Ile Lys Gln Met Glu Lys Ile
            180                 185                 190

Ala Gly Val Lys Phe Asp Glu Lys Lys Phe Glu Gln Ala Cys Ala Asn
        195                 200                 205

Ala Asn Arg Thr Ala Lys Ala Trp Leu Thr Val Cys Asp Tyr Leu Gln
    210                 215                 220

Tyr Lys Pro Ala Pro Met Ser Gly Phe Asp Leu Phe Asn His Met Ala
225                 230                 235                 240

Asp Val Val Thr Ala Arg Gly Lys Val Glu Thr Ala Glu Ala Phe Glu
                245                 250                 255

Leu Leu Ala Ser Glu Leu Glu Gln His Val Lys Asn Gly Thr Ser Thr
            260                 265                 270

Ala Pro Phe Pro Glu Gln Tyr Arg Val Met Phe Glu Gly Ile Pro Cys
        275                 280                 285

Trp Pro Asn Leu Arg Thr Leu Phe Lys Pro Leu Lys Ala Asn Gly Val
    290                 295                 300

Asn Val Thr Ala Val Val Tyr Ala Pro Ala Phe Gly Phe Val Tyr Asn
305                 310                 315                 320

Gly Leu Asp Glu Met Ala Arg Ala Tyr Cys Lys Ala Pro Asn Ser Val
                325                 330                 335

Cys Ile Glu Gln Gly Val Asp Trp Arg Glu Gly Ile Cys Arg Glu Asn
            340                 345                 350

Lys Val Asp Gly Val Leu Val His Tyr Asn Arg Ser Cys Lys Pro Trp
        355                 360                 365

Ser Gly Tyr Met Ala Glu Met Gln Arg Arg Phe Thr Lys Asp Leu Gly
    370                 375                 380

Val Pro Cys Ala Gly Phe Asp Gly Asp Gln Ala Asp Pro Arg Asn Phe
385                 390                 395                 400

Asn Glu Ala Gln Tyr Glu Thr Arg Val Gln Gly Leu Val Glu Ala Met
                405                 410                 415

Glu Glu Asn Lys Lys Gln Lys Glu Ala Arg Ala
            420                 425

<210> SEQ ID NO 84
<211> LENGTH: 380
<212> TYPE: PRT
<213> ORGANISM: Oscillibacter valericigenes

<400> SEQUENCE: 84

Met Ser Ile Glu Thr Ile Val Lys Glu Phe Ala Asp Val Ala Ala Asp

```
            1               5               10              15
        Pro Lys Ala Gln Leu Lys Lys Tyr Lys Ala Glu Gly Lys Lys Cys Ile
                        20                  25                  30
        Gly Val Met Pro Tyr Tyr Ala Pro Glu Glu Leu Val Ala Ala Ala Gly
                        35                  40                  45
        Met Val Pro Phe Gly Met Trp Gly Ser Asn Asp Lys Thr Ile Ser Arg
                        50                  55                  60
        Ala Lys Glu Tyr Cys Ala Thr Phe Tyr Cys Thr Ile Ala Gln Leu Asp
         65                  70                  75                  80
        Leu Glu Met Leu Leu Asp Gly Thr Met Asp Leu Leu Asp Gly Val Ile
                         85                 90                  95
        Thr Pro Thr Ile Cys Asp Thr Leu Arg Pro Met Ser Gln Asn Ile Arg
                        100                 105                 110
        Val Ala Met Gly Glu Lys Leu Pro Cys Ile Phe Leu Ala His Pro Gln
                        115                 120                 125
        Asn Arg Lys Pro Ala Tyr Gly Lys Lys Phe Cys Leu Asp Gln Tyr Thr
                        130                 135                 140
        His Ile Lys Thr Glu Leu Glu Lys Ile Ala Gly Ala Pro Ile Thr Asp
        145                 150                 155                 160
        Ala Ala Leu Ser Glu Thr Ile Lys Val Tyr Asn Lys Ser Arg Ala Ala
                        165                 170                 175
        Arg Arg Glu Phe Val Lys Leu Val Ser Asp His Cys Asp Val Ile Thr
                        180                 185                 190
        Pro Thr Lys Arg Ser Ala Val Leu Lys Ala Ala Trp Phe Met Pro Lys
                        195                 200                 205
        Ala Glu Tyr Thr Glu Lys Leu Lys Ala Leu Asn Ala Glu Leu Lys Ala
                        210                 215                 220
        Leu Pro Val Cys Asp Trp Lys Gly Thr Lys Val Val Thr Ser Gly Ile
        225                 230                 235                 240
        Ile Cys Asp Asn Pro Lys Leu Leu Glu Ile Phe Glu Glu Asn Lys Ile
                        245                 250                 255
        Ala Ile Ala Ala Asp Asp Val Ala His Glu Ser Arg Ser Phe Arg Val
                        260                 265                 270
        Asp Ala Pro Glu Thr Gly Asp Pro Met Glu Ala Leu Ala Gln Gln Phe
                        275                 280                 285
        Ala Asn Gln Asp Tyr Asp Val Leu Leu Tyr Asp Glu His Ser Ser Glu
                        290                 295                 300
        Asn Arg Arg Gly Glu Phe Val Ala Lys Leu Val Lys Asp Ser Gly Ala
        305                 310                 315                 320
        Lys Gly Leu Val Leu Phe Met Gln Gln Phe Cys Asp Pro Glu Glu Met
                        325                 330                 335
        Glu Tyr Pro Ser Leu Lys Lys Ala Leu Asp Glu Ala Lys Ile Pro His
                        340                 345                 350
        Ile Lys Leu Gly Val Asp Gln Gln Met Arg Asp Phe Gly Gln Ala Arg
                        355                 360                 365
        Thr Ala Ile Gln Ala Phe Ala Asp Val Ile Ser Leu
                        370                 375                 380
```

<210> SEQ ID NO 85
<211> LENGTH: 422
<212> TYPE: PRT
<213> ORGANISM: Desulfosporosinus orientis
<220> FEATURE:
<221> NAME/KEY: MISC_FEATURE
<222> LOCATION: (1)..(422)

<223> OTHER INFORMATION: strain ATCC 19365 / DSM 765 /NCIMB 8382 /VKM B-1628

<400> SEQUENCE: 85

```
Met Thr Asp Thr Ala Asn Met Ser Ala Lys Glu Leu Leu Gly Phe Tyr
  1               5                  10                  15

Gln Glu Glu Leu Tyr Glu Ala Arg Gln Ala Lys Lys Glu Gly Lys
             20                  25                  30

Leu Val Cys Trp Ser Ala Ser Val Ala Pro Ser Glu Phe Cys Val Ala
             35                  40                  45

Met Asp Val Ala Met Ile Tyr Pro Glu Thr His Ala Ala Gly Ile Gly
 50                  55                  60

Ala Arg Lys Gly Ala Leu Asp Met Leu Glu Val Ala Asp Glu Lys Gly
 65                  70                  75                  80

Tyr Asn Leu Asp Thr Cys Ser Tyr Ala Arg Val Asn Leu Gly Tyr Met
                 85                  90                  95

Glu Leu Leu Lys Gln Glu Ala Leu Thr Gly Ile Thr Pro Glu Lys Leu
            100                 105                 110

Glu Lys Ser Pro Ala Ala Arg Val Pro Leu Pro Asp Phe Val Ile Thr
            115                 120                 125

Cys Asn Asn Ile Cys Asn Thr Leu Leu Lys Trp Tyr Glu Asn Leu Ala
130                 135                 140

Val Glu Leu Asn Ile Pro Cys Ile Val Ile Asp Val Pro Phe Asn His
145                 150                 155                 160

Thr Met Pro Ile Pro Gln Tyr Ala Lys Asp Tyr Ile Ala Glu Gln Phe
                165                 170                 175

Lys Glu Ala Ile Ala Gln Leu Glu Glu Ile Cys Gly Lys Lys Phe Asp
            180                 185                 190

Tyr Asp Lys Phe Leu Gln Val Gln Glu Gln Thr Gln Arg Ser Val Ala
            195                 200                 205

Gln Trp Asn Arg Ile Ala Ser Leu Ser Gly His Lys Pro Ser Pro Leu
        210                 215                 220

Asn Gly Phe Asp Leu Phe Asn Tyr Met Ala Leu Ile Val Cys Ala Arg
225                 230                 235                 240

Ser Arg Asp Cys Ala Glu Ile Thr Phe Lys Lys Phe Ala Asp Glu Leu
                245                 250                 255

Glu Asp Asn Leu Ser Lys Gly Ile Tyr Ala Phe Lys Gly Asn Glu Gln
            260                 265                 270

Lys Arg Ile Thr Trp Glu Gly Ile Ala Val Trp Pro His Leu Gly His
            275                 280                 285

Thr Phe Lys Gly Leu Lys Asn Leu Gly Asn Ile Met Thr Gly Ser Ala
        290                 295                 300

Tyr Pro Gly Leu Trp Asn Leu Ser Tyr Thr Pro Gly Asp Met Ser Ser
305                 310                 315                 320

Met Ala Glu Ala Tyr Thr Arg Ile Tyr Ile Asn Thr Cys Leu Asp Asn
                325                 330                 335

Lys Val Lys Val Leu Ser Asp Ile Ile Ser Gly Gly Lys Cys Asp Gly
            340                 345                 350

Val Ile Tyr His Gln Asn Arg Ser Cys Lys Leu Met Ser Phe Leu Asn
            355                 360                 365

Val Glu Thr Ala Asp Ile Leu Gln Gln Asn His Leu Pro Tyr Val
        370                 375                 380

Ser Phe Asp Gly Asp Gln Thr Asp Pro Arg Asn Phe Ala Pro Ala Gln
385                 390                 395                 400
```

```
Phe Asp Thr Arg Ile Gln Ala Leu Asp Glu Met Met Lys Gln Asn Lys
                405                 410                 415

Glu Gly Val Ser His Glu
            420

<210> SEQ ID NO 86
<211> LENGTH: 372
<212> TYPE: PRT
<213> ORGANISM: Desulfosporosinus orientis
<220> FEATURE:
<221> NAME/KEY: MISC_FEATURE
<222> LOCATION: (1)..(372)
<223> OTHER INFORMATION: strain ATCC 19365 /DSM 765 /NCIMB 8382 /VKM B-
      1628

<400> SEQUENCE: 86

Met Ser Arg Ile Glu Ala Ile Ile Ser Glu Leu Ser Ser Ile Ala Asn
  1               5                  10                  15

Asn Pro Arg Lys Ala Met Glu Asp Tyr Lys Lys Glu Thr Gly Lys Gly
                 20                  25                  30

Ser Val Gly Ile Met Pro Tyr Tyr Ala Pro Glu Glu Ile Val His Ala
             35                  40                  45

Ala Gly Tyr Leu Pro Val Gly Ile Trp Gly Gly Gln Lys Ser Ile Ser
         50                  55                  60

Lys Ala Arg Ala Tyr Leu Pro Pro Phe Ala Cys Ser Ile Met Gln Ser
 65                  70                  75                  80

Val Val Glu Met Gln Leu Glu Gly Val Tyr Asn Asp Leu Ala Ala Val
                 85                  90                  95

Leu Phe Pro Val Pro Cys Asp Thr Leu Lys Cys Leu Ser Gln Lys Trp
                100                 105                 110

Lys Gly Thr Ser Pro Val Ile Val Met Thr His Pro Gln Asn Arg Lys
            115                 120                 125

Leu Glu Ala Ala Asn Lys Phe Leu Ala Glu Glu Tyr Arg Leu Val Arg
        130                 135                 140

Glu Lys Leu Glu Lys Ile Leu Asn Val Gln Ile Thr Asp Glu Ala Leu
145                 150                 155                 160

Asn His Ser Ile Asp Val Tyr Asn Glu Asn Arg Lys Ala Met Arg Glu
                165                 170                 175

Phe Thr Asp Ile Ala Ala Asn Tyr Leu Asn Ile Ile Asp Pro Arg Lys
            180                 185                 190

Arg His Glu Ile Ile Lys Ala Arg Phe Phe Met Glu Lys Ser Lys His
        195                 200                 205

Thr Ala Leu Val Lys Glu Leu Asn Ser Glu Leu Lys Ser Leu Pro Val
210                 215                 220

Glu Asp Phe Thr Gly Lys Lys Val Ile Leu Thr Gly Ile Met Ala Glu
225                 230                 235                 240

Pro Asn Glu Val Leu Asp Ile Leu Lys Glu Asn Asp Phe Ala Val Val
                245                 250                 255

Ala Asp Asp Leu Ala Gln Glu Ser Arg Leu Phe Arg Ile Asp Val Pro
            260                 265                 270

Ala Gly Pro Asp Pro Leu Tyr Arg Leu Ala Lys Trp Trp Gln Glu Phe
        275                 280                 285

Asp Gly Cys Ser Leu Ala Val Asp Thr Lys Leu Leu Arg Gly Pro Met
    290                 295                 300

Leu Met Asn Met Val Asn Val Asp Lys Ala Asp Ala Val Val Val Cys
305                 310                 315                 320
```

-continued

```
Met Met Lys Phe Cys Asp Pro Glu Glu Phe Asp Tyr Pro Ile Tyr Tyr
                325                 330                 335

Arg Gln Phe Glu Glu Ala Gly Ile Lys Ser Leu Phe Ile Glu Ile Asp
            340                 345                 350

Leu Glu Pro Thr Ser Phe Glu Gln Thr Lys Thr Arg Val Gln Ser Phe
        355                 360                 365

Arg Glu Met Leu
    370

<210> SEQ ID NO 87
<211> LENGTH: 266
<212> TYPE: PRT
<213> ORGANISM: Desulfosporosinus orientis
<220> FEATURE:
<221> NAME/KEY: MISC_FEATURE
<222> LOCATION: (1)..(266)
<223> OTHER INFORMATION: strain ATCC 19365 /DSM 765 /NCIMB 8382 / VKM B-
      1628

<400> SEQUENCE: 87

Met Tyr Thr Met Gly Ile Asp Ile Gly Ser Ser Ser Lys Val Val
  1               5                  10                  15

Ile Leu Glu Asp Gly Val Asn Leu Ile Ala Gly Glu Val Ile Gln Ile
             20                  25                  30

Gly Thr Gly Ser Thr Gly Pro Lys Arg Val Leu Glu Glu Ala Leu Ala
         35                  40                  45

Lys Thr Gly Leu Thr Leu Ala Asp Met Ala Lys Ile Ile Ala Thr Gly
     50                  55                  60

Tyr Gly Arg Ser Ser Val Glu Val Ser Asp Lys Gln Ile Ser Glu Ile
 65                  70                  75                  80

Ser Cys Gln Ala Lys Gly Val Tyr Phe Leu Val Pro Thr Ala Lys Leu
                 85                  90                  95

Ile Ile Asp Ile Gly Gly Gln Asp Val Lys Ala Ile Arg Leu Asp Arg
            100                 105                 110

Ile Gly Gly Val Arg Gln Phe Phe Met Asn Asp Lys Cys Ala Ala Gly
        115                 120                 125

Thr Gly Arg Phe Leu Asp Val Met Ser Arg Val Leu Glu Val Asp Leu
    130                 135                 140

Asp Glu Met Ala Glu Tyr Asp Ala Arg Ala Thr Glu Pro Ala Thr Val
145                 150                 155                 160

Ser Ser Thr Cys Thr Val Phe Ala Glu Ser Glu Val Ile Ser Gln Leu
                165                 170                 175

Ala Asn Gly Val Ala Lys Glu Asn Ile Ile Ala Gly Val His Gln Ser
            180                 185                 190

Val Ala Ser Lys Ala Cys Gly Leu Ala Tyr Arg Cys Gly Val Glu Glu
        195                 200                 205

Asp Val Val Met Cys Gly Gly Val Ala Lys Asp Leu Gly Val Val Arg
    210                 215                 220

Ala Ile Ser Lys Glu Leu Lys Lys Pro Val Ile Val Ala Pro Asn Pro
225                 230                 235                 240

Gln Ile Thr Ala Ala Leu Gly Ala Ala Leu Phe Ala Tyr Glu Glu Val
                245                 250                 255

Met Glu Ala Asn Lys Leu Arg Lys Glu Val
            260                 265

<210> SEQ ID NO 88
```

```
<211> LENGTH: 411
<212> TYPE: PRT
<213> ORGANISM: Peptostreptococcus anaerobius
<220> FEATURE:
<221> NAME/KEY: MISC_FEATURE
<222> LOCATION: (1)..(411)
<223> OTHER INFORMATION: CAG:621

<400> SEQUENCE: 88
```

| Met | Ser | Asn | Thr | Gly | Ala | Val | Glu | Glu | Lys | Pro | Ala | Lys | Val | Leu | Leu |
|---|---|---|---|---|---|---|---|---|---|---|---|---|---|---|---|
| 1 | | | | 5 | | | | | 10 | | | | | 15 | |

| Gly | Glu | Ile | Val | Ala | Lys | His | Tyr | Lys | Glu | Ala | Trp | Glu | Ala | Lys | Glu |
|---|---|---|---|---|---|---|---|---|---|---|---|---|---|---|---|
| | | | 20 | | | | | 25 | | | | | 30 | | |

| Arg | Gly | Glu | Lys | Val | Gly | Trp | Cys | Ala | Ser | Asn | Phe | Pro | Gln | Glu | Ile |
|---|---|---|---|---|---|---|---|---|---|---|---|---|---|---|---|
| | | 35 | | | | | 40 | | | | | 45 | | | |

| Phe | Glu | Thr | Met | Asp | Ile | Lys | Val | Val | Phe | Pro | Glu | Asn | Gln | Ala | Ala |
|---|---|---|---|---|---|---|---|---|---|---|---|---|---|---|---|
| | 50 | | | | | 55 | | | | | 60 | | | | |

| Ala | Ile | Ser | Ala | Lys | Gly | Gly | Gln | Arg | Met | Cys | Glu | Ile | Ala | Glu |
|---|---|---|---|---|---|---|---|---|---|---|---|---|---|---|
| 65 | | | | | 70 | | | | | 75 | | | | 80 |

| Asn | Glu | Gly | Tyr | Ser | Asn | Asp | Ile | Cys | Ala | Tyr | Ala | Arg | Ile | Ser | Leu |
|---|---|---|---|---|---|---|---|---|---|---|---|---|---|---|---|
| | | | | 85 | | | | | 90 | | | | | 95 | |

| Ala | Tyr | Met | Asp | Val | Lys | Asp | Ala | Pro | Glu | Leu | Asn | Met | Pro | Gln | Pro |
|---|---|---|---|---|---|---|---|---|---|---|---|---|---|---|---|
| | | | 100 | | | | | 105 | | | | | 110 | | |

| Asp | Phe | Val | Ala | Cys | Cys | Asn | Asn | Ile | Cys | Asn | Cys | Met | Ile | Lys | Trp |
|---|---|---|---|---|---|---|---|---|---|---|---|---|---|---|---|
| | 115 | | | | | 120 | | | | | 125 | | | | |

| Tyr | Glu | Asn | Ile | Ala | Lys | Glu | Leu | Asn | Ile | Pro | Leu | Ile | Leu | Val | Asp |
|---|---|---|---|---|---|---|---|---|---|---|---|---|---|---|---|
| 130 | | | | | 135 | | | | | 140 | | | | | |

| Val | Pro | Tyr | Asn | Asn | Asp | Tyr | Glu | Ala | Gly | Asp | Asp | Arg | Val | Glu | Tyr |
|---|---|---|---|---|---|---|---|---|---|---|---|---|---|---|---|
| 145 | | | | | 150 | | | | | 155 | | | | | 160 |

| Leu | Arg | Gly | Gln | Phe | Asp | His | Ala | Ile | Lys | Gln | Leu | Glu | Asp | Leu | Thr |
|---|---|---|---|---|---|---|---|---|---|---|---|---|---|---|---|
| | | | | 165 | | | | | 170 | | | | | 175 | |

| Gly | Lys | Lys | Trp | Asp | Glu | Lys | Lys | Phe | Glu | Glu | Val | Met | Ala | Ile | Ser |
|---|---|---|---|---|---|---|---|---|---|---|---|---|---|---|---|
| | | | 180 | | | | | 185 | | | | | 190 | | |

| Gln | Arg | Thr | Gly | Arg | Ala | Trp | Leu | Lys | Ala | Thr | Gly | Tyr | Ala | Lys | Tyr |
|---|---|---|---|---|---|---|---|---|---|---|---|---|---|---|---|
| | 195 | | | | | 200 | | | | | 205 | | | | |

| Thr | Pro | Ser | Pro | Phe | Ser | Gly | Phe | Asp | Val | Phe | Asn | His | Met | Ala | Val |
|---|---|---|---|---|---|---|---|---|---|---|---|---|---|---|---|
| | 210 | | | | | 215 | | | | | 220 | | | | |

| Ala | Val | Cys | Ala | Arg | Gly | Lys | Glu | Glu | Ser | Ala | Ile | Ala | Phe | Glu | Lys |
|---|---|---|---|---|---|---|---|---|---|---|---|---|---|---|---|
| 225 | | | | | 230 | | | | | 235 | | | | | 240 |

| Leu | Ala | Glu | Glu | Phe | Asp | Glu | Asn | Val | Lys | Thr | Gly | Lys | Ser | Thr | Phe |
|---|---|---|---|---|---|---|---|---|---|---|---|---|---|---|---|
| | | | | 245 | | | | | 250 | | | | | 255 | |

| Lys | Gly | Glu | Glu | Lys | Tyr | Arg | Val | Leu | Phe | Glu | Gly | Ile | Ala | Cys | Trp |
|---|---|---|---|---|---|---|---|---|---|---|---|---|---|---|---|
| | | | 260 | | | | | 265 | | | | | 270 | | |

| Pro | His | Leu | Arg | His | Thr | Phe | Lys | Gln | Leu | Lys | Asp | Ser | Gly | Val | Asn |
|---|---|---|---|---|---|---|---|---|---|---|---|---|---|---|---|
| | | 275 | | | | | 280 | | | | | 285 | | | |

| Val | Cys | Gly | Thr | Val | Tyr | Ala | Asp | Ala | Phe | Gly | Tyr | Ile | Tyr | Asp | Asn |
|---|---|---|---|---|---|---|---|---|---|---|---|---|---|---|---|
| | 290 | | | | | 295 | | | | | 300 | | | | |

| Thr | Tyr | Glu | Leu | Met | Gln | Ala | Tyr | Cys | Gly | Thr | Pro | Asn | Ala | Ile | Ser |
|---|---|---|---|---|---|---|---|---|---|---|---|---|---|---|---|
| 305 | | | | | 310 | | | | | 315 | | | | | 320 |

| Tyr | Glu | Arg | Ser | Leu | Asp | Met | Arg | Leu | Lys | Val | Ile | Glu | Glu | Asn | Asn |
|---|---|---|---|---|---|---|---|---|---|---|---|---|---|---|---|
| | | | | 325 | | | | | 330 | | | | | 335 | |

| Ile | Asp | Gly | Met | Leu | Ile | His | Ile | Asn | Arg | Ser | Cys | Lys | Gln | Trp | Ser |
|---|---|---|---|---|---|---|---|---|---|---|---|---|---|---|---|
| | | | 340 | | | | | 345 | | | | | 350 | | |

| Gly | Ile | Met | Tyr | Glu | Met | Glu | Arg | Glu | Ile | Arg | Glu | Arg | Thr | Gly | Ile |
|---|---|---|---|---|---|---|---|---|---|---|---|---|---|---|---|
| | | 355 | | | | | 360 | | | | | 365 | | | |

```
Pro Thr Ala Thr Phe Asp Gly Asp Gln Ala Asp Pro Arg Asn Phe Ser
    370                 375                 380

Glu Ala Gln Tyr Asp Thr Arg Val Gln Gly Leu Ile Glu Val Met Glu
385                 390                 395                 400

Ala Asn Lys Ala Ala Lys Met Lys Glu Glu Asn
                405                 410

<210> SEQ ID NO 89
<211> LENGTH: 372
<212> TYPE: PRT
<213> ORGANISM: Peptostreptococcus anaerobius
<220> FEATURE:
<221> NAME/KEY: MISC_FEATURE
<222> LOCATION: (1)..(372)
<223> OTHER INFORMATION: CAG:621

<400> SEQUENCE: 89

Met Ser Asn Leu Glu Glu Leu Phe Gly Lys Leu Ala Val Cys Pro Leu
  1               5                  10                  15

Glu Gln Ile Asp Lys Tyr Val Ala Asp Gly Lys Lys Val Ile Gly Cys
             20                  25                  30

Ala Pro Val Tyr Ala Pro Glu Glu Leu Val Tyr Ala Ser Gly Met Ile
         35                  40                  45

Pro Met Ala Ile Trp Gly Ala Glu Gly Glu Val Thr Leu Ala Lys Glu
 50                  55                  60

Tyr Phe Pro Ala Phe Tyr Val Ser Ile Ile Leu Arg Leu Leu Asp Leu
 65                  70                  75                  80

Gly Leu Glu Gly Lys Leu Asp Lys Met Ser Gly Met Ile Leu Pro Gly
                 85                  90                  95

Leu Ser Asp Gly Leu Lys Gly Leu Ser Gln Asn Trp Lys Arg Ala Val
            100                 105                 110

Lys Asn Val Pro Ala Leu Tyr Ile Gly Tyr Gly Gln Asn Arg Lys Ile
        115                 120                 125

Glu Ala Gly Ile Val Tyr Asn Ala Arg Gln Tyr Glu Lys Leu Lys Val
    130                 135                 140

Gln Leu Glu Glu Ile Ala Gly Lys Lys Ile Glu Asp Ala Gln Ile Glu
145                 150                 155                 160

Glu Ala Ile Val Leu Tyr Asn Lys His Arg Lys Ala Met Gln Ala Phe
                165                 170                 175

Ser Asp Leu Ala Ala Lys His Leu Asn Thr Val Thr Pro Ser Leu Arg
            180                 185                 190

Ala Lys Val Met Ser Ser Ala Cys Leu Met Asp Lys Ala Glu His Leu
        195                 200                 205

Glu Ile Val Glu Ala Ile Asn Ala Glu Leu Ser Ala Met Pro Glu Glu
    210                 215                 220

Lys Phe Asp Gly Lys Lys Ile Val Thr Thr Gly Leu Leu Ala Asn Ser
225                 230                 235                 240

Pro Glu Ile Leu Lys Ile Phe Glu Glu Phe Lys Leu Gly Ile Val Ala
                245                 250                 255

Asp Asn Ile Asn His Glu Ser Gly Gln Phe Asp Tyr Leu Val Asp Glu
            260                 265                 270

Ala Thr Gly Asn Pro Ile Lys Ala Leu Ser Lys Trp Ile Ser Asp Ile
        275                 280                 285

Glu Gly Ser Thr Leu Leu Tyr Asp Pro Glu Lys Leu Arg Gly Gln Ile
    290                 295                 300

Ile Ile Asp Lys Ala Lys Lys Tyr Asp Ala Asp Gly Val Val Tyr Leu
```

```
                305                 310                 315                 320
Leu Ser Lys Phe Ser Asp Ser Asp Glu Phe Asp Tyr Pro Ile Ile Arg
            325                 330                 335

Lys Gln Leu Glu Glu Ala Gly Tyr Met His Ile Leu Val Glu Val Asp
            340                 345                 350

Gln Gln Met Thr Asn Phe Glu Gln Ala Lys Thr Ala Leu Gln Thr Phe
            355                 360                 365

Ala Asp Met Ile
        370

<210> SEQ ID NO 90
<211> LENGTH: 263
<212> TYPE: PRT
<213> ORGANISM: Peptostreptococcus anaerobius
<220> FEATURE:
<221> NAME/KEY: MISC_FEATURE
<222> LOCATION: (1)..(263)
<223> OTHER INFORMATION: CAG:621

<400> SEQUENCE: 90

Met Ser Asp Ile Tyr Thr Met Gly Ile Asp Ile Gly Ser Thr Ser Ser
  1               5                  10                  15

Lys Cys Val Val Leu Lys Asn Gly Lys Asp Leu Val Ser Ser Gly Val
             20                  25                  30

Val Asn Leu Gly Ala Gly Thr Lys Gly Ala Asp Gln Val Ile Glu Lys
         35                  40                  45

Val Leu Ala Asp Cys Gly Ile Lys Phe Glu Asp Leu Asn Val Ile Val
     50                  55                  60

Ser Thr Gly Tyr Gly Arg Asn Ser Tyr Asp Ser Ala Lys Lys Thr Met
 65                  70                  75                  80

Ser Glu Leu Ser Cys His Ala Lys Gly Gly Thr Tyr Ile Phe Gly Pro
                 85                  90                  95

Val Arg Thr Ile Ile Asp Ile Gly Gly Gln Asp Ile Lys Val Leu Lys
            100                 105                 110

Leu Asn Asp Lys Gly Met Met Thr Asn Phe Leu Met Asn Asp Lys Cys
        115                 120                 125

Ala Ala Gly Thr Gly Arg Phe Leu Glu Val Met Ala Gly Val Leu Asp
    130                 135                 140

Val Lys Leu Ala Glu Leu Gly Asp Leu Asp Lys Leu Ala Thr Glu Lys
145                 150                 155                 160

Thr Pro Ile Ser Ser Thr Cys Thr Val Phe Ala Glu Ser Glu Val Ile
                165                 170                 175

Ser Cys Met Ala Lys Lys Ile Pro Ile Pro Asn Ile Ile Arg Gly Ile
            180                 185                 190

His Ala Ser Val Ala Thr Arg Val Ala Gly Leu Ala Lys Arg Gly Gly
        195                 200                 205

Leu Thr Thr Pro Val Ala Met Thr Gly Gly Val Thr Lys Asn Ser Gly
    210                 215                 220

Ile Val Arg Ala Leu Ser Glu Glu Leu Glu Thr Asp Ile Met Ile Ser
225                 230                 235                 240

Glu Ile Ser Gln Leu Ala Gly Ala Ile Gly Ala Ala Leu Tyr Ala Tyr
                245                 250                 255

Asp Glu Tyr Leu Lys Glu Asn
            260

<210> SEQ ID NO 91
```

<211> LENGTH: 258
<212> TYPE: PRT
<213> ORGANISM: Chloroflexus aggregans
<220> FEATURE:
<221> NAME/KEY: MISC_FEATURE
<222> LOCATION: (1)..(258)
<223> OTHER INFORMATION: strain MD-66 / DSM 9485

<400> SEQUENCE: 91

```
Met Ser Asp Glu Thr Leu Val Leu Ser Thr Ile Glu Gly Pro Val Ala
 1               5                  10                  15

Ile Leu Thr Leu Asn Arg Pro Gln Ala Leu Asn Ala Leu Ser Pro Ala
            20                  25                  30

Leu Ile Asp Ala Leu Ile Arg His Leu Glu His Cys Asp Asn Asp Asp
        35                  40                  45

Thr Ile Arg Val Ile Ile Thr Gly Ala Gly Arg Ala Phe Ala Ala
    50                  55                  60

Gly Ala Asp Ile Lys Ala Met Ala Asp Ala Thr Pro Ile Asp Met Leu
65                  70                  75                  80

Thr Thr Asp Met Ile Ala Arg Trp Ala Arg Ile Ala Ala Val Arg Lys
                85                  90                  95

Pro Val Ile Ala Ala Val Asn Gly Phe Ala Leu Gly Gly Gly Cys Glu
            100                 105                 110

Leu Ala Met Met Cys Asp Ile Ile Leu Ala Ser Glu Thr Ala Gln Phe
        115                 120                 125

Gly Gln Pro Glu Ile Asn Ile Gly Ile Pro Gly Ala Gly Gly Thr
    130                 135                 140

Gln Arg Leu Thr Arg Ala Ile Gly Pro Tyr Arg Ala Met Glu Met Val
145                 150                 155                 160

Leu Thr Gly Ala Thr Ile Ser Ala Gln Glu Ala Tyr Ala Tyr Gly Leu
                165                 170                 175

Val Asn Arg Val Cys Pro Pro Asp Ser Leu Leu Asp Glu Ala Arg Arg
            180                 185                 190

Leu Ala Gln Thr Ile Ala Ala Lys Pro Pro Leu Ala Val Arg Leu Ala
        195                 200                 205

Lys Glu Ala Val Arg Ala Ala Glu Thr Thr Val Arg Glu Gly Leu
    210                 215                 220

Ala Ile Glu Leu Arg Asn Phe Tyr Leu Leu Phe Ala Ser Ala Asp Gln
225                 230                 235                 240

Lys Glu Gly Met Arg Ala Phe Ile Glu Lys Arg Thr Ala Asn Phe Ser
                245                 250                 255

Gly Arg
```

<210> SEQ ID NO 92
<211> LENGTH: 257
<212> TYPE: PRT
<213> ORGANISM: Marivirga tractuosa

<400> SEQUENCE: 92

```
Met Glu Phe Ile Lys Val Asn Thr Gln Tyr Lys Lys His Ile Ala Leu
 1               5                  10                  15

Ile Asn Leu Asn Arg Pro Lys Glu Leu Asn Ala Leu Asn Leu Gln Leu
            20                  25                  30

Met Thr Glu Leu Lys Asp Thr Leu Lys Val Leu Asp Glu Asp Glu Asn
        35                  40                  45

Val Arg Val Ile Ile Leu Thr Gly Asn Glu Lys Ala Phe Ala Ala Gly
    50                  55                  60
```

```
Ala Asp Ile Lys Gln Met Ala Gly Lys Thr Ala Ile Asp Met Leu Asn
 65                  70                  75                  80

Val Asp Gln Phe Ser Thr Trp Asp Gln Ile Lys Lys Thr Lys Lys Pro
                 85                  90                  95

Leu Ile Ala Ala Val Ser Gly Phe Ala Leu Gly Gly Gly Cys Glu Leu
            100                 105                 110

Ala Met Thr Cys Asp Met Ile Val Ala Ser Glu Ser Ala Lys Phe Gly
            115                 120                 125

Gln Pro Glu Ile Lys Ile Gly Val Met Pro Gly Ala Gly Gly Thr Gln
130                 135                 140

Arg Leu Thr Arg Ala Ile Gly Lys Ala Lys Ala Met Glu Leu Val Leu
145                 150                 155                 160

Thr Gly Asn Phe Ile Ser Ala Glu Glu Ala Met His Tyr Gly Leu Val
                165                 170                 175

Asn Lys Val Val Pro Thr Glu Met Tyr Leu Glu Ala Ala Glu Leu
            180                 185                 190

Ala Glu Gln Ile Ala Gln Met Ser Pro Val Ala Ala Lys Leu Ala Lys
            195                 200                 205

Glu Ser Val Asn Arg Ala Phe Glu Thr His Leu Asp Glu Gly Leu His
210                 215                 220

Phe Glu Arg Lys Asn Phe Tyr Leu Thr Phe Ala Ser Glu Asp Gln Thr
225                 230                 235                 240

Glu Gly Met Glu Ala Phe Val Glu Lys Arg Lys Pro Glu Phe Lys Gly
                245                 250                 255

Lys

<210> SEQ ID NO 93
<211> LENGTH: 257
<212> TYPE: PRT
<213> ORGANISM: Marinithermus hydrothermalis
<220> FEATURE:
<221> NAME/KEY: MISC_FEATURE
<222> LOCATION: (1)..(257)
<223> OTHER INFORMATION: strain DSM 14884/JCM 11576/T1

<400> SEQUENCE: 93

Met Tyr Glu Asn Leu Ile Val Glu Thr Leu Glu Gly Gly Val Gly Leu
  1               5                  10                  15

Ile Arg Ile His Arg Pro Lys Arg Leu Asn Ala Leu Asn Gln Ala Thr
                 20                  25                  30

Met Asp Glu Ile Val Arg Ala Val Arg Ala Phe Glu Ala Asp Asp Ala
             35                  40                  45

Val Arg Ala Ile Val Leu Thr Gly Asp Glu Arg Ala Phe Ala Ala Gly
         50                  55                  60

Ala Asp Val Thr Glu Met Asp Gly Ala Asn Val Pro Glu Met Leu Ser
 65                  70                  75                  80

Gly Tyr Arg Phe Glu Gln Trp Gly Thr Leu Arg Arg Thr Thr Lys Pro
                 85                  90                  95

Leu Ile Ala Ala Val Ser Gly Phe Ala Leu Gly Gly Gly Leu Glu Leu
            100                 105                 110

Ala Met Leu Cys Asp Ile Ile Val Ala Ser Glu Thr Ala Arg Leu Gly
            115                 120                 125

Gln Pro Glu Ile Asn Leu Gly Ile Met Pro Gly Ala Gly Gly Thr Gln
130                 135                 140

Arg Leu Thr Arg Gln Val Gly Lys Tyr Leu Ala Met Glu Met Val Leu
```

```
                145                 150                 155                 160
Thr Gly Arg Met Leu Thr Ala Glu Glu Ala Tyr Arg His Gly Leu Val
                    165                 170                 175

Asn Arg Val Val Pro Val Glu Phe Tyr Leu Glu Glu Ala Ile Gln Ile
                180                 185                 190

Ala Arg Glu Ile Ala Lys Lys Ala Pro Val Ala Val Arg Leu Ala Lys
                    195                 200                 205

Asp Ala Ile Leu Lys Ala Glu Asp Thr Pro Leu Glu Val Gly Leu Ala
                210                 215                 220

Tyr Glu Arg His Asn Phe Tyr Leu Leu Phe Gly Thr Glu Asp Lys Gln
225                 230                 235                 240

Glu Gly Ile Arg Ala Phe Leu Glu Lys Arg Lys Pro Glu Trp Lys Gly
                    245                 250                 255

Arg

<210> SEQ ID NO 94
<211> LENGTH: 259
<212> TYPE: PRT
<213> ORGANISM: Chitinophaga pinensis
<220> FEATURE:
<221> NAME/KEY: MISC_FEATURE
<222> LOCATION: (1)..(259)
<223> OTHER INFORMATION: strain ATCC 43595/DSM 2588/NCIB11800/UQM 2034

<400> SEQUENCE: 94

Met Gln Pro Gln Phe Ile Ile Ile His Arg Gln Val Ala Pro Tyr Val
1               5                   10                  15

Ala His Ile Gln Leu Asn Arg Pro Lys Glu Leu Asn Ala Leu Asn Leu
                20                  25                  30

Glu Leu Met Ile Glu Leu Arg Asp Ala Leu Lys Met Leu Asp Ala Asp
            35                  40                  45

Asp Asn Val Arg Ala Ile Val Ile Ser Gly Asn Glu Lys Ala Phe Ala
        50                  55                  60

Ala Gly Ala Asp Ile Lys Gln Met Ala Gly Lys Thr Ala Met Asp Met
65                  70                  75                  80

Tyr Asn Ile Asp Gln Phe Ser Thr Trp Asp Thr Ile Lys Lys Thr Lys
                85                  90                  95

Lys Pro Leu Ile Ala Ala Val Ser Gly Phe Ala Leu Gly Gly Gly Cys
                100                 105                 110

Glu Leu Val Met Leu Cys Asp Met Ile Val Ala Ser Glu Thr Ala Arg
            115                 120                 125

Phe Gly Gln Pro Glu Ile Lys Ile Gly Val Met Pro Gly Ala Gly Gly
        130                 135                 140

Thr Gln Arg Leu Thr Arg Ala Val Gly Lys Ala Leu Ala Met Glu Met
145                 150                 155                 160

Val Leu Thr Gly Arg Phe Ile Thr Ala Gln Glu Ala Ala Arg Ala Gly
                165                 170                 175

Leu Ile Asn Arg Val Ile Pro Val Glu Leu Phe Leu Gln Glu Ala Ile
                180                 185                 190

Arg Leu Ala Thr Glu Val Ala Ala Leu Ser Pro Leu Ala Val Lys Met
            195                 200                 205

Ala Lys Glu Ser Val Leu Lys Ala Phe Asp Ser Ser Leu Glu Glu Gly
        210                 215                 220

Leu His Phe Glu Arg Lys Asn Phe Tyr Leu Leu Phe Ala Ser Glu Asp
225                 230                 235                 240
```

```
Gln Lys Glu Gly Met Gln Ala Phe Val Asp Lys Arg Ser Pro Val Phe
                245                 250                 255

Lys Gly Lys

<210> SEQ ID NO 95
<211> LENGTH: 258
<212> TYPE: PRT
<213> ORGANISM: Megasphaera elsdenii
<220> FEATURE:
<221> NAME/KEY: MISC_FEATURE
<222> LOCATION: (1)..(258)
<223> OTHER INFORMATION: DSM 20460

<400> SEQUENCE: 95

Met Tyr Thr Leu Gly Ile Asp Val Gly Ser Ser Ser Lys Ala Val
  1               5                  10                  15

Ile Leu Glu Asp Gly Lys Lys Ile Val Ala His Ala Val Val Glu Ile
                 20                  25                  30

Gly Thr Gly Ser Thr Gly Pro Glu Arg Val Leu Asp Glu Val Phe Lys
                 35                  40                  45

Asp Thr Asn Leu Lys Ile Glu Asp Met Ala Asn Ile Ile Ala Thr Gly
             50                  55                  60

Tyr Gly Arg Phe Asn Val Asp Cys Ala Lys Gly Glu Val Ser Glu Ile
 65                  70                  75                  80

Thr Cys His Ala Lys Gly Ala Leu Phe Glu Cys Pro Gly Thr Thr Thr
                 85                  90                  95

Ile Leu Asp Ile Gly Gly Gln Asp Val Lys Ser Ile Lys Leu Asn Gly
                100                 105                 110

Gln Gly Leu Val Met Gln Phe Ala Met Asn Asp Lys Cys Ala Ala Gly
                115                 120                 125

Thr Gly Arg Phe Leu Asp Val Met Ser Lys Val Leu Glu Ile Pro Met
                130                 135                 140

Ser Glu Met Gly Asp Trp Tyr Phe Lys Ser Lys His Pro Ala Ala Val
145                 150                 155                 160

Ser Ser Thr Cys Thr Val Phe Ala Glu Ser Glu Val Ile Ser Leu Leu
                165                 170                 175

Ser Lys Asn Val Pro Lys Glu Asp Ile Val Ala Gly Val His Gln Ser
                180                 185                 190

Ile Ala Ala Lys Ala Cys Ala Leu Val Arg Arg Val Gly Val Gly Glu
                195                 200                 205

Asp Leu Thr Met Thr Gly Gly Ser Arg Asp Pro Gly Val Val Asp
                210                 215                 220

Ala Val Ser Lys Glu Leu Gly Ile Pro Val Arg Val Ala Leu His Pro
225                 230                 235                 240

Gln Ala Val Gly Ala Leu Gly Ala Ala Leu Ile Ala Tyr Asp Lys Ile
                245                 250                 255

Lys Lys

<210> SEQ ID NO 96
<211> LENGTH: 428
<212> TYPE: PRT
<213> ORGANISM: Megasphaera elsdenii
<220> FEATURE:
<221> NAME/KEY: MISC_FEATURE
<222> LOCATION: (1)..(428)
<223> OTHER INFORMATION: DSM 20460

<400> SEQUENCE: 96
```

```
Met Ser Glu Glu Lys Thr Val Asp Ile Glu Ser Met Ser Ser Lys Glu
  1               5                  10                  15

Ala Leu Gly Tyr Phe Leu Pro Lys Val Asp Glu Asp Ala Arg Lys Ala
                 20                  25                  30

Lys Lys Glu Gly Arg Leu Val Cys Trp Ser Ala Ser Val Ala Pro Pro
         35                  40                  45

Glu Phe Cys Thr Ala Met Asp Ile Ala Ile Val Tyr Pro Glu Thr His
     50                  55                  60

Ala Ala Gly Ile Gly Ala Arg His Gly Ala Pro Ala Met Leu Glu Val
 65              70                  75                      80

Ala Glu Asn Lys Gly Tyr Asn Gln Asp Ile Cys Ser Tyr Cys Arg Val
                 85                  90                  95

Asn Met Gly Tyr Met Glu Leu Leu Lys Gln Gln Ala Leu Thr Gly Glu
                 100                 105                 110

Thr Pro Glu Val Leu Lys Asn Ser Pro Ala Ser Pro Ile Pro Leu Pro
             115                 120                 125

Asp Val Val Leu Thr Cys Asn Asn Ile Cys Asn Thr Leu Leu Lys Trp
             130                 135                 140

Tyr Glu Asn Leu Ala Lys Glu Leu Asn Val Pro Leu Ile Asn Ile Asp
145                 150                 155                 160

Val Pro Phe Asn His Glu Phe Pro Val Thr Lys His Ala Lys Gln Tyr
                 165                 170                 175

Ile Val Gly Glu Phe Lys His Ala Ile Lys Gln Leu Glu Asp Leu Cys
                 180                 185                 190

Gly Arg Pro Phe Asp Tyr Asp Lys Phe Phe Glu Val Gln Lys Gln Thr
             195                 200                 205

Gln Arg Ser Ile Ala Ala Trp Asn Lys Ile Ala Thr Tyr Phe Gln Tyr
         210                 215                 220

Lys Pro Ser Pro Leu Asn Gly Phe Asp Leu Phe Asn Tyr Met Gly Leu
225                 230                 235                 240

Ala Val Ala Ala Arg Ser Leu Asn Tyr Ser Glu Ile Thr Phe Asn Lys
                 245                 250                 255

Phe Leu Lys Glu Leu Asp Glu Lys Val Ala Asn Lys Lys Trp Ala Phe
                 260                 265                 270

Gly Glu Asn Glu Lys Ser Arg Val Thr Trp Glu Gly Ile Ala Val Trp
                 275                 280                 285

Ile Ala Leu Gly His Thr Phe Lys Glu Leu Lys Gly Gln Gly Ala Leu
                 290                 295                 300

Met Thr Gly Ser Ala Tyr Pro Gly Met Trp Asp Val Ser Tyr Glu Pro
305                 310                 315                 320

Gly Asp Leu Glu Ser Met Ala Glu Ala Tyr Ser Arg Thr Tyr Ile Asn
                 325                 330                 335

Cys Cys Leu Glu Gln Arg Gly Ala Val Leu Glu Lys Val Val Arg Asp
                 340                 345                 350

Gly Lys Cys Asp Gly Leu Ile Met His Gln Asn Arg Ser Cys Lys Asn
                 355                 360                 365

Met Ser Leu Leu Asn Asn Glu Gly Gly Gln Arg Ile Gln Lys Asn Leu
                 370                 375                 380

Gly Val Pro Tyr Val Ile Phe Asp Gly Asp Gln Thr Asp Ala Arg Asn
385                 390                 395                 400

Phe Ser Glu Ala Gln Phe Asp Thr Arg Val Glu Ala Leu Ala Glu Met
                 405                 410                 415

Met Ala Asp Lys Lys Ala Asn Glu Gly Gly Asn His
```

<210> SEQ ID NO 97
<211> LENGTH: 372
<212> TYPE: PRT
<213> ORGANISM: Megasphaera elsdenii
<220> FEATURE:
<221> NAME/KEY: MISC_FEATURE
<222> LOCATION: (1)..(372)
<223> OTHER INFORMATION: DSM 20460

<400> SEQUENCE: 97

Met Ser Gln Ile Asp Glu Leu Ile Ser Lys Leu Gln Glu Val Ser Asn
1               5                   10                  15

His Pro Gln Lys Thr Val Leu Asn Tyr Lys Lys Gln Gly Lys Gly Leu
            20                  25                  30

Val Gly Met Met Pro Tyr Tyr Ala Pro Glu Glu Ile Val Tyr Ala Ala
        35                  40                  45

Gly Tyr Leu Pro Val Gly Met Phe Gly Ser Gln Asn Pro Gln Ile Ser
    50                  55                  60

Ala Ala Arg Thr Tyr Leu Pro Pro Phe Ala Cys Ser Leu Met Gln Ala
65                  70                  75                  80

Asp Met Glu Leu Gln Leu Asn Gly Thr Tyr Asp Cys Leu Asp Ala Val
                85                  90                  95

Ile Phe Ser Val Pro Cys Asp Thr Leu Arg Cys Met Ser Gln Lys Trp
            100                 105                 110

His Gly Lys Ala Pro Val Ile Val Phe Thr Gln Pro Gln Asn Arg Lys
        115                 120                 125

Ile Arg Pro Ala Val Asp Phe Leu Lys Ala Glu Tyr Glu His Val Arg
    130                 135                 140

Thr Glu Leu Glu Arg Ile Leu Asn Val Lys Ile Ser Asp Leu Ala Ile
145                 150                 155                 160

Gln Glu Ala Ile Lys Val Tyr Asn Glu Asn Arg Gln Val Met Arg Glu
                165                 170                 175

Phe Cys Asp Val Ala Ala Gln Tyr Pro Gln Ile Phe Thr Pro Val Lys
            180                 185                 190

Arg His Asp Val Ile Lys Ala Arg Trp Phe Met Asp Lys Ala Glu His
        195                 200                 205

Thr Ala Leu Val Arg Glu Leu Ile Asp Ala Val Lys Lys Glu Pro Val
    210                 215                 220

Gln Pro Trp Asn Gly Lys Lys Val Ile Leu Ser Gly Ile Met Ala Glu
225                 230                 235                 240

Pro Asp Glu Phe Leu Asp Ile Phe Ser Glu Phe Asn Ile Ala Val Val
                245                 250                 255

Ala Asp Asp Leu Ala Gln Glu Ser Arg Gln Phe Arg Thr Asp Val Pro
            260                 265                 270

Ser Gly Ile Asp Pro Leu Glu Gln Leu Ala Gln Gln Trp Gln Asp Phe
        275                 280                 285

Asp Gly Cys Pro Leu Ala Leu Asn Glu Asp Lys Pro Arg Gly Gln Met
    290                 295                 300

Leu Ile Asp Met Thr Lys Lys Tyr Asn Ala Asp Ala Val Val Ile Cys
305                 310                 315                 320

Met Met Arg Phe Cys Asp Pro Glu Glu Phe Asp Tyr Pro Ile Tyr Lys
                325                 330                 335

Pro Glu Phe Glu Ala Ala Gly Val Arg Tyr Thr Val Leu Asp Leu Asp
            340                 345                 350

```
Ile Glu Ser Pro Ser Leu Glu Gln Leu Arg Thr Arg Ile Gln Ala Phe
            355                 360                 365

Ser Glu Ile Leu
    370

<210> SEQ ID NO 98
<211> LENGTH: 258
<212> TYPE: PRT
<213> ORGANISM: Chloroflexus aurantiacus
<220> FEATURE:
<221> NAME/KEY: MISC_FEATURE
<222> LOCATION: (1)..(258)
<223> OTHER INFORMATION: strain ATCC 29364 / DSM 637 / Y-400-fl

<400> SEQUENCE: 98

Met Ser Glu Glu Ser Leu Val Leu Ser Thr Ile Glu Gly Pro Ile Ala
1               5                   10                  15

Ile Leu Thr Leu Asn Arg Pro Gln Ala Leu Asn Ala Leu Ser Pro Ala
            20                  25                  30

Leu Ile Asp Asp Leu Ile Arg His Leu Glu Ala Cys Asp Ala Asp Asp
        35                  40                  45

Thr Ile Arg Val Ile Ile Thr Gly Ala Gly Arg Ala Phe Ala Ala
    50                  55                  60

Gly Ala Asp Ile Lys Ala Met Ala Asn Ala Thr Pro Ile Asp Met Leu
65                  70                  75                  80

Thr Ser Gly Met Ile Ala Arg Trp Ala Arg Ile Ala Ala Val Arg Lys
                85                  90                  95

Pro Val Ile Ala Ala Val Asn Gly Tyr Ala Leu Gly Gly Gly Cys Glu
            100                 105                 110

Leu Ala Met Met Cys Asp Ile Ile Ala Ser Glu Asn Ala Gln Phe
        115                 120                 125

Gly Gln Pro Glu Ile Asn Leu Gly Ile Ile Pro Gly Ala Gly Gly Thr
    130                 135                 140

Gln Arg Leu Thr Arg Ala Leu Gly Pro Tyr Arg Ala Met Glu Leu Ile
145                 150                 155                 160

Leu Thr Gly Ala Thr Ile Ser Ala Gln Glu Ala Leu Ala His Gly Leu
                165                 170                 175

Val Cys Arg Val Cys Pro Pro Glu Ser Leu Leu Asp Glu Ala Arg Arg
            180                 185                 190

Ile Ala Gln Thr Ile Ala Thr Lys Ser Pro Leu Ala Val Gln Leu Ala
        195                 200                 205

Lys Glu Ala Val Arg Met Ala Ala Glu Thr Thr Val Arg Glu Gly Leu
    210                 215                 220

Ala Ile Glu Leu Arg Asn Phe Tyr Leu Leu Phe Ala Ser Ala Asp Gln
225                 230                 235                 240

Lys Glu Gly Met Gln Ala Phe Ile Glu Lys Arg Ala Pro Asn Phe Ser
                245                 250                 255

Gly Arg

<210> SEQ ID NO 99
<211> LENGTH: 900
<212> TYPE: DNA
<213> ORGANISM: Dictyostelium discoideum
<220> FEATURE:
<221> NAME/KEY: MISC_FEATURE
<222> LOCATION: (1)..(900)
<223> OTHER INFORMATION: Slime mold
```

<400> SEQUENCE: 99

```
atgattaata gattattttc aattaataat attaaaaatg gatcaaaatt ttttagttca      60
tcaacaacag ttgaaactaa acaaccatta gttttattag aaaaacattt agtaaatgga     120
aaatatacag gtattcaaat tgttaaatta aataaaccaa acaattgaa tgcattaaca      180
tttgaaatgg gagttgatta taagaaggtg gtggatacat tagcagaaga taaagatttg     240
aaatgtgttg tattgacagg tgaaggtaag gcattttcgg caggtggtga tttagatttc     300
ttaattgaaa gaactaaaga cacaccagaa acaatcaaa gaattatgga aagattctat      360
agaacatttt tatatattcg ttcattacca gtaccaatca tttctgcaat caatggtgca     420
gcaattggtg caggtttctg tttagctta gcaactgata ttcgtgtcgt tagtaataaa      480
gcaccagtgg gtttaacatt caccaaatta ggtattcatc caggtatggg tgtaactcat     540
tcaattacaa atatagttgg tcaagatgtt gcatcctata tgttattatc aagtgatatt     600
atcaaaggtg atgaagctca agattaggt ttagttttaa atcggttga atctgatcaa       660
gttttaccaa ctgctttaaa tctcgctgaa acaatctcaa aaaattcaac tatcgctgta     720
aactctacaa caaaaacttt acgtaataaa tataattcag atttagataa aagtttaact     780
cgtgaagctg atgctcaaag tcaatgttgg gcttcaaaag atatagttga aggtatttta     840
gcaattagag aaagtagaga tccaaaacat aattatttat tatttgatga tcaaaaataa    900
```

<210> SEQ ID NO 100
<211> LENGTH: 786
<212> TYPE: DNA
<213> ORGANISM: Clostridium acetobutylicum

<400> SEQUENCE: 100

```
atggaactaa acaatgtcat ccttgaaaag gaaggtaaag ttgctgtagt taccattaac      60
agacctaaag cattaaatgc gttaaatagt gatacactaa agaaatgga ttatgttata      120
ggtgaaattg aaaatgatag cgaagtactt gcagtaattt taactggagc aggagaaaaa     180
tcatttgtag caggagcaga tatttctgag atgaaggaaa tgaataccat tgaaggtaga     240
aaattcggga tacttggaaa taagtgtttt agaagattag aacttcttga aaagcctgta     300
atagcagctg ttaatggttt tgcttttagga ggcggatgcg aaatagctat gtcttgtgat    360
ataagaatag cttcaagcaa cgcaagattt ggtcaaccag aagtaggtct cggaataaca     420
cctggttttg gtggtacaca aagactttca agattagttg gaatgggcat ggcaaagcag     480
cttatattta ctgcacaaaa tataaaggca gatgaagcat taagaatcgg acttgtaaat    540
aaggtagtag aacctagtga attaatgaat acagcaaaag aaattgcaaa caaaattgtg     600
agcaatgctc cagtagctgt taagttaagc aaacaggcta ttaatagagg aatgcagtgt     660
gatattgata ctgctttagc atttgaatca gaagcatttg gagaatgctt ttcaacagag     720
gatcaaaagg atgcaatgac agctttcata gagaaaagaa aaattgaagg cttcaaaaat     780
agatag                                                                786
```

<210> SEQ ID NO 101
<211> LENGTH: 468
<212> TYPE: DNA
<213> ORGANISM: Clostridium difficile

<400> SEQUENCE: 101

```
aatagtaaaa aagtagtgat agctgctgta acggatttg ctttaggtgg atgtgaactt       60
gcaatggcat gtgatataag aattgcatct gctaaagcta aatttggtca gccagaagta     120
```

```
actcttggaa taactccagg atatggagga actcaaaggc ttacaagatt ggttggaatg    180
gcaaaagcaa aagaattaat ctttacaggt caagttataa aagctgatga agctgaaaaa    240
atagggctag taaatagagt cgttgagcca gacattttaa tagaagaagt tgagaaatta    300
gctaagataa tagctaaaaa tgctcagctt gcagttagat actctaaaga agcaatacaa    360
cttggtgctc aaactgatat aaatactgga atagatatag aatctaattt atttggtctt    420
tgtttttcaa ctaaagacca aaaagaagga attgtcagct ttcgttga                468
```

<210> SEQ ID NO 102
<211> LENGTH: 777
<212> TYPE: DNA
<213> ORGANISM: Clostridium pasteurianum

<400> SEQUENCE: 102

```
atgggaaata ttatctttga agaagaagat ggaatagaaa aagttacaat taacagacct     60
aaagctctta atgcattaaa tagtgaaaca ttaaaagaac ttggtacagt aataaatgac    120
atatctgtaa acgatggaat aaaagctgta ataataacag gttcgggatc aaaagctttt    180
gtagctggtg cagatatagc tgaaatgagt actctaaatt caatagaggc aacaaatttt    240
tcaagacttg cccaaaatgt attttcacaa atagaaaatc tacctaaatt agtagtagca    300
gcagttaacg gttttgctct tggaggagga tgtgagcttg caatggcttg tgatgtaagg    360
tttgcttcaa aaaaagctaa atttggtcaa ccagaagtta atttaggaat attgccaagt    420
ttcggaggaa ctcaacggct tccaaaattg gttggaaagg gaatagcaaa agaattgata    480
ttttctacag atatgattac tgccgatgaa gcttatcgta taggacttgc taataaagtc    540
tatgaacctg aggaattatt agtaaaatca caggagtttg ctgaaaaggt aatgactaaa    600
tctccatggg gtgttaaatt agcaaaagca tgtataaata atggattaga tgtagatttg    660
gaagcaggac ttaaatatga agcaaattca tttggtctgt gtttttcaac ggaagatcaa    720
aaggaaggta tgaaagcatt tttagaaaaa agaaaagcag acttcaaagg actttaa       777
```

<210> SEQ ID NO 103
<211> LENGTH: 789
<212> TYPE: DNA
<213> ORGANISM: Clostridium pasteurianum

<400> SEQUENCE: 103

```
atggatttta ataatattat ccttgaaaaa gaggaaaaaa ttgccgtagt tacaattaat     60
agacctaaag ctcttaatgc tttgaacagt gaaacgttaa ctgagcttga ttctgtaatt    120
gatgaaattg acaaagataa tgaaatttta gcagtggtat taacgggagc gggaaaatcc    180
ttcgtagctg gagccgatat atcagaaatg aaagacatga atgtagtaga aggaagaaaa    240
tttggaatac taggtaataa ggtgttcaga aaacttgaaa atttagaaaa gccagtaata    300
gcagccctta atggatttac attgggtggt ggttgtgaaa ttgctatgtc ttgcgatata    360
agaatagctt ctactaaggc aaaatttgga cagccagagg tacagcttgg aataactcca    420
ggttttggcg gtactcaaag attagctaga ttaataggcc caggagctgc aaaggaactt    480
atatatactg gaaaaattat aaatgctgaa gaggcctata gattaggact tgttaataga    540
gttatagaac cagaaacttt attagatgaa gcaaaacaat tggcaaatac tatagcagcc    600
aatgcaccta tagctgttaa gttggctaaa tcagcaataa atagaggaat tcaaactgat    660
attgatacag gtgtgtcaat tgaatcagaa gtatttggag cttgtttctc tacagaagat    720
```

-continued

```
caaaaagaag gtatgaatac attcttgaat gataaaaaat atttaactgg taattttaag    780
aataaataa                                                            789

<210> SEQ ID NO 104
<211> LENGTH: 783
<212> TYPE: DNA
<213> ORGANISM: Megasphaera elsdenii

<400> SEQUENCE: 104
atggattacc agaacattat ttttgctgta gaagacggta ttgcaacgat tacgatcaat     60
cgcccgaagg ctctgaacgc tttgaaccag gctacggtca gcgaattgaa agacgtcgtt    120
gaaaagattg cagctgataa agctatcaaa gtcgtcatca tcaccggtgc aggcgctaaa    180
tccttcgtcg ctggcgctga catcaaagaa atggcttcca agaacgctgc tgaaggccgc    240
gaatggggcc agttcggtca gaacgtcttc acggaaatcg aaaacctgcc gcagcctgtc    300
atcgcagcta tcaacggctt cgctctcggc ggcggctgcg aactctcctg cgcttgcgat    360
atccgctatg cagctgaaaa cgctaaattc ggccagccgg aagtcggctt gggcatcact    420
ccgggctttg cggcacgca gcgcctgacc cgtgtcgtag ccgcggcca cgcgaaagaa     480
ctcatctaca cgggcggcat gatcgacgct gaaaaagcaa agctatcgg cttggtcaat    540
gaagtcttcc gcaggaaga actgatgccg gctgctgtta aattggctaa gaagatcgct    600
aagaacgctc ctattgcagt acagctctcc aaagctgcca tcaaccgcgg catcaactgc    660
gacgtcgtaa ccggtatcgc ttatgaagct gaagtcttcg gcctctgctt ctccacggct    720
gaccagaagg aaggcatggc tgctttctgc gaaaaacgca agcaacgtt tgaaggtaaa    780
taa                                                                 783

<210> SEQ ID NO 105
<211> LENGTH: 780
<212> TYPE: DNA
<213> ORGANISM: Metallosphaera sedula

<400> SEQUENCE: 105
atggaatttg aaacaataga aactaaaaaa gaaggaaact tgttctggat tacgttaaat     60
agacccgata aactaaacgc actaaacgct aaattacttg aggagttaga tagggcagtc    120
tctcaggcag agtctgaccc agagattagg gttatcatca ttacagggaa aggaaaggcc    180
ttctgcgcag gggctgacat aacccagttt aaccagttaa ccccagcaga agcctggaaa    240
ttctctaaga aggaagaga gatcatggac aagatagagg cactgagcaa acccaccatt    300
gccatgatca atggatatgc ccttgggggt ggactagagc tagccttagc ctgtgatata    360
aggatcgcag cggaggaggc ccaactaggc cttccagaga taaacctagg gatatatccg    420
gggtatgggg ggactcagag gttaaccaga gttataggaa agggaagagc cctggagatg    480
atgatgacgg gcgatcgtat tcctggtaag gatgctgaga atatggtct cgtgaatagg    540
gttgtccccc tagctaactt ggagcaagag acaaggaagc tggcagaaaa gatagccaag    600
aagtctccta tctctctcgc cttaatcaag gaagttgtaa acaggggact agactctccc    660
ctactgtcag gtctagcgtt ggaaagcgta ggatggggag tcgtgttttc tacggaggac    720
aagaaggagg gggtaagtgc cttcctggag aagagagagc ctacgtttaa gggaaaatag    780

<210> SEQ ID NO 106
<211> LENGTH: 779
<212> TYPE: DNA
<213> ORGANISM: Clostridicum kluyvery
```

<400> SEQUENCE: 106

```
atggaattta aaaatatcat tcttgaaaag gatggaaatg tggcttcaat aacgttgaat      60
agacctaagg cattaaatgc attaaatgca gcaactttaa aagagataga tgccgcaata     120
aacgacattg ctgaagatga taacgtatat gctgtgataa ttactgggtc aggtaaagct     180
tttgtagcag gagcagatat agctgagatg aaagatctta ctgcagttga gggaagaaag     240
ttttcagttc ttggcaataa atatttaga aaattagaaa atttagaaaa accagttata      300
gcagctataa atggatttgc actgggtggt ggctgtgaat tgtcattgtc ttgcgatata     360
agaatagctt catcaaaggc taagtttggt caaccagagg ttggtcttgg aattactcca     420
gggtttggag gtactcaaag acttgcaaga gcaataggcg ttggtatggc taaggaactt     480
atataccg aaaagtaat taatgctgaa gaggcattaa aataggtttt ggtaaataaa       540
gtagttgagc cagataaatt attggaagaa gctaaagctt tagtagatgc tattattgtt     600
aatgcaccta tagctgttag aatgtgtaag gctgctataa atcaaggact tcagtgtgat     660
atagatacag gtgtagctta tgaagcagaa gtatttgggg aatgttttgc tacagaagat     720
agagtagaag gaatgacagc atttgtagaa aaagagaca aggcttttaa aaataagta       779
```

<210> SEQ ID NO 107
<211> LENGTH: 1509
<212> TYPE: DNA
<213> ORGANISM: Sulfolobus tokodaii

<400> SEQUENCE: 107

```
atggcaatta gaactggaga gcaatattta gattctataa aaattagaaa taaggctgaa      60
atttacgtaa tgggaaaaga agtaaaggat gtaaccactc atcccttctt gaaaccttct     120
gtaatggcat ttaaggcaac atttgatgct gcttgggaag aggacacaaa agaattagcc     180
agagcatgga gtccttttcat aaatgaagaa gtgaatagat ttaatcacat acacaggtca     240
ccagaagact tagctgctaa agtgaaatta ctgagaaaat taagccataa gaccggtgca     300
tgtttccaaa gatgtgtagg atgggacgct ctgaacactt tgtggattat gacgaatata     360
atggctcaaa aaggtaaaaa agaatataag gatagatttg tcgaatactt aagttacgtc     420
caaaagaagg atttagcatt agctggtgct atgacagatg caaaaggtgt aagaacatta     480
aaaccgcatc aacaaccaaa taagaacgct tatgttagaa ttgaggaagt taccaaagac     540
ggtatttatg tttctggtgc aaaggcaaat attactggtg tagctgcaac agaagaaatt     600
gtggttttac ctactagggc tatggggcca aagataaag attatgctgt tgcattttca     660
ataccgacag atactgaggg tataaaaatt atagttggta gacaattaaa tgatgctaga     720
agattagaag gtggtgacat agatgcttta ccgtacttct ataaccacga gggtttagta     780
atctttgacc atgttttgt accaatggat agagtattct taatgggaga atacgagttt     840
acttcacaat tagttgaagt attctcagca tatcatagac aaggatatgg tggttgcaag     900
gctggtttag gagatgtaat tattggtgca tcaatgaatt tagcaaaaca attaggagta     960
gaaaaagctt cacatgtaca agaaaaacta acggaaatga tattcttaac tgagaccatg    1020
tattctgcag gaattgcagc tagtttaaat gcagttaagg tctgcgataa ttgttggtgg    1080
gttaatccta tgcacgctaa tgttacaaaa catttagtag ctagatttcc agcccagatt    1140
tctcagttat ctatcgatat tgcaggtgga ataataggta ctgcaccaag tgagtgggat    1200
ctcaagaatc ctaaattaag agaatatatt gccaaatact tacaaggtgt tgagggttat    1260
```

| acagctgaag atagattaag aatggttaga ttactggaaa acgttagtct gggtgttgca | 1320 |
| ttccaaattg aatctgtaca cggtgcagga agtccagcag cacaaagaat aatgtttagt | 1380 |
| agactttatg acttaaacta tgctgaggaa gtcgcaaaga ggttagctgg gaagaagact | 1440 |
| gatttacagt ggaaacctaa agcagagcct tggagagaaa gtgagacaga aaaattagta | 1500 |
| aaaagttaa | 1509 |

<210> SEQ ID NO 108
<211> LENGTH: 1452
<212> TYPE: DNA
<213> ORGANISM: Geobacter metallireducens

<400> SEQUENCE: 108

| atggcactaa gagatgggaa ttcctaccgg gaaagccttc gggcgctcaa tatcaaagtc | 60 |
| tatgcctttg gagagaagat tgacagcata gtagatcacc cattgttcca gccccatatc | 120 |
| aatgcggctg cattgacgtt cgacttggcc catgatccga ccacggaagc gctcgtcaca | 180 |
| gccacctcac acctgacggg gagtaaaatc agccgcttca cccatatcca ccagagcacc | 240 |
| gacgatctca taaaaaaggt gaagatgttg cggcttattg cagggaagac gggaagttgc | 300 |
| taccagcgct gtgtggggtg ggatgccctg aacgctaact atacggtaac ctatgagatg | 360 |
| gaccaggagc ttggtaccga ctatcaccag cgttttaggc gttacctcga atatatacag | 420 |
| gacaatgacc tgatggtggc gggagcaatg accgatccca aggggacag ggggctgcct | 480 |
| ccggcaaaac agaaagaccc ggacatgttc gtgcacgtgg tggcaaagaa tgacaagggg | 540 |
| atagtcattc gtggggcaaa ggttcaccag accggaattg tcaattccca tgaaatgctg | 600 |
| attatgccaa ccatggccat ggggggaggag acggcgact atgcggttgc ctgtgctctc | 660 |
| cccacggatt cccccggtgt catccatatc tttggtcgtc aaaccaacga tacacgccgt | 720 |
| ctggaaaagg gagaccttga tcagggtaat gctgagtatg gaactgtcgg aggcgaggct | 780 |
| ttgaccatac ttgaagatgt cttcgtcccg tgggaacgcg tcttcatgtg cggagagtac | 840 |
| aagtatgcgg ggctgctggt tgagcgtttc gcgagctatc atcgacagaa ctatggtgga | 900 |
| tgcaaggcag gcgtgagcga tgtgatcatc ggcgcaacta ccgctatggc agagtacaac | 960 |
| ggagcagcca aggcttccca cgtgcgtgac aagatcgtgg agatggtcca cctcaccgag | 1020 |
| acccttatt gcggttccat cgcctgctcc tgtgagggtg ctcccacgcc gtcaggggcc | 1080 |
| tatttcgtca atcccctgct ggccaatacg gttaagcaga acgtgacccg tttcatctat | 1140 |
| gagattgcac gccttttccca cgatatttcc ggtggctgca tggcaaccat gccttcggag | 1200 |
| aaggatctgc accacgatga gatcggcaaa tatgtagaga agtatttccg gggggtggac | 1260 |
| gaagctccca ctgaagagcg catgcggatg gcccggctcg ttgaaaatat gacgggcggc | 1320 |
| acggctttgg tggaaagcat gcatggtgcc ggctctcccc aggcgcagag agtcatgatc | 1380 |
| ctccgccagg caaatctcgg ccataaggta aagcttgcca agaaactggc cggcataaag | 1440 |
| gaagaaaaat ag | 1452 |

<210> SEQ ID NO 109
<211> LENGTH: 1392
<212> TYPE: DNA
<213> ORGANISM: Sulfolobus solfataricus

<400> SEQUENCE: 109

| atgagatcaa aagaagattt cctaaagtcc ttaaaagatg aagaaatttt gtattatagg | 60 |
| gggaagttag tagaagatat aacaacacat cagatcttaa agacagccgc attgcacgca | 120 |

```
gctaagttat atgaatacgc tgatagagtc tatgaggata ataaaatggg aaaaatgagc    180
aagttcttta aggtaccttg acatctcaa gatttgctag atagacataa actaatttac    240
gatttaacga tgtattgtaa tggggtattt aacatttcac aagcaatagg aagtgatgcg    300
atctttgccc ttatgatcac ggcaaaacaa gttgatagaa aatacggaac tgattactca    360
aaacgtgttg aaaaatattt tgagagagtt gctaaagaag atttaacgtt agccactgcc    420
cagactgacg ttaagggaga tcgaagtaag aggccttctg aacaagttga tccagatatg    480
tatgttagag tagttgatgt gaaaagcgat ggaatagttg ttagaggagc aaaggctcat    540
acaactcaat ctgcggtatc tgatgagatt attgtcatac caaccagagt aatgagggat    600
agcgataaag attacgcagt agcctttgcg gttccagcta atactaaagg tttgaagatg    660
tatattagac caattgatga aattgagggc aattcctcct cagtactcag tagaaaagat    720
tatgagctag aaacattaac cgtcttcaac gacgttttcg ttccttggga tagggtattt    780
ttatttaagg aatacgacta cgctggaaca ttggctatgc tatttgcaac cttccatagg    840
tttactgcat tatcgtatag gtcagcgacc atgaatctat atttgggagc atctaaagtg    900
gcatctcaag taaatggcat tgagaatgaa aagcatgtga gagatgatat agttgatata    960
attctctaca aggaaattat gaggagtagc gcgatagctg cggctgtgta tccagtaaac   1020
atggagggta tagctgtgcc caacccgctt tttactaatg ttggtaaatt atactccaat   1080
atgcatttcc atgatgttgt aagagattta attgacattg ctgggggggat aatagctact   1140 atgccctctc aagaagattt ggaaagtgat gaaggaaaga atattgttaa atatttaagg   1200
ggctcagttg atggagagga aagagcaaaa gtgttaaaac tagctaagga attaggggct   1260
agtacgttta ctggctattt gctaactggt atgatacatg cggaaggttc tatggaagct   1320
agcaaaatag agctattcag aagttataat tttaaggagg ccgagaactt agttaaaagg   1380
gtattaagct ag                                                      1392

<210> SEQ ID NO 110
<211> LENGTH: 1440
<212> TYPE: DNA
<213> ORGANISM: Syntrophobacter fumaroxidans

<400> SEQUENCE: 110
atgggactca aaacgaaggc ggaatatata gaatccttgc gaggcatgaa gccgacggtc     60
tacatgttcg gtgagaagat cgaaagcgtt gtggacaatc cacgcctgcg agcgggcatc    120
gaggcgacgg gggcgacgta cgaactggca gagacggagg agtatcgccc tctcattgtg    180
actgaaagtc ccctcattca cgaacccgtc aaccggtata cgttgccccc gtcgtccatc    240
gcggacctcg tcgccagggt gaagatcaat cgtctcatgg cactcgtgt cgggacctgc    300 tttcaacggt gcacggggct ggactgcctg tccgcccttt ccatcgtgac ctacgacatc    360
gacgccaagc attccacccc ttacttcaaa cggttcatcg agtttctgaa gcatgttcag    420
aaaaacgacc tgacctgcaa cgccggcgtg accgacgtca agggcgaccg ttccctggcc    480
ccccacgagc aggaagacaa ggacatgtac gtgagggtcg tggaacgcaa tgcggacggc    540
atcgtcgtga gggcgccaa ggcgcaccag accggttccc tctcctcgca cgaaatcatc    600
gtcctgccga cgcgtgccct gcgaaagggc gacgaggact acgcgctcgc ttttgccatc    660
cccaacgaca ctcccggcct gattcacgtc gtgggccgat cgagcctcga cacccgccag    720
ctggacggct gcgacctggg caaccttcac tattccaagt actgcccgac cgtgatcttc    780
```

| | |
|---|---:|
| aaggacgtgt tcgttccctg ggagcgggtc ttcatgtgcg gcgaggtgga attcgccgtg | 840 |
| gagatggtga accgcttttc ggcttatcac cgccagagcc acggcggctg caagtcgggc | 900 |
| aagatcgact gcatggtcgg agcggccctc accatgatgg actacaacgg gacggagaag | 960 |
| gccgggcatc tcaagcagaa ggccatcgag atggtccacc gggcggaaac cctctacggc | 1020 |
| tgcagcctgg ccgcgtccta cgagggcaaa aagaacctt ccggaaccta cttcatcgac | 1080 |
| acggtgctgg ccaatgcgtc caagatccac gaaggcaagg aaatgagcga ggccggccgc | 1140 |
| ctgctggtgg acatcgccgg aggcttcgtg gccgatctgc cttcggatcg cgacctggcc | 1200 |
| attcccgaag tcggggaact gctgaaaaaa tacctgaagg gggtggcgtc ggtgccggtg | 1260 |
| gaagaccgcg tcaaaatgta ccggctgatc gaaaagctcg tcatggaaag cgccgatacg | 1320 |
| atttcggaca tccatggagg cggttctccc gaggcccaca ggatcacgat cctgcgggaa | 1380 |
| agcaacctca aggccaagaa ggacgcggcc aagcggttgg cgggaatcga atcgaagtag | 1440 |

<210> SEQ ID NO 111
<211> LENGTH: 1461
<212> TYPE: DNA
<213> ORGANISM: Porphyromonas gingivalis

<400> SEQUENCE: 111

| | |
|---|---:|
| atgatgacta gcgaacagta cgtagaaagt cttcggaaac ttaatctgaa ggtttacttc | 60 |
| atgggtgaaa ggatcgaaaa ccctgtagat catcccatga ttcgtccctc aatgaattca | 120 |
| gtagctatga cttataagct tgctgagatg gacgaataca agcatttaat gacagcaact | 180 |
| tcaaacttga ctggtaagca agtgaatcgt ttctgccatc tacatcagag cacagaggat | 240 |
| ctgaaagaca aagtgaagat gcagcgtctc atgggacaaa aaacagcttc atgcttccag | 300 |
| cgttgtgtgg gaatggatgc attcaatgcc atctattcta ctacttacga aatggatcaa | 360 |
| gctctgggta ccacttatca caagcgtttc atcgagtaca tgaaatatgt acaagacaac | 420 |
| gacttggtcg tagatggagc catgacagac cccaaagggg atcgcggttt atctccctca | 480 |
| gaacaagccg atccggatct ttatctgcac attgttgaag ttcgtgaaga tgggatcgtc | 540 |
| gtttccggtg caaaggcaca ccaaaccgga gcagtcaatt cgcacgagca tctgatcatg | 600 |
| cctacgatcg ctatgcgcga agctgatgct gactatgccg tttcttttgc cgttcccagt | 660 |
| gatgcagagg gcgttattat gatctatggc cgccagtcat gcgacactcg caaaatggaa | 720 |
| gaaggggcag acattgacct cggcaactct gaattcggcg gacatgaagc tcttgttgta | 780 |
| ttcgaccgcg tattcgtgcc caatgaccgc gtgttcatgt gcaaagaata ccagtttgca | 840 |
| ggtatgatgg tagaacgttt cgccggatac caccgtcagt cttatggagg atgtaaagta | 900 |
| ggtgttggtg atgtacttat cggtgcagct gctctcgcag cagactacaa tggagttcct | 960 |
| aaggcatctc acattaagga taaactcatt gagatgatcc acctgaatga aacccttat | 1020 |
| gcttgcggta ttgcatgctc ttcagaggga actcagatga agccggcaa ctatatgatc | 1080 |
| gatttgctgt tagctaatgt ttgtaagcaa aatatcaccc gccttcctta tgaaatagct | 1140 |
| cgcttggcag aagatattgc aggaggtttg atggtaacca tgccttctca acaagacttc | 1200 |
| cgccatccgg aaataggccc gatcgtaaag aaatatcttg caggggcaac aggcaaatcg | 1260 |
| acagaaaacc gtatgcgtgt tctgcgtttg atagagaata tcacgctggg aacagctgcc | 1320 |
| gtcggttatc gaaccgagtc tatgcacgga gccggatctc ctcaagctca gagaatcatg | 1380 |
| atcgctcgtc aggagatctt tgagggcaag aaaaagcttg cacgggcgat tgctcatatc | 1440 |
| gacgaatcac tcgataagta a | 1461 |

<210> SEQ ID NO 112
<211> LENGTH: 1590
<212> TYPE: DNA
<213> ORGANISM: Polynucleobacter necessarius
<220> FEATURE:
<221> NAME/KEY: MISC_FEATURE
<222> LOCATION: (1)..(1590)
<223> OTHER INFORMATION: subsp. Asymbioticus

<400> SEQUENCE: 112

| | | | | | |
|---|---|---|---|---|---|
| atgagtcaaa | gcacctccca | gttcatgaat | agcaaagact | atcaagagtc | attgcgctca |   60 |
| ctaaagccaa | ctgtctatgt | cgatggtcga | ttgatcgaat | ccgtcgccga | tgagccttct |  120 |
| cttcgccctg | gagtccaagc | cttaggagtg | acttatgaca | tggtccatga | cccagcgcta |  180 |
| gcaccgctca | tgttggctga | ctcgaatggc | actcctgtac | caagaatgct | gcacattaat |  240 |
| cagtcttctg | gagatctctt | aaataaatta | gaagcggtac | gtgtactctg | ccaagaaact |  300 |
| ggatgtgccc | aacgctattt | agcccatgat | gcgttaaatg | cgattgcaca | agtttctgcg |  360 |
| cgcattgatg | atgccaaagg | aagtaatgag | catagtgcta | aattttctga | gtatctatcg |  420 |
| catgtacaaa | cgaaggactt | ggcattaggc | attgccatga | cagatgcaaa | aggagatcgc |  480 |
| tcccgcagac | ctcatgagca | agaaaatcca | gatacttacg | tacatatcgt | ttctcaagat |  540 |
| gctaaagggg | tcgtgatctc | gggtacaaaa | gcgattgtga | ctggcgcccc | ttacatgcat |  600 |
| gaattcttag | tcatgccagg | tcgcaatatg | actaagagg | atgcagcctt | gcgatttgc |  660 |
| tgtgctgtcc | ctgtggatgc | caaaggtatt | acgattgtgg | cacgcccagc | gggacgccca |  720 |
| ggcgacaagg | tcgagcatgg | taaaccgata | ttttctagta | aatatggtca | atcgactggg |  780 |
| gtagtgatat | tcgataaagt | attcgttccc | tgggatcgtg | tttttttatgc | tggcgaatgg |  840 |
| gaacactcta | gcgtgctgac | ttataactac | gccacccatc | atcgtcatag | ctgcatcgcg |  900 |
| gcgcgagcag | gctttggaga | tctgttaatt | ggtgctggcg | ctttaatgtg | cgaagcgaac |  960 |
| ggattggatc | cagcaaccaa | atctaattta | cgtgatccga | tggttgaact | cattaagatc | 1020 |
| actgaaggat | tttatgcttg | cggtgtggct | gctagcgtct | atggaacgca | agatccgtac | 1080 |
| agtaaatcat | ttatgcctga | gccggtatt | tctaatatcg | gaaaactctt | attagcaacg | 1140 |
| cagatttatg | acatgcatcg | cttggcacat | gaagtatcgg | gaggattaat | cgtagcgttg | 1200 |
| ccaggaccag | acgaagatca | caacccagca | actgcagcca | ctttggcaga | ggtgttacga | 1260 |
| gccaatccag | ccgtcccctta | tgacaagcga | attgaagttg | cacggtttat | tgaagatctc | 1320 |
| acagcgtctt | atcaaggcgg | ttggtattcc | gtcattagcc | tacatggtgg | cggctctcca | 1380 |
| gcagcaatga | agcaagaaat | ctatcgtcag | taccctattg | gcaataaagt | agagctagtg | 1440 |
| gaacgtttat | tagatcgcgg | agtgctgact | agtagcgaag | agcgggcgat | tacgaaaaat | 1500 |
| aaacaacctg | ggcgctgctg | cgatcaaggc | tgtagcgcgc | caggacaagc | agtgatggta | 1560 |
| cctttgccag | agcctggcag | aagaacttaa | | | | 1590 |

<210> SEQ ID NO 113
<211> LENGTH: 777
<212> TYPE: DNA
<213> ORGANISM: Gordonia terrae
<220> FEATURE:
<221> NAME/KEY: MISC_FEATURE
<222> LOCATION: (1)..(777)
<223> OTHER INFORMATION: C-6

<400> SEQUENCE: 113

| | |
|---|---|
| gtgaccgaac accagaccat cgtcgtcgag accagcggcc gggtgggcat catcaccctc | 60 |
| aaccgcccga aagcgctgaa cgcgctcaac accgagttga tgaacgaagt ggtcggcgcc | 120 |
| gtcaaggagt tcgacgtcga ccaggggatc ggcgccatcg tgatcaccgg ttcggagaag | 180 |
| gcgttcgccg cgggcgccga catcaaggag atgtcatcga agtcctacgc ggatgtggtg | 240 |
| aacgagcagt tcttcggcgc ctgggatgag ctgtcgcggg cgcgtacgcc gatcatcgcc | 300 |
| gcagtgaccg gctacgccct cggcggcggc tgcgaactcg cgatgctgtg cgacaccatc | 360 |
| atcgccggcg acaacgccgt cttcggtcag cccgagatca acctcggcgt catccccggc | 420 |
| atcggtggtt cgcagcgcct cacccgcgcc gtcggcaagg ccaaggcgat ggacatggtg | 480 |
| ctcaccggcc ggcagatgaa ggtcgacgag gccgagcgtc tgggcctggt ctcgcgggtg | 540 |
| gtgcccaagg aggactgccg cgccgccgcg atcgaagtcg ccgagataat cgcctcgaag | 600 |
| tcgctgatcg ccgccgcggc cgccaaggac gcggtcaacc gtgccttcga gtcgagcctg | 660 |
| gtggagggtg tccgcgccga gcgcgcgctg ttctactcga cgttcgcgac cgacgaccag | 720 |
| accgagggca tggccgcctt cgtcgagaag cgggacccga acttcaccca ccgctga | 777 |

<210> SEQ ID NO 114
<211> LENGTH: 777
<212> TYPE: DNA
<213> ORGANISM: Halalkalicoccus jeotgali

<400> SEQUENCE: 114

| | |
|---|---|
| atggcagaca gagtactcat cgaacgagag aatgacatag cgacgatcat cgttaatcgg | 60 |
| cctgagaagc gtaatgcgat ggatatcccg acgcgaaaag ccctctatgc cgccttcgaa | 120 |
| gaggttagcg aggatgacga tgtgcgggca atcgtgctcc gcggagcagg agatgggtcg | 180 |
| tttatcgccg gtggcgatat tgattctttc gccgacttcg accacatgga cggcatggag | 240 |
| tacagcgaga agtacgccca agggctgtac aactatgttg cggaccgcca caaaccaacc | 300 |
| atcgccgcgt tgacggcta cgctctcggt ggaggcaccg aaatcgccct cgcttgcgac | 360 |
| attcgcctcg ccacggacga cgcgaagttc ggcctgcccg aagtcggcat cggcgtcatc | 420 |
| ccagccggtg gtgaacaca gcgactcgtt caagtcgtcg gagcccgggct tgcaagcgaa | 480 |
| cttatcctca ctggccgcat tatcagcgcc gacgaggcaa agagaattgg tcttgcaaac | 540 |
| catgtctacg ccgccgagga attcgataat gaagtccgag ccatggccga agatcttgcc | 600 |
| tcgaaggcgc ctgtcgccca gcgacttgca aaagaatcca tccgacgtag ccttgatatc | 660 |
| gacgccggcc ttgaatacga gcgactggcc ggagcgtttc tgttcggcac cgacgaccag | 720 |
| aaagagggtg caaacgcctt ccttgaggac cgagagccga agtaccgaaa ccggtaa | 777 |

<210> SEQ ID NO 115
<211> LENGTH: 774
<212> TYPE: DNA
<213> ORGANISM: Carboxydothermus hydrogenoformans

<400> SEQUENCE: 115

| | |
|---|---|
| gtggaatttg aaaaaattaa atttgaggtt acggacggtt atgccgttat ttacctaaac | 60 |
| aacccgccgg taaatgctct tggccagaaa gttttaaaag atttacaaaa agcttttgcag | 120 |
| gaaattgaga aaaatcccga gattcgggcg gtaataatta gcggggaagg tagcaaggtt | 180 |
| ttctgtgccg gggcagatat cacggaattt gctgaccggg ctaaagggat tttaccggaa | 240 |
| gtggaaggaa gtgttctttt ccggcaaatt gagcttttcc ccaagccggt gattgctgcg | 300 |
| ctgaacggta gctcctacgg cggaggaacc gaattagcga taagctgtca cctgcgcatt | 360 |

```
ttagcagatg atgcttccat ggctttgccc gaagtaaaac tgggcattat ccctggctgg    420
ggaggtaccc agaggttacc ccggttaatt ggtaaaacca gagccctgga agcaatgctt    480
accggagagc caataacggc agaagaagcc ttaagctacg gtctggtaaa caaagtcgta    540
cccaaagacc aggtactaac agaagcccgg gcgctggcag ctaagcttgc caaggggcg     600 cccatcgcta tgcgggaaat tttaaaggcg gtaactttag ggctggatac ttcaatagaa    660
gaaggtttaa aaattgagaa agaaggttcc aaagtgcgt ttagcagtga agatgcggtg     720
gagggaagaa ctgctttctt tgaaaaacgg ccgccgaatt ttaaaggccg gtaa          774
```

<210> SEQ ID NO 116
<211> LENGTH: 774
<212> TYPE: DNA
<213> ORGANISM: Thermomicrobium roseum

<400> SEQUENCE: 116

```
atgagcgtgc gtgtcgagcg ggagggggcg atcaccctcg tcacggtcga gcgcccggaa     60
cgactgaacg cgctcgatac cgcgacgttg cgtgccttac tcgcggcagt gcaggaactg    120
gcaacggagg aggcgatcgc tgtcgtcgtc ctcaccgggg caggcgatcg cgcgttcatc    180
gccggagccg atatcagcga gatggtagag aagtcgccag ccgaggcgct cgccttcgcc    240
gagttgggac acgccgtttg ccgggcgatc gaggaagcgc cgcaaccgta catcgcagcg    300
gtcaatggct acgcgctagg aggcggctgc gagatcgcgc tggcgtgcga tatccgcctc    360
gccagcgagc gcgccgtctt cgcccagccg gaagtaacgc tgggtattcc accaggctgg    420
ggcggatcgc aacggctgcc gcgcgtcgtt cctcctggta tcgcgcgcga gttgctctat    480
acggggcgcc gcgtcgatgc gcaggaagca ctgcggatcg ggctcgtcaa tgccgtctat    540
ccggctgacc aactcctcga gcgagctcgg gaactggcga accggatcgc ggccaacggg    600
ccactcgcgg tccgcttgac caaggcgcg gttcgcttcg gtctcgagca ggggctggaa     660
gctggactga cctacgagcg gcaggtgttc gcgtacgcgt tcaccaccga ggatcagcgg    720 gagggatgc gggcatttct ggaaaagcgt cgtccggctt ttcgcgggcg ctga           774
```

<210> SEQ ID NO 117
<211> LENGTH: 825
<212> TYPE: DNA
<213> ORGANISM: Methylobacterium extorquens

<400> SEQUENCE: 117

```
atgaacgctg acgccgagac cgcctcgacc gacgaactgc tcttcgcggt ggatgcggcg     60
ggcatcgccc gcatcaccct caaccggccg aaggcgcgca acgcgctgac cttcgcgatg    120
tatcgcgggc tggtggagtt gtgcgagcgg atcgaggcgg accacgcgat caaggcggtg    180
atcatcaccg gcgccgggga caaggcgttc gcggcgggta ccgacatcgc ccagttccgt    240
agcttcagca aaccggaaga gcgcgatcgg tacgagcgct tcatggaccg ggtgctcggc    300
ggcctggagc gcctgcgggt gccgaccatc gcggcggtcg ccggagcctg caccggggc     360 ggtgcagcga tcgctgcggc ctgcgacatg gcatcgcca gccgcgacgc ccgcttcggc    420
atccccatcg cccgcacgct cggcaattgc ctctcgcaga acaccctgag gcggctggcg    480
aacctcattg ggcgccccg cgtgaaggac attctgttca ccgctcggct cgtcgaggcg    540
caggaggctc tggcgatcgg cctcgtcaac gaggtggtcg aggatgccgc ggccgtcgcg    600
gcccgagcgg atgcgctggc caccctgctc gcgagccacg cgcccctcac cctccaggcc    660
```

```
accaaggaag gcctgcgccg catcggcgag gagggcgcgg cggaggccgc cgagggcgag      720
cggcccggcg acgacctgat cgtgatgacc tatatgagcg cggatttccg ggagggcatg      780
gaagccttcc tgggcaagcg cccgccgaac ttcaaagggc gctga                      825
```

<210> SEQ ID NO 118
<211> LENGTH: 1224
<212> TYPE: DNA
<213> ORGANISM: Clostridium sporogenes

<400> SEQUENCE: 118

```
atgagtgata gaaataagga agtaaaagaa aaaaaggcaa agcattatct tagagagatt       60
actgcaaagc attacaaaga agctctcgaa gcaaagaaa ggggagaaaa ggttggttgg       120
tgtgcatcta acttcccaca agaaatagct acaacattgg gggtaaaagt tgtttatcca      180
gaaaatcatg cagcagctgt agcagctaga gggaatggac aaaatatgtg tgaacatgct      240
gaggctatgg gttttttctaa tgatgtatgt ggttatgcaa gagtaaattt agctgttatg     300
gacataggtc atagtgaaga tcaaccaata cctatgccag actttgtact ttgctgtaat     360
aacatttgta atcaaatgat taaatggtat gagcatatag caaaaacttt agatatacca     420
atgattctta tagatatacc atacaataca gaaaatactg tttcacaaga tagaattaaa     480
tatattagag cacaatttga tgatgcaata aaacaattgg aagaaataac aggcaaaaaa     540
tgggatgaaa ataaatttga agaagttatg aaaatatccc aagaaagtgc aaaacaatgg     600
ttaagagcag catcctatgc aaagtataaa ccttcaccat ttagcggatt tgatttattt     660
aatcatatgc ctgtagcagt ttgtgcaaga ggtacacaag aagctgcaga tgcatttaag     720
atgttagcag atgaatatga ggagaatgta aaaactggaa atccactta tagggagaa      780 gaaaaacaac gtatattatt tgaagggatt gcctgttggc catatttgag acataaatta    840
actaagctta gtgaatatgg tatgaacgta actgcaactg tatacgcaga agcctttggt    900
gttatatatg agaatatgga tgaattaatg gctgcttata taaagttcc taattcaatt    960 agttttgaaa acgcattaaa aatgagatta atgctgtta caagcactaa tacagaaggt   1020
gctgttattc atataaatag aagctgtaaa ttatggagtg attttttata tgagctagca   1080
agaagattag aaaaggaaac aggaattcct gtagtatcat ttgatgggga ccaggcagac   1140
ccaagaaatt tctcgaaagc tcaatatgat actagaattc aaggacttaa tgaagtaatg   1200
gttgctaaaa aggaggctga ataa                                          1224
```

<210> SEQ ID NO 119
<211> LENGTH: 1125
<212> TYPE: DNA
<213> ORGANISM: Clostridium sporogenes

<400> SEQUENCE: 119

```
atgtcaaatt cagataaatt ttttaatgac tttaaggata ttgtagaaaa tcctaaaaaa       60
tatataatga agcatatgga acaaactgga caaaaggcta taggatgtat gccattatat      120
actcctgagg aacttgtatt agctgctgga atgtttccag taggggtatg gggaagcaat      180
acagaacttt caaaagctaa aacatatttc ccagcattta tttgttcaat attacaaaca      240
acattggaaa atgcattaaa tggagaatat gatatgttat ctggtatgat gattacaaat      300
tattgtgatt cattaaaatg catgggacaa aattttaaac taaccgttga aaatattgag     360
tttatcccag taacagttcc acaaaataga aaatgaag ctggaaaaga gttttttaaa       420
agtcaatata aaatgaatat tgagcaatta gaaaagattt ctggtaataa aataacagat     480
```
gaatctttag aaaaagctat agaaatatat gatgaacaca gaaaagtaat gaatgacttt 540
tcaatgttag catcaaaata tccaggtata ataacaccaa ctaaacgtaa ttatgttatg 600
aaatctgctt attatatgga taaaaaagaa catactgaaa aagttagaca attaatggat 660
gaaattaaag ctatagaacc aaaaccattt gaaggaaaga gagttataac tacaggtata 720
attgcagatt cagaagattt acttaaaata ttagaagaaa ataatatagc tatagttggt 780
gatgatatag cacatgaatc tagacaatat agaacattga ctccagaagc gaacacacca 840
atggataggt tagctgagca atttgctaat agagaatgta gtactttata tgatcctgaa 900
aagaaaaggg gtcaatatat agtagaaatg gctaaagaga gaaaagcaga tggaattata 960
tttttcatga caaaattctg tgacccagag gaatatgatt atccacaaat gaaaaaggat 1020
tttgaagaag caggcattcc acatgtacta atagaaactg atatgcaaat gaaaaattat 1080
gaacaagcta gaactgcaat tcaggctttt tcagaaacac tttaa 1125

<210> SEQ ID NO 120
<211> LENGTH: 795
<212> TYPE: DNA
<213> ORGANISM: Clostridium sporogenes

<400> SEQUENCE: 120
atggcagaca tttatactat gggtgtagac ataggttcaa ctgcatcaaa aacagtagta 60
ttaaaaaatg gtaaagaaat tgtaagtcaa gcagtaataa gtgtaggggc cggaacaagt 120
ggccccaaga gagctataga ttctgtatta aaagatgcta aattatccat tgaagattta 180
gactatattg tatccactgg atatggaaga aatagtttcg attttgctaa caaacaaatt 240
tctgaattaa gttgtcatgc aaaaggggtc tatttcgata acaataaagc tagaacagtt 300
attgatatag gcggacaaga tattaaagta ttaaaattag cggatagtgg aagactttta 360
aactttataa tgaatgataa atgtgctgca ggaacgggac gatttttaga tgtaatgtct 420
agagtaatag aagttccagt tgatgagtta ggaaaaaaag cattagaaag caaaaatcct 480
tgtactatta gttctacctg tacagtattt gcagagtcag aagtaatttc tcaacttgca 540
agaggagtta aaactgaaga tttgatagca ggaatttgta aatctgtagc atcaagagtg 600
gctagccttg caaagagaag tggtatagaa gaattagtag ttatgagtgg aggagtagct 660
aaaaatatag gtgtagtaaa ggcaatggaa gcagaattgg gaagagacat atatatatct 720
aaaaattctc aattaaatgg agcattggga gcaagtctat acgcttatga aagttttcaa 780
aaagaaagga gctaa 795

<210> SEQ ID NO 121
<211> LENGTH: 1239
<212> TYPE: DNA
<213> ORGANISM: Clostridium sporogenes

<400> SEQUENCE: 121
atggaaaaca atacaaatat gtttagtgga gtaaaggtta ttgaattagc aaattttata 60
gctgctccag cagcaggtag attttttgct gatggtggtg cagaggtaat aaaaattgaa 120
tcacctgctg gagatccttt aagatatact gctccttcag aaggaagacc attaagccaa 180
gaagaaaata ctacttatga tttggaaaat gcaaataaaa aagcaatagt attaaatctt 240
aaaagcgaaa aaggtaaaaa gatattacat gaaatgttag cagaagcaga tatattatta 300
actaattgga gaacaaaggc tttagttaaa caaggattag actatgaaac actaaaagaa 360

```
aaatatccta aattagttttt tgcacaaata actggttatg gtgaaaaagg accagataaa    420
gatcttccag gctttgatta tactgcattt ttcgctagag gcggtgtttc aggtactctt    480
tatgaaaaag gaactgtgcc tccaaatgtt gttccaggac ttggagacca tcaagctggg    540
atgtttttag cagcgggtat ggcaggagct ttatataaag caaaaacaac aggacaagga    600
gataaagtaa cagtaagttt aatgcatagt gctatgtatg gactaggtat tatgatacaa    660
gctgctcaat ataaagatca tggattagta tatccgataa atcgtaatga aactccaaat    720
ccttttatag tttcatataa atctaaggat gattactttg ttcaagtatg tatgccacca    780
tatgatgttt tctatgatag atttatgacc gctttaggaa gagaagattt agttggagac    840
gaaagataca ataaaataga aaatttaaaa gatggacgtg ctaaggaagt atacagtata    900
atcgaacaac aaatggttac aaagacaaag gatgaatggg ataacatatt tagagatgca    960
gacattccat ttgctatcgc acaaacttgg gaagatttat tagaagatga acaagcttgg   1020
gcaaatgatt atttgtataa gatgaaatat ccaacaggaa acgaaagagc attagtaaga   1080
cttccagtat tctttaaaga agcaggatta ccagaatata atcaatcacc acaaatagca   1140
gaaaatactg tagaagttttt aaaagaaatg ggatatacag aacaagagat tgaggaatta   1200 gaaaagata aagatataat ggtaaggaag gaaaaataa                            1239

<210> SEQ ID NO 122
<211> LENGTH: 1107
<212> TYPE: DNA
<213> ORGANISM: Lachnoanaerobaculum saburreum

<400> SEQUENCE: 122
atgtggcatt gtttagaaac tttaaaaaag attagtgcgt ctccaaagga acagcttaat     60
aaataccttg aagaaggaaa aaagttatt gctgttgcac cggtttatac acctgaggag    120
attatccatg cttttggatt tgtacctatg ggggtatggg gcgcagatat tgaaattaat    180
gagtcaaaaa aatattatcc tgcatttatt tgctcaataa tgcagacagt attggagctg    240
ggaataaagg gaaattataa cggagttagt gctatagtgg ttccttcgct atgtgactca    300
ttaaaaactt tgggacaaaa ttggaaatat gcggtaaagg acattccttt tataccaatg    360
acctatccac aaaatagaaa atctgattat gctgttgatt tcacattgga gatgtataag    420
agagtgatca gtgatttgga aaatattacc ggagaaaagt ttgatgaagg taaactcaaa    480
aacacttatg aaatttataa tgagcataat aggggttatga gagaatttac aaaagtttcg    540
gaagagtatg aagtttcggc aacagataga agtgcagtat ttaaaagtgc ttggtttatg    600
cttaaggagg aacatacaga acttgttagg gaattgatcg aacttataaa aaaagagggt    660
aaaatatcta gaagctaag aatttataca acaggaatat tggcggatgc accggattta    720
ctcaatattt ttgacagcaa taatatgcaa atcgtaggtg atgatattgc ttatgaatcc    780
agacagtata gaacagatat acccgatgga aatggtttat atgctcttgc aaagaagttt    840
tcaaatatgg acaactgtac tcttttatat gataaggata agagaagggt tgactttatt    900
attgaagaag caagaaaaa aagagctgac ggaatagtag ttcttatgac caagttttgc    960
gatcctgaag aatttgacta tgtgcctata aagagggcgg caaatgaagc aggtattcca   1020
catatcaata tagaagtgga tagacaaatg aaaaattatc aacaggcaaa tactatgtta   1080
caaacatttg cagacatgtt ggtttag                                       1107

<210> SEQ ID NO 123
<211> LENGTH: 1230
```

```
<212> TYPE: DNA
<213> ORGANISM: Lachnoanaerobaculum saburreum

<400> SEQUENCE: 123
gtggaagaag ctaaaaaaca aaagcctaca gttgatccaa acagcgcaaa ggctagattg      60
ggcaggatag cagcaaaagc atatagtgac tgtgttgagg ctaaaaagcg aggagaattg     120
gtaggatggt gtgcaagtaa ttttccggtg gagatacctg agaccttggg attgtacgta     180
tgttaccctg agaatcaggc ggcaggtatt gctgccagag gcggtggaga acgaatgtgc     240
agtgagagtg aaggtgacgg atactctaat gatatatgcg catatgcaag aatttcgctt     300
gcatatatga agctgaagga agctcctgaa caggatatgc cacagcctga ctttgttcta     360
tgttgtaata atatatgcaa ctgcatgatt aagtggtatg aaaatatagc aaaagaactt     420
aatattccta tgattatgat tgatatacct tttaatcctg attatgaagt ttcagatgct     480
atgacagcat atatcagaaa tcagttttgg gatgcaatac atcaattgga ggaaattaca     540
ggcaaaaaat ggagtaatga agatatgaa gaggtaagga aatatcagg aagaagctcc     600
agagcatggc ttgaggctac agcgactgcc aaatattcac catctccgtt taacggattt     660
gatttattaa atcatatggc ggttatggtt actgccagag gaaaacttga agctgcagaa     720
gcaatggaaa cacttttgca ggagtacaag gataatcatg agaagggaga gtctacgttc     780
aagggagaag aaaaatatag aataatgttt gagggtatag catgctggcc atggcttcgt     840
gctactgcta caggacttaa gagtcgtgga atcaatatgg ttacaactat atatgcggat     900
gctttcggat ttatctatga tgactttgac ggaatgtgca gagcatatgc caatgttcct     960
aattgtatga atatagagca tgcaagagat aagagaataa aactttgtaa ggacaatagt    1020
gttgaagggc ttctcgttca cacaaacagg tcttgtaaac tttggtcagg atttatgtct    1080
gaaatgagca ggcaaatagg tgaagaatgt ggtattccgg ttgtaagctt tgatggagac    1140
caagcagatc caagaaattt ctcagaggct caatatgata cgagagttca gggattgaca    1200
gagataatgg aagcaaataa ggaaatttaa                                     1230

<210> SEQ ID NO 124
<211> LENGTH: 771
<212> TYPE: DNA
<213> ORGANISM: Lachnoanaerobaculum saburreum

<400> SEQUENCE: 124
atgtacacat tgggtgttga tataggctca actacatcca aagcggtaat attggaggat      60
ggagaaaata tagttgcatc ttcaattgtt atagcaactg taggaacggc aggagtagaa     120
gaggctgtaa aaaatgtact aaacttttca aaactcgaac taaatgacat taaagcagtg     180
gttgctacag gatatggaag aatgaattat gatgtagcag attacaaggt tagtgaattg     240
acatgtcatg cattaggtgt acataaggag ttcccgaatg tcagaactgt aattgatatc     300
ggaggtcagg atgccaaggt aatatctctt gcggcaaacg gtaagatgac aaatttttgtt     360
atgaatgata atgtgcggc agggacaggt agatttcttg atgtaatggc taatatatta     420
aatcttgata tacaggattt ggaggtggaa gccttaaaat cagataatcc ggcaaatata     480
tcaagtactt gtacagtttt tgcggaatcg gaagtcatat cacagcttgc tacaggaaga     540
aatattcctg atttggttgc agggatatgc aaatctgttg cagtaagggt tgccgccctg     600
gctaaacgag taggtatagt tgaagaagtg tgtatgagcg gcggagtggc aaaaaactcg     660
ggtgtgagga atgctatgag taagagcctt ggtgtagata tagtgtttag taaggatgct     720
```
caacttatgg gagcacttgg agccgcaata tacggtttta aaaagttata a    771

<210> SEQ ID NO 125
<211> LENGTH: 795
<212> TYPE: DNA
<213> ORGANISM: Peptostreptococcus stomatis

<400> SEQUENCE: 125
atgagcagtg tatacacaat gggtattgac attggatcaa catcatcaaa gtgtgtgata     60
atgaaggatg gtaaggaaat tgtaagtgaa ggtgtagtta gcttgggtgc tggaactaag    120
ggttctgacc tagttattga ggaagtgctt ggtaaggcag aatgactttt cgatgaaata    180
gacctaatcg tatcgactgg atatggtaga aatagctatg aaagagctgc caagactgtt    240
agtgagctta gttgtcatgc caagggtggt ggatatatct ttggtggtgc cggaactatt    300
atagatatcg gtggtcagga tataaaggta ttgaagctaa atgacaaggg tggtcttgtt    360
aacttcctga tgaatgataa gtgtgctgcc ggtacaggta ggttcttgga agttatgtct    420
ggcgtattgg atgtaaagct agatgaacta ggggaactag atgccaaggc tacagaagtt    480
acaccaatca gttctacatg tacagttttt gctgagtcag aagttatatc atgtatggct    540
aagaagattc ctctagaaaa tatcataaga ggtatacacg catctgttgc aacaaggggtt    600
gctagtttgg caagaagagg tggtttgaag actcctgtag ccatgacagg tggagttagt    660
aagaacaagg gtatagtaag ggctcttaaa gaagaactag aatgtgatat cttgatatct    720
cctgattctc agatggctgg tgctataggt gcagccctat atgcatatga cgaataccag    780
aagcaaaacg cttaa                                                     795

<210> SEQ ID NO 126
<211> LENGTH: 1119
<212> TYPE: DNA
<213> ORGANISM: Peptostreptococcus stomatis

<400> SEQUENCE: 126
atgagtaata tagatgtatt gttaggtaaa cttgatgtaa gtcttttggg acaggtagac     60
aagtatgttt cagaaggtaa gaaggtaata ggttgcgcgc cagtttatac accagaagaa    120
ttagtatatg ctgcaggcat ggtaccaatt ggtgtatggg gtgcagaagg tgaagtaggt    180
ctatcaaagg aatacttccc agcatttat gcagctataa tccttagatt aatggacctt    240
ggtttagaag gtaagcttga caagatgtca ggtatgatta ccgggact aagtgacggt     300
ctaaagggac ttagccagaa ctggaagagg gctataaagc aggttccggc cctatacata    360
ggctatggtc agaacagaaa aattgaagct ggtattactt acaatgaaaa gcagtacatc    420
aagctaagag gacagttaga agaaatagct ggttgcaaga tagaagatgc taaggttgaa    480
gaggctatag ttctttacaa caagcacaga aaggcaatgc aggaattcag ttctctagca    540
gctagtcact aaatactat tacacctatt ctaagagcta gagtaatgac aagtgccttc    600
ttgttcgaca aggcagaaca tttagctata ttggaagaat tgaataaaga attaaaggcg    660
ttacctgaag aaaaatttgc tggcaagaag gtagttacta ctggtattct tgcaaatagc    720
ccaggtatgc tagaaaatact agatgagtac aaacttggta tagttgatga caatatcaac    780
catgaatcag gccagtttga ctacctagtt gatgaaggta ctggtaatcc agttagagcc    840
ttatctaagt ggatttcaga tatagaagga agtactttgt tgtatgatcc agaaaaactt    900
agggggacaga taataattga caaggttaag aagcatcagg cagatggtgt tatataccta    960
atgactaagt ttagtgattc tgatgaattc gactatccaa tcatcagaaa agaattagaa   1020

```
aatgcaggta tcttgcatat actagttgag gttgatcagc aaatgactaa ctttgaacag   1080
gcgaaaacag cattacagac tttcgctgat atgatttaa                          1119

<210> SEQ ID NO 127
<211> LENGTH: 1236
<212> TYPE: DNA
<213> ORGANISM: Peptostreptococcus stomatis

<400> SEQUENCE: 127
atgagtaata caggaatggt agaagaaaag ccggcaaaag tattgttagg agaaattgtt     60
gcaaagcact ataaggaagc ttgggaggca aagaataatg gtgaactagt tggatggtgt   120
gcatctaact tcccacagga aatattcgaa actatggata taaaggttgt ttatccagaa   180
aaccaggctg ctgctatatc tgctaagggt ggcggacaga gaatgtgcga aatagctgaa   240
aatgaaggat attcaaatga tatctgtgct tacgctagaa tatctttggc atacatggac   300
gttaaggatc tccagaatt aaatatgcca cagccagact tcgttgcttg ctgtaacaat   360
atttgtaact gtatgatcaa gtggtatgaa aatatagcta aggaattgaa tatacctta   420 attttaatag acgttcctta caacaatgac tacgaggctg aagacgatag agttgaatat   480
ctaagaggtc agtttgatta tgctatcaag cagttagaag aactaactgg caagaagtgg   540
gatgaaaaga gtttgaaga agtaatgaa gtttctcaga gaacaggtag ggcttggtta   600
aaggctactg gatatgctaa gtatactcca tcaccattct caggctttga cgtattcaac   660
cacatggctg ttgcagtttg tgcaagaggt aagatagaat cagctatagc attcgaaaag   720
ctagctgaag aatttgacga aaacgtaaga actggtaagt caacatttaa gggcgaagaa   780
aagttcaggg tgttatttga aggtatagca tgttggccac acctaagaca tacattcaag   840
cagcttaagg atgctggtgt taatgtctgt ggtacagtat atgcggatgc tttcggatat   900
atctatgaca atacatatca gttaatgcag gcttactgcg gaactccaaa tgctatttca   960
tacgaaaggg caactgatat gagactaaag gttattgaag aaaacaatat agatggtatg  1020
ttaatccaca tcaacagaag ttgtaagcag tggtcaggta tcatgtacga gatggaaaga  1080
gatattagag aaaagactgg tataccaaca gctacattcg atggtgacca ggccgatcca  1140
agaaacttct ctgaagctca gtatgatact agagtacagg gtcttataga actaatggaa  1200
gctaataaag ctgcaaagat gaaggaggcg cactaa                            1236

<210> SEQ ID NO 128
<211> LENGTH: 1227
<212> TYPE: DNA
<213> ORGANISM: Clostridium difficile

<400> SEQUENCE: 128
atgtctgaaa aaaagaaagc tagagtagta attaatgatt tattagctga acaatatgca    60 aatgcatttta aagctaaaga agaaggaaga cctgtaggtt ggtcaacatc agtatttcct   120
caagagttag cagaagtatt tgacttaaac gtattatatc cagaaaacca agcagctgga   180
gtagcagcta aaaaaggttc tttagaatta tgtgaaatag ctgaatctaa aggatattct   240
attgacctat gtgcatatgc aagaacaaat tttggtcttt tagaaaatgg tggatgtgaa   300
gctttggata tgccagctcc agatttccta ctttgctgta acaatatatg taaccaagtt   360
ataaaatggt atgaaaatat ttcaagagaa ttagatatac ttttaataat gattgataca   420 acttctcaata tgaagacgaa gttactcaa tcaagaatag attatattaa agctcaatttt  480
```

```
gaagaagcta taaaacaact agaaattata tcaggaaaga aatttgaccc taagaagttt    540
gaagaagtaa tgaaaatatc agctgaaaac ggaagactat ggaagtattc tatgagttta    600
ccagcagatt cttctccttc tccaatgaat ggatttgact tatttactta catggctgta    660
atagtttgtg ctagaggtaa aaaagaaact acagaagcat ttaagttact tatagaagaa    720
ttagaggaca acatgaaaac tggtaaatct tctttcagag gggaagaaaa atacagaata    780
atgatggaag gtataccttg ttggccatat ataggataca agatgaaaac attagctaaa    840
tttggagtta acatgacagg tagtgtttac ccacatgctt gggcattaca atatgaagtt    900
aatgatttag atggaatggc agtagcatat agtactatgt ttaacaatgt aaacctagac    960
cgtatgacaa aatatagagt tgattcttta gtagagggta aatgtgatgg agcattctat   1020
catatgaaca gaagctgtaa acttatgagt ttaatacaat atgaaatgca aagaagagca   1080
gctgaagaaa ctggattacc atatgctgga tttgatggtg accaagcaga ccctagagct   1140
ttcactaatg ctcaatttga aacaagaatt caaggtttag ttgaagtaat ggaagaaaga   1200
aaaaaactta atagaggtga gatataa                                       1227
```

<210> SEQ ID NO 129
<211> LENGTH: 1125
<212> TYPE: DNA
<213> ORGANISM: Clostridium difficile

<400> SEQUENCE: 129

```
atggaagcta ttttatctaa aatgaaagaa gtagttgaaa atccaaatgc ggctgtaaaa     60
aaatataaaa gtgaaactgg taaaaaagct ataggttgtt tcccagttta ttgcccagaa    120
gaaattatac atgcagctgg aatgcttcca gttggtatat ggggaggaca aacagaatta    180
gatttagcta aacaatattt ccctgcattt gcatgttcaa taatgcaatc atgtttagaa    240
tatggattaa aaggtgctta tgatgaatta tctggagtta ttataccagg tatgtgtgat    300
acactaattt gtttaggaca aaactggaaa tcagcagtac ctcatataaa atatatatca    360
ttagtacacc cacaaaatag aaaacttgaa gctggtgtaa aatacttaat cagtgagtac    420
aaaggcgtaa aaagagaact tgaagaaatt tgtggatatg aaatagaaga agcaaaaatt    480
catgaaagta tagaagttta caatgaacat agaaaaacta tgagagactt tgttgaagta    540
gcttataaac attctaatac tataaaacca tcaataagaa gcttagtaat taagagtggg    600
ttctttatga gaaaagaaga acatactgag ctagtgaaag atttaatagc aaaattaaat    660
gctatgccag aagaagtctg ttctggaaag aaagttttat taacaggtat attagctgat    720
tctaaagata tattagacat tttagaagac aacaatatat cagttgtagc tgacgactta    780
gcacaagaaa caagacaatt cagaacagat gtaccagcag gtgatgatgc gttagagaga    840
ttagcaagac aatggtcaaa catagaagga tgttcattag cttatgaccc taagaaaaaa    900
cgtgggtcac ttatagtaga tgaagttaaa aagaaagata tagatggtgt tatcttctgt    960
atgatgaaat tctgtgaccc agaagaatac gattatcctt tagttagaaa agatatagaa   1020
gatagtggaa tacctacttt atatgttgaa atcgaccaac aaactcagaa taatgaacaa   1080
gccagaactc gtattcaaac ttttgctgag atgatgagtt tagcg                   1125
```

<210> SEQ ID NO 130
<211> LENGTH: 798
<212> TYPE: DNA
<213> ORGANISM: Clostridium difficile

<400> SEQUENCE: 130

```
atgtacacaa tgggattaga tataggttca actgcatcaa agggagtaat cttaaagaat      60
ggggaagata ttgtagcttc tgaaacaata tcctctggta ctgggactac tggaccatca     120
agagttttag aaaaattata tggcaagaca ggtcttgcaa agaagatat taaaaaagtt     180 gtagttacag gatatggaag aatgaactat tcagatgctg ataagcaaat aagtgaatta     240
agctgtcatg ctagaggggt aaatttcata attccagaga caagaaccat tattgacata     300
ggtggtcaag atgcaaaggt attaaaatta gataataatg gaagactatt aaactttctt     360
atgaatgaca atgtgctgc aggtacagga agattttttag atgtaatggc aaaaataata     420
gaggttgatg tatctgaact cggaagtata tctatgaatt ctcaaaatga agtatcaata     480
agcagtacat gtacagtatt tgcagagtct gaggttatat cacatttatc tgaaaatgca     540
aaaattgaag atatagtggc aggtattcat acttcagtag caagagagt ttctagccta     600 gtaaaaagaa taggagtaca agaaatgta gttatggttg gtggggttgc tagaaatagt     660
ggtattgtaa gagctatggc aagagaaatc aacacagaaa ttattgtacc tgatatacct     720
caattaactg gtgctttagg agcagcgtta tatgcttttg atgaagcaaa agaatcacaa     780
aaagaagtga aaaatata                                                   798

<210> SEQ ID NO 131
<211> LENGTH: 1194
<212> TYPE: DNA
<213> ORGANISM: Clostridium difficile

<400> SEQUENCE: 131
cttttagaag gagttaaagt agtagaactt tcaagtttca tcgcagcacc atgttgtgca      60
aaaatgttag gtgactgggg tgcagaggtt attaagattg aacctataga aggtgatgga     120
ataagagtta tgggtggaac atttaaatct ccagcatcag atgatgaaaa ccctatgttt     180
gaattagaaa atggaaataa aaagggtgta agtattaatg taaaatcaaa agaaggagta     240
gaaatattac ataaattatt atcagaagca gacatatttg taactaatgt tagagttcaa     300
gcattagaaa aaatgggtat agcttatgac caaataaaag ataagtatcc aggattaata     360
ttctctcaaa tattaggata tggtgaaaaa ggaccttttaa aagataaacc aggatttgac     420
tatactgcat acttcgcaag aggaggagtt agccaatctg ttatggaaaa aggaacatct     480
ccagcaaata cagcagcagg atttggtgac cactatgcag gtctagcact agcagcagga     540
agtttagcag cattacataa aaaagctcaa actggtaaag gtgagagagt aacagtaagt     600
cttttccata cagctatata tggaatggga acaatgataa caacagcaca atacggaaat     660
gaaatgcctt tatcaagaga aaatccaaac agcccattaa tgactacata taaatgtaaa     720
gatggaagat ggattcaatt agctttaata caatacaaca gtggttagg caaattctgt     780 aaggttataa atagagaata tatattagaa gacgatagat ataataacat agattcaatg     840
gttaatcatg ttgaagattt agttaagata gttggagaag ctatgttaga aaaaacatta     900
gacgagtggt cagctttatt agaagaagca gacttaccat ttgaaaaaat tcaaagctgt     960
gaagatttat tagatgacga acaagcttgg gcaaatgact tcttatttaa gaaaacatac    1020
gatagcggaa atacaggtgt cttagttaat actccagtta tgtttagaaa tgaaggaatt    1080
aaagaatata taccagcacc aaaagtaggt caacatactg tagaagtatt aaaatcttta    1140
ggctacgatg aagagaaaat aaataacttt aaagatagta agttgtaag atat           1194

<210> SEQ ID NO 132
```

```
<211> LENGTH: 768
<212> TYPE: DNA
<213> ORGANISM: Escherichia coli
<220> FEATURE:
<221> NAME/KEY: MISC_FEATURE
<222> LOCATION: (1)..(768)
<223> OTHER INFORMATION: strain K12

<400> SEQUENCE: 132
atgagcgaac tgatcgtcag ccgtcagcaa caagtattgt tgctgaccct taaccgtccc      60
gccgcacgta atgcgctaaa taatgcccct ctgacgcaac tggtaaatga actggaagct     120
gcggctaccg atagcagcat ttcggtctgt gtgattaccg gtaatgcacg ctttttttgcc    180 gctggggccg atctcaacga aatggcagaa aaagatctcg cggccacctt aaacgataca     240
cgcccgcagc tatgggcgcg attgcaggcc ttcaacaaac ctctcatcgc agccgtcaac     300
ggttacgcgc ttggtgcggg ttgcgaactg gcattgttgt gcgatgtggt ggttgccgga    360
gagaacgcgc gttttggttt gccggaaatc actctcggca tcatgccagg cgcaggagga     420
acgcaacgtt taatccgtag tgtcggtaaa tcgttagcca gcaaaatggt gctgagcgga     480
gaaagtatca ccgctcagca agcacagcag gccgggctgg ttagcgacgt cttccccagc     540
gatttaaccc tcgaatacgc cttacagctg gcatcgaaaa tggcacgtca ctcgccgctg     600
gccttacaag cggcaaagca agcgctgcgc cagtcgcagg aagtggcttt gcaagccgga     660
cttgcccagg agcgacagtt attcaccttg ctggcggcaa cagaagatcg tcatgaaggc     720
atctccgctt tcttacaaaa acgcacgccc gactttaaag gacgctaa                  768

<210> SEQ ID NO 133
<211> LENGTH: 774
<212> TYPE: DNA
<213> ORGANISM: Rhodobacter capsulatus

<400> SEQUENCE: 133
atgagctatc acacgatccg ctacgagatc tccgaagggc tggcggtgat cacgctcgat      60
cgccccgagg tgatgaatgc gctgaacgcg gcgatgcggc acgaattgac cgcggcgctg     120
caccgcgcgc ggggcgaggc gcgggcgatc gtgctgaccg gatcggggcg ggccttttgc    180
tctgggcagg atctgggcga tggcgcggcc gaggggctga acctggaaac cgtgctgcgc    240
gaggaatacg agccgctttt gcaggcgatt tacagctgtc cgctgccggt tctggcggcg    300
gtgaacggcg cggcggcggg ggcggggggcc aatctggctc tggcggccga tgtggtgatc    360
gcggcgcaat ctgcggcctt catgcaggct ttcacccgga tcgggctgat gccggatgcg    420
ggcgggacct ggtggctgcc gcggcaggtc ggcatggccc gcgccatggg gatggccctg    480
ttcgccgaga gatcggcgc cgaagaggcc gcgcgcatgg ggctgatctg ggaagccgtg    540
cccgatgtcg atttcgagca tcactggcgg gcccgggcgg cgcatctggc gcggggccct    600
tcggcggcct ttgcgcggt gaagaaggcc tttcatgccg gtctgagcaa tcccctgccc    660
gcgcagctgg cgctggaagc ccggttgcag ggcgaactgg gccagagcgc ggatttccgc    720
gagggcgtgc aggcctttct ggaaaagcgc ccgccgcatt tcaccgggcg ctag           774

<210> SEQ ID NO 134
<211> LENGTH: 2106
<212> TYPE: DNA
<213> ORGANISM: Pseudomonas stutzeri

<400> SEQUENCE: 134
atgacggatg tcattcggct cgaacgccgg ggcgatatcg ctctgatcct ggtcaacaac      60
```

```
ccgccggtca acgcccttgg ccatgccgta cgaaaaggcc tgttggatgc ctttcaagag      120
gctgacgagg cgcccgaggt gacggccgtg gtgctggtct gcgaaggccc gaccttcatg      180
gccggcgccg atatcaagga gttcggcaaa ccgccgcagg caccgagcct gccggaggtg      240
atcgaggtga tcgagggctg ccgcaagccg agcgtcgcgg tgatccacgg caccgccctg      300
ggtggtgggc tggaggtcgc gctgggctgc cattaccgta tcgcccggtc ggacgccaag      360
gtcggcctgc cggaggtgaa gctgggcctg ctgcccggcg ccggcggtac ccagcgcttg      420
ccgcggctgg ccggtgtcga aggcgctg gagatgatcg tcagcggcca gcccatcggt        480
gcggcggagg cgctggagca ctatatcgtc gacgagctgt tcgaaggcga tctgatcgag      540
gccggtctga cctatgcgcg tcgccttgtc gaggagggcc gcggtccgcg ccgcagtggc      600
gagcagaccc gcggtctgga aggcgtcgac aacgaggcgc tgattcgcgc caagcacgcc      660
gaggtggcca agcgcatgcc ggggctgttc tcgccgctgc gctgcattgc cgcggtggaa      720
gccgccacca ggctgccgct ggccgaaggc ctcaagcgcg agcgcgagtt gttcaccgag      780
tgcctgaatt caccgcagcg cggcgcgctg atccattcgt tcttcgccga gcgtcaggcc      840
ggcaagatcg acgacctacc atccgacgtc accccccgcc cgatcaggac cgccgcggtg      900
atcggcggcg gcaccatggg cgtcggcatc gccttgagct cgccaacgc cggggtgccg       960 gtgaagctgc tggaaatcaa tgacgaggcg ttgcaacgcg gcctgcagcg tgcccgcgaa      1020
acctacgcgg cgagcgtcaa gcgcggcagc ctgaccgagg atgcgatgga gcagcgcctc      1080
gcgctgatcg ctggcgtcac cgactacggc gccctggctg atgccgacgt ggtggtcgag      1140
gccgtgttcg aagagatggg cgtcaagcag caggtcttcg agcaactgga tgcggtgtgc      1200
aagccgggtg cgatcctcgc ctccaacacc tcgtcgctgg acctgaacgc catcgccggc      1260
ttcaccaggc gccccgagga tgtggtcggc atgcacttct tcagcccggc caatgtcatg      1320
cgcctgctgg aagtggtgcg cggtgagcgg accagcgatg aagtgctcgc cgccgccatg      1380
gcgatcggca agcagctgaa gaaggtctcg gtggtggtcg gcgtctgcga cggcttcgtc      1440
ggcaaccgca tggtcttcca gtacggccgc gaggcggagt tcctgctgga ggaaggcgcc      1500
acgccacaac aggtcgacgc tgccctgcgc aatttcggca tggccatggg accgttcgcc      1560
atgcgcgatc tgtccggtct cgacatcggc caggcgatcc gcaagcgcca gcgcgcgacg      1620
ctgccggcgc acctggattt tcccaccgtc tcggacaagc tctgcgccgc cggcatgctg      1680
gggcagaaga ccggtgccgg ctactaccgc tacgaacccg gcaaccgcac cccgcaggag      1740
aatcccgacc tcgcgcccat gctggaagcc gcgtcgcggg aaaagggcat cgagcggcag      1800
gcgctggacg agcagtacat cgtcgagcgc tgcatcttcg cgctggtcaa cgagggcgcg      1860
aagattctcg aggaaggcat tgcccagcgc tccagcgaca tcgacgtcat ctacctcaac      1920
ggctacggct tcccggcctt ccgccggcggg ccgatgtact acgccgacag cgtcggcctg     1980
gacaaggtgc tggcgcgagt aaaagaactg cacgcgcgtt gcggcgactg gtggaagccg      2040
gcgccactgc tggaaaaact ggccgccgaa ggccgcacct tcaccgaatg gcaggccggg      2100
caatga                                                                2106
```

<210> SEQ ID NO 135
<211> LENGTH: 1968
<212> TYPE: DNA
<213> ORGANISM: Haliangium ochraceum

<400> SEQUENCE: 135

```
atgatcgtcg gagtcatcgg gtcgggcgcc atcggcccag acctcgccta cggattcgcc    60
tcggccctgg ccagcgttcc cggcgccagg gtctatctac acgatatcaa gcaggaggcc   120
ctcgacgccg gtatgcagcg catccgcggc tacatcgcca agggcctggc ccgcggcaag   180
atcagcgaac gcgtcgccgg cgccctggag acggtgctcg tgcccacgct ctcgctcgcc   240
gatctcgcgc cgtgcagcta cgtgctcgag gccgccaccg aggagctcgg ggtcaagcgc   300
gccatcttgc gcagcctcga ggatacagtc gatagcgagt gcctcatcgg cttcgccacc   360
tcgggcctgc cgcgcgcgat catcgccgcc gaggtcaaac atcccgagcg ctgcttcgtc   420
aatcacccct tctacccgc ctggcgttcg ctgcccgtcg aggtcgtgct ctcgggtagc    480
ccggcgcacg ccagcgcat gctggccacc ctcgaggccc tgggcaaagt ccccgtcatc    540
accgcggacg cgccctgctt cgcggccgac gacatctttt gcaactactg ctcggaggcc   600
gcgcgcatcg tcgaggaagg catcgccaat cccgcccagg tcgacgccat cgtccacggc   660
gccatcggcg gcggcggccc gctcaacgtc ctcgacgcca cccgcggcaa cctgctcacc   720
gtgcactgcc aggagctgat gcgcgacgcc gacaccggca cgccgtggtt cgagccgccc   780
gccatcctgc gcgagcgcgg cgacgccctg tggcacgatc ccaaggcccc gcacgacccc   840
gccttcgacg aggccctgcg cgagcgcgtg ctcgaccgca tcctggccgt gctgctcgcg   900
cgcacagtgt tcgtgctcga tcacggcatc tgccgccgca ccgagctcga ctggatgacg   960
cgcaccgcgc tcggcttccg caccggcttg gtcgacctgg tggacgaact cggccccgag  1020
cgcgtggccg agctgtgcca gcgctacgcc gccgagcacc ccggcttcgt catcccggac  1080
agcatccgcg agcagcacaa gccgcgcttc tacggcaacc tgcgcgtcac cgccaggac   1140 gagctggcca tcgtgcgcat cttccgcccc gaggtgaaga acgcgctcga ccgccgcacc  1200
ctgagcgagc tcgaccacct catggccgcg ctgtcggccg acgacagcgt cgagggcgtg  1260
gtcctgagca gcgccggcgg cgcgctggcc ggcgccgaca tcaccgagct agcgcgcgtg  1320
cgcaccaccg aggaggcggt gtccacctgc gctttcggac aagcggtctt gaaccgcatc  1380
gcggccatgg acaagcccgt ggtcgccgcc gtcgacggcc cggtgctggg cggcggcgcc  1440
gagctgtcga tggcgtgcca tgcgcgcgtc gtcggcccgc gcctgagcat gggccaaccc  1500
gaggtcaacc tcggcatcat ccccggctac ggcggcaccc agcggctgcc gcggctcatc  1560
ggcgtggagc gcgcgctggc catgatgcgc acggcgcaga gcatcgacgc gcagaccgcg  1620
tgcgagtggg gctgggccag cggcacgccg atggtcgact tcgtcggcgc ggccgcgacc  1680
ctcatccgca gccacctcgc cggcgaggcc gagctcgcgc gctcgacccc gcgcccatg   1740 agcgtacccg ccgcggccgc ccccgtggac atcgccacc gctcgcgcgt catcgacgag  1800
atcctcgtgg atgtggtcca gtccggcttg cgcgcgccgc tgagcgaggg cctgccacc   1860 gaggccgccg gcttcggccg ctgcgtgctc accgtggacc tcgacatcgg actcaagaac  1920
ttcatgcaga acggcccccg ggttccggcg ctgttcctcc acgagtag               1968
```

<210> SEQ ID NO 136
<211> LENGTH: 768
<212> TYPE: DNA
<213> ORGANISM: Anoxybacillus flavithermus

<400> SEQUENCE: 136

```
atgtttctcta ttcaacaaga ggggtatgtg gcgattttag cacttcatcg tccaccagca    60
aacgctttag catcttctgt tttgaaagag ctttcagaac ggcttgatgc attaaaagaa   120
gacgaacaag tacgtgtcat cgttcttcac ggagaaggaa gatttttctc agctggtgcc   180
```

```
gatattaaag agtttacagc gatcgaggcg agcgaacaag cggctgaact tgctcgagct    240
ggacaacaag tgatggagaa aattgaacag tttccgaaac cgattattgc cgcgattcac    300
ggtgctgcac ttggcggagg gctcgagtta gctatgagtt gccatctgcg catcgtagcg    360
gaaaacgcca aacttggctt accagaattg cagctcggca tcattccggg atttgcagga    420
acacaacgct tattgcgtca tgtcggtatg gcaaaagcgc tagaaatgat gtggacaagc    480
gaaccgatca caggtgcaga agctgtgcag tggggactag caaacaaagc cgtcccagaa    540
gaacaattgc ttgatacagc gaagcaactt gcacaaaaaa ttgctcaaaa gagcccgatt    600
tctgttcaag cggtattgaa actagttaat gaagctcgca caaaacgtt ccatgaatgc     660 gttgaaaaag aggctcaact gtttggacaa gtctttgtaa cagaagatgc gaaagagggc    720
atttcggcat ttatcgaaaa acggacacca cagtttcaag gaaaataa                 768
```

<210> SEQ ID NO 137
<211> LENGTH: 783
<212> TYPE: DNA
<213> ORGANISM: Streptomyces avermitilis

<400> SEQUENCE: 137

```
atgagcacgg cgcccgaagc tgccgacttg gtgctccacg agcgtcacgg cggcgtactg    60
accatcacca tcaaccgccc cgcgcagaag aacgccgtcg accacgaggc cgcggtacag   120
ctcgcggcgg ccgtggatct gctcgacgcg gacccggagc tgtcggtcgg cgtcctcacg   180
ggcgcgggcg gggtgttcag cgcgggcatg gacctgaagg cgttcgccaa gggcgagctg   240
cccttgctgc ccagccgggg cctgggcggg ctcacccgcg cgtcggtgcg aaagccgctg   300
gtcgccgcgg tcgagggctg ggcgctcggc ggtggcttcg agctggtcct cgcctgcgac   360
ctgatcgtcg ccgcggagga cgcccgcttc gggtttcccg aggtcatgcg tggtctcgtg   420
gcggcggagg cggactggt caggctgccg cgccgacttc cgtaccacgt cgccgcgcgc    480
gtactgctga cgggcgagcc gctgaccgcc gtcgaagcca aggagtacgg gctcgtcaat   540
gagctgaccc cgcccggcgc cgcgctggac gcggcccggg agctcgcggg ccgcgtcgcg   600
cggaacgcac cgcttgcact ggcggccgtc aaggaggtcc tgcgcgagac acagggcctg    660
aaggagagcg acgcgttcag acgccaggac gagctcacga gcggactggc cgccagcgag   720
gacgcgcggg aaggcgcaca ggcgttcgcc gagaaacgcg ccccggtctg gcacggccgc   780
tga                                                                 783
```

<210> SEQ ID NO 138
<211> LENGTH: 1683
<212> TYPE: DNA
<213> ORGANISM: Advenella kashmirensis

<400> SEQUENCE: 138

```
gtggacaatg ccgtaagct gattgaacgt ggctggcatt tattcaaccg tatcgaaaag     60
ctagcctttc ctacactggc actcatgcac ggcccctgcc tgggtggcgg gctggaactg   120
gcactggcgt gccgttatcg aatcgcgatc gattctccca agccggtgat cggcctgcct   180
gaagtcaaat tgggcatctt ccccgcctgg ggcggcctga tgcgactacc ccgcctgatt   240
ggtccgcaaa ccgccctgaa catgatgctg accggtcgca cactggatgg ccgcaaggcc   300
aggtctgccg gtctggtaga tttgctggtc gcacccgag ttgcagagaa atcgcgatc    360 gatctggtca cgtcgggcaa accggcgcgt caggctcgcg gcctggccgg cttgctcaat   420
```

| | |
|---|---|
| cgtgcaccgt tcaagtcgct ggtggctgcc caggcacgca aaagcgtcaa gcaaaaagac | 480 |
| ccttatggcc actaccccgc caccctgacc atgctggatc tgtgggaaaa acatgatggc | 540 |
| gacccgttgg ccgatcccca ggcgctgacc cggctgctgc aatcggatgt cacccgcaat | 600 |
| ctgatccgtg tatttcacct gcaggagcgg ctcaaggcgt ttggcaagaa ggataatgcc | 660 |
| actcccgtca accatgttca tgtgatcggg gccggcgtga tgggcggtgg catcgctgcc | 720 |
| tggtgcgcgc tgcagggcat caaaaccacc ttgcaggata ccgacgccca gcgcatcgcc | 780 |
| ggggcgttca aaacgccgt ctccatttat gcccgcaagg atcggtatac cgcgcaggca | 840 |
| gcccgcgatc gcctgattcc ggacctggcg ggccacggta tcgcgacggc tgatctggtg | 900 |
| attgaagcga tcagcgaaaa tccgcaagcc aagcaatcgc tctaccagca gatcgaacca | 960 |
| aaaatgaaag aaggcgccat tttagccacc aatacatcca gtctgtccat tgcgcagtta | 1020 |
| cgcagcgtgc tggtgcaccc cgaacgtttt gtcggtattc attttttcaa tccagtctca | 1080 |
| cgcatgccgc tggtagaagt ggtacatgcc gatggcatcg cccaggaaac tctggacacc | 1140 |
| gctgccgcct tgtcggcaa atcggcaaa ctgccgctgc cggttcagga cacgccgggc | 1200 |
| tttctggtca cgccgtgct tgctccctat atgctgcaag ccatgcggtg cattgacgaa | 1260 |
| ggcatggatc ccgaagtcat cgataccgca atgctggagt tcggcatgcc catggggccg | 1320 |
| atcacgctgg ccgatacggt tggtctggat attgccatgg cagccggcaa acagctgtcc | 1380 |
| gaaggccagg agccgccacg ctgcctgcaa gagaagattg cccaaggcaa gctgggtgtc | 1440 |
| aaaagcggcg aaggctttta cgtgtggaaa gaccgcaagc atgaccagcg cagtagcaaa | 1500 |
| gccatcccgc aaggcctggc acagcgcctg atcaagccgc tgatagagca gaccgaaaaa | 1560 |
| caacttgcga caacatcgt gcaagatgca gatcttgccg atgcaggcgt gatattcgga | 1620 |
| accgggtttg cgccttttac cggaggaccc attcattaca acaaagtaa aggaggacta | 1680 |
| tga | 1683 |

<210> SEQ ID NO 139
<211> LENGTH: 714
<212> TYPE: DNA
<213> ORGANISM: Oligotropha carboxidovorans

<400> SEQUENCE: 139

| | |
|---|---|
| gtgagccttt cgccgcttgc caacggcgta cgcgttctca cactggatcg tccgtccaag | 60 |
| gccaacgcgt tgaatgcgga ggtcgtggac cagttgcttg cgtgtgtcgc ccaggccgag | 120 |
| gcggaggatt gccgcgtgct gatcctcgcc gccaacggca aggcgttttg cggcgggttt | 180 |
| gatttcggtg gttatgaatc gatgtcggcg ggcgacctgc tgctgcgctt tgtccggatc | 240 |
| gaggagttgc tgcagcggat gcgccagtcg tcgtttgtca gcattgctct ggtgcatggt | 300 |
| gcggcgatgg gggcggggc ggacatcgtc gcgtcttgca cctatcgcat cggcaccgac | 360 |
| gcaagccggt ttcgctttcc gggattccgt ttcggcgtgg cgcttggcac gcggcatctg | 420 |
| gcgcagcttg tcgcccgca acgggcgcgc gatatcctgc tgaccaatgc aacgatcgat | 480 |
| gcattgaccg ctgtcgatat cggattgctg acgcacctcg tcgatgccgg gagcatgcgg | 540 |
| cagaaagcgg acgagattat tgcgcagatt ggctcgctgg accgtgtcgc acgcaaccgg | 600 |
| attttgcatc tgacctcggc tcagaacaat gacggtgaca tggctgagct ggtgaaatcg | 660 |
| gtgagcgcgc ccgggctaca cgagcgcatt gcgcagtacc gcgccgggca ttga | 714 |

<210> SEQ ID NO 140
<211> LENGTH: 801

```
<212> TYPE: DNA
<213> ORGANISM: Riemerella anatipestifer

<400> SEQUENCE: 140
atgtacaaat taatagatgt agataaccat tttgaaggaa agcttcaaat cgcatatatc    60
aatcagccag aatcgtttaa tagtcttaat aaggttgttt tagaagagtt attgcacttt   120
ataaaagctt gtgacgcaga ttctagtgta cgctgtattg caattagtgg caaaggtaag   180
gcgttttgtt ctggtcagaa tttaaaggag gctttagatt ataaagcaga agccaatgag   240
gaacgcttta tccaaaggat tgtgatagat tattataatc cgttagtgaa ggctattgtc   300
tatgctaaaa aaccagtaat tgcattggtt aatggtcctg cggttggtgc aggagcaatg   360
ttagctctca tctgtgattt tgcagtggcg tcagagtcag cgtattttt cttagctttt    420 tctaatatag gactagtgcc agatacggca ggtacttact atttgcctaa acttttaggg   480
cgttccttag cgagttattt ggcatttaca gggaagaagc tatctgctaa agagtcttta   540
gaaagaggtt tggtggtaga tgtttttca gatgctactt tttcggaaca atctttacaa    600
gtcctagaac atattactca tcagcctact gtggcattgg gcttacaaa aaaagccttt    660 aataaatctt atcagaatag tctatcggag cagttagatt tggagagtat tctccagcaa   720
gatgctgcag aaacttggga ttttcaagag gggatagccg ctttttagc aaaaagaaaa    780 cctcagtata aaggtaagta a                                              801

<210> SEQ ID NO 141
<211> LENGTH: 1269
<212> TYPE: DNA
<213> ORGANISM: Fusobacterium necrophorum
<220> FEATURE:
<221> NAME/KEY: MISC_FEATURE
<222> LOCATION: (1)..(1269)
<223> OTHER INFORMATION: subsp. funduliforme Fnf 1007

<400> SEQUENCE: 141
atgtcagaaa caatcaattt agatgaaatg tcagcaaaac aattattggg ttattatcaa    60
gaaaaattgg atgaagaagc aagacaggca aaaagagaag gaaaattagt tgttggtct   120 gcttccgttg ctccaccaga attctgtgta gctatggata ttgccatggt gtatccagaa   180
actcatgcag cagggattgg agctagaaaa gggtcgttag atctgctaga agtagcagat   240
gaaaaagggt attcttaga tatttgttct tatgcaagag taaatttggg gtatatggaa    300
ttgttaaaac aacaagcctt aactggagaa actcctgaaa aattagcaaa ctctccggct   360
gcaaaagttc ctttaccgga tttagttatt acatgtaata acatttgtaa tactttgtta   420
aaatggtacg aaaatttggc aaaggaatta aatattccat gtattgtaat tgacgttccg   480
ttcaatcata ctatgccaat tacaaaacat tcaaaagaat atattgcaga tcaatttaaa   540
tatgcaattc aacaattaga agaaattaca ggaaagaaat ttgactatga taaattctta   600
gaagtgcaag agcaaacaca aagatctgta tatcaatgga atcgtttagc agctcttgct   660
cactacaaac cttctccatt aaatggtttc gatttattta acttcatggc tttaattgta   720
tgtgctagaa gtagagatta tgcagaaatc actttcaaga aatttgcaga tgaattggaa   780
gaaaacttga aaatgaagt atatgcgttc aaaggagctg aaaagaacag agttacttgg   840
gaaggaattg cagtatggcc ttaccttgga cacactttca gtctttaaa aggaatggga   900 agtatcatga ccggttctgc atatccagga atctggaact tgacatatac tcctggagat   960
atggaatcta tggcggaagc atatacaaga gtctacatta atacttgctt acaaaataaa  1020
```

| | |
|---|---|
| gcggatgtcc tttctaaaat tgtaacagac ggaaaatgtg atggaatact atatcatttg | 1080 |
| aatagaagtt gtaaactgat gagtttcttg aatgtggaaa ctgctgaatt agttgaaaaa | 1140 |
| gcgactggag tgccatatgt aagtttcgat ggagaccaaa cagatccgag aaatttcgca | 1200 |
| ccggctcaat ttgatacaag agtcaaagct taaatgaaa tgatggaagt taataacgaa | 1260 |
| acaaaataa | 1269 |

```
<210> SEQ ID NO 142
<211> LENGTH: 834
<212> TYPE: DNA
<213> ORGANISM: Fusobacterium necrophorum
<220> FEATURE:
<221> NAME/KEY: MISC_FEATURE
<222> LOCATION: (1)..(834)
<223> OTHER INFORMATION: subsp. funduliforme Fnf 1007

<400> SEQUENCE: 142
```

| | |
|---|---|
| gtgcaagatg acagaagttt taagaaagga aagagaagag gaatgtatac agttggagtg | 60 |
| gatataggtt cttcttcttc aaaagtagtg atattaaagg atggaacaga gattgtaagt | 120 |
| caatcggcaa ttcagtcggg aattggaagt aatcgagcca ttgttgcttt ggaagataat | 180 |
| ttaaaaaaag caaacttgac gaaggaagat attggtttta cagttgttac tggatatgga | 240 |
| cgctttactt tgaaggagc agataaacaa atcagcgaga ttagttgtca tgccagggg | 300 |
| attcattttt tattaccgaa tgtgagaacc attattgata tggtggaca agatgccaaa | 360 |
| gcgatcagct tagatgaaaa aggtcatgta agacaatttt ttatgaatga caaatgtgca | 420 |
| gcaggaacag gacgattttt aactgtaatg gcacgcgtac tagagatttc cctagatgag | 480 |
| atgggaactt atgatgctct ttctaaaaat ccttgtaata ttagtagtac ttgtgctgta | 540 |
| tttgcagaat cagaagtcat ttctcaattg gcaaagggaa ataccaaaga ggatgtcatt | 600 |
| gcaggagtac ataattctgt cgctcataag atattaggtt tagtatatcg tacttctatg | 660 |
| gaagaaaaat ttgcgatttg tggtggtgtt gctcagaata caggtgcatt gcgtgcaata | 720 |
| cgggaagctt tgaaaaaaga agtaatcgtt gctcctaatc cacaattaac aggagcatta | 780 |
| ggagctgcaa tttttgctta tgatgagctg aaaaaattaa gaaagggtga ataa | 834 |

```
<210> SEQ ID NO 143
<211> LENGTH: 1125
<212> TYPE: DNA
<213> ORGANISM: Fusobacterium necrophorum
<220> FEATURE:
<221> NAME/KEY: MISC_FEATURE
<222> LOCATION: (1)..(1125)
<223> OTHER INFORMATION: subsp. funduliforme Fnf 1007

<400> SEQUENCE: 143
```

| | |
|---|---|
| atgaaaggca gattagaaga attaattcat atatttgaag atgttgcaaa caaccccaaa | 60 |
| aaaatggtag cagaatataa aaaagaagta gggaaagaag tgattggagt catgccagta | 120 |
| tatgctccag aagaaattat tcacgctgct ggatgtttac ctattggatt atggggagga | 180 |
| aaaaaagaag tttctaaagc aagagcatat ttacctcctt ttgcatgttc tattatgcaa | 240 |
| actgttatgg aattacaaat tggaggaaca tatgacattt tagatgcagt attattctct | 300 |
| gtaccttgtg atactttgaa atgtttaagt caaaaatgga aggaaaatc tcctgtaatt | 360 |
| gtatttactc atcctcaaaa cagagtaatt gaaggagcaa atgcttactt agtaaaggaa | 420 |
| tatcaagcag taaagaaaa attagaagga atcttaggaa gaaccattcc tatggaagcg | 480 |
| attgaagaaa gcgtaaaagt atataatgaa aatagaagag ttatgagaga atttgtagaa | 540 |

```
gtggcggcac aatatccaca aattatcgat ccaattgtta gacataatgt gatgaaatcc     600
agatggttct taagaaaaga aaaacatact gaatatgtaa agaattaat cgctgaatta      660 aaaaaagaaa ctattgttcc ttgggacgga agaaagtaa tcttaacagg aattatgaca      720
gaaccagtag aattgttgca aatctttaaa gatgaaaaac ttgctattgt agccgatgat    780
ttagctcatg aaagccgaca atttagagga gatgttcctg aagaaggagg agatgttcta    840
tacagaatgg caaaatggtg gcaaaattta gaaggatgtt ctttagcaac ggatactaat    900
aaaggtagag gacaaatgct aatggatatg tgtaaggata cgaaagcaga tgccgttatc    960
gtgtgtatga tgaaattctg tgatcctgaa gaatttgact atccggtata ctatagagaa    1020
tttactgaat ccggaattaa aaatattaca gtggaagtgg acttagaagt ttcttctttt    1080
gaacaaatta gaacaagaat acaaacattt aaagatattt ataa                      1125

<210> SEQ ID NO 144
<211> LENGTH: 1269
<212> TYPE: DNA
<213> ORGANISM: Desulfosporosinus youngiae
<220> FEATURE:
<221> NAME/KEY: MISC_FEATURE
<222> LOCATION: (1)..(1269)
<223> OTHER INFORMATION: DSM 17734

<400> SEQUENCE: 144
atgacggata caacaactat gagtgccaaa gaattgttag gtttctatca ggaagaattg      60
tatgaagaag cgagacaggc caaaaaagaa ggaaaacttg tttgttggtc tgcatcggtt     120
gctccttcgg agttttgtgt ggctatggat gtggcgatga tctatcctga aacacatgct    180
gcggggattg gggcaagaaa aggtgcctta gatgtgctgg aagttgccga tgaaaaaggc    240
tataacctgg atacttgctc ctatgcaaga gtcaatatgg gttatatgga acttctgaaa    300
caagaggctt taacaggaat aacgccggaa aagcttgaaa atccccggc ggccagaata    360 ccgctgcccg atttttgtcat aacctgcaac aacatttgca acaccttgct taagtggtat    420
gagaatcttg ccgttgaatt aaatattccc tgcatcatca ttgatgttcc ctttaatcat    480
accatgccca ttccccagta tgctaaggac tatattgcgg aacagtttaa ggaggctatt    540
actcagcttg aggaaatttg cggcaggaaa ttcgactacg acaaattttt gaaagtacag    600
gaacaaaccc agcgttctgt ggcccagtgg aacagaattg ctgctttgtc gggacataaa    660
ccatctcctt taaatggttt tgatcttttc aactatatgg ccctgatcgt ttgtgccaga    720
agcagagact acgcggaaat tacctttaaa agtttgccg atgaacttga agaaaacctc    780
aaaaacggta tctacgccct taaaggaaat gaacaaaagc gtgtaacttg ggagggcata    840
gctgtttggc cgcatctggg ccatacattt aaaggcttaa agaatctggg caatatcatg    900
acaggttcgg cttatcccgg tttgtggaat cttacctaca cacctgggga tatgagttcc    960
atggcggaag cttataccag aatttatatc aatacttgtc tcgataacaa agttaaggtg    1020
cttagtgacg tcatcagcgg cggaaagtgt gacggggtta tttatcatca gaacagaagc    1080
tgtaagctca tgagtcttct caatgtcgaa acggctgata tactccaaaa acaaaatcat    1140
ttaccctatg tcagctttga tggggaccaa acggatcctc gtaactttgc tcctgcccag    1200
tttgatacac gtatccaggc cttagatgaa atgatgaagc agaataagga gggagtttcc    1260
aatgagtag                                                            1269

<210> SEQ ID NO 145
```

<211> LENGTH: 1119
<212> TYPE: DNA
<213> ORGANISM: Desulfosporosinus youngiae
<220> FEATURE:
<221> NAME/KEY: MISC_FEATURE
<222> LOCATION: (1)..(1119)
<223> OTHER INFORMATION: DSM 17734

<400> SEQUENCE: 145

```
atgagtagaa ttgaaacgat tatcagtgaa ttaacgtcca ttgccaataa tccccgccag      60
gctatggaag attataaaaa agaaaccggc aaagggtcgg ttggggttat gccttattat     120
gctcctgaaa aaatcattca tgccgcaggg tatctgcccg taggtatttg gggaggacaa     180
aagagtattt ccaaggcccg ggcctatttg cctcccttty cttgttcaat tatgcaatcc     240
gtggtggaaa tgcagcttga agggtctat gacgatttag aagcggtcct tttccctgtt     300
ccttgtgaca ccttaaaatg tcttagccaa aaatggaaag gaacctcccc tgtcatcgtt     360
ttaactcatc ctcaaaacag aaaactggaa gcagccaata agtttcttgc tgaggaatat     420
aggcttgtgc gtgaaaaact ggaaaaaatc ctgaatgtta agattacaga cgaggcactt     480
aaccaaagca ttgaaattta taacgaaaat cgtaaagtaa tgcgtgaatt tacagagata     540
gctgctaatt atcccaacat tattgatccc gtaaaacgtc atgcgcttat caaagccaga     600
ttctttatgg aaaaagccaa acataccgct ctggtcaaag aattgaatgc agagcttaaa     660
gcgttaccgg tggaagcctt tacaggcaaa aaggttgttt tgacaggcat tatggctgaa     720
cccaatgaag tattggacat tttgcaagat aacggttttg ctgttgtggc agatgacctg     780
gcccaggaat ccagactgtt cagaaatgat gttccctcag gacagaccc actctatcgc     840
ttggctaaat ggtggcagga attcgatggt tgttctctgg ctgtcgatgc gaaaaaacca     900
agaggcccca tgctgatgga tatggttaaa gcatctaagg ccgatgccgt tgtggtttgc     960
atgatgaagt tctgtgaccc tgaagaattt gactatccaa tctactacag acagtttgaa    1020
gaagccggaa ttaagagctt atttatagaa attgacctgg aaccaacctc ctttgaacag    1080
actaaaacca gagttcaaag ttttagagaa atgctgtga                           1119
```

<210> SEQ ID NO 146
<211> LENGTH: 819
<212> TYPE: DNA
<213> ORGANISM: Desulfosporosinus youngiae
<220> FEATURE:
<221> NAME/KEY: MISC_FEATURE
<222> LOCATION: (1)..(819)
<223> OTHER INFORMATION: DSM 17734

<400> SEQUENCE: 146

```
atgtttacaa tggggattga tattgggtcc tcatcctcaa aggttgtaat ccttgaagat     60
ggagttaata ttatcgccgg agaagttatt cagattggaa caggttctac gggacctaaa    120
cgtgtactgg atgaagctct tgccaaagca ggtcttacat tgcaagacat ggctaaaatt    180
attgctacag gctatggaag atcgtctgtg gaagaagcac acaaacaaat cagcgaaatc    240
agttgtcagg ctaagggagt tttctttttta gttccttcag caaaattaat tattgatatt    300
ggcggtcagg atgttaaggc cattaaactt gacagtaaag gctgtgttaa gcagtttttt    360
atgaatgata aatgtgccgc cggaacagga cgttttctcg atgttatgtc gcgggtactg    420
gaagttaatc ttgatgaaat ggcggaatac gatgcccggg caacagaacc tgccacggtc    480
agcagcactt gcacagtttt tgcagaatct gaggtaatat ctcagcttgc caacggagtt    540
gctaaagaga acattattgc aggggttcac cagtcagttg ctagcaaagc ctgtggactt    600
```

```
gcctatcgat gtggggtgga agaggacatc gtgatgtgcg gaggcgttgc taaggactta      660
ggggttgtca gagcaatcag caaagaactg aaaaaaccgg tcattgtagc tcctaatcca      720
caaattacag ctgcacttgg agctgctata tttgccttcg aagaagttat ggaaactgtt      780
atggttgcct tcgaagaagt taggggagct aataaataa                             819
```

<210> SEQ ID NO 147
<211> LENGTH: 1269
<212> TYPE: DNA
<213> ORGANISM: Peptoniphilus indolicus
<220> FEATURE:
<221> NAME/KEY: MISC_FEATURE
<222> LOCATION: (1)..(1269)
<223> OTHER INFORMATION: ATCC 29427

<400> SEQUENCE: 147

```
atgaatacta tagatatatc aaatatgaaa gctaaagaaa tgcttggata ttttcaaaac       60
aaacttgacg aagaagcacg tgaagctaaa aaaaatggaa aattagtttg ctggtcagcc      120
tctgtagctc catctgaatt ttgtgtaacc atggatatcg cattagttta tccagaaact      180
cacgcagccg gtataggtgc tagaaaaggc tctttagcta tgttagatgt tgctgataga      240
aaaggttata atacagatat atgttcttat gccagagtaa acttaggata tatggaactt      300
ttaaaagaat atgctaagac aggagtgaaa cctaaagaac ttgaagaatc tcctgctgca      360
gatgttcctc tacctgattt agtaataact tgcaataata tatgcaacac tttactaaaa      420
tggtatgaaa atttagctgc agaattaaat attccttgta tagttataga cgttcctttt      480
aatcatacta tgcctattcc taagtattct aaagaatata ttgctgacca atttaaggaa      540
gcaataagac aacttgaaga ataacagga aaagattttg actatgataa attttttagaa      600 gttcaagagc aaacgcaaag atctgttgct caatggaata gacttgctgc actttctaaa      660
tatgaaccgt ctcctctaaa tggatttgat ttatttaact atatggctct tatagttttgt      720 gcaagaagta aaaattatgc tgaattaact tttaaaaaat ttgccgatga acttgaagaa      780
aatatgcaaa atggagtgta tccttacaag gctggagaac aatccagaat tacttgggaa      840
ggtatagcta tttggccata tttaggacac acttttaaga ctcttaaagg ctatggctca      900
ataatgacag gctctgctta tcctggactt tggaacttag aatacacacc tggagatatg      960
ctttcaatgg cagaagctta tacgagaata tatataaaca cttgccttga caataaagtt     1020
gatgtattga gaaaaatcat taaaaacggt aaatgtgatg gggtcgcata ccatctaaat     1080
agaagttgta aattgatgag tcttctaaac gttgagacag ctgaaatttt aaataaagaa     1140
aataatcttc catatgttag ttttgatggt gatcaaactg atcctagaaa tttctcagaa     1200
gcacaatatg ataacagaat acaaactctt actgagatga tgtctgccaa taaaaaaatg     1260
aggggttga                                                             1269
```

<210> SEQ ID NO 148
<211> LENGTH: 792
<212> TYPE: DNA
<213> ORGANISM: Peptoniphilus indolicus
<220> FEATURE:
<221> NAME/KEY: MISC_FEATURE
<222> LOCATION: (1)..(792)
<223> OTHER INFORMATION: ATCC 29427

<400> SEQUENCE: 148

```
atgtacacta tgggagtaga tatcggttct acatcatcta aaatcataat acttgaagat       60
```

```
ggaataaaaa ttatcggaaa tattgtagta caatctggaa ccggtacaag tgggccaaca      120
attgctactg caaaagctaa gtcctttctt tcaaataata atttaacttt agatgatata      180
tctaaaatcg ttgtcacagg ttacggcaga ttttcatttg atattgccga taaacaaata      240
agtgaaataa cttgtcatac aaaaggtatt aacttttag tgcctgaagc tcgaactatt      300
ttagatatag gtggacaaga tacaaaagct atttcagtta atgataaagg tcaagttcta      360 caattttca tgaatgacaa atgtgccgcc ggcactggca gattttaga agtcatggct      420 aaaatttag aaatacctt agaaaaatg ggtgaatatg atagattatc aactaatccg      480
gtagctataa gtagtacttg taccgttttt gctgagtctg aagttatttc tcagctatca      540
aagggcatat ctaaagaaaa tatattagcc ggtgtacata attcaactgc taacaaagtt      600
tgtggtcttt tatatcgtac aggaattaag gaaaaaatag ttttatgtgg aggagttgct      660
caaaaccaag gtgttgttag agcgctccaa gaggaattaa aaaagaaat aaccatagct      720 cctcacccac aaatgacagg cgccataggt gctgcttat ttgcttatga agaggcgaat      780
aaaaatttat ag                                                          792
```

<210> SEQ ID NO 149
<211> LENGTH: 1119
<212> TYPE: DNA
<213> ORGANISM: Peptoniphilus indolicus
<220> FEATURE:
<221> NAME/KEY: MISC_FEATURE
<222> LOCATION: (1)..(1119)
<223> OTHER INFORMATION: ATCC 29427

<400> SEQUENCE: 149

```
atgaacaaaa ttaatgaaat aataaattta ttggatgaag tttctaaaga tcctaaacta      60
acagttaaaa aatataaaga aaaacagga aaggtgttg taggtgtcat gccattatat      120
gcacctgaag aaattattca tgctgcaggt tttctaccta tgggactttg gggtgcacaa      180
aaagaagtat ctaaagcaag aatttattta cctccttttg catgttcaat aatgcaaact      240
aatatggaac ttcaaataga aggtgcctat gatgacttag atgcagttgt atttctgta       300 ccgtgcgata ctctaaaatg tatgagtcaa aaatggaagg gtaaaagtcc tgttatagta      360
tttactcatc ctcaaaacag aaaattagaa tctgcaaata aattttggt tacagaatat       420 gaaatcttaa aagataaatt agaaagata ttaaatgtaa aatatctga tgaatccata       480 acaaatagta ttgaaattta caatgaaaat agaaaagtca tgagagaatt ttcagaccta      540
gctggtcaat atcctaatat aattgaccct attcaaagac atattgtatt taagtccaga      600
tggtttatgg aaaaatcaga acatactaaa ttagttaaag aactaatatc tgaaattaaa      660
aaattaccta ttgaagaatg ggatggctat aaagttatag caactggtat tatgatagaa      720
cctgaagaaa tacttcaaat atttaaagat aagaaaatag ctattgttgc agatgattta      780
gctcaagaat caagacaatt tagacatgac gtacctgaag gagatcaacc tctttaaga       840 cttgctaagt ggtggcaaaa tttagaagga tgtgctcttg caactgatac aaaaaaatta      900
agaggccaaa tgctaattga tatggcgaaa aaatataatg ccgatgctgt attgatatgt      960
atgatgaaat tctgcgatcc tgaagaattt gactaccctg tatactatag agagttccaa     1020
gaagctggca taaagaattt actaattgaa attgacttag aaatgacagc ttttgaacaa     1080
actaacacaa gacttcaaac tcttgtagaa actctctaa                            1119
```

<210> SEQ ID NO 150
<211> LENGTH: 1269

```
<212> TYPE: DNA
<213> ORGANISM: Desulfosporosinus meridiei
<220> FEATURE:
<221> NAME/KEY: MISC_FEATURE
<222> LOCATION: (1)..(1269)
<223> OTHER INFORMATION: strain ATCC BAA-275/DSM 3257/ NCIMB 13706/S10

<400> SEQUENCE: 150
atgactgata caacagctat gagcgccaaa gaattgttag gtttctatca ggaagaattg      60
tatgaagaag cgagacgggc aaaaaaagaa ggaaaacttg tttgttggtc tgcatccgtt     120
gctccttcgg agttttgtgt ggctatggat gtagctatga tatatcctga aacccatgct     180
gcgggtattg gggccagaaa aggtgcctta gatgtgcttg aagttgcgga tgaaaaaggc     240
tataacgtgg atacttgctc ctatgcaaga gtaaatcttg gttatatgga acttttaaaa     300
caggaggctt taacaggaat aacaccggaa aagcttgaaa atccccagc ggccagaata     360
cccccttccg attttgtcat aacctgtaac aacatttgta acaccttgct taagtggtat     420
gagaatcttg ccgttgaatt aaatattcct tgcatcatca ttgatgttcc ctttaatcat     480
acaatgccca ttccacagta tgccaaggat tatattgcgg aacagtttaa ggaagctatt     540
actcagcttg aggaaatttg cggcaagaaa ttcgactatg acaaattttt aaaagtacag     600
gaacaaaccc aacgttctgt tgcccaatgg aatagaatcg ctgctttgtc atcacataaa     660
ccatcccctt aaatggttt tgatcttttc aactatatgg ccctgatcgt tgtgcaagg     720
agtaaagact acgcagaaat tacctttaaa agtttgctg atgaacttga agaaaatctt     780
aataagggta tcttcgcctt taaaggaaat gaacaaaagc gggtaacttg gaaggcata     840
gctgtttggc cgcacctggg acatacattt aaaggcttaa agaatcttgg caatataatg     900
acaggttcag cctatccggg tctgtggaat gttagttata caccaggtga tatgagttca     960
atggcggaag cttatactag aatttatatc aatacttgtc ttgataataa agttaaggtt    1020
cttagtgacg taattagtgg cggaaagtgt gacggtgtta tttatcatca gaacagaagc    1080
tgtaagctca tgagttttct gaatgtagaa actgctgata tcctccaaaa agaaaatggt    1140
ttaccctatg taagctttga tggagaccaa actgatcctc gtaacttttc tcctgcccag    1200
tttgacacac gtatccaggc cttagatgaa atgatgaagc agaataagga gggagtttcc    1260
aatgagtag                                                            1269

<210> SEQ ID NO 151
<211> LENGTH: 1119
<212> TYPE: DNA
<213> ORGANISM: Desulfosporosinus meridiei
<220> FEATURE:
<221> NAME/KEY: MISC_FEATURE
<222> LOCATION: (1)..(1119)
<223> OTHER INFORMATION: strain ATCC BAA-275/DSM 13257/NCIMB13706/S10

<400> SEQUENCE: 151
atgagtagaa ttgaaactat tattagtgaa ttatcttcaa tttcaaataa tccccgcaag      60
gctatggaag attataaaaa agaaaccggt aaagggtcgg taggggttat gccttattat     120
gcccctgaag aaataattca tgctgctggt tttcttcccg taggtatttg gggaggacaa     180
aagagtattt caaaagcccg tgcctattta cctcccttg cttgttcaat tatgcaatca     240
gttatggaaa tgcagcttga agggtatat gacgatttag aagcagtact tttccccgtt     300
ccttgtgaca ctttaaaatg tctcagccaa aaatggaaag gaacatcacc tgtcatcgta     360
tttactcatc ctcaaaacag aaaactcgaa gcagccaata agtttcttgc tgaggaatat     420
```

```
cgacttgttc gtgaaaagct ggaaacaata ttgaatgtaa agattactga tgaagcactc    480
aaccaaagta ttgaaactta taacgaaaat cgtaaagtaa tgcgtgaatt tacggaccta    540
gctgctaatt atcctcagat tattgatccc agaatacgtc atgcaattat aaaagctaga    600 tttttttatgg aaaaatctaa acataccgct atggtaaaag aattgaattc agagcttaaa    660
tcgttacctg ttgaagcctt tacaggtaaa aaggttgttt taacaggaat tatggctgaa    720
cccaatgaag tattagacat tttaaaagat aacggttttg ctgttgtggc agacgacctg    780
gcccaggaat ccagactgtt cagaaatgat gttccgtcag gtacagaccc actatatcga    840
ttggctaaat ggtggcaaga attcgatggt tgttctcttg ctacagatgc gaaaaaatca    900
agaggcccca tgctgatgga gatggttaaa gggtctaagg ccgatgcagt tgtggtttgc    960
atgatgaagt tctgtgaccc tgaagaattt gactatccaa tctactatag acagtttgaa    1020
gaagctggaa ttaagagcct attatatagaa attgacctgg aaacaacatc ctttgaacag    1080
actaaaacca gagttcaaag ttttagtgaa atgctgtga                           1119
```

<210> SEQ ID NO 152
<211> LENGTH: 786
<212> TYPE: DNA
<213> ORGANISM: Desulfosporosinus meridiei
<220> FEATURE:
<221> NAME/KEY: MISC_FEATURE
<222> LOCATION: (1)..(786)
<223> OTHER INFORMATION: strain ATCC BAA-275/DSM 13257/NCIMB 13706/S10

<400> SEQUENCE: 152

```
atgtttacaa tggggattga tattgggtcc tcatcctcaa aggttgtaat acttgaagat    60
ggagttaata ttatcgctgg agaagtcatt cagattggaa caggttcgac aggacctaaa    120
cgtgtactga tgaagctct ttccaaagca ggtcttaaat tggaagacat ggctaaaatt    180
attgctacag gctacggaag atcttctgtg gaagaagcac acaaacaaat tagcgaaatc    240
agttgtcagg ctaagggagt tttcttttta gttccttcag caaaattaat tattgatatc    300
ggcggtcaag atgttaaggc aattagactt gacagtaaag gcggcgttaa gcagtttttt    360
atgaatgata atgtgccgc cggaacagga cgttttctcg atgttatgtc acgagtactt    420
gaagttaatc ttgatgaaat ggcagaatac gatgctcgtg caacagaacc tgccacggtc    480
agcagcactt gcacagtttt tgcagaatct gaggtaatat ctcagctttc caacggagtt    540
gctaaagaga atattattgc aggggttcac cagtcagttg ctagcaaagc ctgtggactt    600
gcctatagat gtggggtgga agaggacatt gttatgtgcg gaggtgttgc taaggactta    660
ggggttgtcc gggcaataag caaagaacta aaaaaacctg tcattgtagc tcctaatcca    720
caaattacag ctgcccttgg agctgctatc tttgccttcg aagaagtcag gggagctaat    780
aaataa                                                              786
```

<210> SEQ ID NO 153
<211> LENGTH: 1434
<212> TYPE: DNA
<213> ORGANISM: Acidaminococcus fermentans

<400> SEQUENCE: 153

```
atgccaaaga cagtaagccc tggcgttcag gcattgagag atgtagttga aaaggtttac    60
agagaactgc gggaaccgaa agaaagagga gaaaaagtag ctggtcctc ttccaagttc    120 ccctgcgaac tggctgaatc ttttcggctg catgttgggt atccggaaaa ccaggctgct    180
ggtatcgctg ccaaccgtga cggcgaagtg atgtgccagg ctgcagaaga tatcggttat    240
```

```
gacaacgata tctgcggcta tgcccgtatt tccctggctt atgctgccgg gttccggggt    300
gccaacaaaa tggacaaaga tggcaactat gtcatcaacc cccacagcgg caaacagatg    360
aaagatgcca atggcaaaaa ggtattcgac gcagatggca aacccgtaat cgatcccaag    420
accctgaaac cctttgccac caccgacaac atctatgaaa tcgctgctct gccggaaggg    480
gaagaaaaga cccgccgcca gaatgccctg cacaaatatc gtcagatgac catgcccatg    540
ccggacttcg tgctgtgctg caacaacatc tgcaactgca tgaccaaatg gtatgaagac    600
attgcccgtc ggcacaacat tcctttgatc atgatcgacg ttccttacaa cgaattcgac    660
catgtcaacg aagccaacgt gaaatacatc cggtcccagc tggatacggc catccgtcaa    720
atggaagaaa tcaccggcaa gaagttcgat gaagacaaat cgaacagtg ctgccagaac    780 gccaaccgta ctgccaaagc atggctgaag gtttgcgact acctgcagta caaaccggct    840
ccgttcaacg ggttcgacct gttcaaccat atggctgacg tggttaccgc ccgtggccgt    900
gtggaagctg ctgaagcttt cgaactgctg gccaaggaac tggaacagca tgtgaaggaa    960
ggcaccacca ccgctcccct caaagaacag catcgtatca tgttcgaagg gatcccctgc   1020
tggccgaaac tgccgaacct gttcaaaccg ctgaaagcca acggcctgaa catcaccggc   1080
gttgtatatg ctcctgcttt cgggttcgtg tacaacaacc tggacgaatt ggtcaaagcc   1140
tactgcaaag ccccgaactc cgtcagcatc gaacagggtg ttgcctggcg tgaaggcctg   1200
atccgcgaca acaaggttga cggcgtactg gttcactaca accggtcctg caaaccctgg   1260
agcggctaca tgcctgaaat gcagcgtcgt ttcaccaaag acatgggtat ccccactgct   1320
ggattcgacg gtgaccaggc tgacccgaga aacttcaacg cggctcagta tgagacccgt   1380
gttcagggct tggtcgaagc catggaagca aatgatgaaa agaagggaa ataa           1434

<210> SEQ ID NO 154
<211> LENGTH: 1140
<212> TYPE: DNA
<213> ORGANISM: Acidaminococcus fermentans

<400> SEQUENCE: 154
atggctatca gtgcacttat tgaagagttc caaaaagtat ctgccagccc gaagaccatg     60
ctggccaaat ataaagccca gggcaaaaaa gccatcggct gcctgccgta ctatgttccg    120
gaagaactgg tctatgctgc aggcatggtt cccatgggtg tatggggctg caatggcaaa    180
caggaagtcc gttccaagga atactgtgct tccttctact gcaccattgc ccagcagtct    240
ctggaaatgc tgctggacgg gaccctggat gggttggacg ggatcatcac tccggtactg    300
tgtgataccc tgcgtcccat gagccagaac ttcaaagtgg ccatgaaaga caagatgccg    360
gttattttcc tggctcatcc ccaggtccgt cagaatgccg ccggcaagca gttcacctat    420
gatgcctaca gcgaagtgaa aggccatctg gaagaaatct gcggccatga aatcaccaat    480
gatgccatcc tggatgccat caaagtgtac aacaagagcc gtgctgcccg ccgcgaattc    540
tgcaaactgg ccaacgaaca tcctgatctg atcccggctt ccgtacgggc accgtactg     600 cgtgccgctt acttcatgct gaaggatgaa tacaccgaaa agctggaaga actgaacaag    660
gaactggcag ctgctcctgc cggcaagttc gacgccaca aagtggttgt tccggcatc     720 atctacaaca cgcccggcat cctgaaagcc atggatgaca caaactggc cattgctgct    780 gatgactgcg cttatgaaag ccgcagcttt gccgtggatg ctccggaaga tctggacaac    840
ggactgcatg ctctggctgt acagttctcc aaacagaaga acgatgttct gctgtacgat    900
```

| | |
|---|---|
| cctgaatttg ccaagaatac ccgttctgaa cacgttggca atctggtaaa agaaagcggc | 960 |
| gcagaaggac tgatcgtgtt catgatgcag ttctgcgatc cggaagaaat ggaatatcct | 1020 |
| gatctgaaga aggctctgga tgcccaccac attcctcatg tgaagattgg tgtggaccag | 1080 |
| atgacccggg actttggtca ggcccagacc gctctggaag ctttcgcaga aagcctgtaa | 1140 |

<210> SEQ ID NO 155
<211> LENGTH: 783
<212> TYPE: DNA
<213> ORGANISM: Acidaminococcus fermentans

<400> SEQUENCE: 155

| | |
|---|---|
| atgagtatct ataccttggg aatcgatgtt ggatctactg catccaagtg cattatcctg | 60 |
| aaagatggaa agaaaatcgt ggcgaaatcc ctggtagccg tggggaccgg aacttccggt | 120 |
| cccgcacggt ctatttcgga agtcctggaa atgcccaca tgaaaaaaga agacatggcc | 180 |
| tttaccctgg ctaccggcta cggacgcaat tcgctggaag gcattgccga caagcagatg | 240 |
| agcgaactga gctgccatgc catgggcgcc agctttatct ggcccaacgt ccataccgtc | 300 |
| atcgatatcg gcgggcagga tgtgaaggtc atccatgtgg aaaacgggac catgaccaat | 360 |
| ttccagatga atgataaatg cgctgccggg actggccgtt cctggatgt tatggccaat | 420 |
| atcctggaag tgaaggtttc cgacctggct gagctgggag ccaaatccac caaacgggtg | 480 |
| gctatcagct ccacctgtac tgtgtttgca gaaagtgaag tcatcagcca gctgtccaaa | 540 |
| ggaaccgaca agatcgacat cattgccggg atccatcgtt ctgtagccag ccgggtcatt | 600 |
| ggtcttgcca atcgggtggg gattgtgaaa acgtggtca tgaccggcgg tgtagcccag | 660 |
| aactatggcg tgagaggagc cctggaagaa ggccttggcg tggaaatcaa gacgtctccc | 720 |
| ctggctcagt acaacggtgc cctgggtgcc gctctgtatg cgtataaaaa agcagccaaa | 780 |
| taa | 783 |

<210> SEQ ID NO 156
<211> LENGTH: 1011
<212> TYPE: DNA
<213> ORGANISM: Carboxydothermus hydrogenoformans

<400> SEQUENCE: 156

| | |
|---|---|
| atgaaattaa actatttttg cagttactgg ccggtggaaa tatccgaagg agcggggatt | 60 |
| tctacggtcc gttatttccc gtccgatgaa agcaaagctc cggtaaggct tcctgcttac | 120 |
| tgctgttctt atgccagggg aagccttgcc gaaattgaag aagaaggaga cggtgacttt | 180 |
| tggggatttg cccacagttg cgacacgatg cagagtttat acggcattac taagagttta | 240 |
| ctggagacg accgggtttt tcttttcgtt ccgccggttg acttaaccac cgcttttgcc | 300 |
| cggaatact accgggaagc tttaattat ctctggcggg aactttccca aaaaagcggg | 360 |
| gttaatggtg aggaaaagtt aaagcttacc tgggaaaagt tgaaggagtt aagaaataag | 420 |
| gttaaatctt tggaaaactt gacgtcaatt attccttcct ccgaaatttt tgagcttta | 480 |
| aaaaagcttc agaccctgcc gctggatgag ctttggatt acctcgaggc caaaaagcg | 540 |
| gaatttacca gttatctgt ggctcaaaag gctataggga ttattttaac gggagcggta | 600 |
| gtcactaaca gtaaacttta ccttgcttta gaacaacagg gatttagagt agtttatgat | 660 |
| gatacctgta ccggctttcg tcattttgct ggagagatag aggataaaga cgatattttg | 720 |
| gaggcaatag tttccttacta ccttttcaaag cccccctgtc cctgcaggca taggggagta | 780 |
| tgggcgaggg cggagtattt aaaaaaatctt tatcataaca aaaatgcccg gccattgta | 840 |

```
cttttacaaa ataaattttg tgaccccttt gcctgggatg ttccctattt agtggactac    900
tttaaaaaac agggagttcc ggttttagtt ttagaggtgg aaggcggaga atcggcgag     960 caaaataaaa ctcgcctcca ggccttccgg gaaagcgtgg gtggagtgta a            1011
```

<210> SEQ ID NO 157
<211> LENGTH: 1215
<212> TYPE: DNA
<213> ORGANISM: Carboxydothermus hydrogenoformans

<400> SEQUENCE: 157

```
atggctaaaa aaatctttaa gcctcttaag gcttcagaga aaataaataa aattttaaaa     60
aatcattatt taaaagcaaa gtatttgcca acgcttggaa aattttttgg ttataaaacc    120
gcctggatta ccagcggagc tccggtggaa ctactgcggg cctttggtat agagccggtt    180
tatccggaga attacggtgc catttgcggt gcccgcaagg tttcgccgag tctttgccag    240
gtagcggaaa cagggggtta ttctctcgat ttgtgttctt atgccaagag taatctcgga    300
agtatctgga atccgaaaga aagtccattt aacggcttac cccggccgga tttactggtg    360
gtttgcaaca catttgcggg acggttttta agtggtacg  aaactttaag ccgggaattt    420
aatattcccc ttttatcat  tgatacccct tttatcaccg gtgaaccccca accctggcaa   480 atccagtatg tggccaaaca gatagaaaaa ctggcgattg aactgaaaaa attttttccgg   540 aaaaagttgg atttaaaccg tttggaaaaa gtaattctcc ttgccaatga dacggtggat    600
ttatggaagg ggataagaaa ttttgccaaa ataaaccctt cgccggtaaa cgttaccgat    660
ttatttatta atctggggcc aatggtggtt ttaagggtgg ccgaagttgc ccgggatttt    720
tacgaggaag tttaccggga agtggaagaa aggtacaaag ccgggggtcc ggcggtagag    780
ggagaaaaat accgtttagt ctgggacaac attcccatct ggtacggact gtaccgtttt    840
tacggttatt ttgccgaaag gggagcggtt tttgttaccg attcctatac cggtggctgg    900
gcggtcaaca taaaaaaggg tcctccctt  tatgcattag ccgagaccta tgccggcgtc    960
tttttaaatc gggatttaga atttcgcaaa atcagttgc  aatctttcat tgaggaattt   1020
tctgccgatg gctttgtcat gcactccaat cgttcgtgca aagcttattc ttttgtgcag   1080
gaggaaatcc ggcgccaaat catgaggtca ctaggagtgc cggggttaat agtggatgcc   1140
gatatgaccg cagccggct  ttattccgaa gaaacgggttt taaaccgggt ccaggctttc   1200
ctggagagcc tgtag                                                    1215
```

<210> SEQ ID NO 158
<211> LENGTH: 765
<212> TYPE: DNA
<213> ORGANISM: Carboxydothermus hydrogenoformans

<400> SEQUENCE: 158

```
ttgtatcttg gagttgatat tggttcgctt acgaccaagg ttgtcttaat tgaccgggga     60
aaaaatctta ttgcttatcg ttacagtaaa accggacctg ccggaaagga aacggccgag    120
cggttaattc aagaggtttt gataaaagcg aatatttccc gggacgatat tcagggaata    180
gttgctaccg gttacggcag ggttctcttt tccggaaagg agttttcgga gataacctgt    240
caggcccggg ggattgggca tttatacccg gaggcaaaaa cgattatcga tattggtggc    300
caggatagca aagtaatttc tctgggaaaa aacggaaagg tactggactt tgccatgaac    360
gataaatgtg ctgctggcac cggacgtttt ttggaggtga tgagtcaggc ccttgaagtt    420
```

| | |
|---|---|
| cgtctggaag agatagggga acttgccgaa aagagccagg aggcagctaa gatatcttcg | 480 |
| gtttgtaccg tttttgccga atcggaagtg atatccaatt tatcccgggg gcagagccgg | 540 |
| gaagcggtag cacggggaat tgtgaggcg gtggcggccc gaacggctat actggcgcaa | 600 |
| aaagtggggg tggtagaacc ggtggttttt accggagggg tggccaaaaa tactggagtt | 660 |
| gtggcggctt tggagcgaaa gcttggggtt aagttattaa ttccggaaga ttccacgatt | 720 |
| accgcagctc tgggggcggc tttattagcc gctgaaaatt cttaa | 765 |

<210> SEQ ID NO 159
<211> LENGTH: 786
<212> TYPE: DNA
<213> ORGANISM: Oscillibacter valericigenes

<400> SEQUENCE: 159

| | |
|---|---|
| atgaacaata tttacacgat gggcatcgac gtggggtcca ccgcatccaa gtgcctcatc | 60 |
| ctgaaagacg gcagcgaaat cgttgccaag tctctggtag atgtgggcgc gggtaccagc | 120 |
| ggccctaccc gtgctattgc ggaggtactg gaagccgcgg ggatgaagaa ggaggacatg | 180 |
| gcttttattc tggctaccgg ctatggccgc aattcactgg acgacattgc cgaccaccag | 240 |
| atgagcgagc tgagctgcca tgccaaaggc gcgttttttcc tgtttccgga tgtccacacc | 300 |
| gtcatcgaca tcggcgggca ggatgtgaag attcttgaga ttgagaacgg cgttatggtg | 360 |
| aattttgcca tgaatgacaa gtgcgccgcc gggacgggcc ggttcctgga cgtgatggcc | 420 |
| cgggtgctgg aggtgaaggt ggaggatctg gcggacctgg gagcccagtc caccaagaat | 480 |
| gtggagatca gctccacatg caccgtgttc gctgagagcg aggtcatcag ccagctggcc | 540 |
| aagggcagcg acaagcgcga catcatccac ggcatccaca gtctgtggc atcccgggtg | 600 |
| gttggccttg ccaaccgtat cggtgtgcgg gacgcgtgg tgatgaccgg cggcgtcgcc | 660 |
| cagaacggcg gcgtggtctc cgcgcttcag gaggcgttgg gccatcccat tcacacttcg | 720 |
| cctctgacgc agtacaacgg cgcgctgggc cggcgttgt ttgcatggca gaaggcaacc | 780 |
| aaataa | 786 |

<210> SEQ ID NO 160
<211> LENGTH: 1284
<212> TYPE: DNA
<213> ORGANISM: Oscillibacter valericigenes

<400> SEQUENCE: 160

| | |
|---|---|
| atggccgaaa acgaaaaagc cactgcggcc gctcccgagg cggctcctgt taagaaagct | 60 |
| ccgaagccgg tcagccccgg tacgcaggcg ctgcgcgacg ttgtcaccaa ggtgtacgcc | 120 |
| gccgcgtggg atgcgaaaaa ggcggccgc ccgtgggct ggtcgtcttc caagttcccc | 180 |
| tgcgagatcg ccgaggcgct gggccttgca gtcgtatatc cggaaaacca ggctgccggt | 240 |
| atcggcgccc agcacgatgg ccagcggatg tgtgaatctg ccgagtcctt gggcttcgac | 300 |
| ccagatatct gcggatacgc ccggatttcc ctggcttatt ccgcgggcgt tgagacgacc | 360 |
| aatgagtccc gccgggttcc catgccggac ttcgtgctgt gctgcaacaa tatttgtaac | 420 |
| tgcatgacca gtggtatga gaatattgcc cggatgcaca acattcccct gattatgatc | 480 |
| gacgtgccct ataacaacga ggtcaccgtc agcgattccc aggtggctta cattcgcggc | 540 |
| cagttcgatg acgccattaa gcagatggag aagattgccg gcgtgaagtt cgacgaaaag | 600 |
| aagtttgaac aggcctgcgc caatgccaac cgcactgcca aggcgtggct gacggtctgt | 660 |
| gactatttgc agtataagcc cgctcccatg agcggcttcg atctgtttaa ccatatggct | 720 |

```
gatgtggtga ctgcccgcgg caaggtggag actgccgagg cgttcgagct gctggcaagc      780
gagctggaac agcacgtaaa aaacggaacc agcaccgctc cgttccccga gcagtaccgc      840
gtcatgttcg agggcattcc ctgctggccc aacctaagga cgcttttcaa gcccctgaaa      900
gccaacggcg tcaacgtcac cgccgtggtg tacgcgcccg cgttcggttt tgtgtataac      960
gggctggacg agatggcccg cgcatactgc aaggccccca acagcgtgtg cattgagcag     1020
ggcgtggact ggcgcgaggg catctgtcgc gagaacaagg tagacggcgt gctggtgcac     1080
tataaccgat cctgcaagcc ctggtccggc tacatggccg agatgcagcg ccgtttcacc     1140
aaggatctgg gcgtcccctg cgccgggttc gacgagatc aggccgatcc ccgcaacttc      1200
aacgaggctc agtatgagac ccgtgtccag ggcctggtag aggctatgga ggagaataaa     1260
aagcagaagg aggcccgggc atga                                            1284

<210> SEQ ID NO 161
<211> LENGTH: 1143
<212> TYPE: DNA
<213> ORGANISM: Oscillibacter valericigenes

<400> SEQUENCE: 161
atgagtatcg aaacgattgt aaaggagttt gccgacgttg cggccgaccc gaaagcacag       60
ctgaagaaat acaaggcgga gggcaaaaaa tgcattggtg tgatgccgta ttacgcgccc      120
gaggagctgg tggccgccgc cggtatggtg ccgtttggta tgtggggcag caatgacaag      180
accatttctc gcgccaagga atactgcgct acatttttact gcaccatcgc ccagctggat      240
cttgagatgc tgctggacgg caccatggat cttttagacg gagtcatcac ccccaccatc      300
tgcgacacgc tccgtcccat gagccagaac atccgcgtgg ccatgggcga gaagctcccc      360 tgcatttttcc tggcccatcc ccagaaccgc aagcccgctt acggcaagaa gttctgcctg      420
gaccaatata cccacatcaa gactgagctt gagaagatcg ccggcgcgcc catcaccgac      480
gccgcactgt ccgagaccat caaggtctat aataagagcc gcgccgcccg ccgtgagttc      540
gtgaagctgg tcagcgacca ctgcgatgtt atcaccccca ccaaacgcag cgctgttttg      600
aaagccgcgt ggtttatgcc caaggcggag tacaccgaga agctgaaggc cctcaacgca      660
gagctgaagg ctctgcctgt gtgcgactgg aaggggacca aggtggtcac ctccggcatc      720
atatgcgaca accctaagct tctggagatc ttcgaggaga caaaatcgc catcgccgcc       780 gacgacgtgg ctcatgagtc ccgctccttc cgcgtagacg ctcccgagac cggcgatccc      840
atggaggcac tcgcccagca gtttgccaat caggattacg atgttctgct gtacgatgag      900
cattccagcg agaaccgccg gggcgagttt gtggccaagc tggtgaagga cagcggcgcc      960
aaggggctgg tcctgtttat gcagcagttc tgcgacccgg aggagatgga gtatccctcc     1020
ctcaaaaagg cgctggacga agccaagatc ccccacatca agctgggtgt ggatcaacag     1080
atgcgggact tcggtcaggc tcgcaccgcg attcaggcgt tgccgatgt gatctccctc     1140 taa                                                                  1143

<210> SEQ ID NO 162
<211> LENGTH: 1269
<212> TYPE: DNA
<213> ORGANISM: Desulfosporosinus orientis
<220> FEATURE:
<221> NAME/KEY: MISC_FEATURE
<222> LOCATION: (1)..(1269)
<223> OTHER INFORMATION: strain ATCC 19365 / DSM 765 / NCIMB 8382 /
      VKM B-1628
```

<400> SEQUENCE: 162

```
atgactgata cagccaatat gagtgctaaa gaattgttag gtttctatca ggaagaattg      60
tatgaagaag cgagacaggc caaaaaagaa ggaaaacttg tttgctggtc ggcttccgtt     120
gctccttcgg agttttgtgt agctatggac gtggccatga tctatcctga aacccatgct    180
gcagggatcg gggccagaaa aggcgcctta gatatgcttg aagttgccga tgaaaaaggg    240
tataacctgg acacttgctc ctatgccaga gtgaatctgg gttatatgga acttttaaaa    300
caagaggctt taaccggaat aaccccggag aaactggaaa atctccggc ggccagagta     360
cccctgcctg attttgtcat aacctgcaac aacatttgta acaccttgct taagtggtat    420
gaaaatcttg ccgttgagct aaatattccc tgcatcgtca ttgatgttcc ctttaatcac    480
accatgccca ttccccagta tgctaaagac tatattgcgg aacagtttaa ggaggcaatt    540
gctcagcttg aagagatttg cggcaagaaa ttcgactatg acaaattctt gcaagtccag    600
gaacaaaccc agcgctctgt ggcccaatgg aaccggattg cttctttgtc agggcataaa    660
ccatccccct aaatggtttt tgatcttttc aactatatgg ccctgatcgt tgtgcccgc     720
agcagggact gcgcagaaat tacccttaaa agtttgccg atgaactgga agacaatcta     780
agcaaaggaa tctacgcctt taaaggcaat gaacaaaagc gtatcacttg ggaaggcatc    840
gctgtttggc cgcacctggg ccataccttt aaaggcttaa agaatcttgg caatatcatg    900
accggttcag cctatcccgg tttgtggaat ctttcttata cgcccggtga tatgagttcc    960
atggcagaag cttacaccag aatttatatc aatacttgtc tggataacaa agttaaggtt    1020
cttagtgaca tcatcagcgg cggaaagtgt gacggtgtta tttatcatca aacagaagc     1080
tgtaagctca tgagttttct caatgtcgaa acgccgata tcctccaaca acaaaatcat     1140
ttaccctatg tcagctttga tggagaccaa accgatcccc gtaactttgc tcctgcccag   1200
tttgatacac ggatccaagc cttagatgaa atgatgaagc agaataagga gggagttttcc 1260
catgagtag                                                           1269
```

<210> SEQ ID NO 163
<211> LENGTH: 1119
<212> TYPE: DNA
<213> ORGANISM: Desulfosporosinus orientis
<220> FEATURE:
<221> NAME/KEY: MISC_FEATURE
<222> LOCATION: (1)..(119)
<223> OTHER INFORMATION: strain ATCC 19365 / DSM 765 / NCIMB 8382 / VKM B-1628

<400> SEQUENCE: 163

```
atgagtagaa ttgaagcgat tatcagtgaa ttatcttcta ttgccaataa tccccgtaag     60
gccatggaag attataagaa agaaacgggc aaagggtcgg tagggattat gccttattat    120
gctccggaag aaatcgttca tgccgccggt tacctgcccg taggaatttg ggagggcaa     180
aagagtattt ctaaagcccg tgcttatta cctccttttg cttgttcaat catgcaatcc    240
gttgtggaaa tgcagctgga aggggtctat aacgacttag cggcggtcct tttccccgtt    300
ccttgtgaca ctttaaaatg tctcagccaa aaatggaaag gcacatcccc ggtcatcgtc    360
atgactcatc ctcaaaaccg aaaactcgaa gcagccaata agtttctggc tgaggaatat    420
cgccttgttc gtgaaaagct ggaaaaaatc ttaaatgttc agattaccga tgaggcactg    480
aaccacagca ttgatgttta taacgaaaat cgcaaggcaa tgcgtgaatt tacgacata     540
gccgctaatt attttgaacat tattgatccc agaaagcgtc atgagattat caaggccaga   600
```

```
ttctttatgg aaaaatccaa acataccgcc ttggtcaaag aattgaattc cgagcttaaa      660
tctttacctg tggaagattt tacaggcaaa aaggtgattt taaccggaat catggctgaa      720
cccaatgaag tattagacat tttgaaagag aatgattttg ctgttgtggc agatgacctg      780
gcccaggaat ccagactgtt caggattgat gttccggctg gtccagaccc actctaccgc      840
ttggctaaat ggtggcaaga attcgacggt tgttctctgg ctgtagatac gaaaaaatta      900
agaggaccca tgctgatgaa tatggttaac gtggataagg ccgatgccgt ggtggtttgc      960
atgatgaagt tctgtgaccc tgaagaattt gactatccca tctactacag acagtttgaa     1020
gaagccggaa ttaagagctt atttatagaa attgacctgg agccaacctc ctttgaacag     1080
actaaaacca gagttcaaag ttttcgtgaa atgctgtga                            1119
```

<210> SEQ ID NO 164
<211> LENGTH: 801
<212> TYPE: DNA
<213> ORGANISM: Desulfosporosinus orientis
<220> FEATURE:
<221> NAME/KEY: MISC_FEATURE
<222> LOCATION: (1)..(801)
<223> OTHER INFORMATION: strain ATCC 19365 / DSM 765 / NCIMB 8382 / VKM B-1628

<400> SEQUENCE: 164

```
atgtatacta tggggattga tatcggttcc tcatcctcaa aggttgtcat acttgaagat       60
ggagttaacc tcatcgccgg cgaagtcatt cagattggaa caggctcgac aggtcctaaa      120
cgggtactgg aggaagctct tgccaaaaca ggtctcacct ggcagacat ggctaaaatt       180 attgctaccg gctacggccg atcttctgtg gaagtatccg acaagcaaat cagcgaaatc      240
agctgtcagg ctaagggagt ttactttta gttcctacag caaaattaat cattgatatc      300
ggcggtcagg atgtgaaggc cattagactt gaccgtatag gcggcgtcag gcagtttttt      360
atgaatgata atgtgccgc cggaacagga cgttttctcg atgtgatgtc acgagtactg      420
gaagtggatc tggatgaaat ggcagaatac gatgcccggg ccacagaacc cgccacggtc      480
agcagcacct gcacagtgtt tgccgaatcc gaggtaatat ctcagcttgc caacggagtt      540
gctaaagaga atattattgc cggggttcac cagtccgttg ccagcaaagc ctgtggactc      600
gcctatcgat gcggggtgga agaggacgtt gtgatgtgcg gaggagttgc taaggactta      660
ggagttgtcc gggccatcag caaagaacta aaaaaaccgg tcattgtagc tcctaatccc      720
caaattacag ccgcccttgg cgctgcccta tttgcttatg aagaagttat ggaagctaat      780
aaattaagga agaggtatg a                                                801
```

<210> SEQ ID NO 165
<211> LENGTH: 1236
<212> TYPE: DNA
<213> ORGANISM: Peptostreptococcus anaerobius
<220> FEATURE:
<221> NAME/KEY: MISC_FEATURE
<222> LOCATION: (1)..(1236)
<223> OTHER INFORMATION: CAG:621

<400> SEQUENCE: 165

```
atgagtaaca caggtgcagt tgaagaaaag ccggcaaaag tattgttagg cgagatagtt       60
gcaaaacatt ataaggaagc ttgggaagct aagaaaagag gcgaaaaagt tggttggtgt      120
gcttctaact tcccacagga aatatttgaa acaatggata tcaaggttgt attccctgaa      180
aaccaggcag cagcaatttc tgctaagggt ggtggacaga ggatgtgcga aatcgcagaa      240
```

```
aacgaaggat attcaaacga catatgtgct tacgctagaa tatctctagc atacatggac        300
gttaaagatg ctccagagtt aaatatgcct cagccagact tgttgcatg  ctgtaacaat        360 atctgtaact gtatgatcaa gtggtatgaa aatatagcta agaactaaa  tatacctcta        420 atccttgttg acgtgccata taacaatgac tatgaagcag gcgatgacag agtagaatac        480
ttaagaggac agttcgatca cgctataaag cagttagaag acttaactgg taaaaagtgg        540
gatgaaaaga agttcgaaga agtaatggca atatctcaga gaacaggtag agcttggtta        600
aaggctactg gatatgctaa gtacactcca tcaccattct caggatttga cgtattcaac        660
catatggcag ttgctgtatg tgctagaggt aaggaagaat cagcaatagc atttgaaaag        720
ctagctgaag aatttgatga aaatgtaaag actggtaagt ctacattcaa gggagaagaa        780
aagtacagag tactatttga aggtatagct tgttggccac acctaagaca tacatttaag        840
cagctaaagg attcaggagt aaacgtttgt ggtactgttt atgcagatgc attcggatac        900
atctacgaca atacttatga attaatgcag gcttattgtg gaactcctaa tgcaatatct        960
tatgaaagat cattagatat gagacttaag gttatagaag aaaataatat agacggtatg       1020
ttgatacata taaacagaag ctgtaagcag tggtctggta tcatgtacga aatggaaaga       1080
gaaataagag aaagaactgg tataccaaca gctacattcg atggtgatca ggctgaccca       1140
agaaacttct cagaagcaca gtacgacaca agagtacagg gtctaataga agttatggaa       1200
gcaaacaaag ctgcaaagat gaaggaggaa aactag                                  1236
```

<210> SEQ ID NO 166
<211> LENGTH: 1119
<212> TYPE: DNA
<213> ORGANISM: Megasphaera elsdenii
<220> FEATURE:
<221> NAME/KEY: MISC_FEATURE
<222> LOCATION: (1)..(1119)
<223> OTHER INFORMATION: DSM 20460

<400> SEQUENCE: 166

```
atgagtcaga tcgacgaact tatcagcaaa ttacaggaag tatccaacca tccccagaag         60
acggttttga attataaaaa acagggtaaa ggcctcgtag gcatgatgcc ctactacgct        120
ccggaagaaa tcgtatatgc tgcaggctac ctcccggtag gcatgttcgg ttcccagaac        180
ccgcagatct ccgcagctcg tacgtacctt cctccgttcg cttgctcctt gatgcaggct        240
gacatggaac tccagctcaa cggcacctat gactgcctcg acgctgttat cttctccgtt        300
ccttgcgaca ctctccgctg catgagccag aaatggcacg gcaaagctcc ggtcatcgtc        360
ttcacacagc cgcagaaccg taagatccgc ccggctgtcg atttcctcaa gctgaatac         420 gaacatgtcc gtacggaatt ggaacgtatc ctcaacgtaa aaatctccga cctggctatc        480
caggaagcta tcaaagtata taacgaaaac cgtcaggtta tgcgtgaatt ctgcgacgta        540
gctgctcagt acccgcagat cttcactccg gtaaaacgtc atgacgtcat caaagcccgc        600
tggttcatgg acaaagctga acacaccgct ttggtccgcg aactcatcga cgctgtcaag        660
aaagaaccgg tacagccgtg gaatggcaaa aaagtcatcc tctccggtat catggcagaa        720
ccggatgaat tcctcgatat cttcagcgaa ttcaacatcg ctgtcgtcgc tgacgacctc        780
gctcaggaat cccgccagtt ccgtacagac gtaccgtccg gcatcgatcc cctcgaacag        840
ctcgctcagc agtggcagga cttcgatggc tgcccgctcg cttgaacga agacaaaccg         900 cgtggccaga tgctcatcga catgactaag aaatacaatg ctgacgccgt cgtcatctgc        960
```

```
atgatgcgtt tctgcgatcc tgaagaattc gactatccga tttacaaacc ggaatttgaa    1020
gctgctggcg ttcgttacac ggtcctcgac ctcgacatcg aatctccgtc cctcgaacag    1080
ctccgcaccc gtatccaggc tttctcggaa atcctctaa                           1119
```

<210> SEQ ID NO 167
<211> LENGTH: 1119
<212> TYPE: DNA
<213> ORGANISM: Peptostreptococcus anaerobius
<220> FEATURE:
<221> NAME/KEY: MISC_FEATURE
<222> LOCATION: (1)..(1119)
<223> OTHER INFORMATION: CAG:621

<400> SEQUENCE: 167

```
atgagtaact tagaagaact atttggaaaa cttgctgtat gtccattaga gcagatagat     60
aaatatgttg ctgatggtaa gaaagttatt ggttgcgcgc agtatatgc tccagaagaa    120 cttgtatacg catcaggtat gattcctatg caatatggg gagcagaggg tgaagtaact    180
cttgcaaaag aatatttccc agctttctac gtatcaatca tcttaagact tttagatcta    240
ggtctagaag gcaagcttga taagatgtca ggaatgattc taccaggtct aagtgacgga    300
ctaaagggac ttagccagaa ctggaaaaga gctgtaaaga atgttccagc attatatata    360
ggatatggac agaacagaaa gatagaagct ggtatagttt acaatgctag acagtatgaa    420
aagctaaaag tacagttaga agaaatagct ggaaagaaga tagaagatgc tcagatagaa    480
gaagcaatcg ttttatacaa caagcacaga aaagctatgc aggcattctc agaccttgca    540
gctaaacact aaatacagt tactcctagc ctaagagcta aggtaatgtc aagtgcatgc    600
ctaatggaca aggctgaaca tttagaaata gtagaagcaa tcaacgctga actttcagct    660
atgccagaag aaaaatttga tggtaagaag attgtaacta ctggactact agctaacagt    720
cctgaaatat taagatatt tgaagaattt aaacttggta ttgttgctga caacataaac    780
cacgaatcag acagtttga ttatttagtt gatgaagcta ctggtaaccc aataaaggcg    840
ttgtctaagt ggatttcaga tattgaagga agtactttgc tatacgatcc agaaaaacta    900
agaggacaga taatcatcga taaggctaaa aaatacgatg cagatggtgt agtataccta    960
ctatctaaat tctctgattc agatgaattt gactacccaa tcattagaaa acagctagaa   1020
gaggctggat atatgcacat cttagttgaa gtagatcagc aaatgactaa cttcgaacaa   1080
gcaaaaactg cattgcagac ttttgcagac atgatatag                          1119
```

<210> SEQ ID NO 168
<211> LENGTH: 792
<212> TYPE: DNA
<213> ORGANISM: Peptostreptococcus anaerobius
<220> FEATURE:
<221> NAME/KEY: MISC_FEATURE
<222> LOCATION: (1)..(792)
<223> OTHER INFORMATION: CAG:621

<400> SEQUENCE: 168

```
atgagtgata tatacacaat gggtattgac attggatcaa catcatctaa atgtgtagtg     60
cttaagaatg gtaaagattt agttagtagc ggcgtcgtca atcttggcgc cggtactaaa    120
ggtgccgatc aggttataga aaaggtacta gctgactgtg gtatcaagtt cgaagatctg    180
aatgtgattg tttccacagg atatggtaga aattcttacg acagtgcaaa gaagactatg    240
agtgaactta gctgtcatgc taagggtggt acatatatct tcggacctgt aagaactatt    300
atagatatag gcggacagga cataaaggta ctaaaactaa atgacaaagg tatgatgaca    360
```

```
aatttcttga tgaatgataa atgtgcagct ggtacaggta gattcttaga ggttatggct    420
ggagtacttg atgttaagct agcagaacta ggtgacttag acaagttagc aactgaaaaa    480
acaccaatat cttcaacttg tacagtattt gcagaatcag aagtaatatc ttgtatggct    540
aagaaaatac ctattcctaa tataattagg ggtatacacg cttctgttgc tacaagagtt    600
gcaggtcttg ctaagagagg tggattaaca actccagtcg ctatgactgg tggtgttact    660
aagaactcag gaatagtaag ggcacttagc gaagagttag aaacagatat catgatttcg    720
gaaatttctc agttggcagg cgcaattgga gcggcattgt acgcttacga tgagtatctg    780
aaggaaaatt ag                                                        792

<210> SEQ ID NO 169
<211> LENGTH: 777
<212> TYPE: DNA
<213> ORGANISM: Chloroflexus aggregans
<220> FEATURE:
<221> NAME/KEY: MISC_FEATURE
<222> LOCATION: (1)..(777)
<223> OTHER INFORMATION: strain MD-66 / DSM 9485

<400> SEQUENCE: 169
atgagcgatg aaacgcttgt gctcagcact atcgaaggcc ccgttgcaat ccttacgctc     60
aatcgaccac aagcactcaa tgcccttagc cctgccctca tcgacgcact catccgccat    120
cttgagcatt gcgataacga cgatacgatc cgggtgatca ttatcaccgg cgccggtcgc    180
gcctttgccg ccggcgccga catcaaggcg atggccgatg cgacgccgat cgatatgctt    240
acaaccgata tgattgcccg ctgggcgcgg attgcggcgg tgcgcaaacc cgtgatcgca    300
gccgtgaacg gatttgccct cggtggtggc tgcgagttgg ctatgatgtg tgacatcatt    360
cttgccagtg aaacagccca attcggtcaa cccgaaatca catcggcat atccccggc     420 gccggtggca cccaacgcct gacccgcgca attgggcccat accgtgcaat ggagatggtc    480
ttaaccggtg ctaccatcag tgcccaagaa gcttacgcct acggcctggt gaatcgggta    540 tgccacccg atagcctgct tgatgaagcc cgccggttgg cccagaccat tgcagccaag    600
ccgccgctcg ctgtgcgttt agccaaggaa gccgtgcgcg ctgcggctga aacgaccgtg    660
cgtgaagggt tagccattga attgcgtaac ttttatctgc tctttgccag tgccgatcag    720
aaagagggca tgcgagcctt tatcgaaaag cgtacagcca acttcagtgg tcgctaa      777

<210> SEQ ID NO 170
<211> LENGTH: 774
<212> TYPE: DNA
<213> ORGANISM: Marivirga tractuosa
<220> FEATURE:
<221> NAME/KEY: MISC_FEATURE
<222> LOCATION: (1)..(774)
<223> OTHER INFORMATION: strain ATCC 23168/DSM 4126/NBRC 15989/NCIMB
      1408/VKM B-1430/H-43

<400> SEQUENCE: 170
atggaattca taaagtaaa cacacaatat aaaaagcata ttgcgctcat caatcttaac     60
agacctaaag aattaaatgc cttgaactta cagttaatga ctgaattgaa ggacacttta    120
aaggtcttgg atgaggatga aaatgttaga gttataattt taacaggtaa tgagaaggct    180
tttgccgctg gagcagacat taagcaaatg gcaggtaaaa cggctattga catgctcaat    240
gttgatcaat tcagcacttg ggatcaaatc aaaaaaacaa agaagccatt gattgcagcc    300
gtttcaggat ttgcattggg cggtggttgc gaattagcga tgacttgcga tatgattgta    360
```

```
gcgtcagaat ctgctaaatt cggtcagcct gaaataaaaa tcggagtaat gccgggagca      420
ggtggtacac aaaggttaac tagggcaatt ggtaaagcca agcgatgga attagtcttg      480 actggtaatt ttattagtgc agaggaagca atgcattatg cttagttaa taaagttgtt      540 cctacagaga tgtatctgga agcagctgct gaactggctg agcaaatagc acaaatgtct      600
cctgtagcag ctaagttggc aaaagaatca gttaacaggg cttttgaaac gcatttggac      660
gaaggcttgc actttgagag aaaaaacttc tatttaacat ttgcttcaga agatcagact      720
gaaggtatgg aagcttttgt agagaaaaga agcctgaat tcaaggggaa ataa           774
```

```
<210> SEQ ID NO 171
<211> LENGTH: 774
<212> TYPE: DNA
<213> ORGANISM: Marinithermus hydrothermalis
<220> FEATURE:
<221> NAME/KEY: MISC_FEATURE
<222> LOCATION: (1)..(774)
<223> OTHER INFORMATION: strain DSM 14884 / JCM 11576 / T1

<400> SEQUENCE: 171
```

```
atgtacgaga acctcatcgt ggagacgctc gagggcggcg tggggctcat tcgcatccac      60
cggcccaagc gcctcaacgc cctgaaccag gccaccatgg acgagatcgt ccgcgcagta      120
cgcgcgtttg aagcggatga cgcggtgcgc gcgatcgtcc tcacggggga cgagcgggcg      180
ttcgccgcgg gcgcggacgt caccgagatg gacgcgcgca acgtgccgga gatgctctcc      240
gggtaccgct tcgagcagtg ggagaccctc cggcgcacca cgaaacccct gatcgccgcg      300
gtctcggggt tcgcgctcgg ggcgggctc gagctcgcga tgctgtgcga catcatcgta      360
gcctcggaga ccgcgcggct cggccagccc gagatcaacc tcgggatcat gccgggggcg      420
ggcggcacgc aacggctcac gcggcaggtg ggcaagtacc tcgcgatgga gatggtcctc      480
acggggcgca tgctcaccgc ggaggaggcg taccgtcacg gcctggtgaa ccgggtcgtc      540
ccggtcgagt tctacctgga ggaagccatc cagatcgcgc gggagatcgc gaagaaagcc      600
ccggtggcgg tgcgcctggc caaggacgcg atcctcaagg cagaggacac gccgctcgag      660
gtgggcctcg cgtacgagcg ccacaacttc tacctgctct tcggcaccga ggacaagcaa      720
gaagggatcc gcgctttcct cgagaagcgc aagcccgaat ggaaagggag gtag           774
```

```
<210> SEQ ID NO 172
<211> LENGTH: 780
<212> TYPE: DNA
<213> ORGANISM: Chitinophaga pinensis
<220> FEATURE:
<221> NAME/KEY: MISC_FEATURE
<222> LOCATION: (1)..(780)
<223> OTHER INFORMATION: strain ATCC 43595 / DSM 2588 / NCIB 11800 /
      UQM 2034

<400> SEQUENCE: 172
```

```
atgcaaccac aatttataat catacaccgg caggtagccc catatgtggc tcatatacag      60
ttaaaccgcc ccaaagaact caatgcactg aaccttgaac tgatgattga gctcagggat      120
gcattaaaaa tgttggatgc ggatgacaat gttcgtgcaa tcgtcatcag cggtaatgaa      180
aaagcattcg ctgcaggcgc ggatatcaaa cagatggcgg ggaaaactgc catggacatg      240
tataacattg accagttcag cacctgggac acaataaaaa aaactaaaaa gccgttgatt      300
gcggcagtaa gcggcttcgc gctgggaggg ggatgtgagc tggtgatgct atgcgatatg      360
atagtagcca gtgaaacagc gcggttcgga cagccggaaa taaaaattgg cgtcatgcct      420
```

| | |
|---|---|
| ggcgcaggtg gtacacaacg cctgacccgc gccgtaggta aagccctggc catggaaatg | 480 |
| gtattgacag gtcgctttat cactgcacaa gaagctgcac gtgcaggtct tatcaaccgg | 540 |
| gtaataccgg tggaactttt cctgcaggaa gccatccggc tggcgactga agtagctgcg | 600 |
| cttagtccgt tggcagtaaa gatggctaaa gaatctgtac tgaaagcatt tgatagctcc | 660 |
| ctcgaagaag gactacattt tgaacgtaaa aactttatc tgctgtttgc ctctgaagat | 720 |
| cagaaagaag gcatgcaggc ttttgttgat aagagatcac ctgtttttaa aggaaaataa | 780 |

<210> SEQ ID NO 173
<211> LENGTH: 777
<212> TYPE: DNA
<213> ORGANISM: Megasphaera elsdenii
<220> FEATURE:
<221> NAME/KEY: MISC_FEATURE
<222> LOCATION: (1)..(777)
<223> OTHER INFORMATION: DSM 20460

<400> SEQUENCE: 173

| | |
|---|---|
| gtgtatactc tcggaatcga cgttggttct tcttcttcca aggcagtcat cctggaagat | 60 |
| ggcaagaaga tcgtcgccca tgccgtcgtt gaaatcggca ccggttcgac cggtccggaa | 120 |
| cgcgtcctgg acgaagtctt caaagatacc aacttaaaaa ttgaagacat ggcgaacatc | 180 |
| atcgccacag gctatggccg tttcaatgtc gactgcgcca aggcgaagt cagcgaaatc | 240 |
| acgtgccatg ccaaaggggc cctctttgaa tgccccggta cgacgaccat cctcgatatc | 300 |
| ggcggtcagg acgtcaagtc catcaaattg aatggcagg gcctggtcat gcagtttgcc | 360 |
| atgaacgaca aatgcgccgc tggtacgggc cgtttcctcg acgtcatgtc gaaggtactg | 420 |
| gaaatcccca tgtctgaaat gggggactgg tacttcaaat cgaagcatcc cgctgccgtc | 480 |
| agcagtacct gcacggtttt tgctgaatcg gaagtcattt cccttctttc caagaatgtc | 540 |
| ccgaaagaag atatcgtagc cggtgtccat cagtccatcg ccgccaaagc ctgcgctctc | 600 |
| gtgcgccgcg tcggtgtcgg tgaagacctg accatgaccg gcggtggctc ccgcgatccc | 660 |
| ggcgtcgtcg atgccgtatc gaaagaatta ggtattcctg tcagagtcgc tctgcatccc | 720 |
| caagcggtgg gtgctctcgg agctgctttg attgcttatg ataaaatcaa gaaataa | 777 |

<210> SEQ ID NO 174
<211> LENGTH: 1287
<212> TYPE: DNA
<213> ORGANISM: Megasphaera elsdenii
<220> FEATURE:
<221> NAME/KEY: MISC_FEATURE
<222> LOCATION: (1)..(1287)
<223> OTHER INFORMATION: DSM 20460

<400> SEQUENCE: 174

| | |
|---|---|
| atgagtgaag aaaaaacagt agatattgaa agcatgagct ccaaggaagc ccttggttac | 60 |
| ttcttgccga agtcgatga agacgcacgt aaagcgaaaa agaaggccg cctcgtttgc | 120 |
| tggtccgctt ctgtcgctcc tccggaattc tgcacggcta tggacatcgc catcgtctat | 180 |
| ccggaaactc acgcagctgg tatcggtgcc cgtcacggtg ctccggccat gctcgaagtt | 240 |
| gctgaaaaca aaggttacaa ccaggacatc tgttcctact gccgcgtcaa catgggctac | 300 |
| atggaactcc tcaaacagca ggctctgaca ggcgaaacgc cggaagtcct caaaaactcc | 360 |
| ccggcttctc cgattcccct tccggatgtt gtcctcactt gcaacaacat ctgcaatacc | 420 |
| ttgctcaaat ggtatgaaaa cttggctaaa gaattgaacg tacctctcat caacatcgac | 480 |

| | |
|---|---|
| gtaccgttca accatgaatt ccctgttacg aaacacgcta acagtacat cgtcggcgaa | 540 |
| ttcaaacatg ctatcaaaca gctcgaagac ctttgcggcc gtcccttcga ctatgacaaa | 600 |
| ttcttcgaag tacagaaaca gacacagcgc tccatcgctg cctggaacaa aatcgctacg | 660 |
| tacttccagt acaaaccgtc gccgctcaac ggcttcgacc tcttcaacta catgggcctc | 720 |
| gccgttgctg cccgctcctt gaactactcg gaaatcacgt tcaacaaatt cctcaaagaa | 780 |
| ttggacgaaa aagtagctaa taagaaatgg ctttcggtg aaaacgaaaa atcccgtgtt | 840 |
| acttgggaag gtatcgctgt ctggatcgct ctcggccaca ccttcaaaga actcaaaggt | 900 |
| cagggcgctc tcatgactgg ttccgcttat cctggcatgt gggacgtttc ctacgaaccg | 960 |
| ggcgacctcg aatccatggc agaagcttat tcccgtacat acatcaactg ctgcctcgaa | 1020 |
| cagcgcggtg ctgttcttga aaagttgtc cgcgatggca aatgcgacgg cttgatcatg | 1080 |
| caccagaacc gttcctgcaa gaacatgagc ctcctcaaca acgaaggcgg ccagcgcatc | 1140 |
| cagaagaacc tcggcgtacc gtacgtcatc ttcgacggcg accagaccga tgctcgtaac | 1200 |
| ttctcggaag cacagttcga tacccgcgta gaagctttgg cagaaatgat ggcagacaaa | 1260 |
| aaagccaatg aaggaggaaa ccactaa | 1287 |

<210> SEQ ID NO 175
<211> LENGTH: 1119
<212> TYPE: DNA
<213> ORGANISM: Megasphaera elsdenii
<220> FEATURE:
<221> NAME/KEY: MISC_FEATURE
<222> LOCATION: (1)..(1119)
<223> OTHER INFORMATION: DSM 20460

<400> SEQUENCE: 175

| | |
|---|---|
| atgagtcaga tcgacgaact tatcagcaaa ttacaggaag tatccaacca tccccagaag | 60 |
| acggttttga attataaaaa acagggtaaa ggcctcgtag gcatgatgcc ctactacgct | 120 |
| ccggaagaaa tcgtatatgc tgcaggctac ctcccggtag gcatgttcgg ttcccagaac | 180 |
| ccgcagatct ccgcagctcg tacgtacctt cctccgttcg cttgctcctt gatgcaggct | 240 |
| gacatggaac tccagctcaa cggcacctat gactgcctcg acgctgttat cttctccgtt | 300 |
| ccttgcgaca ctctccgctg catgagccag aaatggcacg gcaaagctcc ggtcatcgtc | 360 |
| ttcacacagc cgcagaaccg taagatccgc ccggctgtcg atttcctcaa agctgaatac | 420 |
| gaacatgtcc gtacggaatt ggaacgtatc ctcaacgtaa aaatctccga cctggctatc | 480 |
| caggaagcta tcaaagtata taacgaaaac cgtcaggtta tgcgtgaatt ctgcgacgta | 540 |
| gctgctcagt acccgcagat cttcactccg gtaaaacgtc atgacgtcat caaagcccgc | 600 |
| tggttcatgg acaaagctga acacaccgct ttggtccgcg aactcatcga cgctgtcaag | 660 |
| aaagaaccgg tacagccgtg gaatggcaaa aaagtcatcc tctccggtat catggcagaa | 720 |
| ccggatgaat tcctcgatat cttcagcgaa ttcaacatcg ctgtcgtcgc tgacgacctc | 780 |
| gctcaggaat cccgccagtt ccgtacagac gtaccgtccg gcatcgatcc cctcgaacag | 840 |
| ctcgctcagc agtggcagga cttcgatggc tgcccgctcg ctttgaacga agacaaaccg | 900 |
| cgtggccaga tgctcatcga catgactaag aaatacaatg ctgacgccgt cgtcatctgc | 960 |
| atgatgcgtt tctgcgatcc tgaagaattc gactatccga tttacaaacc ggaatttgaa | 1020 |
| gctgctggcg ttcgttacac ggtcctcgac ctcgacatcg aatctccgtc cctcgaacag | 1080 |
| ctccgcaccc gtatccaggc tttctcggaa atcctctaa | 1119 |

<210> SEQ ID NO 176
<211> LENGTH: 777
<212> TYPE: DNA
<213> ORGANISM: Chloroflexus aurantiacus
<220> FEATURE:
<221> NAME/KEY: MISC_FEATURE
<222> LOCATION: (1)..(777)
<223> OTHER INFORMATION: strain ATCC 29364 / DSM 637 / Y-400-fl

<400> SEQUENCE: 176

```
atgagtgaag agtctctggt tctcagcaca attgaaggcc ccatcgccat cctcaccctc      60
aatcgccccc aggccctcaa tgcgctcagt ccggccttga ttgatgacct cattcgccat     120
ttagaagcct gcgatgccga tgacacaatc gcgtgatca ttatcaccgg cgccggacgg     180
gcatttgctg ccggcgctga catcaaagcg atggccaatg ccacgcctat tgatatgctc     240
accagtggca tgattgcgcg ctgggcacgc atcgccgcgg tgcgcaaacc ggtgattgct     300
gccgtgaatg gtatgcgct cggtggtggt tgtgaattgg caatgatgtg cgacatcatc     360
atcgccagtg aaaacgcgca gttcggacaa ccggaaatca atctgggcat cattcccggt     420
gctggtggca cccaacggct gacccgcgcc cttggcccgt atcgcgcaat ggaattgatc     480
ctgaccggcg cgaccatcag tgctcaggaa gctctcgccc acggcctggt gtgccgggtc     540
tgcccgcctg aaagcctgct cgatgaagcc cgtcggatcg cgcaaaccat tgccaccaaa     600
tcaccactgg ctgtacagtt ggcgaaagag gcagtccgta tggccgccga aaccactgtg     660
cgcgaggggt tggctatcga gctgcgtaac ttctatctgc tgtttgccag tgctgaccaa     720
aaagagggga tgcaggcatt tatcgagaaa cgcgctccca acttcagtgg tcgttga       777
```

<210> SEQ ID NO 177
<211> LENGTH: 132
<212> TYPE: PRT
<213> ORGANISM: Escherichia coli

<400> SEQUENCE: 177

Met Ser Thr Thr His Asn Val Pro Gln Gly Asp Leu Val Leu Arg Thr
1               5                   10                  15

Leu Ala Met Pro Ala Asp Thr Asn Ala Asn Gly Asp Ile Phe Gly Gly
            20                  25                  30

Trp Leu Met Ser Gln Met Asp Ile Gly Gly Ala Ile Leu Ala Lys Glu
        35                  40                  45

Ile Ala His Gly Arg Val Val Thr Val Arg Val Glu Gly Met Thr Phe
    50                  55                  60

Leu Arg Pro Val Ala Val Gly Asp Val Val Cys Cys Tyr Ala Arg Cys
65                  70                  75                  80

Val Gln Lys Gly Thr Thr Ser Val Ser Ile Asn Ile Glu Val Trp Val
                85                  90                  95

Lys Lys Val Ala Ser Glu Pro Ile Gly Gln Arg Tyr Lys Ala Thr Glu
            100                 105                 110

Ala Leu Phe Lys Tyr Val Ala Val Asp Pro Glu Gly Lys Pro Arg Ala
        115                 120                 125

Leu Pro Val Glu
    130

<210> SEQ ID NO 178
<211> LENGTH: 132
<212> TYPE: PRT
<213> ORGANISM: Klebsiella oxytoca
<220> FEATURE:
<221> NAME/KEY: MISC_FEATURE

<222> LOCATION: (1)..(132)
<223> OTHER INFORMATION: 10-5245

<400> SEQUENCE: 178

Met Thr Thr Thr Asp Leu Ala Pro Lys Gly Glu Leu Val Leu Arg Thr
1               5                   10                  15

Leu Ala Met Pro Ala Asp Thr Asn Ala Asn Gly Asp Ile Phe Gly Gly
                20                  25                  30

Trp Leu Met Ser Gln Met Asp Ile Gly Gly Ala Ile Met Ala Lys Glu
            35                  40                  45

Ile Ala His Gly Arg Val Val Thr Val Arg Val Asp Gly Met Thr Phe
        50                  55                  60

Leu Arg Pro Val Ala Val Gly Asp Val Val Cys Cys Tyr Ala Asn Cys
65                  70                  75                  80

Val Lys Arg Gly Asn Thr Ser Ile Thr Ile Asn Met Glu Val Trp Val
                85                  90                  95

Lys Lys Val Ser Ser Glu Pro Ile Gly Gln Arg Tyr Lys Ala Thr Glu
                100                 105                 110

Ala Leu Phe Ile Tyr Val Ala Val Asp Asn Gln Gly Lys Pro Arg Ala
            115                 120                 125

Leu Pro Thr Leu
    130

<210> SEQ ID NO 179
<211> LENGTH: 133
<212> TYPE: PRT
<213> ORGANISM: Cronobacter turicensis

<400> SEQUENCE: 179

Met Thr Thr Glu Gln Thr Thr Pro Gln Gly Glu Leu Val Leu Arg Thr
1               5                   10                  15

Leu Ala Met Pro Ala Asp Thr Asn Ala Asn Gly Asp Ile Phe Gly Gly
                20                  25                  30

Trp Leu Met Ala Gln Met Asp Ile Gly Gly Ala Ile Leu Ala Lys Glu
            35                  40                  45

Ile Ala His Gly Arg Val Val Thr Val Arg Val Asp Gly Met Thr Phe
        50                  55                  60

Leu Arg Pro Val Ala Val Gly Asp Val Val Cys Cys Tyr Ala Arg Cys
65                  70                  75                  80

Val Lys Arg Gly Asn Thr Ser Val Thr Ile Asn Ile Glu Val Trp Val
                85                  90                  95

Lys Lys Val Ser Ser Glu Pro Leu Gly Gln Arg Tyr Arg Ala Thr Glu
                100                 105                 110

Ala Leu Phe Ile Tyr Val Ala Val Asp Asp Asn Gly Lys Pro Arg Pro
            115                 120                 125

Leu Pro Pro Val Ala
    130

<210> SEQ ID NO 180
<211> LENGTH: 133
<212> TYPE: PRT
<213> ORGANISM: Citrobacter freundii

<400> SEQUENCE: 180

Met Thr Thr Thr Asn Asn Thr Pro Gln Gly Glu Leu Val Leu Arg Thr
1               5                   10                  15

Leu Ala Met Pro Ala Asp Thr Asn Ala Asn Gly Asp Ile Phe Gly Gly

-continued

```
                    20                  25                  30
Trp Leu Met Ser Gln Met Asp Ile Gly Gly Ala Ile Gln Ala Lys Glu
            35                  40                  45
Ile Ala His Gly Arg Val Val Thr Val Arg Val Glu Gly Met Ser Phe
        50                  55                  60
Leu Arg Pro Val Ala Val Gly Asp Val Val Cys Cys Tyr Ala Arg Cys
 65                  70                  75                  80
Val Lys Arg Gly Thr Thr Ser Ile Ser Ile Asn Ile Glu Val Trp Val
                85                  90                  95
Lys Lys Val Ala Ser Glu Pro Ile Gly Gln Arg Tyr Lys Ala Thr Glu
            100                 105                 110
Ala Leu Phe Ile Tyr Val Ala Val Asp Lys Asp Gly Lys Pro Arg Pro
        115                 120                 125
Ile Pro Thr Leu Ala
    130

<210> SEQ ID NO 181
<211> LENGTH: 130
<212> TYPE: PRT
<213> ORGANISM: Salmonella enterica

<400> SEQUENCE: 181

Met Asp Asn Thr Pro Gln Gly Glu Leu Val Leu Arg Thr Leu Ala Met
 1               5                  10                  15
Pro Ala Asp Thr Asn Ala Asn Gly Asp Ile Phe Gly Gly Trp Leu Met
                20                  25                  30
Ser Gln Met Asp Ile Gly Gly Ala Ile Leu Ala Lys Glu Ile Ala His
            35                  40                  45
Gly Arg Val Val Thr Val Arg Val Glu Gly Met Thr Phe Leu Arg Pro
        50                  55                  60
Val Ala Val Gly Asp Val Val Cys Cys Tyr Ala Arg Cys Val Lys Arg
 65                  70                  75                  80
Gly Thr Thr Ser Ile Ser Ile Asn Ile Glu Val Trp Val Lys Lys Val
                85                  90                  95
Ala Ser Glu Pro Ile Gly Gln Arg Tyr Lys Ala Thr Glu Ala Leu Phe
            100                 105                 110
Ile Tyr Val Ala Val Asp Pro Asp Gly Lys Pro Arg Pro Leu Pro Val
        115                 120                 125
Gln Gly
    130

<210> SEQ ID NO 182
<211> LENGTH: 133
<212> TYPE: PRT
<213> ORGANISM: Shigella flexneri
<220> FEATURE:
<221> NAME/KEY: MISC_FEATURE
<222> LOCATION: (1)..(133)
<223> OTHER INFORMATION: 1235-66

<400> SEQUENCE: 182

Met Thr Thr Thr Asn Asn Thr Pro Gln Gly Glu Leu Val Leu Arg Thr
 1               5                  10                  15
Leu Ala Met Pro Ala Asp Thr Asn Ala Asn Gly Asp Ile Phe Gly Gly
                20                  25                  30
Trp Leu Met Ser Gln Met Asp Ile Gly Gly Ala Ile Gln Ala Lys Glu
            35                  40                  45
```

```
Ile Ala His Gly Arg Val Val Thr Val Arg Val Glu Gly Met Ser Phe
    50                  55                  60

Leu Arg Pro Val Ala Val Gly Asp Val Val Cys Cys Tyr Ala Arg Cys
65                  70                  75                  80

Val Lys Arg Gly Thr Thr Ser Ile Ser Ile Asn Ile Glu Val Trp Val
                85                  90                  95

Lys Lys Val Ala Ser Glu Pro Ile Gly Gln Arg Tyr Lys Ala Thr Glu
                100                 105                 110

Ala Leu Phe Ile Tyr Val Ala Val Asp Lys Asp Gly Lys Pro Arg Pro
            115                 120                 125

Ile Pro Lys Gln Val
    130
```

<210> SEQ ID NO 183
<211> LENGTH: 554
<212> TYPE: PRT
<213> ORGANISM: Ilyobacter polytropus
<220> FEATURE:
<221> NAME/KEY: MISC_FEATURE
<222> LOCATION: (1)..(554)
<223> OTHER INFORMATION: DhaB1 protein

<400> SEQUENCE: 183

```
Met Lys Ser Lys Arg Phe Glu Val Leu Lys Glu Arg Pro Val Asn Lys
1               5                   10                  15

Asp Gly Phe Ile Ser Glu Trp Ile Glu Gly Leu Ile Ala Met Glu
                20                  25                  30

Ser Pro Asn Asp Pro Asn Pro Ser Leu Lys Ile Glu Asn Gly Gln Ile
            35                  40                  45

Thr Glu Leu Asp Gly Lys Ser Arg Glu Glu Phe Asp Met Ile Asp Arg
    50                  55                  60

Phe Ile Ala Asp Tyr Ala Ile Asn Met Glu Asn Ala Glu Lys Ala Met
65                  70                  75                  80

Lys Met Ser Ser Met Glu Ile Ser Lys Lys Leu Val Asp Ile Asn Val
                85                  90                  95

Ser Arg Asp Glu Val Leu Glu Ile Thr Thr Gly Ile Thr Pro Ala Lys
                100                 105                 110

Ile Ile Lys Val Met Glu His Met Asn Val Val Glu Met Met Met Ala
            115                 120                 125

Val Gln Lys Met Arg Ala Arg Lys Thr Pro Ser Asn Gln Cys His Val
        130                 135                 140

Thr Asn Leu Arg Asp Asn Pro Val Leu Ile Ala Ala Asp Ala Ala Glu
145                 150                 155                 160

Ala Ser Val Arg Gly Phe Asp Glu Gln Glu Thr Thr Ile Gly Ile Val
                165                 170                 175

Arg Tyr Ala Pro Phe Asn Ala Ile Ser Ile Phe Val Gly Ser Gln Val
                180                 185                 190

Gly Arg Gly Gly Ile Leu Thr Gln Cys Ser Val Glu Glu Ala Thr Glu
            195                 200                 205

Leu Glu Leu Gly Met Lys Gly Phe Thr Ser Tyr Ala Glu Thr Val Ser
        210                 215                 220

Val Tyr Gly Thr Glu Gln Val Phe Ile Asp Gly Asp Thr Pro Trp
225                 230                 235                 240

Ser Lys Ala Phe Leu Ala Ser Ala Tyr Ala Ser Arg Gly Leu Lys Met
                245                 250                 255

Arg Phe Thr Ser Gly Thr Gly Ser Glu Ala Leu Met Gly Asn Ala Glu
```

```
            260                 265                 270
Gly Lys Ser Met Leu Tyr Leu Glu Ala Arg Cys Ile Tyr Val Thr Arg
        275                 280                 285

Gly Ser Gly Val Gln Gly Leu Gln Asn Gly Ser Val Ser Cys Ile Gly
        290                 295                 300

Met Pro Gly Ser Leu Pro Gly Gly Ile Arg Ala Val Leu Ala Glu Asn
305                 310                 315                 320

Leu Ile Ala Met Leu Leu Asp Leu Glu Cys Ala Ser Ala Asn Asp Gln
                325                 330                 335

Thr Phe Ser His Ser Glu Tyr Arg Arg Thr Ala Arg Thr Leu Met Gln
                340                 345                 350

Met Leu Pro Gly Thr Asp Phe Ile Phe Ser Gly Tyr Ser Ala Val Pro
                355                 360                 365

Asn Cys Asp Asn Met Phe Ala Gly Ser Asn Phe Asp Ala Glu Asp Phe
            370                 375                 380

Asp Asp Tyr Asn Ala Leu Gln Arg Asp Leu Lys Ile Asp Gly Gly Leu
385                 390                 395                 400

Lys Pro Val Thr Glu Asp Glu Ile Val Lys Val Arg Asn Lys Ala Ala
                405                 410                 415

Arg Ala Ile Gln Gly Leu Phe Lys Glu Leu Asp Leu Pro Glu Ile Thr
                420                 425                 430

Asp Glu Glu Val Glu Ala Ala Thr Tyr Ala His Gly Ser Val Asp Met
            435                 440                 445

Pro Ala Arg Asn Val Val Glu Asp Leu Lys Ala Glu Glu Leu Leu
450                 455                 460

Ser Ser Gly Ile Thr Gly Val Asp Leu Val Lys Gly Leu Ser Arg Ser
465                 470                 475                 480

Gly Phe Asp Asp Val Ala Glu His Val Leu Gly Met Leu Lys Gln Arg
                485                 490                 495

Val Ser Gly Asp Tyr Leu Gln Thr Ser Ala Ile Leu Asp Lys Gly Phe
            500                 505                 510

Lys Ile Lys Ser Ala Ile Asn Asp Arg Asn Asp Tyr Met Gly Pro Gly
        515                 520                 525

Ser Gly Tyr Arg Ile Ser Glu Glu Arg Trp Glu Glu Ile Lys Asn Ile
        530                 535                 540

Pro Ser Ala Ile Lys Pro Glu Ser Ile Glu
545                 550

<210> SEQ ID NO 184
<211> LENGTH: 187
<212> TYPE: PRT
<213> ORGANISM: Ilyobacter polytropus
<220> FEATURE:
<221> NAME/KEY: MISC_FEATURE
<222> LOCATION: (1)..(187)
<223> OTHER INFORMATION: DhaB2 protein

<400> SEQUENCE: 184

Met Glu Asn Lys Phe Val Pro Ser Val Lys Ile Glu Glu Ile Gly Glu
1               5                   10                  15

Ala Lys Lys Gly Ser Arg Ser Glu Glu Val Val Ile Gly Leu Ala Pro
            20                  25                  30

Ala Phe Lys Lys Phe Gln His Lys Thr Ile Thr Asp Val Pro His Asp
        35                  40                  45

Glu Val Leu Thr Glu Leu Ile Ala Gly Ile Glu Glu Glu Gly Leu Lys
    50                  55                  60
```

Ala Arg Ile Val Arg Val Thr Arg Thr Ser Asp Val Ser Phe Met Ala
65                  70                  75                  80

Leu Asp Ala Ala Lys Leu Ser Gly Ser Gly Ile Gly Ile Gly Ile Gln
            85                  90                  95

Ser Lys Gly Thr Thr Val Ile His Gln Lys Asp Leu Leu Pro Leu Asn
        100                 105                 110

Asn Leu Glu Leu Phe Pro Gln Ala Pro Leu Leu Thr Pro Glu Thr Phe
    115                 120                 125

Arg Leu Ile Gly Lys Asn Ala Ala Lys Tyr Ala Lys Gly Glu Ser Pro
130                 135                 140

Asn Pro Val Pro Val Ala Ser Asp Gln Met Ala Arg Pro Lys Tyr Gln
145                 150                 155                 160

Ala Lys Ala Ala Leu Leu His Ile Lys Glu Thr Lys His Val Val Gln
                165                 170                 175

His Gly Lys Pro Val Glu Ile Lys Tyr Glu Phe
            180                 185

<210> SEQ ID NO 185
<211> LENGTH: 143
<212> TYPE: PRT
<213> ORGANISM: Ilyobacter polytropus
<220> FEATURE:
<221> NAME/KEY: MISC_FEATURE
<222> LOCATION: (1)..(143)
<223> OTHER INFORMATION: DhaB3 protein

<400> SEQUENCE: 185

Met Asn Ile Asp Val Lys Asn Ile Asn Pro Ile Ser Asp Tyr Pro Leu
1               5                   10                  15

Gly Glu Lys Arg Lys Glu Trp Leu Lys Thr Ser Thr Gly Lys Thr Leu
            20                  25                  30

Asp Glu Ile Thr Leu Glu Asn Val Ile Asn Gly Asp Ile Lys Pro Glu
        35                  40                  45

Asp Ile Arg Ile Ser Pro Glu Thr Leu Lys Leu Gln Gly Glu Ile Ala
    50                  55                  60

Lys Lys Gly Asn Arg Pro Thr Ile Thr Lys Asn Phe Glu Arg Ala Ser
65                  70                  75                  80

Glu Met Val Ala Ile Pro Asp Asp Lys Ile Leu Ala Thr Tyr Asn Ala
                85                  90                  95

Leu Arg Pro Tyr Arg Ser Ser Lys Glu Glu Leu Phe Glu Ile Ala Asp
            100                 105                 110

Glu Leu Glu Ser Lys Tyr Ser Ala Val Val Ile Ser Ala Phe Ile Lys
        115                 120                 125

Glu Ala Ala Glu Val Tyr Glu Gln Arg Gly Gln Leu Arg Lys Asp
130                 135                 140

<210> SEQ ID NO 186
<211> LENGTH: 1665
<212> TYPE: DNA
<213> ORGANISM: Ilyobacter polytropus
<220> FEATURE:
<221> NAME/KEY: Gene
<222> LOCATION: (1)..(1665)
<223> OTHER INFORMATION: dhaB1 gene

<400> SEQUENCE: 186
atgaaatcaa aaagatttga agtattgaag gaacgtcctg taaataaaga tggcttttata         60 agtgaatgga tagaagaagg actaatcgca atggaaagtc ctaacgatcc taatccaagt        120

| | |
|---|---|
| ttgaaaatag aaaatggtca aataacagag ttagacggta aaagcagaga agaatttgac | 180 |
| atgatcgaca gatttatagc agattatgca ataaatatgg aaaatgctga aaaagctatg | 240 |
| aaaatgtcat ctatggaaat atctaaaaaa ctagtagaca taaatgtatc aagagatgaa | 300 |
| gtgctggaaa taacaacagg aattacccca gcaaaaataa ttaaagttat ggaacacatg | 360 |
| aatgttgtag agatgatgat ggccgtacaa aaaatgagag ccagaaaaac tccttccaat | 420 |
| cagtgtcatg taactaactt gagagacaat cctgtattaa ttgccgctga tgctgccgaa | 480 |
| gcgtcagtaa gaggttttga tgaacaggag actacaatcg gtatagtaag atatgcacct | 540 |
| ttcaatgcca tctcaatatt tgtaggttca caagtaggta gaggaggaat actgactcag | 600 |
| tgttctgtag aagaagctac tgaattagag cttggaatga aaggattcac aagttatgca | 660 |
| gaaacagtgt ctgtatatgg tacagagcaa gtgtttatag acggtgacga cactccttgg | 720 |
| tcaaaagcct tccttgcttc agcatatgca tcaagaggat taaaaatgag atttacatct | 780 |
| ggaactggtt cagaggctct tatgggaaat gctgaaggga atcaatgct ttaccttgaa | 840 |
| gcaagatgta tctacgtaac aagagggtct ggagtacaag gactacaaaa tggttctgta | 900 |
| agctgcatag ggatgcctgg gtcactacct ggaggaataa gggctgtact ggctgaaaac | 960 |
| ctgatagcaa tgttacttga cttagaatgt gcatcagcaa atgaccagac attctctcac | 1020 |
| tcagaatata gaaggacagc aagaactcta atgcagatgc ttcctggaac agacttcata | 1080 |
| ttctcaggat atagtgccgt accaaactgt gataacatgt ttgctggatc aaattttgat | 1140 |
| gcagaggatt ttgatgacta taatgctctt cagagagacc ttaaaataga cggtggttta | 1200 |
| aaacctgtaa ctgaagatga gattgtcaaa gtaagaaata aagcagccag agcaatacag | 1260 |
| gggttattca aagaacttga tcttcctgaa ataacagatg aagaagtgga agcagcaaca | 1320 |
| tatgcccacg gaagtgttga tatgcctgca agaaatgtgg ttgaagattt aaaagcggca | 1380 |
| gaagaacttt taagctctgg aataacagga gtagatcttg ttaaaggact tagcagaagc | 1440 |
| ggatttgacg atgtagctga gcatgtttta ggtatgttaa acagagagt ttcaggagat | 1500 |
| tacctgcaaa cttcagctat attagacaaa ggctttaaaa taagagtgc cataaacgat | 1560 |
| agaaatgatt acatgggtcc tggaagcgga tatagaataa gcgaggaaag atgggaagag | 1620 |
| atcaaaaata tcccatcagc tataaaacca gaaagtatag aatag | 1665 |

<210> SEQ ID NO 187
<211> LENGTH: 564
<212> TYPE: DNA
<213> ORGANISM: Ilyobacter polytropus
<220> FEATURE:
<221> NAME/KEY: Gene
<222> LOCATION: (1)..(564)
<223> OTHER INFORMATION: dhaB2 gene

<400> SEQUENCE: 187

| | |
|---|---|
| atggaaaata aatttgtacc atctgtaaag atagaagaaa tcggagaagc aaaaaaagga | 60 |
| agcagatctg aagaagtagt tataggactg gctcctgcat ttaaaaaatt tcaacataaa | 120 |
| acaataacag atgtccctca cgatgaagtc ctgactgaac ttatcgcagg tatagaggaa | 180 |
| gagggattaa aggcaagaat cgtaagagta acaagaactt ctgatgtttc atttatggcg | 240 |
| ctggatgctg caaagttaag tggttctgga ataggaatag gaattcagtc aaagggaaca | 300 |
| acagtaatcc accaaaagga tctgcttcct ctaaacaatc tagaactttt cccacaggct | 360 |
| ccactattaa cacctgaaac attcagatta ataggaaaaa atgctgcaaa atatgcaaag | 420 |

```
ggagaatctc caaatccagt acctgtagcc agtgaccaga tggcgagacc taaatatcag        480
gcaaaagcag cattactaca tataaaagag acaaaacatg tcgttcaaca cggaaaacca        540
gtagagataa agtatgaatt ttag                                               564
```

<210> SEQ ID NO 188
<211> LENGTH: 432
<212> TYPE: DNA
<213> ORGANISM: Ilyobacter polytropus
<220> FEATURE:
<221> NAME/KEY: Gene
<222> LOCATION: (1)..(432)
<223> OTHER INFORMATION: dhaB3 gene

<400> SEQUENCE: 188

```
atgaatatag atgttaaaaa tataaatcca atctctgatt atccattagg agaaaagaga         60
aaagaatggt tgaaaacatc cacaggtaaa actttggatg aaataacttt agaaaatgta        120
ataaatggag atataaagcc tgaagatata agaatctcac ctgaaactct aaaattacag        180
ggagagatag caaagaaagg taacaggcca actataacaa agaactttga aagagccagt        240
gaaatggttg ccattccaga tgataaaata ttagcaactt acaacgcttt gagaccttac        300
agatcttcaa aggaagaatt atttgaaata gccgatgaac tagaaagtaa gtattcagct        360
gttgtaatat ctgcatttat caaggaagcc gcagaagttt atgaacaaag aggtcaactt        420
agaaaagatt ag                                                            432
```

<210> SEQ ID NO 189
<211> LENGTH: 490
<212> TYPE: PRT
<213> ORGANISM: Escherichia coli
<220> FEATURE:
<221> NAME/KEY: MISC_FEATURE
<222> LOCATION: (1)..(490)
<223> OTHER INFORMATION: gabD1

<400> SEQUENCE: 189

```
Met Thr Ile Asn Val Ser Glu Leu Leu Ala Lys Val Pro Thr Gly Leu
  1               5                  10                  15

Leu Ile Gly Asp Ser Trp Val Glu Ala Ser Asp Gly Gly Thr Phe Asp
             20                  25                  30

Val Glu Asn Pro Ala Thr Gly Glu Thr Ile Ala Thr Leu Ala Ser Ala
         35                  40                  45

Thr Ser Glu Asp Ala Leu Ala Ala Leu Asp Ala Ala Cys Ala Val Gln
     50                  55                  60

Ala Glu Trp Ala Arg Met Pro Ala Arg Glu Arg Ser Asn Ile Leu Arg
 65                  70                  75                  80

Arg Gly Phe Glu Leu Val Ala Glu Arg Ala Glu Glu Phe Ala Thr Leu
                 85                  90                  95

Met Thr Leu Glu Met Gly Lys Pro Leu Ala Glu Ala Arg Gly Glu Val
            100                 105                 110

Thr Tyr Gly Asn Glu Phe Leu Arg Trp Phe Ser Glu Glu Ala Val Arg
        115                 120                 125

Leu Tyr Gly Arg Tyr Gly Thr Thr Pro Glu Gly Asn Leu Arg Met Leu
    130                 135                 140

Thr Ala Leu Lys Pro Val Gly Pro Cys Leu Leu Ile Thr Pro Trp Asn
145                 150                 155                 160

Phe Pro Leu Ala Met Ala Thr Arg Lys Val Ala Pro Ala Ile Ala Ala
                165                 170                 175
```

```
Gly Cys Val Met Val Leu Lys Pro Ala Arg Leu Thr Pro Leu Thr Ser
            180                 185                 190

Gln Tyr Phe Ala Gln Thr Met Leu Asp Ala Gly Leu Pro Ala Gly Val
        195                 200                 205

Leu Asn Val Val Ser Gly Ala Ser Ala Ser Ala Ile Ser Asn Pro Ile
    210                 215                 220

Met Glu Asp Asp Arg Leu Arg Lys Val Ser Phe Thr Gly Ser Thr Pro
225                 230                 235                 240

Val Gly Gln Gln Leu Leu Lys Lys Ala Asp Lys Val Leu Arg Thr
                245                 250                 255

Ser Met Glu Leu Gly Gly Asn Ala Pro Phe Ile Val Phe Glu Asp Ala
        260                 265                 270

Asp Leu Asp Leu Ala Ile Glu Gly Ala Met Gly Ala Lys Met Arg Asn
        275                 280                 285

Ile Gly Glu Ala Cys Thr Ala Ala Asn Arg Phe Leu Val His Glu Ser
        290                 295                 300

Val Ala Asp Glu Phe Gly Arg Arg Phe Ala Ala Arg Leu Glu Glu Gln
305                 310                 315                 320

Val Leu Gly Asn Gly Leu Asp Glu Gly Val Thr Val Gly Pro Leu Val
                325                 330                 335

Glu Glu Lys Ala Arg Asp Ser Val Ala Ser Leu Val Asp Ala Ala Val
                340                 345                 350

Ala Glu Gly Ala Thr Val Leu Thr Gly Gly Lys Ala Gly Thr Gly Ala
            355                 360                 365

Gly Tyr Phe Tyr Glu Pro Thr Val Leu Thr Gly Val Ser Thr Asp Ala
370                 375                 380

Ala Ile Leu Asn Glu Glu Ile Phe Gly Pro Val Ala Pro Ile Val Thr
385                 390                 395                 400

Phe Gln Thr Glu Glu Glu Ala Leu Arg Leu Ala Asn Ser Thr Glu Tyr
                405                 410                 415

Gly Leu Ala Ser Tyr Val Phe Thr Gln Asp Thr Ser Arg Ile Phe Arg
            420                 425                 430

Val Ser Asp Gly Leu Glu Phe Gly Leu Val Gly Val Asn Ser Gly Val
            435                 440                 445

Ile Ser Asn Ala Ala Ala Pro Phe Gly Gly Val Lys Gln Ser Gly Met
    450                 455                 460

Gly Arg Glu Gly Gly Leu Glu Gly Ile Glu Glu Tyr Thr Ser Val Gln
465                 470                 475                 480

Tyr Ile Gly Ile Arg Asp Pro Tyr Ala Gly
                485                 490

<210> SEQ ID NO 190
<211> LENGTH: 453
<212> TYPE: PRT
<213> ORGANISM: Escherichia coli
<220> FEATURE:
<221> NAME/KEY: MISC_FEATURE
<222> LOCATION: (1)..(453)
<223> OTHER INFORMATION: gabD2

<400> SEQUENCE: 190

Met Ser Leu Thr Phe Pro Val Ile Asn Pro Ser Asp Gly Ser Thr Ile
  1               5                  10                  15

Thr Glu Leu Glu Asn His Asp Ser Thr Gln Trp Met Ser Ala Leu Ser
             20                  25                  30

Asp Ala Val Ala Ala Gly Pro Ser Trp Ala Ala Lys Thr Pro Arg Glu
```

```
                35                  40                  45
Arg Ser Val Val Leu Thr Ala Ile Phe Glu Ala Leu Thr Glu Arg Ala
 50                  55                  60
Gln Glu Leu Ala Glu Ile Ile His Leu Glu Ala Gly Lys Ser Val Ala
 65                  70                  75                  80
Glu Ala Leu Gly Glu Val Ala Tyr Gly Ala Glu Tyr Phe Arg Trp Phe
                 85                  90                  95
Ala Glu Glu Ala Val Arg Leu Pro Gly Arg Tyr Gly Gln Ser Pro Ser
                100                 105                 110
Gly Ile Gly His Ile Ala Val Thr Arg Ala Pro Val Gly Pro Val Leu
                115                 120                 125
Ala Ile Thr Pro Trp Asn Phe Pro Ile Ala Met Ala Thr Arg Lys Ile
                130                 135                 140
Ala Pro Ala Leu Ala Ala Gly Cys Pro Val Leu Val Lys Pro Ala Ser
145                 150                 155                 160
Glu Thr Pro Leu Thr Met Val Lys Val Gly Glu Ile Ile Ala Ser Val
                165                 170                 175
Phe Asp Thr Phe Asn Ile Pro Gln Gly Leu Val Ser Ile Ile Thr Thr
                180                 185                 190
Thr Arg Asp Ala Glu Leu Ser Ala Glu Leu Met Ala Asp Pro Arg Leu
                195                 200                 205
Ala Lys Val Thr Phe Thr Gly Ser Thr Asn Val Gly Arg Ile Leu Val
210                 215                 220
Arg Gln Ser Ala Asp Arg Leu Leu Arg Thr Ser Met Glu Leu Gly Gly
225                 230                 235                 240
Asn Ala Ala Phe Val Ile Asp Glu Ala Ala Asp Leu Asp Glu Ala Val
                245                 250                 255
Ser Gly Ala Ile Ala Ala Lys Leu Arg Asn Ala Gly Gln Val Cys Ile
                260                 265                 270
Ala Ala Asn Arg Phe Leu Val His Glu Ser Arg Ala Ala Glu Phe Thr
                275                 280                 285
Ser Lys Leu Ala Thr Ala Met Gln Asn Thr Pro Ile Gly Pro Val Ile
290                 295                 300
Ser Ala Arg Gln Arg Asp Arg Ile Ala Ala Leu Val Asp Glu Ala Ile
305                 310                 315                 320
Thr Asp Gly Ala Arg Leu Ile Ile Gly Gly Glu Val Pro Asp Gly Ser
                325                 330                 335
Gly Phe Phe Tyr Pro Ala Thr Ile Leu Ala Asp Val Pro Ala Gln Ser
                340                 345                 350
Arg Ile Val His Glu Glu Ile Phe Gly Pro Val Ala Thr Ile Ala Thr
                355                 360                 365
Phe Thr Asp Leu Ala Glu Gly Val Ala Gln Ala Asn Ser Thr Glu Phe
                370                 375                 380
Gly Leu Ala Ala Tyr Gly Phe Ser Asn Asn Val Lys Ala Thr Gln Tyr
385                 390                 395                 400
Met Ala Glu His Leu Glu Ala Gly Met Val Gly Ile Asn Arg Gly Ala
                405                 410                 415
Ile Ser Asp Pro Ala Ala Pro Phe Gly Gly Ile Gly Gln Ser Gly Phe
                420                 425                 430
Gly Arg Glu Gly Gly Thr Glu Gly Ile Glu Glu Tyr Leu Ser Val Arg
                435                 440                 445
Tyr Leu Ala Leu Pro
        450
```

<210> SEQ ID NO 191
<211> LENGTH: 521
<212> TYPE: PRT
<213> ORGANISM: Escherichia coli
<220> FEATURE:
<221> NAME/KEY: MISC_FEATURE
<222> LOCATION: (1)..(521)
<223> OTHER INFORMATION: gabD3

<400> SEQUENCE: 191

```
Met Ile Lys Arg Leu Pro Leu Gly Pro Leu Pro Lys Glu Leu His Gln
  1               5                  10                  15

Thr Leu Leu Asp Leu Thr Ala Asn Ala Gln Asp Ala Ala Lys Val Glu
                 20                  25                  30

Val Ile Ala Pro Phe Thr Gly Glu Thr Leu Gly Phe Val Phe Asp Gly
             35                  40                  45

Asp Glu Gln Asp Val Glu His Ala Phe Ala Leu Ser Arg Ala Ala Gln
 50                  55                  60

Lys Lys Trp Val His Thr Thr Ala Val Glu Arg Lys Lys Ile Phe Leu
 65                  70                  75                  80

Lys Phe His Asp Leu Val Leu Lys Asn Arg Glu Leu Leu Met Asp Ile
                 85                  90                  95

Val Gln Leu Glu Thr Gly Lys Asn Arg Ala Ser Ala Ala Asp Glu Val
            100                 105                 110

Leu Asp Val Ala Ile Thr Thr Arg Phe Tyr Ala Asn Asn Ala Gly Lys
        115                 120                 125

Phe Leu Asn Asp Lys Lys Arg Pro Gly Ala Leu Pro Ile Ile Thr Lys
130                 135                 140

Asn Thr Gln Gln Tyr Val Pro Lys Gly Val Val Gly Gln Ile Thr Pro
145                 150                 155                 160

Trp Asn Tyr Pro Leu Thr Leu Gly Val Ser Asp Ala Val Pro Ala Leu
                165                 170                 175

Leu Ala Gly Asn Ala Val Val Ala Lys Pro Asp Leu Ala Thr Pro Phe
            180                 185                 190

Ser Cys Leu Ile Met Val His Leu Leu Ile Glu Ala Gly Leu Pro Arg
        195                 200                 205

Asp Leu Met Gln Val Val Thr Gly Pro Gly Asp Ile Val Gly Gly Ala
    210                 215                 220

Ile Ala Ala Gln Cys Asp Phe Leu Met Phe Thr Gly Ser Thr Ala Thr
225                 230                 235                 240

Gly Arg Ile Leu Gly Arg Thr Met Gly Glu Arg Leu Val Gly Phe Ser
                245                 250                 255

Ala Glu Leu Gly Gly Lys Asn Pro Leu Ile Val Ala Lys Asp Ala Asp
            260                 265                 270

Leu Asp Lys Val Glu Ala Glu Leu Pro Gln Ala Cys Phe Ser Asn Ser
        275                 280                 285

Gly Gln Leu Cys Val Ser Thr Glu Arg Ile Tyr Val Glu Glu Asp Val
    290                 295                 300

Tyr Glu Glu Val Ile Ala Arg Phe Ser Lys Ala Ala Lys Ala Met Ser
305                 310                 315                 320

Ile Gly Ala Gly Phe Glu Trp Lys Tyr Glu Met Gly Ser Leu Ile Asn
                325                 330                 335

Gln Ala Gln Leu Asp Arg Val Ser Thr Phe Val Asp Gln Ala Lys Ala
            340                 345                 350
```

Ala Gly Ala Thr Val Leu Cys Gly Gly Lys Ser Arg Pro Asp Ile Gly
        355                 360                 365

Pro Phe Phe Tyr Glu Pro Thr Val Leu Ala Asp Val Pro Glu Gly Thr
    370                 375                 380

Pro Leu Leu Thr Glu Glu Val Phe Gly Pro Val Val Phe Ile Glu Lys
385                 390                 395                 400

Val Ala Thr Leu Glu Glu Ala Val Asp Lys Ala Asn Gly Thr Pro Tyr
                405                 410                 415

Gly Leu Asn Ala Ser Val Phe Gly Ser Ser Glu Thr Gly Asn Leu Val
            420                 425                 430

Ala Gly Gln Leu Glu Ala Gly Gly Ile Gly Ile Asn Asp Gly Tyr Ala
        435                 440                 445

Ala Thr Trp Ala Ser Val Ser Thr Pro Leu Gly Gly Met Lys Gln Ser
    450                 455                 460

Gly Leu Gly His Arg His Gly Ala Glu Gly Ile Thr Lys Tyr Ala Glu
465                 470                 475                 480

Ile Arg Asn Ile Ala Glu Gln Arg Trp Met Ser Met Arg Gly Pro Ala
                485                 490                 495

Lys Met Pro Arg Lys Val Tyr Ser Asp Thr Val Ala Thr Ala Leu Lys
            500                 505                 510

Leu Gly Lys Ile Phe Lys Val Leu Pro
        515                 520

<210> SEQ ID NO 192
<211> LENGTH: 1194
<212> TYPE: DNA
<213> ORGANISM: Cupriavidus necator
<220> FEATURE:
<221> NAME/KEY: MISC_FEATURE
<222> LOCATION: (1)..(1194)
<223> OTHER INFORMATION: succinate semialdehyde dehydrogenase (SSADH)
      protein gene: gabD gene

<400> SEQUENCE: 192
atgcacgccg ccacgcaagc catcctcacc ttcaaccatg ccgcgatcc cgagcggctg      60 acccgcaagc ttgcggcgat cgccgcggac ccgtttgcct tctttcgcgg caccaaccat    120
ctctatgccg catcgctgcg cgatgaggcg gcaatgtgca atgcgcccat cacctacgtc    180
tgcggcgatc tgcacctgga gaacttcggc agcttcaagg cgacaacgg gctggtctat    240 ttcgacctga cgactttga cgatgccctg gtcgcgccgc ttacggtgga tgtggtccgg    300
atgctgtcga gcgtgctggt ggccgccggc cagctgggcc tttccgaggc cggcgccatg    360
cgcgcctgcg aggccatgct gtccacctat gccgccgtgc tgcagacagg caagcctcgc    420
tggctcgagc gtgccacggc ggtcggcatg gtggccaccc tgctgcgccg ggtcaagggc    480
cgcaagcgcg gcgcgctgct ggccgagctc accacgctgc gcaagggcaa acggcgcctg    540
gtatgcaacg gccgccatgc gctgccggcg gacaagccgg ccgtgagcg cgctcgcgcg    600 atccttgcgg cctactcgaa gcagggccac catggccacc gcctggccct cgacgatgcc    660
gcgcggcgcg tggcgggcat tggcagcctc gggctggaac gctatatggt gctggcgcgg    720
gacgaactga gcggcatgca gcgactggtc gacatcaagc gcgccgcgcc gagtccatgg    780
caggacctgc ccagcctgtc cctgccaccc tggggcagcg atgcaaggcg ggtggcggcg    840
gtgcagcaag tcatgcaggc ggcttcgccg gcgctgctgt cggctgtcga catgggcaag    900
gcttcctatc tggtcaagag cctgcagcca actgccgacc gcgtcgacct ggcgcattgc    960
agcaactttg cagcgctacg cgagttgctg ggcaccatgg cgcatgccgc ggcatgggcg   1020

-continued

```
catctgcgtg gctgcgggca ccaggccgcg gaccggatcg agcagctgca ggcgtttgcc    1080
ggcggcaccc gctggcgcac cggcgtcctg cggctggcac ggcatggctg cgcggtgtcg    1140
gtggtgcagt ggaaggcgta tgcggacgat taccgcgagg cgcggggagg gtga          1194
```

<210> SEQ ID NO 193
<211> LENGTH: 397
<212> TYPE: PRT
<213> ORGANISM: Cupriavidus necator
<220> FEATURE:
<221> NAME/KEY: MISC_FEATURE
<222> LOCATION: (1)..(397)
<223> OTHER INFORMATION: gabD protein

<400> SEQUENCE: 193

```
Met His Ala Ala Thr Gln Ala Ile Leu Thr Phe Asn His Gly Arg Asp
  1               5                  10                  15

Pro Glu Arg Leu Thr Arg Lys Leu Ala Ala Ile Ala Ala Asp Pro Phe
             20                  25                  30

Ala Phe Phe Arg Gly Thr Asn His Leu Tyr Ala Ala Ser Leu Arg Asp
         35                  40                  45

Glu Ala Ala Met Cys Asn Ala Pro Ile Thr Tyr Val Cys Gly Asp Leu
     50                  55                  60

His Leu Glu Asn Phe Gly Ser Phe Lys Gly Asp Asn Gly Leu Val Tyr
 65                  70                  75                  80

Phe Asp Leu Asn Asp Phe Asp Ala Leu Val Ala Pro Leu Thr Val
                 85                  90                  95

Asp Val Val Arg Met Leu Ser Ser Val Leu Val Ala Ala Gly Gln Leu
            100                 105                 110

Gly Leu Ser Glu Ala Gly Ala Met Arg Ala Cys Glu Ala Met Leu Ser
        115                 120                 125

Thr Tyr Ala Ala Val Leu Gln Thr Gly Lys Pro Arg Trp Leu Glu Arg
    130                 135                 140

Ala Thr Ala Val Gly Met Val Ala Thr Leu Leu Arg Arg Val Lys Gly
145                 150                 155                 160

Arg Lys Arg Gly Ala Leu Leu Ala Glu Leu Thr Thr Leu Arg Lys Gly
                165                 170                 175

Lys Arg Arg Leu Val Cys Asn Gly Arg His Ala Leu Pro Ala Asp Lys
            180                 185                 190

Pro Ala Arg Glu Arg Ala Arg Ala Ile Leu Ala Ala Tyr Ser Lys Gln
        195                 200                 205

Gly His His Gly His Arg Leu Ala Leu Asp Asp Ala Ala Arg Arg Val
    210                 215                 220

Ala Gly Ile Gly Ser Leu Gly Leu Glu Arg Tyr Met Val Leu Ala Arg
225                 230                 235                 240

Asp Glu Leu Ser Gly Met Gln Arg Leu Val Asp Ile Lys Arg Ala Ala
                245                 250                 255

Pro Ser Pro Trp Gln Asp Leu Pro Leu Ser Leu Pro Pro Trp Gly
            260                 265                 270

Ser Asp Ala Arg Arg Val Ala Ala Val Gln Gln Val Met Gln Ala Ala
        275                 280                 285

Ser Pro Ala Leu Leu Ser Ala Val Asp Met Gly Lys Ala Ser Tyr Leu
    290                 295                 300

Val Lys Ser Leu Gln Pro Thr Ala Asp Arg Val Asp Leu Ala His Cys
305                 310                 315                 320
```

```
Ser Asn Phe Ala Ala Leu Arg Glu Leu Leu Gly Thr Met Ala His Ala
            325                 330                 335

Ala Ala Trp Ala His Leu Arg Gly Cys Gly His Gln Ala Ala Asp Arg
        340                 345                 350

Ile Glu Gln Leu Gln Ala Phe Ala Gly Gly Thr Arg Trp Arg Thr Gly
        355                 360                 365

Val Leu Arg Leu Ala Arg His Gly Cys Ala Val Ser Val Val Gln Trp
370                 375                 380

Lys Ala Tyr Ala Asp Asp Tyr Arg Glu Ala Arg Gly Gly
385                 390                 395

<210> SEQ ID NO 194
<211> LENGTH: 1473
<212> TYPE: DNA
<213> ORGANISM: Escherichia coli
<220> FEATURE:
<221> NAME/KEY: MISC_FEATURE
<222> LOCATION: (1)..(1473)
<223> OTHER INFORMATION: gabD1

<400> SEQUENCE: 194
atgactatta atgtctccga actacttgcc aaagtcccca cgggtctact gattggtgat      60
tcctgggtgg aagcatccga cggcggtact ttcgatgtgg aaaacccagc gacgggtgaa     120
acaatcgcaa cgctcgcgtc tgctacttcc gaggatgcac tggctgctct tgatgctgca     180
tgcgctgttc aggccgagtg ggctaggatg ccagcgcgcg agcgttctaa tattttacgc     240
cgcggttttg agctcgtagc agaacgtgca gaagagttcg ccaccctcat gaccttggaa     300
atgggcaagc ctttggctga agctcgcggc gaagtcacct acggcaacga attcctgcgc     360
tggttctctg aggaagcagt tcgtctgtat ggccgttacg gaaccacacc agaaggcaac     420
ttgcggatgc tgaccgccct caagccagtt ggcccgtgcc tcctgatcac ccatggaaac     480
ttcccactag caatggctac ccgcaaggtc gcacctgcga tcgctgcagg ttgtgtcatg     540
gtgctcaagc cagctcgact taccccgctg acctcccagt attttgctca gaccatgctt     600
gatgccggtc ttccagcagg tgtcctcaat gtggtctccg gtgcttccgc ctctgcgatt     660
tccaacccga ttatggaaga cgatcgcctt cgtaaagtct ccttcaccgg ctccacccca     720
gttggccagc agctgctcaa aaaggctgcc gataaagttc tgcgcacctc catggaactt     780
ggtggcaacg cacctttcat tgtcttcgag gacgccgacc tagatctcgc gatcgaaggt     840
gccatgggtg ccaaaatgcg caacatcggc gaagcttgca ccgcagccaa ccgtttctta     900
gtccacgaat ccgtcgccga tgaattcggc cgtcgcttcg ctgcccgcct tgaagagcaa     960
gtcctaggca acggcctcga cgaaggcgtc accgtgggcc ccctggttga ggaaaaagca    1020
cgagacagcg ttgcatcgct tgtcgacgcc gccgtcgccg aaggtgccac cgtcctcacc    1080
ggcggcaagg ccggcacagg tgcaggctac ttctacgaac caacggtgct cacgggagtt    1140
tcaacagatg cggctatcct gaacgaagag atcttcggtc ccgtcgcacc gatcgtcacc    1200
ttccaaaccg aggaagaagc cctgcgtcta gccaactcca ccgaatacgg actggcctcc    1260
tatgtgttca cccaggacac ctcacgtatt ttccgcgtct ccgatggtct cgagttcggc    1320
ctagtgggcg tcaattccgg tgtcatctct aacgctgctg cacctttggg tggcgtaaaa    1380
caatccggaa tgggccgcga aggtggtctc gaaggaatcg aggagtacac ctccgtgcag    1440
tacatcggta tccgggatcc ttacgccggc tag                                 1473

<210> SEQ ID NO 195
```

<211> LENGTH: 1362
<212> TYPE: DNA
<213> ORGANISM: Escherichia coli
<220> FEATURE:
<221> NAME/KEY: Gene
<222> LOCATION: (1)..(1362)
<223> OTHER INFORMATION: gabD2 gene

<400> SEQUENCE: 195

| | | | | |
|---|---|---|---|---|
| gtgtctttga | ccttcccagt | aatcaaccccc | agcgatggct | ccaccatcac | cgagctagaa | 60 |
| aaccacgatt | ccacccagtg | gatgtccgcg | ctctctgatg | cagttgcagc | tggtccttca | 120 |
| tgggctgcga | aaactccccg | cgaaagatcc | gtggtactca | ccgcaatctt | cgaagcactg | 180 |
| accgaacgcg | cccaagaact | tgcagagatc | atccacctgg | aagctggaaa | atccgttgca | 240 |
| gaagctcttg | gtgaagtcgc | ttatggtgca | gaatacttcc | gttggtttgc | ggaagaagca | 300 |
| gtgcgcctgc | ccggccgcta | cggacagtca | ccttccggaa | tcggtcacat | cgccgtcacc | 360 |
| cgcgcacccg | tgggaccagt | gctggcgatc | accccatgga | atttccccat | cgccatggcc | 420 |
| acccgcaaaa | tcgccccagc | cctggccgct | ggttgccccg | tgttggtgaa | acctgcttcc | 480 |
| gaaaccccac | tgaccatggt | caaagtgggg | gagatcatcg | cctccgtctt | tgataccttt | 540 |
| aatatcccgc | agggcttggt | ctcaatcatc | accaccactc | gagatgcaga | gctatcggca | 600 |
| gaactcatgg | ctgatcctcg | cttggctaaa | gtcaccttca | ctggatcaac | caacgtggga | 660 |
| cgcatcctgt | ccgccaatc | cgcggaccga | ctgctgcgca | cctccatgga | actcggcgga | 720 |
| aatgcagctt | tgttatcga | cgaagccgca | gacctcgacg | aagccgtatc | cggtgccatc | 780 |
| gccgcaaaac | tccgcaacgc | cggccaagta | tgcatcgcag | ctaaccgttt | cttggttcat | 840 |
| gaatcccgcg | ctgccgaatt | cacctcaaag | ctggcgacag | ccatgcagaa | cactcccatt | 900 |
| gggccggtga | tttctgcccg | ccaacgcgac | cggatcgcag | cactagtgga | tgaagccatc | 960 |
| accgacggcg | cccgcctcat | catcggtggg | gaggtccccg | acggctccgg | cttcttctat | 1020 |
| ccagccacca | tcttggccga | tgtccctgca | cagtcacgga | ttgtgcatga | ggaaatcttc | 1080 |
| ggacctgtgg | ccaccattgc | cactttcacc | gacttggccg | aaggcgttgc | acaagcaaat | 1140 |
| tccaccgaat | tcggcctcgc | agcctacgga | ttcagcaaca | atgtgaaagc | aacacagtac | 1200 |
| atggcggaac | acttggaagc | cggaatggtc | ggaatcaaca | gaggcgccat | ctctgaccca | 1260 |
| gcagcacctt | tggcggcat | cggacaatcc | ggcttcggca | gagaaggcgg | aaccgaagga | 1320 |
| atcgaagaat | atctctccgt | gcgttacctc | gctttgccgt | ga | 1362 |

<210> SEQ ID NO 196
<211> LENGTH: 1566
<212> TYPE: DNA
<213> ORGANISM: Escherichia coli
<220> FEATURE:
<221> NAME/KEY: Gene
<222> LOCATION: (1)..(1566)
<223> OTHER INFORMATION: gabD3 gene

<400> SEQUENCE: 196

| | | | | | |
|---|---|---|---|---|---|
| atgatcaaac | gtcttccttt | aggtccgctg | cctaaagaac | ttcatcagac | tctgcttgat | 60 |
| ctgaccgcaa | atgcccaaga | tgcggcgaaa | gtggaggtta | tagcgccatt | tactggcgag | 120 |
| accctcggat | ttgttttttga | tggtgatgag | caagacgtcg | agcatgcttt | tgcactttca | 180 |
| agggcagccc | agaaaaagtg | ggtgcacacc | acggcagtgg | aacggaagaa | gatcttcctg | 240 |
| aagtttcatg | atctggtatt | gaaaaaccgt | gagctgctca | tggacatcgt | gcagttggaa | 300 |
| acaggcaaaa | atcgagcatc | ggctgccgat | gaggtgttgg | acgttgcgat | caccacccgc | 360 |

-continued

```
ttctacgcaa acaatgcagg aaagttttta aatgacaaga aacgccccgg cgcgcttccg    420
atcatcacga aaacacaca acagtatgtg cccaagggag tggtcgggca gatcacgccg    480
tggaattacc ctttaacttt gggagtatct gatgctgttc cggcgctgct ggcaggaaac    540
gcagtggtgg ctaaacctga cctcgcgaca cctttctcct gcttgatcat ggtgcacctg    600
ctcattgaag ccggtctgcc gcgtgatttg atgcaggttg tcaccggccc tggcgatatt    660
gttggcggtg cgattgcagc tcagtgtgat ttcctcatgt tcactggatc cacggccacg    720
ggccggatct tgggtcggac aatgggtgag cgtttggtgg gtttctctgc ggaattaggc    780
ggaaagaacc ctcttattgt ggccaaggat gcagatctgg acaaggtgga agctgagctt    840
ccgcaggcgt gttttccaa ctcggggcaa ttgtgtgtct ccactgaacg tatttatgtc    900
gaggaagacg tgtacgagga ggtgattgca cggtttagca aggcggcgaa agccatgtcc    960
attggtgccg gatttgagtg gaaatatgag atgggttcgt tgatcaatca ggcgcagctg    1020
gatcgggtga gcacctttgt tgatcaggct aaagctgcgg cgccacggt gctgtgcggt    1080 ggcaagtcac gccctgatat tggtcccttc ttctatgagc ccacggtatt ggcggatgtc    1140
ccagagggca ccccactgct cacggaggaa gtcttcgggc cggtggtgtt catcgaaaag    1200
gtagccacac tggaagaagc cgtcgataag gcaaatggca cgccctacgg cctgaatgcg    1260
tccgtctttg ggtcgtcgga aaccggcaat cttgttgcag ccagctgga agctggcggt    1320 atcggtatta tgatggcta cgccgcgacg tgggcgagcg tgtccacgcc tctgggtggc    1380
atgaagcagt cggggctggg gcaccgccat ggtgcgagg gaattacaaa atatgcggag    1440
atccgaaaca tcgcggagca cgctggatg tctatgcgtg ggccggccaa aatgccgcga    1500
aaggtgtact cagacaccgt ggccacagcg ctaaagctgg gcaaaatctt taaagttttg    1560
ccgtag                                                              1566
```

<210> SEQ ID NO 197
<211> LENGTH: 607
<212> TYPE: PRT
<213> ORGANISM: Klebsiella pneumoniae
<220> FEATURE:
<221> NAME/KEY: MISC_FEATURE
<222> LOCATION: (1)..(607)
<223> OTHER INFORMATION: gdrA protein

<400> SEQUENCE: 197

```
Met Pro Leu Ile Ala Gly Ile Asp Ile Gly Asn Ala Thr Thr Glu Val
  1               5                  10                  15

Ala Leu Ala Ser Asp Asp Pro Gln Ala Arg Ala Phe Val Ala Ser Gly
                 20                  25                  30

Ile Val Ala Thr Thr Gly Met Lys Gly Thr Arg Asp Asn Ile Ala Gly
             35                  40                  45

Thr Leu Ala Ala Leu Glu Gln Ala Leu Ala Lys Thr Pro Trp Ser Val
         50                  55                  60

Ser Asp Val Ser Arg Ile Tyr Leu Asn Glu Ala Ala Pro Val Ile Gly
 65                  70                  75                  80

Asp Val Ala Met Glu Thr Ile Thr Glu Thr Ile Ile Thr Glu Ser Thr
                 85                  90                  95

Met Ile Gly His Asn Pro Gln Thr Pro Gly Gly Val Gly Val Gly Val
                100                 105                 110

Gly Thr Thr Ile Ala Leu Gly Arg Leu Ala Thr Leu Pro Ala Ala Gln
            115                 120                 125
```

```
Tyr Ala Glu Gly Trp Ile Val Leu Ile Asp Asp Ala Val Asp Phe Leu
130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                165                 170                 175

Leu Arg Lys Thr Leu Pro Val Val Asp Glu Val Thr Leu Leu Glu Gln
            180                 185                 190

Val Pro Glu Gly Val Met Ala Ala Val Glu Val Ala Ala Pro Gly Gln
        195                 200                 205

Val Val Arg Ile Leu Ser Asn Pro Tyr Gly Ile Ala Thr Phe Phe Gly
    210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
                245                 250                 255

Gln Ser Arg Val Ile Pro Ala Gly Asn Leu Tyr Ile Ser Gly Glu Lys
            260                 265                 270

Arg Arg Gly Glu Ala Asp Val Ala Glu Gly Ala Glu Ala Ile Met Gln
        275                 280                 285

Ala Met Ser Ala Cys Ala Pro Val Arg Asp Ile Arg Gly Glu Pro Gly
    290                 295                 300

Thr His Ala Gly Gly Met Leu Glu Arg Val Arg Lys Val Met Ala Ser
305                 310                 315                 320

Leu Thr Asp His Glu Met Ser Ala Ile Tyr Ile Gln Asp Leu Leu Ala
                325                 330                 335

Val Asp Thr Phe Ile Pro Arg Lys Val Gln Gly Gly Met Ala Gly Glu
            340                 345                 350

Cys Ala Met Glu Asn Ala Val Gly Met Ala Ala Met Val Lys Ala Asp
        355                 360                 365

Arg Leu Gln Met Gln Val Ile Ala Arg Glu Leu Ser Ala Arg Leu Gln
    370                 375                 380

Thr Glu Val Val Val Gly Gly Val Glu Ala Asn Met Ala Ile Ala Gly
385                 390                 395                 400

Ala Leu Thr Thr Pro Gly Cys Ala Ala Pro Leu Ala Ile Leu Asp Leu
                405                 410                 415

Gly Ala Gly Ser Thr Asp Ala Ala Ile Val Asn Ala Glu Gly Gln Ile
            420                 425                 430

Thr Ala Val His Leu Ala Gly Ala Gly Asn Met Val Ser Leu Leu Ile
        435                 440                 445

Lys Thr Glu Leu Gly Leu Glu Asp Leu Ser Leu Ala Glu Ala Ile Lys
    450                 455                 460

Lys Tyr Pro Leu Ala Lys Val Glu Ser Leu Phe Ser Ile Arg His Glu
465                 470                 475                 480

Asn Gly Ala Val Glu Phe Phe Arg Glu Ala Leu Ser Pro Ala Val Phe
                485                 490                 495

Ala Lys Val Val Tyr Ile Lys Glu Gly Glu Leu Val Pro Ile Asp Asn
            500                 505                 510

Ala Ser Pro Leu Glu Lys Ile Arg Leu Val Arg Arg Gln Ala Lys Glu
        515                 520                 525

Lys Val Phe Val Thr Asn Cys Leu Arg Ala Leu Arg Gln Val Ser Pro
    530                 535                 540

Gly Gly Ser Ile Arg Asp Ile Ala Phe Val Val Leu Val Gly Gly Ser
```

```
                545                 550                 555                 560
Ser Leu Asp Phe Glu Ile Pro Gln Leu Ile Thr Glu Ala Leu Ser His
                    565                 570                 575

Tyr Gly Val Val Ala Gly Gln Gly Asn Ile Arg Gly Thr Glu Gly Pro
                580                 585                 590

Arg Asn Ala Val Ala Thr Gly Leu Leu Leu Ala Gly Gln Ala Asn
                595                 600                 605
```

<210> SEQ ID NO 198
<211> LENGTH: 117
<212> TYPE: PRT
<213> ORGANISM: Klebsiella pneumoniae
<220> FEATURE:
<221> NAME/KEY: MISC_FEATURE
<222> LOCATION: (1)..(117)
<223> OTHER INFORMATION: gdrB protein

<400> SEQUENCE: 198

```
Met Ser Leu Ser Pro Pro Gly Val Arg Leu Phe Tyr Asp Pro Arg Gly
 1               5                  10                  15

His His Ala Gly Ala Ile Asn Glu Leu Cys Trp Gly Leu Glu Glu Gln
                20                  25                  30

Gly Val Pro Cys Gln Thr Ile Thr Tyr Asp Gly Gly Asp Ala Ala
            35                  40                  45

Ala Leu Gly Ala Leu Ala Ala Arg Ser Ser Pro Leu Arg Val Gly Ile
        50                  55                  60

Gly Leu Ser Ala Ser Gly Glu Ile Ala Leu Thr His Ala Gln Leu Pro
65                  70                  75                  80

Ala Asp Ala Pro Leu Ala Thr Gly His Val Thr Asp Ser Asp His
                85                  90                  95

Leu Arg Thr Leu Gly Ala Asn Ala Gly Gln Leu Val Lys Val Leu Pro
                100                 105                 110

Leu Ser Glu Arg Asn
        115
```

<210> SEQ ID NO 199
<211> LENGTH: 607
<212> TYPE: PRT
<213> ORGANISM: Ilyobacter polytropus
<220> FEATURE:
<221> NAME/KEY: MISC_FEATURE
<222> LOCATION: (1)..(607)
<223> OTHER INFORMATION: gdrA protein

<400> SEQUENCE: 199

```
Met Lys Ile Ile Val Gly Val Asp Ile Gly Asn Ala Thr Thr Glu Val
 1               5                  10                  15

Ala Leu Ala Lys Val Asp Asn Ile Glu Cys Lys Phe Leu Ser Ser Ala
                20                  25                  30

Leu His Glu Thr Thr Gly Leu Lys Gly Thr Lys Asp Asn Val Leu Gly
            35                  40                  45

Ile Lys Arg Ala Ile Lys Lys Ala Met Lys Arg Ala Asp Leu Lys Asn
        50                  55                  60

Ala Asp Leu Ser Leu Ile Arg Ile Asn Glu Ala Thr Pro Val Ile Gly
65                  70                  75                  80

Asp Val Ser Met Glu Thr Ile Thr Glu Thr Ile Ile Thr Glu Ser Thr
                85                  90                  95

Met Ile Gly His Asn Pro Ser Thr Pro Gly Gly Ile Gly Leu Gly Ile
                100                 105                 110
```

```
Gly Glu Thr Ile Leu Phe Gln Glu Leu Gly Asn Phe Glu Asn Asp Lys
            115                 120                 125

Asp Tyr Ile Val Ile Val Glu Lys Ser Phe Ser Phe Leu Glu Val Ala
        130                 135                 140

His Arg Ile Asn Glu Ala Phe Lys Asn Gly Cys Lys Ile Lys Gly Ala
145                 150                 155                 160

Ile Ile Gln Lys Asp Asp Gly Val Leu Ile Asn Asn Arg Leu Ile Asn
                165                 170                 175

Lys Ile Pro Ile Val Asp Glu Val Leu Phe Val Lys Lys Val Pro Thr
                180                 185                 190

Gly Met Lys Ala Ala Val Glu Val Ala Pro Gln Gly Lys Ile Ile Glu
            195                 200                 205

Val Ile Ser Asn Pro Tyr Gly Ile Ala Thr Ile Phe Ser Leu Thr Ser
        210                 215                 220

Glu Glu Thr Lys Lys Ile Val Pro Ile Ser Lys Ala Leu Ile Gly Asn
225                 230                 235                 240

Arg Ser Gly Val Val Ile Lys Thr Pro His Gly Asp Val Lys Glu Lys
                245                 250                 255

Val Ile Pro Ala Gly Arg Ile Gln Ile Asp Gly Asn Tyr Arg Ser Lys
            260                 265                 270

Ser Val Asn Ile Glu Glu Gly Ser Lys Arg Ile Met Lys Ala Leu Gly
        275                 280                 285

Ser Ile Glu His Val Gln Asp Ile Asn Gly Glu Ser Gly Thr Asn Ile
290                 295                 300

Gly Gly Met Leu Lys Asn Val Lys Ser Val Met Gly Asn Phe Thr Asn
305                 310                 315                 320

Glu Ser Ile Asp Asn Ile Lys Ile Lys Asp Ile Leu Ala Val Asp Thr
                325                 330                 335

Phe Val Pro Gln Lys Ile Lys Gly Gly Ile Ala Glu Glu Phe Val Phe
            340                 345                 350

Glu Asn Ala Val Gly Ile Ala Ala Met Val Asn Thr Lys Lys Asn Gln
        355                 360                 365

Met Ser Glu Val Ala Lys Glu Ile Glu Lys Glu Leu Gly Val Lys Val
        370                 375                 380

Glu Val Gly Gly Val Glu Ala Asp Met Ala Ile Thr Gly Ala Leu Thr
385                 390                 395                 400

Thr Pro Gly Thr Gly Thr Pro Leu Val Ile Val Asp Ile Gly Ala Gly
                405                 410                 415

Ser Thr Asp Ala Cys Ser Ile Asp Arg Tyr Gly Asn Lys Glu Leu Val
                420                 425                 430

His Leu Ala Gly Ala Gly Asn Met Thr Thr Leu Leu Ile Gln Lys Glu
            435                 440                 445

Leu Gly Ile Glu Asp Phe Asn Leu Ala Glu Asp Ile Lys Lys Tyr Pro
        450                 455                 460

Leu Ala Lys Val Glu Ser Leu Phe Tyr Ile Arg His Glu Asp Gly Asn
465                 470                 475                 480

Val Gln Phe Phe Glu Asn Ser Leu Ser Pro Lys Val Phe Ala Lys Asn
                485                 490                 495

Val Leu Ile Lys Glu Gly Glu Leu Ile Pro Ile Asp Leu Asp Met Ser
                500                 505                 510

Leu Glu Lys Ile Arg Ile Arg Arg Ser Ala Lys Arg Lys Ile Phe
            515                 520                 525
```

```
Ile Thr Asn Val Leu Arg Ser Leu Arg Lys Val Ser His Thr Lys Asn
            530                 535                 540

Ile Arg Asp Phe Glu Phe Val Ile Val Gly Gly Ser Ala Leu Asp
545                 550                 555                 560

Phe Glu Ile Ser Gln Met Ile Thr Glu Ala Leu Ser Glu Tyr Gly Ile
                565                 570                 575

Val Ala Gly Cys Gly Asn Ile Arg Gly Thr Glu Gly Pro Arg Asn Ala
            580                 585                 590

Val Ala Thr Gly Leu Val Met Gly Val Asn Asp Gly Gln Gln Ala
            595                 600                 605

<210> SEQ ID NO 200
<211> LENGTH: 107
<212> TYPE: PRT
<213> ORGANISM: Ilyobacter polytropus
<220> FEATURE:
<221> NAME/KEY: MISC_FEATURE
<222> LOCATION: (1)..(107)
<223> OTHER INFORMATION: gdrB

<400> SEQUENCE: 200

Met Asp Asn Arg Pro Asn Ile Thr Leu Phe Cys Ser Asp Asn Ile Asp
 1                5                  10                  15

Arg Glu Tyr Ile Asn Glu Ile Leu Trp Gly Ile Glu Glu Glu Glu Ile
                20                  25                  30

Pro Tyr Leu Leu Lys Ile Val Pro Ser Lys Glu Val Val Lys Glu Asn
            35                  40                  45

Tyr Val Ser Gly Thr Leu Glu Ile Gly Ile Gly Val Leu Glu Asn Gly
    50                  55                  60

Asp Ala Leu Leu Thr Thr Arg Lys Tyr Asp Lys Glu Tyr Ile Gln Lys
65                  70                  75                  80

Ala Asn Ile Phe Val Glu Lys Asn Lys Leu Arg Asp Leu Gly Ser Asn
                85                  90                  95

Gly Ala Arg Leu Val Lys Gly Leu Pro Leu Arg
            100                 105

<210> SEQ ID NO 201
<211> LENGTH: 1824
<212> TYPE: DNA
<213> ORGANISM: Ilyobacter polytropus
<220> FEATURE:
<221> NAME/KEY: Gene
<222> LOCATION: (1)..(1824)
<223> OTHER INFORMATION: gdrA gene

<400> SEQUENCE: 201
atgaagatca tagtgggtgt agatattgga aatgctacaa cagaagtagc tttggcaaag        60
gtagacaata tagaatgtaa gtttttatcc agtgccttac atgaaacaac aggtttaaaa       120
ggtactaaag ataatgtttt gggaataaaa agagccatta agaaggcaat gaaaagagct       180
gatttaaaaa atgcagattt atctttaatc aggataaatg aagctactcc tgttatagga       240
gacgtttcta tggaaactat aacagaaaca ataattacag agtctactat gattggacat       300 aaccccttcaa ctcctggggg aataggtctt gggataggag aaacaatcct attccaagag      360
cttggaaatt ttgaaaatga taagattac atagtaatag tggaaaaaag tttcagcttc       420
ttagaggtag ctcacagaat caatgaagct tttaaaaatg gatgcaaaat aaagggtgct       480
attattcaaa aagatgatgg ggttctcata aataacagac tcataaataa aatccccata      540
gttgatgagg tactttttgt taaaaaagta cctacaggga tgaaggctgc tgtagaagta       600
```

```
gctccacagg gaaaaataat agaggttatt tcaaatccat atggcattgc cacaattttt      660
tccctcactt cagaagagac taaaaaaata gttcctattt ctaaagcact tataggcaac      720
aggtctggag tagttatcaa gacacctcac ggagatgtaa aagagaaggt tatccctgct      780
ggaaggatac agattgacgg aaactacagg tcaaaaagtg taaatataga agagggttcc      840
aaaagaataa tgaaagccct gggaagtatt gagcatgtcc aagatataaa tggagaatct      900
ggaaccaata tcgaggaat gctaaaaaat gtaaaaagtg taatgggaa tttcaccaat       960 gagtccattg ataatataaa ataaaagac atattggcag tagatacctt tgtcccacaa     1020
aagataaagg ggggaattgc agaagaattt gtatttgaaa atgctgtagg aatagctgca     1080
atggtaaata ccaaaaaaaa tcaaatgtcc gaagtagcga aagagattga aaaagaactg     1140
ggagtaaaag tagaagtagg aggagtagag gcagatatgg ctataaccgg tgctctaact     1200
actccaggca caggaacacc tctggtaatt gtagatatag gagcaggttc gacagatgca     1260
tgttccattg acagatatgg aaataaagaa ctggttcatc tggccggagc tggtaatatg     1320
acaacacttc ttattcaaaa agagctgggt atagaggatt ttaatcttgc tgaagatata     1380
aaaaaatatc ctctggcaaa agtagaatct ctatttata taagcacga ggatggaaat       1440 gttcaatttt ttgaaaactc tctttctccg aaagtatttg ctaaaaatgt ccttataaaa     1500
gaaggtgaac ttattccaat cgaccttgat atgtctctgg aaaaaatcag aattatcaga     1560
aggtctgcca aaagaaaaat ttttataacc aatgtactta gatcattaag gaaagtttct     1620
catacaaaaa atattaggga ttttgaattt gtagttattg ttggaggatc tgcattggat     1680
tttgaaatat ctcagatgat aactgaagct ttatctgagt atggaatagt agcaggatgc     1740
ggaaatataa gaggaacaga gggccctaga aatgctgtag ccactggact tgtaatgggg     1800
gtgaatgatg gacaacaggc ctaa                                            1824

<210> SEQ ID NO 202
<211> LENGTH: 324
<212> TYPE: DNA
<213> ORGANISM: Ilyobacter polytropus
<220> FEATURE:
<221> NAME/KEY: Gene
<222> LOCATION: (1)..(324)
<223> OTHER INFORMATION: gdrB gene

<400> SEQUENCE: 202
atggacaaca ggcctaatat aacattattt tgctcagata atattgacag ggaatatatt       60
aatgaaattt gtggggtat agaggaggaa gagataccat atcttctgaa aattgtacct      120
tctaaagaag ttgtcaaaga aaattatgtt tcaggaactc tagagatagg tatcggagta     180
ttagaaaatg gcgacgccct tctaacaaca aggaagtacg ataaggaata tatacaaaag     240
gcaaacattt ttgtagaaaa aaataaattg agagatttag gaagcaacgg agcaagactt     300
gtaaagggtc tgccacttag ataa                                            324

<210> SEQ ID NO 203
<211> LENGTH: 1824
<212> TYPE: DNA
<213> ORGANISM: Klebsiella pneumoniae
<220> FEATURE:
<221> NAME/KEY: Gene
<222> LOCATION: (1)..(1824)
<223> OTHER INFORMATION: gdrA gene

<400> SEQUENCE: 203
```

-continued

| | |
|---|---|
| atgccgttaa tagccgggat tgatatcggc aacgccacca ccgaggtggc gctggcgtcc | 60 |
| gacgacccgc aggcgagggc gtttgttgcc agcgggatcg tcgcgacgac gggcatgaaa | 120 |
| gggacgcggg acaatatcgc cggaccctc gccgcgctgg agcaggccct ggcgaaaaca | 180 |
| ccgtggtcgg tgagcgatgt ctctcgcatc tatcttaacg aagccgcgcc ggtgattggc | 240 |
| gatgtggcga tggagaccat caccgagacc attatcaccg aatcgaccat gatcggtcat | 300 |
| aacccgcaga cgccgggcgg ggtgggcgtt ggcgtgggga cgactatcgc cctcgggcgg | 360 |
| ctggcgacgc tgccggcggc gcagtatgcc gaggggtgga tcgtactgat tgacgacgcc | 420 |
| gtcgatttcc ttgacgccgt gtggtggctc aatgaggcgc tcgaccgggg gatcaacgtg | 480 |
| gtggcggcga tcctcaaaaa ggacgacggc gtgctggtga acaaccgcct gcgtaaaacc | 540 |
| ctgccggtgg tagatgaagt gacgctgctg gagcaggtcc ccgaggggt aatggcggcg | 600 |
| gtggaagtgg ccgcgccggg ccaggtggtg cggatcctgt cgaatcccta cgggatcgcc | 660 |
| accttcttcg ggctaagccc ggaagagacc caggccatcg tccccatcgc ccgcgccctg | 720 |
| attggcaacc gttcagcgt ggtgctcaag accccgcagg gggatgtgca gtcgcgggtg | 780 |
| atcccggcgg gcaacctcta cattagcggc gaaaagcgcc gcggagaggc cgatgtcgcc | 840 |
| gagggcgcgg aagccatcat gcaggcgatg agcgcctgcc ctccggtacg cgacatccgc | 900 |
| ggcgaaccgg gcactcacgc cggcggcat cttgagcggg tgcgcaaggt aatggcgtcc | 960 |
| ctgaccgacc atgagatgag cgcgatatac atccaggatc tgctggcggt ggatacgttt | 1020 |
| attccgcgca aggtgcaggg cgggatggcc ggcgagtgcg ccatggaaaa tgccgtcggg | 1080 |
| atggcggcga tggtgaaagc ggatcgtctg caaatgcagg ttatcgcccg cgaactgagc | 1140 |
| gcccgactgc agaccgaggt ggtggtgggc ggcgtggagg ccaacatggc catcgccggg | 1200 |
| gcgttaacca ctcccggctg tgcggcgccg ctggcgatcc tcgacctcgg cgccggctcg | 1260 |
| acggatgcgg cgatcgtcaa cgcggagggg cagataacgg cggtccatct cgccggggcg | 1320 |
| gggaatatgg tcagcctgtt gattaaaacc gagctgggcc tcgaggatct ttcgctggcg | 1380 |
| gaagcgataa aaaatacccc gctggccaaa gtggaaagcc tgttcagtat tcgtcacgag | 1440 |
| aatggcgcgt tggagttctt tcgggaagcc ctcagcccgg cggtgttcgc caaagtggtg | 1500 |
| tacatcaagg agggcgaact ggtgccgatc gataacgcca gcccgctgga aaaaattcgt | 1560 |
| ctcgtgcgcc ggcaggcgaa agagaaagtg tttgtcacca actgcctgcg cgcgctgcgc | 1620 |
| caggtctcac ccggcggttc cattcgcgat atcgcctttg tggtgctggt gggcggctca | 1680 |
| tcgctggact ttgagatccc gcagcttatc acggaagcct tgtcgcacta tggcgtggtc | 1740 |
| gccgggcagg gcaatattcg gggaacagaa gggccgcgca acgcggtcgc caccgggctg | 1800 |
| ctactggccg gtcaggcgaa ttaa | 1824 |

<210> SEQ ID NO 204
<211> LENGTH: 354
<212> TYPE: DNA
<213> ORGANISM: Klebsiella pneumoniae
<220> FEATURE:
<221> NAME/KEY: Gene
<222> LOCATION: (1)..(354)
<223> OTHER INFORMATION: gdrB gene

<400> SEQUENCE: 204

| | |
|---|---|
| atgtcgcttt caccgccagg cgtacgcctg ttttacgatc cgcgcgggca ccatgccggc | 60 |
| gccatcaatg agctgtgctg ggggctggag gagcaggggg tccctgcca gaccataacc | 120 |
| tatgacggag gcggtgacgc cgctgcgctg ggcgccctgg cggccagaag ctcgcccctg | 180 |

```
cgggtgggta ttgggctcag cgcgtccggc gagatagccc tcactcatgc ccagctgccg    240
gcggacgcgc cgctggctac cggacacgtc accgatagcg acgatcatct gcgtacgctc    300
ggcgccaacg ccgggcagct ggttaaagtc ctgccgttaa gtgagagaaa ctga          354
```

<210> SEQ ID NO 205
<211> LENGTH: 314
<212> TYPE: PRT
<213> ORGANISM: Corynebacterium glutamicum

<400> SEQUENCE: 205

| | | | | | | | | | | | | | | |
|---|---|---|---|---|---|---|---|---|---|---|---|---|---|---|
| Met | Lys | Glu | Thr | Val | Gly | Asn | Lys | Ile | Val | Leu | Ile | Gly | Ala | Gly Asp |
| 1 | | | | 5 | | | | | 10 | | | | | 15 |
| Val | Gly | Val | Ala | Tyr | Ala | Tyr | Ala | Leu | Ile | Asn | Gln | Gly | Met | Ala Asp |
| | | | 20 | | | | | 25 | | | | | 30 | |
| His | Leu | Ala | Ile | Ile | Asp | Ile | Asp | Glu | Lys | Lys | Leu | Glu | Gly | Asn Val |
| | | 35 | | | | | 40 | | | | | 45 | | |
| Met | Asp | Leu | Asn | His | Gly | Val | Val | Trp | Ala | Asp | Ser | Arg | Thr | Arg Val |
| | 50 | | | | | 55 | | | | | 60 | | | |
| Thr | Lys | Gly | Thr | Tyr | Ala | Asp | Cys | Glu | Asp | Ala | Ala | Met | Val | Val Ile |
| 65 | | | | | 70 | | | | | 75 | | | | | 80 |
| Cys | Ala | Gly | Ala | Ala | Gln | Lys | Pro | Gly | Glu | Thr | Arg | Leu | Gln | Leu Val |
| | | | | 85 | | | | | 90 | | | | | 95 |
| Asp | Lys | Asn | Val | Lys | Ile | Met | Lys | Ser | Ile | Val | Gly | Asp | Val | Met Asp |
| | | | 100 | | | | | 105 | | | | | 110 | |
| Ser | Gly | Phe | Asp | Gly | Ile | Phe | Leu | Val | Ala | Ser | Asn | Pro | Val | Asp Ile |
| | | 115 | | | | | 120 | | | | | 125 | | |
| Leu | Thr | Tyr | Ala | Val | Trp | Lys | Phe | Ser | Gly | Leu | Glu | Trp | Asn | Arg Val |
| | 130 | | | | | 135 | | | | | 140 | | | |
| Ile | Gly | Ser | Gly | Thr | Val | Leu | Asp | Ser | Ala | Arg | Phe | Arg | Tyr | Met Leu |
| 145 | | | | | 150 | | | | | 155 | | | | | 160 |
| Gly | Glu | Leu | Tyr | Glu | Val | Ala | Pro | Ser | Ser | Val | His | Ala | Tyr | Ile Ile |
| | | | | 165 | | | | | 170 | | | | | 175 |
| Gly | Glu | His | Gly | Asp | Thr | Glu | Leu | Pro | Val | Leu | Ser | Ser | Ala | Thr Ile |
| | | | 180 | | | | | 185 | | | | | 190 | |
| Ala | Gly | Val | Ser | Leu | Ser | Arg | Met | Leu | Asp | Lys | Asp | Pro | Glu | Leu Glu |
| | | 195 | | | | | 200 | | | | | 205 | | |
| Gly | Arg | Leu | Glu | Lys | Ile | Phe | Glu | Asp | Thr | Arg | Asp | Ala | Ala | Tyr His |
| | 210 | | | | | 215 | | | | | 220 | | | |
| Ile | Ile | Asp | Ala | Lys | Gly | Ser | Thr | Ser | Tyr | Gly | Ile | Gly | Met | Gly Leu |
| 225 | | | | | 230 | | | | | 235 | | | | | 240 |
| Ala | Arg | Ile | Thr | Arg | Ala | Ile | Leu | Gln | Asn | Gln | Asp | Val | Ala | Val Pro |
| | | | | 245 | | | | | 250 | | | | | 255 |
| Val | Ser | Ala | Leu | Leu | His | Gly | Glu | Tyr | Gly | Glu | Glu | Asp | Ile | Tyr Ile |
| | | | 260 | | | | | 265 | | | | | 270 | |
| Gly | Thr | Pro | Ala | Val | Val | Asn | Arg | Arg | Gly | Ile | Arg | Val | Val | Glu |
| | | 275 | | | | | 280 | | | | | 285 | | |
| Leu | Glu | Ile | Thr | Asp | His | Glu | Met | Glu | Arg | Phe | Lys | His | Ser | Ala Asn |
| | 290 | | | | | 295 | | | | | 300 | | | |
| Thr | Leu | Arg | Glu | Ile | Gln | Lys | Gln | Phe | Phe | | | | | |
| 305 | | | | | 310 | | | | | | | | | |

<210> SEQ ID NO 206
<211> LENGTH: 43
<212> TYPE: DNA

```
<213> ORGANISM: Artificial Sequence
<220> FEATURE:
<223> OTHER INFORMATION: Synthetic Forward primer

<400> SEQUENCE: 206
tcatcaccac agccaggatc cgatgagaaa ggttcccatt att                        43

<210> SEQ ID NO 207
<211> LENGTH: 42
<212> TYPE: DNA
<213> ORGANISM: Artificial Sequence
<220> FEATURE:
<223> OTHER INFORMATION: Synthetic reverse primer

<400> SEQUENCE: 207
gcattatgcg ccgcaagct tttaggactt catttccttc ag                          42

<210> SEQ ID NO 208
<211> LENGTH: 44
<212> TYPE: DNA
<213> ORGANISM: Artificial Sequence
<220> FEATURE:
<223> OTHER INFORMATION: Synthetic primer

<400> SEQUENCE: 208
tcatcaccac agccaggatc cgatgaaacc tgtaaaacca cctc                       44

<210> SEQ ID NO 209
<211> LENGTH: 41
<212> TYPE: DNA
<213> ORGANISM: Artificial Sequence
<220> FEATURE:
<223> OTHER INFORMATION: Synthetic primer

<400> SEQUENCE: 209
gcattatgcg ccgcaagct tttaatgagc cgcttcaggc a                           41

<210> SEQ ID NO 210
<211> LENGTH: 48
<212> TYPE: DNA
<213> ORGANISM: Artificial Sequence
<220> FEATURE:
<223> OTHER INFORMATION: Synthetic primer

<400> SEQUENCE: 210
tcatcaccac agccaggatc cgatgaaggt gatcaccgca cgcgaagc                   48

<210> SEQ ID NO 211
<211> LENGTH: 42
<212> TYPE: DNA
<213> ORGANISM: Artificial Sequence
<220> FEATURE:
<223> OTHER INFORMATION: Synthetic primer

<400> SEQUENCE: 211
gcattatgcg ccgcaagct tttacaggtg caggggcccg gc                          42

<210> SEQ ID NO 212
<211> LENGTH: 52
<212> TYPE: DNA
<213> ORGANISM: Artificial Sequence
<220> FEATURE:
<223> OTHER INFORMATION: Synthetic primer

<400> SEQUENCE: 212
tcatcaccac agccaggatc cgatgaccac ctcaacgcaa acggaactta ag              52
```

<210> SEQ ID NO 213
<211> LENGTH: 42
<212> TYPE: DNA
<213> ORGANISM: Artificial Sequence
<220> FEATURE:
<223> OTHER INFORMATION: Synthetic primer

<400> SEQUENCE: 213
gcattatgcg gccgcaagct tttaccattt tccatctccg at     42

<210> SEQ ID NO 214
<211> LENGTH: 46
<212> TYPE: DNA
<213> ORGANISM: Artificial Sequence
<220> FEATURE:
<223> OTHER INFORMATION: Synthetic primer

<400> SEQUENCE: 214
tcatcaccac agccaggatc cgatggcata tcaggacgta tacgag     46

<210> SEQ ID NO 215
<211> LENGTH: 44
<212> TYPE: DNA
<213> ORGANISM: Artificial Sequence
<220> FEATURE:
<223> OTHER INFORMATION: Synthetic primer

<400> SEQUENCE: 215
gcattatgcg gccgcaagct tttattggcg tagcccagcg attg     44

<210> SEQ ID NO 216
<211> LENGTH: 45
<212> TYPE: DNA
<213> ORGANISM: Artificial Sequence
<220> FEATURE:
<223> OTHER INFORMATION: Synthetic primer

<400> SEQUENCE: 216
tcatcaccac agccaggatc cgatgaagaa ggttatcgtt ctgac     45

<210> SEQ ID NO 217
<211> LENGTH: 42
<212> TYPE: DNA
<213> ORGANISM: Artificial Sequence
<220> FEATURE:
<223> OTHER INFORMATION: Synthetic primer

<400> SEQUENCE: 217
gcattatgcg gccgcaagct tttatttttt caagttcatt ag     42

<210> SEQ ID NO 218
<211> LENGTH: 44
<212> TYPE: DNA
<213> ORGANISM: Artificial Sequence
<220> FEATURE:
<223> OTHER INFORMATION: Synthetic primer

<400> SEQUENCE: 218
tcatcaccac agccaggatc cgatgctgga aaaggtagt acac     44

<210> SEQ ID NO 219
<211> LENGTH: 42
<212> TYPE: DNA
<213> ORGANISM: Artificial Sequence
<220> FEATURE:

<223> OTHER INFORMATION: Synthetic primer

<400> SEQUENCE: 219
gcattatgcg gccgcaagct tttaaatgtt atttaaaaat tt                42

<210> SEQ ID NO 220
<211> LENGTH: 45
<212> TYPE: DNA
<213> ORGANISM: Artificial Sequence
<220> FEATURE:
<223> OTHER INFORMATION: Synthetic primer

<400> SEQUENCE: 220
tcatcaccac agccaggatc cgatgaagaa ggttaatatt ctcac            45

<210> SEQ ID NO 221
<211> LENGTH: 43
<212> TYPE: DNA
<213> ORGANISM: Artificial Sequence
<220> FEATURE:
<223> OTHER INFORMATION: Synthetic primer

<400> SEQUENCE: 221
gcattatgcg gccgcaagct tttatttctt caagttcatt agt              43

<210> SEQ ID NO 222
<211> LENGTH: 45
<212> TYPE: DNA
<213> ORGANISM: Artificial Sequence
<220> FEATURE:
<223> OTHER INFORMATION: Synthetic primer

<400> SEQUENCE: 222
tcatcaccac agccaggatc cgatgaggaa ggttaagatt atgac            45

<210> SEQ ID NO 223
<211> LENGTH: 43
<212> TYPE: DNA
<213> ORGANISM: Artificial Sequence
<220> FEATURE:
<223> OTHER INFORMATION: Synthetic primer

<400> SEQUENCE: 223
gcattatgcg gccgcaagct tttattctcc ctcgttgttt ttc              43

<210> SEQ ID NO 224
<211> LENGTH: 42
<212> TYPE: DNA
<213> ORGANISM: Artificial Sequence
<220> FEATURE:
<223> OTHER INFORMATION: Synthetic primer

<400> SEQUENCE: 224
tcatcaccac agccaggatc cgatgagcac aagaaagaga cc                42

<210> SEQ ID NO 225
<211> LENGTH: 43
<212> TYPE: DNA
<213> ORGANISM: Artificial Sequence
<220> FEATURE:
<223> OTHER INFORMATION: Synthetic primer

<400> SEQUENCE: 225
gcattatgcg gccgcaagct tttatttgtc ttcccaaaca tat              43

<210> SEQ ID NO 226
<211> LENGTH: 42
<212> TYPE: DNA
<213> ORGANISM: Artificial Sequence
<220> FEATURE:
<223> OTHER INFORMATION: Synthetic primer

<400> SEQUENCE: 226
tcatcaccac agccaggatc cgatgattaa tagattattt tc                        42

<210> SEQ ID NO 227
<211> LENGTH: 43
<212> TYPE: DNA
<213> ORGANISM: Artificial Sequence
<220> FEATURE:
<223> OTHER INFORMATION: Synthetic primer

<400> SEQUENCE: 227
gcattatgcg gccgcaagct tttattttg atcatcaaat aat                        43

<210> SEQ ID NO 228
<211> LENGTH: 43
<212> TYPE: DNA
<213> ORGANISM: Artificial Sequence
<220> FEATURE:
<223> OTHER INFORMATION: Synthetic primer

<400> SEQUENCE: 228
tcatcaccac agccaggatc cgatggaact aaacaatgtc atc                       43

<210> SEQ ID NO 229
<211> LENGTH: 42
<212> TYPE: DNA
<213> ORGANISM: Artificial Sequence
<220> FEATURE:
<223> OTHER INFORMATION: Synthetic primer

<400> SEQUENCE: 229
gcattatgcg gccgcaagct tttatctatt tttgaagcct tc                        42

<210> SEQ ID NO 230
<211> LENGTH: 44
<212> TYPE: DNA
<213> ORGANISM: Artificial Sequence
<220> FEATURE:
<223> OTHER INFORMATION: Synthetic primer

<400> SEQUENCE: 230
tcatcaccac agccaggatc cgaatagtaa aaaagtagtg atag                      44

<210> SEQ ID NO 231
<211> LENGTH: 43
<212> TYPE: DNA
<213> ORGANISM: Artificial Sequence
<220> FEATURE:
<223> OTHER INFORMATION: Synthetic primer

<400> SEQUENCE: 231
gcattatgcg gccgcaagct tttaaacgaa agctgacaat tcc                       43

<210> SEQ ID NO 232
<211> LENGTH: 44
<212> TYPE: DNA
<213> ORGANISM: Artificial Sequence
<220> FEATURE:
<223> OTHER INFORMATION: Synthetic primer

<400> SEQUENCE: 232
tcatcaccac agccaggatc cgatgggaaa tattatcttt gaag        44

<210> SEQ ID NO 233
<211> LENGTH: 42
<212> TYPE: DNA
<213> ORGANISM: Artificial Sequence
<220> FEATURE:
<223> OTHER INFORMATION: Synthetic primer

<400> SEQUENCE: 233
gcattatgcg gccgcaagct tttaaagtcc tttgaagtct gc        42

<210> SEQ ID NO 234
<211> LENGTH: 44
<212> TYPE: DNA
<213> ORGANISM: Artificial Sequence
<220> FEATURE:
<223> OTHER INFORMATION: Synthetic primer

<400> SEQUENCE: 234
tcatcaccac agccaggatc cgatggattt taataatatt atcc        44

<210> SEQ ID NO 235
<211> LENGTH: 42
<212> TYPE: DNA
<213> ORGANISM: Artificial Sequence
<220> FEATURE:
<223> OTHER INFORMATION: Synthetic primer

<400> SEQUENCE: 235
gcattatgcg gccgcaagct tttatttatt cttaaaatta cc        42

<210> SEQ ID NO 236
<211> LENGTH: 49
<212> TYPE: DNA
<213> ORGANISM: Artificial Sequence
<220> FEATURE:
<223> OTHER INFORMATION: Synthetic primer

<400> SEQUENCE: 236
tcatcaccac agccaggatc cgatggcact aagagatggg aattcctac        49

<210> SEQ ID NO 237
<211> LENGTH: 43
<212> TYPE: DNA
<213> ORGANISM: Artificial Sequence
<220> FEATURE:
<223> OTHER INFORMATION: Synthetic primer

<400> SEQUENCE: 237
gcattatgcg gccgcaagct tttattttc ttcctttatg ccg        43

<210> SEQ ID NO 238
<211> LENGTH: 44
<212> TYPE: DNA
<213> ORGANISM: Artificial Sequence
<220> FEATURE:
<223> OTHER INFORMATION: Synthetic primer

<400> SEQUENCE: 238
tcatcaccac agccaggatc cgatgagatc aaaagaagat ttcc        44

<210> SEQ ID NO 239
<211> LENGTH: 41

<212> TYPE: DNA
<213> ORGANISM: Artificial Sequence
<220> FEATURE:
<223> OTHER INFORMATION: Synthetic primer

<400> SEQUENCE: 239
gcattatgcg gccgcaagct tttaagctta ataccctttt a        41

<210> SEQ ID NO 240
<211> LENGTH: 47
<212> TYPE: DNA
<213> ORGANISM: Artificial Sequence
<220> FEATURE:
<223> OTHER INFORMATION: Synthetic primer

<400> SEQUENCE: 240
tcatcaccac agccaggatc cgatgggact caaaacgaag gcggaat        47

<210> SEQ ID NO 241
<211> LENGTH: 43
<212> TYPE: DNA
<213> ORGANISM: Artificial Sequence
<220> FEATURE:
<223> OTHER INFORMATION: Synthetic primer

<400> SEQUENCE: 241
gcattatgcg gccgcaagct tttacttcga ttcgattccc gcc        43

<210> SEQ ID NO 242
<211> LENGTH: 44
<212> TYPE: DNA
<213> ORGANISM: Artificial Sequence
<220> FEATURE:
<223> OTHER INFORMATION: Synthetic primer

<400> SEQUENCE: 242
tcatcaccac agccaggatc cgatgatgac tagcgaacag tacg        44

<210> SEQ ID NO 243
<211> LENGTH: 43
<212> TYPE: DNA
<213> ORGANISM: Artificial Sequence
<220> FEATURE:
<223> OTHER INFORMATION: Synthetic primer

<400> SEQUENCE: 243
gcattatgcg gccgcaagct tttaacttat cgagtgattc gtc        43

<210> SEQ ID NO 244
<211> LENGTH: 41
<212> TYPE: DNA
<213> ORGANISM: Artificial Sequence
<220> FEATURE:
<223> OTHER INFORMATION: Synthetic primer

<400> SEQUENCE: 244
tcatcaccac agccaggatc cgatgagtca aagcacctcc c        41

<210> SEQ ID NO 245
<211> LENGTH: 42
<212> TYPE: DNA
<213> ORGANISM: Artificial Sequence
<220> FEATURE:
<223> OTHER INFORMATION: Synthetic primer

<400> SEQUENCE: 245
gcattatgcg ccgcaagct tttaagttct tctgccaggc tc           42

<210> SEQ ID NO 246
<211> LENGTH: 45
<212> TYPE: DNA
<213> ORGANISM: Artificial Sequence
<220> FEATURE:
<223> OTHER INFORMATION: Synthetic primer

<400> SEQUENCE: 246
tcatcaccac agccaggatc cgatggaatt tgaaacaata gaaac       45

<210> SEQ ID NO 247
<211> LENGTH: 44
<212> TYPE: DNA
<213> ORGANISM: Artificial Sequence
<220> FEATURE:
<223> OTHER INFORMATION: Synthetic primer

<400> SEQUENCE: 247
gcattatgcg ccgcaagct tttaattttc ccttaaacgt aggc         44

<210> SEQ ID NO 248
<211> LENGTH: 40
<212> TYPE: DNA
<213> ORGANISM: Artificial Sequence
<220> FEATURE:
<223> OTHER INFORMATION: Synthetic primer

<400> SEQUENCE: 248
tcatcaccac agccaggatc cgatggaaac aattgttata             40

<210> SEQ ID NO 249
<211> LENGTH: 42
<212> TYPE: DNA
<213> ORGANISM: Artificial Sequence
<220> FEATURE:
<223> OTHER INFORMATION: Synthetic primer

<400> SEQUENCE: 249
gcattatgcg ccgcaagct tttatttacc cttaaactga gc           42

<210> SEQ ID NO 250
<211> LENGTH: 40
<212> TYPE: DNA
<213> ORGANISM: Artificial Sequence
<220> FEATURE:
<223> OTHER INFORMATION: Synthetic primer

<400> SEQUENCE: 250
tcatcaccac agccaggatc cgatgaccga acaccagacc             40

<210> SEQ ID NO 251
<211> LENGTH: 43
<212> TYPE: DNA
<213> ORGANISM: Artificial Sequence
<220> FEATURE:
<223> OTHER INFORMATION: Synthetic primer

<400> SEQUENCE: 251
gcattatgcg ccgcaagct tttagcggtg ggtgaagttc ggg          43

<210> SEQ ID NO 252
<211> LENGTH: 40
<212> TYPE: DNA
<213> ORGANISM: Artificial Sequence

```
<220> FEATURE:
<223> OTHER INFORMATION: Synthetic primer

<400> SEQUENCE: 252
tcatcaccac agccaggatc cgatggcaga cagagtactc                               40

<210> SEQ ID NO 253
<211> LENGTH: 42
<212> TYPE: DNA
<213> ORGANISM: Artificial Sequence
<220> FEATURE:
<223> OTHER INFORMATION: Synthetic primer

<400> SEQUENCE: 253
gcattatgcg gccgcaagct tttaccggtt tcggtacttc gg                            42

<210> SEQ ID NO 254
<211> LENGTH: 46
<212> TYPE: DNA
<213> ORGANISM: Artificial Sequence
<220> FEATURE:
<223> OTHER INFORMATION: Synthetic primer

<400> SEQUENCE: 254
tcatcaccac agccaggatc cgatggaaac aattgttata aaaaaa                        46

<210> SEQ ID NO 255
<211> LENGTH: 45
<212> TYPE: DNA
<213> ORGANISM: Artificial Sequence
<220> FEATURE:
<223> OTHER INFORMATION: Synthetic primer

<400> SEQUENCE: 255
gcattatgcg gccgcaagct tttatttacc cttaaactga gcctt                         45

<210> SEQ ID NO 256
<211> LENGTH: 43
<212> TYPE: DNA
<213> ORGANISM: Artificial Sequence
<220> FEATURE:
<223> OTHER INFORMATION: Synthetic primer

<400> SEQUENCE: 256
tcatcaccac agccaggatc cggtgaccga acaccagacc atc                           43

<210> SEQ ID NO 257
<211> LENGTH: 47
<212> TYPE: DNA
<213> ORGANISM: Artificial Sequence
<220> FEATURE:
<223> OTHER INFORMATION: Synthetic primer

<400> SEQUENCE: 257
gcattatgcg gccgcaagct tttagcggtg ggtgaagttc gggtccc                       47

<210> SEQ ID NO 258
<211> LENGTH: 43
<212> TYPE: DNA
<213> ORGANISM: Artificial Sequence
<220> FEATURE:
<223> OTHER INFORMATION: Synthetic primer

<400> SEQUENCE: 258
tcatcaccac agccaggatc cgatggcaga cagagtactc atc                           43
```

<210> SEQ ID NO 259
<211> LENGTH: 45
<212> TYPE: DNA
<213> ORGANISM: Artificial Sequence
<220> FEATURE:
<223> OTHER INFORMATION: Synthetic primer

<400> SEQUENCE: 259
gcattatgcg gccgcaagct tttaccggtt tcggtacttc ggctc            45

<210> SEQ ID NO 260
<211> LENGTH: 44
<212> TYPE: DNA
<213> ORGANISM: Artificial Sequence
<220> FEATURE:
<223> OTHER INFORMATION: Synthetic primer

<400> SEQUENCE: 260
tcatcaccac agccaggatc cggtggaatt tgaaaaaatt aaat              44

<210> SEQ ID NO 261
<211> LENGTH: 43
<212> TYPE: DNA
<213> ORGANISM: Artificial Sequence
<220> FEATURE:
<223> OTHER INFORMATION: Synthetic primer

<400> SEQUENCE: 261
gcattatgcg gccgcaagct tttaccggcc tttaaaattc ggc               43

<210> SEQ ID NO 262
<211> LENGTH: 43
<212> TYPE: DNA
<213> ORGANISM: Artificial Sequence
<220> FEATURE:
<223> OTHER INFORMATION: Synthetic primer

<400> SEQUENCE: 262
tcatcaccac agccaggatc cgatgagcgt gcgtgtcgag cgg               43

<210> SEQ ID NO 263
<211> LENGTH: 44
<212> TYPE: DNA
<213> ORGANISM: Artificial Sequence
<220> FEATURE:
<223> OTHER INFORMATION: Synthetic primer

<400> SEQUENCE: 263
gcattatgcg gccgcaagct tttagcgccc gcgaaaagcc ggac              44

<210> SEQ ID NO 264
<211> LENGTH: 43
<212> TYPE: DNA
<213> ORGANISM: Artificial Sequence
<220> FEATURE:
<223> OTHER INFORMATION: Synthetic primer

<400> SEQUENCE: 264
tcatcaccac agccaggatc cgatgaacgc tgacgccgag acc               43

<210> SEQ ID NO 265
<211> LENGTH: 43
<212> TYPE: DNA
<213> ORGANISM: Artificial Sequence
<220> FEATURE:
<223> OTHER INFORMATION: Synthetic primer

<400> SEQUENCE: 265
gcattatgcg gccgcaagct tttagcgccc tttgaagttc ggc        43

<210> SEQ ID NO 266
<211> LENGTH: 40
<212> TYPE: DNA
<213> ORGANISM: Artificial Sequence
<220> FEATURE:
<223> OTHER INFORMATION: Synthetic primer

<400> SEQUENCE: 266
tcatcaccac agccaggatc cgatgagtga tagaaataag        40

<210> SEQ ID NO 267
<211> LENGTH: 37
<212> TYPE: DNA
<213> ORGANISM: Artificial Sequence
<220> FEATURE:
<223> OTHER INFORMATION: Synthetic primer

<400> SEQUENCE: 267
gcattatgcg gccgcaagct tttaattcag cctcctt        37

<210> SEQ ID NO 268
<211> LENGTH: 41
<212> TYPE: DNA
<213> ORGANISM: Artificial Sequence
<220> FEATURE:
<223> OTHER INFORMATION: Synthetic primer

<400> SEQUENCE: 268
tcatcaccac agccaggatc cgatgtcaaa ttcagataaa t        41

<210> SEQ ID NO 269
<211> LENGTH: 43
<212> TYPE: DNA
<213> ORGANISM: Artificial Sequence
<220> FEATURE:
<223> OTHER INFORMATION: Synthetic primer

<400> SEQUENCE: 269
gcattatgcg gccgcaagct tttaaaagtg tttctgaaaa agc        43

<210> SEQ ID NO 270
<211> LENGTH: 43
<212> TYPE: DNA
<213> ORGANISM: Artificial Sequence
<220> FEATURE:
<223> OTHER INFORMATION: Synthetic primer

<400> SEQUENCE: 270
tcatcaccac agccaggatc cgatggcaga catttatact atg        43

<210> SEQ ID NO 271
<211> LENGTH: 43
<212> TYPE: DNA
<213> ORGANISM: Artificial Sequence
<220> FEATURE:
<223> OTHER INFORMATION: Synthetic primer

<400> SEQUENCE: 271
gcattatgcg gccgcaagct tttaagctcc tttcttttg aaa        43

<210> SEQ ID NO 272

<211> LENGTH: 41
<212> TYPE: DNA
<213> ORGANISM: Artificial Sequence
<220> FEATURE:
<223> OTHER INFORMATION: Synthetic primer

<400> SEQUENCE: 272
tcatcaccac agccaggatc cgatggaaaa caatacaaat a         41

<210> SEQ ID NO 273
<211> LENGTH: 40
<212> TYPE: DNA
<213> ORGANISM: Artificial Sequence
<220> FEATURE:
<223> OTHER INFORMATION: Synthetic primer

<400> SEQUENCE: 273
gcattatgcg gccgcaagct tttatttttc cttccttacc         40

<210> SEQ ID NO 274
<211> LENGTH: 43
<212> TYPE: DNA
<213> ORGANISM: Artificial Sequence
<220> FEATURE:
<223> OTHER INFORMATION: Synthetic primer

<400> SEQUENCE: 274
tcatcaccac agccaggatc cgatgtggca ttgtttagaa act         43

<210> SEQ ID NO 275
<211> LENGTH: 42
<212> TYPE: DNA
<213> ORGANISM: Artificial Sequence
<220> FEATURE:
<223> OTHER INFORMATION: Synthetic primer

<400> SEQUENCE: 275
gcattatgcg gccgcaagct tttaaaccaa catgtctgca aa         42

<210> SEQ ID NO 276
<211> LENGTH: 43
<212> TYPE: DNA
<213> ORGANISM: Artificial Sequence
<220> FEATURE:
<223> OTHER INFORMATION: Synthetic primer

<400> SEQUENCE: 276
tcatcaccac agccaggatc cggtggaaga agctaaaaaa caa         43

<210> SEQ ID NO 277
<211> LENGTH: 43
<212> TYPE: DNA
<213> ORGANISM: Artificial Sequence
<220> FEATURE:
<223> OTHER INFORMATION: Synthetic primer

<400> SEQUENCE: 277
gcattatgcg gccgcaagct tttaaatttc cttatttgct tcc         43

<210> SEQ ID NO 278
<211> LENGTH: 42
<212> TYPE: DNA
<213> ORGANISM: Artificial Sequence
<220> FEATURE:
<223> OTHER INFORMATION: Synthetic primer

<400> SEQUENCE: 278

-continued tcatcaccac agccaggatc cgatgtacac attgggtgtt ga  42

<210> SEQ ID NO 279
<211> LENGTH: 43
<212> TYPE: DNA
<213> ORGANISM: Artificial Sequence
<220> FEATURE:
<223> OTHER INFORMATION: Synthetic primer

<400> SEQUENCE: 279
gcattatgcg gccgcaagct tttataactt tttaaaaccg tat  43

<210> SEQ ID NO 280
<211> LENGTH: 45
<212> TYPE: DNA
<213> ORGANISM: Artificial Sequence
<220> FEATURE:
<223> OTHER INFORMATION: Synthetic primer

<400> SEQUENCE: 280
tcatcaccac agccaggatc cgatgagcag tgtatacaca atggg  45

<210> SEQ ID NO 281
<211> LENGTH: 43
<212> TYPE: DNA
<213> ORGANISM: Artificial Sequence
<220> FEATURE:
<223> OTHER INFORMATION: Synthetic primer

<400> SEQUENCE: 281
gcattatgcg gccgcaagct tttaagcgtt ttgcttctgg tat  43

<210> SEQ ID NO 282
<211> LENGTH: 48
<212> TYPE: DNA
<213> ORGANISM: Artificial Sequence
<220> FEATURE:
<223> OTHER INFORMATION: Synthetic primer

<400> SEQUENCE: 282
tcatcaccac agccaggatc cgatgagtaa tatagatgta ttgttagg  48

<210> SEQ ID NO 283
<211> LENGTH: 43
<212> TYPE: DNA
<213> ORGANISM: Artificial Sequence
<220> FEATURE:
<223> OTHER INFORMATION: Synthetic primer

<400> SEQUENCE: 283
gcattatgcg gccgcaagct tttaaatcat atcagcgaaa gtc  43

<210> SEQ ID NO 284
<211> LENGTH: 42
<212> TYPE: DNA
<213> ORGANISM: Artificial Sequence
<220> FEATURE:
<223> OTHER INFORMATION: Synthetic primer

<400> SEQUENCE: 284
tcatcaccac agccaggatc cgatgagtaa tacaggaatg gt  42

<210> SEQ ID NO 285
<211> LENGTH: 42
<212> TYPE: DNA

<213> ORGANISM: Artificial Sequence
<220> FEATURE:
<223> OTHER INFORMATION: Synthetic primer

<400> SEQUENCE: 285
gcattatgcg gccgcaagct tttagtgcgc ctccttcatc tt    42

<210> SEQ ID NO 286
<211> LENGTH: 44
<212> TYPE: DNA
<213> ORGANISM: Artificial Sequence
<220> FEATURE:
<223> OTHER INFORMATION: Synthetic primer

<400> SEQUENCE: 286
tcatcaccac agccaggatc cgatgtctga aaaaaaagaa gcta    44

<210> SEQ ID NO 287
<211> LENGTH: 40
<212> TYPE: DNA
<213> ORGANISM: Artificial Sequence
<220> FEATURE:
<223> OTHER INFORMATION: Synthetic primer

<400> SEQUENCE: 287
gcattatgcg gccgcaagct tttatatctc acctctatta    40

<210> SEQ ID NO 288
<211> LENGTH: 47
<212> TYPE: DNA
<213> ORGANISM: Artificial Sequence
<220> FEATURE:
<223> OTHER INFORMATION: Synthetic primer

<400> SEQUENCE: 288
tcatcaccac agccaggatc cgatggaagc tattttatct aaaatga    47

<210> SEQ ID NO 289
<211> LENGTH: 43
<212> TYPE: DNA
<213> ORGANISM: Artificial Sequence
<220> FEATURE:
<223> OTHER INFORMATION: Synthetic primer

<400> SEQUENCE: 289
gcattatgcg gccgcaagct tttactaaac tcatcatctc agc    43

<210> SEQ ID NO 290
<211> LENGTH: 42
<212> TYPE: DNA
<213> ORGANISM: Artificial Sequence
<220> FEATURE:
<223> OTHER INFORMATION: Synthetic primer

<400> SEQUENCE: 290
tcatcaccac agccaggatc cgatgtacac aatgggatta ga    42

<210> SEQ ID NO 291
<211> LENGTH: 42
<212> TYPE: DNA
<213> ORGANISM: Artificial Sequence
<220> FEATURE:
<223> OTHER INFORMATION: Synthetic primer

<400> SEQUENCE: 291
gcattatgcg gccgcaagct tttaattttt cacttctttt tg    42

<210> SEQ ID NO 292
<211> LENGTH: 44
<212> TYPE: DNA
<213> ORGANISM: Artificial Sequence
<220> FEATURE:
<223> OTHER INFORMATION: Synthetic primer

<400> SEQUENCE: 292
tcatcaccac agccaggatc cgcttttaga aggagttaaa gtag            44

<210> SEQ ID NO 293
<211> LENGTH: 45
<212> TYPE: DNA
<213> ORGANISM: Artificial Sequence
<220> FEATURE:
<223> OTHER INFORMATION: Synthetic primer

<400> SEQUENCE: 293
gcattatgcg gccgcaagct tttatcttac aactttacta tcttt           45

<210> SEQ ID NO 294
<211> LENGTH: 42
<212> TYPE: DNA
<213> ORGANISM: Artificial Sequence
<220> FEATURE:
<223> OTHER INFORMATION: Synthetic primer

<400> SEQUENCE: 294
tcatcaccac agccaggatc cgatgagcga actgatcgtc ag              42

<210> SEQ ID NO 295
<211> LENGTH: 43
<212> TYPE: DNA
<213> ORGANISM: Artificial Sequence
<220> FEATURE:
<223> OTHER INFORMATION: Synthetic primer

<400> SEQUENCE: 295
gcattatgcg gccgcaagct tttagcgtcc tttaaagtcg ggc             43

<210> SEQ ID NO 296
<211> LENGTH: 43
<212> TYPE: DNA
<213> ORGANISM: Artificial Sequence
<220> FEATURE:
<223> OTHER INFORMATION: Synthetic primer

<400> SEQUENCE: 296
tcatcaccac agccaggatc cgatgagcta tcacacgatc cgc             43

<210> SEQ ID NO 297
<211> LENGTH: 42
<212> TYPE: DNA
<213> ORGANISM: Artificial Sequence
<220> FEATURE:
<223> OTHER INFORMATION: Synthetic primer

<400> SEQUENCE: 297
gcattatgcg gccgcaagct tttaagcgcc cggtgaaatg cg              42

<210> SEQ ID NO 298
<211> LENGTH: 44
<212> TYPE: DNA
<213> ORGANISM: Artificial Sequence
<220> FEATURE:

<223> OTHER INFORMATION: Synthetic primer

<400> SEQUENCE: 298
tcatcaccac agccaggatc cgatgacgga tgtcattcgg ctcg            44

<210> SEQ ID NO 299
<211> LENGTH: 36
<212> TYPE: DNA
<213> ORGANISM: Artificial Sequence
<220> FEATURE:
<223> OTHER INFORMATION: Synthetic primer

<400> SEQUENCE: 299
gcattatgcg gccgcaagct tttattgccc ggcctg                     36

<210> SEQ ID NO 300
<211> LENGTH: 45
<212> TYPE: DNA
<213> ORGANISM: Artificial Sequence
<220> FEATURE:
<223> OTHER INFORMATION: Synthetic primer

<400> SEQUENCE: 300
tcatcaccac agccaggatc cgatgatcgt cggagtcatc gggtc           45

<210> SEQ ID NO 301
<211> LENGTH: 43
<212> TYPE: DNA
<213> ORGANISM: Artificial Sequence
<220> FEATURE:
<223> OTHER INFORMATION: Synthetic primer

<400> SEQUENCE: 301
gcattatgcg gccgcaagct tttactcgtg gaggaacagc gcc             43

<210> SEQ ID NO 302
<211> LENGTH: 44
<212> TYPE: DNA
<213> ORGANISM: Artificial Sequence
<220> FEATURE:
<223> OTHER INFORMATION: Synthetic primer

<400> SEQUENCE: 302
tcatcaccac agccaggatc cgatgttttc tattcaacaa gagg            44

<210> SEQ ID NO 303
<211> LENGTH: 44
<212> TYPE: DNA
<213> ORGANISM: Artificial Sequence
<220> FEATURE:
<223> OTHER INFORMATION: Synthetic primer

<400> SEQUENCE: 303
gcattatgcg gccgcaagct tttattttcc ttgaaactgt ggtg            44

<210> SEQ ID NO 304
<211> LENGTH: 43
<212> TYPE: DNA
<213> ORGANISM: Artificial Sequence
<220> FEATURE:
<223> OTHER INFORMATION: Synthetic primer

<400> SEQUENCE: 304
tcatcaccac agccaggatc cgatgagcac ggcgcccgaa gct             43

```
<210> SEQ ID NO 305
<211> LENGTH: 42
<212> TYPE: DNA
<213> ORGANISM: Artificial Sequence
<220> FEATURE:
<223> OTHER INFORMATION: Synthetic primer

<400> SEQUENCE: 305
gcattatgcg gccgcaagct tttagcggcc gtgccagacc gg              42

<210> SEQ ID NO 306
<211> LENGTH: 43
<212> TYPE: DNA
<213> ORGANISM: Artificial Sequence
<220> FEATURE:
<223> OTHER INFORMATION: Synthetic primer

<400> SEQUENCE: 306
tcatcaccac agccaggatc cggtggacaa tggccgtaag ctg             43

<210> SEQ ID NO 307
<211> LENGTH: 43
<212> TYPE: DNA
<213> ORGANISM: Artificial Sequence
<220> FEATURE:
<223> OTHER INFORMATION: Synthetic primer

<400> SEQUENCE: 307
gcattatgcg gccgcaagct tttaatagtc ctcctttact ttg             43

<210> SEQ ID NO 308
<211> LENGTH: 43
<212> TYPE: DNA
<213> ORGANISM: Artificial Sequence
<220> FEATURE:
<223> OTHER INFORMATION: Synthetic primer

<400> SEQUENCE: 308
tcatcaccac agccaggatc cggtgagcct ttcgccgctt gcc             43

<210> SEQ ID NO 309
<211> LENGTH: 43
<212> TYPE: DNA
<213> ORGANISM: Artificial Sequence
<220> FEATURE:
<223> OTHER INFORMATION: Synthetic primer

<400> SEQUENCE: 309
gcattatgcg gccgcaagct tttaatgccc ggcgcggtac tgc             43

<210> SEQ ID NO 310
<211> LENGTH: 41
<212> TYPE: DNA
<213> ORGANISM: Artificial Sequence
<220> FEATURE:
<223> OTHER INFORMATION: Synthetic primer

<400> SEQUENCE: 310
tcatcaccac agccaggatc cgatgtacaa attaatagat g               41

<210> SEQ ID NO 311
<211> LENGTH: 42
<212> TYPE: DNA
<213> ORGANISM: Artificial Sequence
<220> FEATURE:
<223> OTHER INFORMATION: Synthetic primer
```

<400> SEQUENCE: 311
gcattatgcg gccgcaagct tttacttacc tttatactga gg          42

<210> SEQ ID NO 312
<211> LENGTH: 42
<212> TYPE: DNA
<213> ORGANISM: Artificial Sequence
<220> FEATURE:
<223> OTHER INFORMATION: Synthetic primer

<400> SEQUENCE: 312
tcatcaccac agccaggatc cgatgtcaga acaatcaat tt          42

<210> SEQ ID NO 313
<211> LENGTH: 43
<212> TYPE: DNA
<213> ORGANISM: Artificial Sequence
<220> FEATURE:
<223> OTHER INFORMATION: Synthetic primer

<400> SEQUENCE: 313
gcattatgcg gccgcaagct tttaattttg tttcgttatt aac         43

<210> SEQ ID NO 314
<211> LENGTH: 41
<212> TYPE: DNA
<213> ORGANISM: Artificial Sequence
<220> FEATURE:
<223> OTHER INFORMATION: Synthetic primer

<400> SEQUENCE: 314
tcatcaccac agccaggatc cggtgcaaga tgacagaagt t           41

<210> SEQ ID NO 315
<211> LENGTH: 42
<212> TYPE: DNA
<213> ORGANISM: Artificial Sequence
<220> FEATURE:
<223> OTHER INFORMATION: Synthetic primer

<400> SEQUENCE: 315
gcattatgcg gccgcaagct tttattcacc ctttcttaat tt          42

<210> SEQ ID NO 316
<211> LENGTH: 42
<212> TYPE: DNA
<213> ORGANISM: Artificial Sequence
<220> FEATURE:
<223> OTHER INFORMATION: Synthetic primer

<400> SEQUENCE: 316
tcatcaccac agccaggatc cgatgaaagg cagattagaa ga          42

<210> SEQ ID NO 317
<211> LENGTH: 43
<212> TYPE: DNA
<213> ORGANISM: Artificial Sequence
<220> FEATURE:
<223> OTHER INFORMATION: Synthetic primer

<400> SEQUENCE: 317
gcattatgcg gccgcaagct tttataaaat atctttaaat gtt         43

<210> SEQ ID NO 318
<211> LENGTH: 42

<212> TYPE: DNA
<213> ORGANISM: Artificial Sequence
<220> FEATURE:
<223> OTHER INFORMATION: Synthetic primer

<400> SEQUENCE: 318
tcatcaccac agccaggatc cgatgacgga tacaacaact at        42

<210> SEQ ID NO 319
<211> LENGTH: 43
<212> TYPE: DNA
<213> ORGANISM: Artificial Sequence
<220> FEATURE:
<223> OTHER INFORMATION: Synthetic primer

<400> SEQUENCE: 319
gcattatgcg gccgcaagct tttaactcat tggaaactcc ctc        43

<210> SEQ ID NO 320
<211> LENGTH: 43
<212> TYPE: DNA
<213> ORGANISM: Artificial Sequence
<220> FEATURE:
<223> OTHER INFORMATION: Synthetic primer

<400> SEQUENCE: 320
tcatcaccac agccaggatc cgatgagtag aattgaaacg att        43

<210> SEQ ID NO 321
<211> LENGTH: 44
<212> TYPE: DNA
<213> ORGANISM: Artificial Sequence
<220> FEATURE:
<223> OTHER INFORMATION: Synthetic primer

<400> SEQUENCE: 321
gcattatgcg gccgcaagct tttaacagca tttctctaaa actt        44

<210> SEQ ID NO 322
<211> LENGTH: 41
<212> TYPE: DNA
<213> ORGANISM: Artificial Sequence
<220> FEATURE:
<223> OTHER INFORMATION: Synthetic primer

<400> SEQUENCE: 322
tcatcaccac agccaggatc cgatgtttac aatggggatt g        41

<210> SEQ ID NO 323
<211> LENGTH: 45
<212> TYPE: DNA
<213> ORGANISM: Artificial Sequence
<220> FEATURE:
<223> OTHER INFORMATION: Synthetic primer

<400> SEQUENCE: 323
gcattatgcg gccgcaagct tttatttatt agctccccta acttc        45

<210> SEQ ID NO 324
<211> LENGTH: 42
<212> TYPE: DNA
<213> ORGANISM: Artificial Sequence
<220> FEATURE:
<223> OTHER INFORMATION: Synthetic primer

<400> SEQUENCE: 324
tcatcaccac agccaggatc cgatgaatac tatagatata tc    42

<210> SEQ ID NO 325
<211> LENGTH: 44
<212> TYPE: DNA
<213> ORGANISM: Artificial Sequence
<220> FEATURE:
<223> OTHER INFORMATION: Synthetic primer

<400> SEQUENCE: 325
gcattatgcg gccgcaagct tttaacccct cattttttta ttgg    44

<210> SEQ ID NO 326
<211> LENGTH: 41
<212> TYPE: DNA
<213> ORGANISM: Artificial Sequence
<220> FEATURE:
<223> OTHER INFORMATION: Synthetic primer

<400> SEQUENCE: 326
tcatcaccac agccaggatc cgatgtacac tatgggagta g    41

<210> SEQ ID NO 327
<211> LENGTH: 42
<212> TYPE: DNA
<213> ORGANISM: Artificial Sequence
<220> FEATURE:
<223> OTHER INFORMATION: Synthetic primer

<400> SEQUENCE: 327
gcattatgcg gccgcaagct tttataaatt tttattcgcc tc    42

<210> SEQ ID NO 328
<211> LENGTH: 38
<212> TYPE: DNA
<213> ORGANISM: Artificial Sequence
<220> FEATURE:
<223> OTHER INFORMATION: Synthetic primer

<400> SEQUENCE: 328
tcatcaccac agccaggatc cgatgaacaa aattaatg    38

<210> SEQ ID NO 329
<211> LENGTH: 44
<212> TYPE: DNA
<213> ORGANISM: Artificial Sequence
<220> FEATURE:
<223> OTHER INFORMATION: Synthetic primer

<400> SEQUENCE: 329
gcattatgcg gccgcaagct tttaagagag tttctacaag agtt    44

<210> SEQ ID NO 330
<211> LENGTH: 43
<212> TYPE: DNA
<213> ORGANISM: Artificial Sequence
<220> FEATURE:
<223> OTHER INFORMATION: Synthetic primer

<400> SEQUENCE: 330
tcatcaccac agccaggatc cgatgactga tacaacagct atg    43

<210> SEQ ID NO 331
<211> LENGTH: 43
<212> TYPE: DNA
<213> ORGANISM: Artificial Sequence

```
<220> FEATURE:
<223> OTHER INFORMATION: Synthetic primer

<400> SEQUENCE: 331
gcattatgcg ccgcaagct tttactcatt ggaaactccc tcc                          43

<210> SEQ ID NO 332
<211> LENGTH: 41
<212> TYPE: DNA
<213> ORGANISM: Artificial Sequence
<220> FEATURE:
<223> OTHER INFORMATION: Synthetic primer

<400> SEQUENCE: 332
tcatcaccac agccaggatc cgagaagctg gaattaagag c                           41

<210> SEQ ID NO 333
<211> LENGTH: 42
<212> TYPE: DNA
<213> ORGANISM: Artificial Sequence
<220> FEATURE:
<223> OTHER INFORMATION: Synthetic primer

<400> SEQUENCE: 333
gcattatgcg ccgcaagct tttaacagca tttcactaaa ac                           42

<210> SEQ ID NO 334
<211> LENGTH: 41
<212> TYPE: DNA
<213> ORGANISM: Artificial Sequence
<220> FEATURE:
<223> OTHER INFORMATION: Synthetic primer

<400> SEQUENCE: 334
tcatcaccac agccaggatc cgatgtttac aatggggatt g                           41

<210> SEQ ID NO 335
<211> LENGTH: 43
<212> TYPE: DNA
<213> ORGANISM: Artificial Sequence
<220> FEATURE:
<223> OTHER INFORMATION: Synthetic primer

<400> SEQUENCE: 335
gcattatgcg ccgcaagct tttaatttat tagctcccct gac                          43

<210> SEQ ID NO 336
<211> LENGTH: 42
<212> TYPE: DNA
<213> ORGANISM: Artificial Sequence
<220> FEATURE:
<223> OTHER INFORMATION: Synthetic primer

<400> SEQUENCE: 336
tcatcaccac agccaggatc cgatgccaaa gacagtaagc cc                          42

<210> SEQ ID NO 337
<211> LENGTH: 42
<212> TYPE: DNA
<213> ORGANISM: Artificial Sequence
<220> FEATURE:
<223> OTHER INFORMATION: Synthetic primer

<400> SEQUENCE: 337
gcattatgcg ccgcaagct tttatttccc cttcttttca tc                           42
```

<210> SEQ ID NO 338
<211> LENGTH: 44
<212> TYPE: DNA
<213> ORGANISM: Artificial Sequence
<220> FEATURE:
<223> OTHER INFORMATION: Synthetic primer

<400> SEQUENCE: 338
tcatcaccac agccaggatc cgatggctat cagtgcactt attg         44

<210> SEQ ID NO 339
<211> LENGTH: 45
<212> TYPE: DNA
<213> ORGANISM: Artificial Sequence
<220> FEATURE:
<223> OTHER INFORMATION: Synthetic primer

<400> SEQUENCE: 339
gcattatgcg ccgcaagct tttacaggct ttctgcgaaa gcttc         45

<210> SEQ ID NO 340
<211> LENGTH: 42
<212> TYPE: DNA
<213> ORGANISM: Artificial Sequence
<220> FEATURE:
<223> OTHER INFORMATION: Synthetic primer

<400> SEQUENCE: 340
tcatcaccac agccaggatc cgatgagtat ctataccttg gg         42

<210> SEQ ID NO 341
<211> LENGTH: 44
<212> TYPE: DNA
<213> ORGANISM: Artificial Sequence
<220> FEATURE:
<223> OTHER INFORMATION: Synthetic primer

<400> SEQUENCE: 341
gcattatgcg ccgcaagct tttatttggc tgctttttta tacg         44

<210> SEQ ID NO 342
<211> LENGTH: 45
<212> TYPE: DNA
<213> ORGANISM: Artificial Sequence
<220> FEATURE:
<223> OTHER INFORMATION: Synthetic primer

<400> SEQUENCE: 342
tcatcaccac agccaggatc cgatgaaatt aaactatttt tgcag         45

<210> SEQ ID NO 343
<211> LENGTH: 43
<212> TYPE: DNA
<213> ORGANISM: Artificial Sequence
<220> FEATURE:
<223> OTHER INFORMATION: Synthetic primer

<400> SEQUENCE: 343
gcattatgcg ccgcaagct tttacactcc acccacgctt tcc         43

<210> SEQ ID NO 344
<211> LENGTH: 43
<212> TYPE: DNA
<213> ORGANISM: Artificial Sequence
<220> FEATURE:
<223> OTHER INFORMATION: Synthetic primer

<400> SEQUENCE: 344
tcatcaccac agccaggatc cgatggctaa aaaaatcttt aag        43

<210> SEQ ID NO 345
<211> LENGTH: 45
<212> TYPE: DNA
<213> ORGANISM: Artificial Sequence
<220> FEATURE:
<223> OTHER INFORMATION: Synthetic primer

<400> SEQUENCE: 345
gcattatgcg gccgcaagct tttacaggct ctccaggaaa gcctg        45

<210> SEQ ID NO 346
<211> LENGTH: 49
<212> TYPE: DNA
<213> ORGANISM: Artificial Sequence
<220> FEATURE:
<223> OTHER INFORMATION: Synthetic primer

<400> SEQUENCE: 346
tcatcaccac agccaggatc cgttgtatct tggagttgat attggttcg        49

<210> SEQ ID NO 347
<211> LENGTH: 47
<212> TYPE: DNA
<213> ORGANISM: Artificial Sequence
<220> FEATURE:
<223> OTHER INFORMATION: Synthetic primer

<400> SEQUENCE: 347
gcattatgcg gccgcaagct tttaagaatt ttcagcggct aataaag        47

<210> SEQ ID NO 348
<211> LENGTH: 46
<212> TYPE: DNA
<213> ORGANISM: Artificial Sequence
<220> FEATURE:
<223> OTHER INFORMATION: Synthetic primer

<400> SEQUENCE: 348
tcatcaccac agccaggatc cgatgaacaa tatttacacg atgggc        46

<210> SEQ ID NO 349
<211> LENGTH: 45
<212> TYPE: DNA
<213> ORGANISM: Artificial Sequence
<220> FEATURE:
<223> OTHER INFORMATION: Synthetic primer

<400> SEQUENCE: 349
gcattatgcg gccgcaagct tttatttggt tgccttctgc catgc        45

<210> SEQ ID NO 350
<211> LENGTH: 43
<212> TYPE: DNA
<213> ORGANISM: Artificial Sequence
<220> FEATURE:
<223> OTHER INFORMATION: Synthetic primer

<400> SEQUENCE: 350
tcatcaccac agccaggatc cgatggccga aaacgaaaaa gcc        43

<210> SEQ ID NO 351

<210> SEQ ID NO 351
<211> LENGTH: 43
<212> TYPE: DNA
<213> ORGANISM: Artificial Sequence
<220> FEATURE:
<223> OTHER INFORMATION: Synthetic primer

<400> SEQUENCE: 351
gcattatgcg gccgcaagct tttatgcccg ggcctccttc tgc        43

<210> SEQ ID NO 352
<211> LENGTH: 41
<212> TYPE: DNA
<213> ORGANISM: Artificial Sequence
<220> FEATURE:
<223> OTHER INFORMATION: Synthetic primer

<400> SEQUENCE: 352
tcatcaccac agccaggatc cgatgagtat cgaaacgatt g          41

<210> SEQ ID NO 353
<211> LENGTH: 43
<212> TYPE: DNA
<213> ORGANISM: Artificial Sequence
<220> FEATURE:
<223> OTHER INFORMATION: Synthetic primer

<400> SEQUENCE: 353
gcattatgcg gccgcaagct tttaagaggg agatcacatc ggc        43

<210> SEQ ID NO 354
<211> LENGTH: 43
<212> TYPE: DNA
<213> ORGANISM: Artificial Sequence
<220> FEATURE:
<223> OTHER INFORMATION: Synthetic primer

<400> SEQUENCE: 354
tcatcaccac agccaggatc cgatgactga tacagccaat atg        43

<210> SEQ ID NO 355
<211> LENGTH: 43
<212> TYPE: DNA
<213> ORGANISM: Artificial Sequence
<220> FEATURE:
<223> OTHER INFORMATION: Synthetic primer

<400> SEQUENCE: 355
gcattatgcg gccgcaagct tttactcatg ggaaactccc tcc        43

<210> SEQ ID NO 356
<211> LENGTH: 46
<212> TYPE: DNA
<213> ORGANISM: Artificial Sequence
<220> FEATURE:
<223> OTHER INFORMATION: Synthetic primer

<400> SEQUENCE: 356
tcatcaccac agccaggatc cgatgagtag aattgaagcg attatc     46

<210> SEQ ID NO 357
<211> LENGTH: 41
<212> TYPE: DNA
<213> ORGANISM: Artificial Sequence
<220> FEATURE:
<223> OTHER INFORMATION: Synthetic primer

<400> SEQUENCE: 357

```
gcattatgcg gccgcaagct tttacagcat ttcacgaaaa c                           41
```

<210> SEQ ID NO 358
<211> LENGTH: 46
<212> TYPE: DNA
<213> ORGANISM: Artificial Sequence
<220> FEATURE:
<223> OTHER INFORMATION: Synthetic primer

<400> SEQUENCE: 358

```
tcatcaccac agccaggatc cgatgtatac tatggggatt gatatc                     46
```

<210> SEQ ID NO 359
<211> LENGTH: 45
<212> TYPE: DNA
<213> ORGANISM: Artificial Sequence
<220> FEATURE:
<223> OTHER INFORMATION: Synthetic primer

<400> SEQUENCE: 359

```
gcattatgcg gccgcaagct tttatacctc tttccttaat ttatt                      45
```

<210> SEQ ID NO 360
<211> LENGTH: 44
<212> TYPE: DNA
<213> ORGANISM: Artificial Sequence
<220> FEATURE:
<223> OTHER INFORMATION: Synthetic primer

<400> SEQUENCE: 360

```
tcatcaccac agccaggatc cgatgagtaa cacaggtgca gttg                       44
```

<210> SEQ ID NO 361
<211> LENGTH: 44
<212> TYPE: DNA
<213> ORGANISM: Artificial Sequence
<220> FEATURE:
<223> OTHER INFORMATION: Synthetic primer

<400> SEQUENCE: 361

```
gcattatgcg gccgcaagct tttagttttc ctccttcatc tttg                       44
```

<210> SEQ ID NO 362
<211> LENGTH: 48
<212> TYPE: DNA
<213> ORGANISM: Artificial Sequence
<220> FEATURE:
<223> OTHER INFORMATION: Synthetic primer

<400> SEQUENCE: 362

```
tcatcaccac agccaggatc cgatgagtaa cttagaagaa ctatttgg                   48
```

<210> SEQ ID NO 363
<211> LENGTH: 45
<212> TYPE: DNA
<213> ORGANISM: Artificial Sequence
<220> FEATURE:
<223> OTHER INFORMATION: Synthetic primer

<400> SEQUENCE: 363

```
gcattatgcg gccgcaagct tttatatcat gtctgcaaaa gtctg                      45
```

<210> SEQ ID NO 364
<211> LENGTH: 45
<212> TYPE: DNA

<213> ORGANISM: Artificial Sequence
<220> FEATURE:
<223> OTHER INFORMATION: Synthetic primer

<400> SEQUENCE: 364
tcatcaccac agccaggatc cgatgagtga tatatacaca atggg    45

<210> SEQ ID NO 365
<211> LENGTH: 43
<212> TYPE: DNA
<213> ORGANISM: Artificial Sequence
<220> FEATURE:
<223> OTHER INFORMATION: Synthetic primer

<400> SEQUENCE: 365
gcattatgcg gccgcaagct tttaaatttt ccttcagata ctc    43

<210> SEQ ID NO 366
<211> LENGTH: 44
<212> TYPE: DNA
<213> ORGANISM: Artificial Sequence
<220> FEATURE:
<223> OTHER INFORMATION: Synthetic primer

<400> SEQUENCE: 366
tcatcaccac agccaggatc cgatgagcga tgaaacgctt gtgc    44

<210> SEQ ID NO 367
<211> LENGTH: 44
<212> TYPE: DNA
<213> ORGANISM: Artificial Sequence
<220> FEATURE:
<223> OTHER INFORMATION: Synthetic primer

<400> SEQUENCE: 367
gcattatgcg gccgcaagct tttagcgacc actgaagttg gctg    44

<210> SEQ ID NO 368
<211> LENGTH: 45
<212> TYPE: DNA
<213> ORGANISM: Artificial Sequence
<220> FEATURE:
<223> OTHER INFORMATION: Synthetic primer

<400> SEQUENCE: 368
tcatcaccac agccaggatc cgatggaatt cataaaagta aacac    45

<210> SEQ ID NO 369
<211> LENGTH: 43
<212> TYPE: DNA
<213> ORGANISM: Artificial Sequence
<220> FEATURE:
<223> OTHER INFORMATION: Synthetic primer

<400> SEQUENCE: 369
gcattatgcg gccgcaagct tttatttccc cttgaattca ggc    43

<210> SEQ ID NO 370
<211> LENGTH: 41
<212> TYPE: DNA
<213> ORGANISM: Artificial Sequence
<220> FEATURE:
<223> OTHER INFORMATION: Synthetic primer

<400> SEQUENCE: 370
tcatcaccac agccaggatc cgatgtacga gaacctcatc g    41

<210> SEQ ID NO 371
<211> LENGTH: 43
<212> TYPE: DNA
<213> ORGANISM: Artificial Sequence
<220> FEATURE:
<223> OTHER INFORMATION: Synthetic primer

<400> SEQUENCE: 371
gcattatgcg gccgcaagct tttacctccc tttccattcg ggc         43

<210> SEQ ID NO 372
<211> LENGTH: 47
<212> TYPE: DNA
<213> ORGANISM: Artificial Sequence
<220> FEATURE:
<223> OTHER INFORMATION: Synthetic primer

<400> SEQUENCE: 372
tcatcaccac agccaggatc cgatgcaacc acaatttata atcatac     47

<210> SEQ ID NO 373
<211> LENGTH: 44
<212> TYPE: DNA
<213> ORGANISM: Artificial Sequence
<220> FEATURE:
<223> OTHER INFORMATION: Synthetic primer

<400> SEQUENCE: 373
gcattatgcg gccgcaagct tttattttcc tttaaaaaca ggtg        44

<210> SEQ ID NO 374
<211> LENGTH: 41
<212> TYPE: DNA
<213> ORGANISM: Artificial Sequence
<220> FEATURE:
<223> OTHER INFORMATION: Synthetic primer

<400> SEQUENCE: 374
tcatcaccac agccaggatc cggtgtatac tctcggaatc g           41

<210> SEQ ID NO 375
<211> LENGTH: 45
<212> TYPE: DNA
<213> ORGANISM: Artificial Sequence
<220> FEATURE:
<223> OTHER INFORMATION: Synthetic primer

<400> SEQUENCE: 375
gcattatgcg gccgcaagct tttatttctt gattttatca taagc       45

<210> SEQ ID NO 376
<211> LENGTH: 44
<212> TYPE: DNA
<213> ORGANISM: Artificial Sequence
<220> FEATURE:
<223> OTHER INFORMATION: Synthetic primer

<400> SEQUENCE: 376
tcatcaccac agccaggatc cgatgagtga agaaaaaaca gtag        44

<210> SEQ ID NO 377
<211> LENGTH: 45
<212> TYPE: DNA
<213> ORGANISM: Artificial Sequence
<220> FEATURE:

<223> OTHER INFORMATION: Synthetic primer

<400> SEQUENCE: 377
gcattatgcg gccgcaagct tttagtggtt tcctccttca ttggc        45

<210> SEQ ID NO 378
<211> LENGTH: 46
<212> TYPE: DNA
<213> ORGANISM: Artificial Sequence
<220> FEATURE:
<223> OTHER INFORMATION: Synthetic primer

<400> SEQUENCE: 378
tcatcaccac agccaggatc cgatgagtca gatcgacgaa cttatc        46

<210> SEQ ID NO 379
<211> LENGTH: 45
<212> TYPE: DNA
<213> ORGANISM: Artificial Sequence
<220> FEATURE:
<223> OTHER INFORMATION: Synthetic primer

<400> SEQUENCE: 379
gcattatgcg gccgcaagct tttagaggat ttccgagaaa gcctg        45

<210> SEQ ID NO 380
<211> LENGTH: 41
<212> TYPE: DNA
<213> ORGANISM: Artificial Sequence
<220> FEATURE:
<223> OTHER INFORMATION: Synthetic primer

<400> SEQUENCE: 380
tcatcaccac agccaggatc cgatgagtga agagtctctg g        41

<210> SEQ ID NO 381
<211> LENGTH: 45
<212> TYPE: DNA
<213> ORGANISM: Artificial Sequence
<220> FEATURE:
<223> OTHER INFORMATION: Synthetic primer

<400> SEQUENCE: 381
gcattatgcg gccgcaagct tttaacgacc actgaagttg ggagc        45

<210> SEQ ID NO 382
<211> LENGTH: 43
<212> TYPE: DNA
<213> ORGANISM: Artificial Sequence
<220> FEATURE:
<223> OTHER INFORMATION: Synthetic primer

<400> SEQUENCE: 382
tcatcaccac agccaggatc cgatgtctac aacacataac gtc        43

<210> SEQ ID NO 383
<211> LENGTH: 40
<212> TYPE: DNA
<213> ORGANISM: Artificial Sequence
<220> FEATURE:
<223> OTHER INFORMATION: Synthetic primer

<400> SEQUENCE: 383
gcattatgcg gccgcaagct tttactcaac aggtaaggcg        40

<210> SEQ ID NO 384
<211> LENGTH: 45
<212> TYPE: DNA
<213> ORGANISM: Artificial Sequence
<220> FEATURE:
<223> OTHER INFORMATION: Synthetic primer

<400> SEQUENCE: 384
tcatcaccac agccaggatc cgatgacaac aacagatctt gcgcc          45

<210> SEQ ID NO 385
<211> LENGTH: 41
<212> TYPE: DNA
<213> ORGANISM: Artificial Sequence
<220> FEATURE:
<223> OTHER INFORMATION: Synthetic primer

<400> SEQUENCE: 385
gcattatgcg gccgcaagct tttacagagt cggcagtgcg c              41

<210> SEQ ID NO 386
<211> LENGTH: 45
<212> TYPE: DNA
<213> ORGANISM: Artificial Sequence
<220> FEATURE:
<223> OTHER INFORMATION: Synthetic primer

<400> SEQUENCE: 386
tcatcaccac agccaggatc cgatgacgac agagcaaacc acgcc          45

<210> SEQ ID NO 387
<211> LENGTH: 42
<212> TYPE: DNA
<213> ORGANISM: Artificial Sequence
<220> FEATURE:
<223> OTHER INFORMATION: Synthetic primer

<400> SEQUENCE: 387
gcattatgcg gccgcaagct tttacgccac aggcggcagc gg             42

<210> SEQ ID NO 388
<211> LENGTH: 46
<212> TYPE: DNA
<213> ORGANISM: Artificial Sequence
<220> FEATURE:
<223> OTHER INFORMATION: Synthetic primer

<400> SEQUENCE: 388
tcatcaccac agccaggatc cgatgacaac aacgaataac actccc         46

<210> SEQ ID NO 389
<211> LENGTH: 44
<212> TYPE: DNA
<213> ORGANISM: Artificial Sequence
<220> FEATURE:
<223> OTHER INFORMATION: Synthetic primer

<400> SEQUENCE: 389
gcattatgcg gccgcaagct tttaggccaa cgtggggatt ggac           44

<210> SEQ ID NO 390
<211> LENGTH: 43
<212> TYPE: DNA
<213> ORGANISM: Artificial Sequence
<220> FEATURE:
<223> OTHER INFORMATION: Synthetic primer

```
<400> SEQUENCE: 390
tcatcaccac agccaggatc cgatggataa tactcctcag ggc                43

<210> SEQ ID NO 391
<211> LENGTH: 40
<212> TYPE: DNA
<213> ORGANISM: Artificial Sequence
<220> FEATURE:
<223> OTHER INFORMATION: Synthetic primer

<400> SEQUENCE: 391
gcattatgcg gccgcaagct tttaaccctg aaccgggagc                    40

<210> SEQ ID NO 392
<211> LENGTH: 44
<212> TYPE: DNA
<213> ORGANISM: Artificial Sequence
<220> FEATURE:
<223> OTHER INFORMATION: Synthetic primer

<400> SEQUENCE: 392
tcatcaccac agccaggatc cgatgacaac aacgaataac accc               44

<210> SEQ ID NO 393
<211> LENGTH: 44
<212> TYPE: DNA
<213> ORGANISM: Artificial Sequence
<220> FEATURE:
<223> OTHER INFORMATION: Synthetic primer

<400> SEQUENCE: 393
gcattatgcg gccgcaagct tttagacctg tttaggtatc ggac               44

<210> SEQ ID NO 394
<211> LENGTH: 32
<212> TYPE: DNA
<213> ORGANISM: Artificial Sequence
<220> FEATURE:
<223> OTHER INFORMATION: Synthetic primer: dhaB123_F

<400> SEQUENCE: 394
tcatgaaatc aaaaagattt gaagtattga ag                            32

<210> SEQ ID NO 395
<211> LENGTH: 36
<212> TYPE: DNA
<213> ORGANISM: Artificial Sequence
<220> FEATURE:
<223> OTHER INFORMATION: Synthetic primer: dhaB123_R

<400> SEQUENCE: 395
ggatccctaa tcttttctaa gttgacctct ttgttc                        36

<210> SEQ ID NO 396
<211> LENGTH: 30
<212> TYPE: DNA
<213> ORGANISM: Artificial Sequence
<220> FEATURE:
<223> OTHER INFORMATION: Synthetic primer: gdrAB_F

<400> SEQUENCE: 396
ggatccaaag gttcggggat agttatgaag                               30

<210> SEQ ID NO 397
<211> LENGTH: 33
```

<212> TYPE: DNA
<213> ORGANISM: Artificial Sequence
<220> FEATURE:
<223> OTHER INFORMATION: Synthetic primer: gdrAB_R

<400> SEQUENCE: 397
gagctcttat ctaagtggca gacccttac aag                          33

<210> SEQ ID NO 398
<211> LENGTH: 1194
<212> TYPE: DNA
<213> ORGANISM: Cupriavidus necator
<220> FEATURE:
<221> NAME/KEY: Gene
<222> LOCATION: (1)..(1194)
<223> OTHER INFORMATION: succinate semialdehyde dehydrogenase (SSADH)
      protein gene: gabD gene

<400> SEQUENCE: 398

| | | |
|---|---|---|
| atgcacgccg ccacgcaagc catcctcacc ttcaaccatg ccgcgatcc cgagcggctg | 60 |
| acccgcaagc ttgcggcgat cgccgcggac ccgtttgcct tctttcgcgg caccaaccat | 120 |
| ctctatgccg catcgctgcg cgatgaggcg gcaatgtgca atgcgcccat cacctacgtc | 180 |
| tgcggcgatc tgcacctgga gaacttcggc agcttcaagg cgacaacgg ctggtctat | 240 |
| ttcgacctga cgactttga cgatgccctg gtcgcgccgc ttacggtgga tgtggtccgg | 300 |
| atgctgtcga gcgtgctggt ggccgccggc cagctgggcc tttccgaggc cggcgccatg | 360 |
| cgcgcctgcg aggccatgct gtccacctat gccgcgtgc tgcagacagg caagcctcgc | 420 |
| tggctcgagc gtgccacggc ggtcggcatg gtggccaccc tgctgcgccg ggtcaagggc | 480 |
| cgcaagcgcg gcgcgctgct ggccgagctc accacgctgc gcaagggcaa acggcgcctg | 540 |
| gtatgcaacg gccgccatgc gctgccggcg gacaagccgg ccgtgagcg cgctcgcgcg | 600 |
| atccttgcgg cctactcgaa gcagggccac catggccacc gcctggccct cgacgatgcc | 660 |
| gcgcggcgcg tggcgggcat ggcagcctc gggctggaac gctatatggt gctggcgcgg | 720 |
| gacgaactga gcggcatgca gcgactggtc gacatcaagc gcgccgcgcc gagtccatgg | 780 |
| caggacctgc ccagcctgtc cctgccaccc tggggcagcg atgcaaggcg ggtgcggcg | 840 |
| gtgcagcaag tcatgcaggc ggcttcgccg gcgctgctgt cggctgtcga catgggcaag | 900 |
| gcttcctatc tggtcaagag cctgcagcca actgccgacc gcgtcgacct ggcgcattgc | 960 |
| agcaactttg cagcgctacg cgagttgctg ggcaccatgg cgcatgccgc ggcatgggcg | 1020 |
| catctgcgtg gctgcgggca ccaggccgcg gaccggatcg agcagctgca ggcgtttgcc | 1080 |
| ggcggcaccc gctggcgcac cggcgtcctg cggctggcac ggcatggctg cgcggtgtcg | 1140 |
| gtggtgcagt ggaaggcgta tgcggacgat taccgcgagg cgcggggagg gtga | 1194 |

<210> SEQ ID NO 399
<211> LENGTH: 28
<212> TYPE: DNA
<213> ORGANISM: Artificial Sequence
<220> FEATURE:
<223> OTHER INFORMATION: Synthetic primer: gabD_F

<400> SEQUENCE: 399
aaagctagca tgtaccagga tctcgccc                               28

<210> SEQ ID NO 400
<211> LENGTH: 30
<212> TYPE: DNA
<213> ORGANISM: Artificial Sequence -continued

```
<220> FEATURE:
<223> OTHER INFORMATION: Synthetic primer: gabD_R

<400> SEQUENCE: 400
aatggtacct caggcctggg tgatgaactt                                           30

<210> SEQ ID NO 401
<211> LENGTH: 258
<212> TYPE: PRT
<213> ORGANISM: Ruegeria pomeroyi
<220> FEATURE:
<221> NAME/KEY: MISC_FEATURE
<222> LOCATION: (1)..(258)
<223> OTHER INFORMATION: DSS-3

<400> SEQUENCE: 401
```

Met Ala Phe Glu Thr Ile Ile Val Glu Val Asp His Val Ala Leu
 1               5                  10                  15

Ile Arg Leu Asn Arg Pro Asp Ala Leu Asn Ala Leu Asn Thr Gln Leu
            20                  25                  30

Leu Gly Glu Leu Cys Thr Ala Leu Glu Glu Ala Asp Gly Asn Asp Lys
        35                  40                  45

Val Arg Cys Ile Val Ile Thr Gly Ser Asp Lys Ala Phe Ala Ala Gly
    50                  55                  60

Ala Asp Ile Arg Glu Met Ser Gln Lys Thr Tyr Val Glu Val Tyr Ser
65                  70                  75                  80

Glu Asn Leu Phe Ala Ala Ala Asn Asp Arg Val Ser Ala Ile Arg Lys
                85                  90                  95

Pro Ile Ile Ala Ala Val Ala Gly Tyr Ala Leu Gly Gly Gly Cys Glu
            100                 105                 110

Leu Ala Met Leu Cys Asp Phe Ile Ile Ala Ala Asp Thr Ala Lys Phe
        115                 120                 125

Gly Gln Pro Glu Ile Asn Leu Gly Val Ile Ala Gly Ile Gly Gly Thr
    130                 135                 140

Gln Arg Leu Thr Arg Leu Val Gly Lys Ser Lys Ser Met Asp Leu Asn
145                 150                 155                 160

Leu Thr Gly Arg Phe Met Asp Ala Glu Ala Glu Arg Ala Gly Leu
                165                 170                 175

Val Ser Arg Val Val Pro Ala Lys Lys Leu Val Glu Glu Ala Leu Ser
            180                 185                 190

Ala Ala Gln Lys Ile Ala Glu Lys Ser Met Ile Ser Ala Tyr Ala Val
        195                 200                 205

Lys Glu Ala Val Asn Arg Ser Tyr Glu Thr Thr Leu Ser Glu Gly Leu
    210                 215                 220

Leu Phe Glu Arg Arg Val Phe His Ser Met Phe Ala Thr Glu Asp Gln
225                 230                 235                 240

Lys Glu Gly Met Ala Ala Phe Leu Glu Lys Arg Ala Ala Gln Phe Arg
                245                 250                 255

Asp Lys

```
<210> SEQ ID NO 402
<211> LENGTH: 777
<212> TYPE: DNA
<213> ORGANISM: Ruegeria pomeroyi
<220> FEATURE:
<221> NAME/KEY: MISC_FEATURE
<222> LOCATION: (1)..(777)
<223> OTHER INFORMATION: DSS-3
```

<400> SEQUENCE: 402

```
atggcctttg agacgatcat cgtcgaagtt gaagaccacg tagccctgat caggctgaac      60
cgtcccgatg cgctcaatgc gctcaacacc cagttgctgg gcgagttgtg taccgcgctg     120
gaagaggccg acggcaatga caaggtgcgc tgcatcgtca tcaccggcag cgacaaggca     180
tttgccgccg gggccgatat ccgcgagatg tcccaaaaga cctatgtcga ggtgtatagc     240
gagaacctgt tcgcggccgc caacgaccgt gtcagcgcca tccgcaagcc gatcatcgcc     300
gcagtggcgg gctatgcgct gggcggtggc tgtgaactgg cgatgctgtg cgatttcatc     360
atcgcggcgg acaccgcaaa gttcggccag cccgagatca acctgggcgt gatcgccggt     420
atcggcggca cccagcgtct gacccggctg gtgggcaagt ccaagtcgat ggacctgaac     480
ctgaccgggc ggttcatgga tgccgaagag gccgagcgcg ccgggctggt cagccgcgtg     540
gttccggcca agaagctggt cgaagaggcg ctgagcgcag cccagaagat cgccgagaaa     600
tcgatgatct cggcctatgc ggtcaaggag gcggtcaacc gctcttacga gaccacgctg     660
agcgaggggc tgctgttcga cgccgggtg ttccattcga tgttcgccac cgaagatcag     720
aaggaaggca tggccgcttt cctcgagaag cgggcggcac agttccgcga caagtga       777
```

<210> SEQ ID NO 403
<211> LENGTH: 44
<212> TYPE: DNA
<213> ORGANISM: Artificial Sequence
<220> FEATURE:
<223> OTHER INFORMATION: Synthetic primer

<400> SEQUENCE: 403

```
tcatcaccac agccaggatc cgatggcctt tgagacgatc atcg                       44
```

<210> SEQ ID NO 404
<211> LENGTH: 45
<212> TYPE: DNA
<213> ORGANISM: Artificial Sequence
<220> FEATURE:
<223> OTHER INFORMATION: Synthetic primer

<400> SEQUENCE: 404

```
gcattatgcg gccgcaagct tttacttgtc gcggaactgt gccgc                      45
```

<210> SEQ ID NO 405
<211> LENGTH: 399
<212> TYPE: DNA
<213> ORGANISM: Escherichia coli
<220> FEATURE:
<221> NAME/KEY: Gene
<222> LOCATION: (1)..(399)
<223> OTHER INFORMATION: yciA gene

<400> SEQUENCE: 405

```
atgtctacaa cacataacgt ccctcagggc gatcttgttt acgtactttt agccatgccc      60
gccgatacca atgccaatgg tgacatcttt ggtggttggt taatgtcaca aatggatatt     120
ggcggcgcta ttctggcaaa agaaattgcc cacggtcgcg tagtgactgt gcgggttgaa     180
ggaatgactt tcttacggcc ggttgcggtc ggcgatgtgg tgtgctgcta tgcacgctgt     240
gtccagaaag ggacgacatc ggtcagcatt aatattgaag tgtgggtgaa aaaagtagcg     300
tctgaaccaa ttgggcaacg ctataaagcg acagaagcat atttaagta tgtcgcggtt     360
gatcctgaag gaaaacctcg cgccttacct gttgagtaa                            399
```

```
<210> SEQ ID NO 406
<211> LENGTH: 399
<212> TYPE: DNA
<213> ORGANISM: Klebsiella oxytoca
<220> FEATURE:
<221> NAME/KEY: MISC_FEATURE
<222> LOCATION: (1)..(399)
<223> OTHER INFORMATION: 10-5245 HMPREF9689

<400> SEQUENCE: 406
atgacaacaa cagatcttgc gccgaagggc gaattggttt tacgcaccct ggcgatgccg      60
gcggacacca acgcaaacgg cgatattttc ggcggctggc tgatgtcgca aatggatatt     120
ggcggggcca ttatggccaa agaaattgcc cacggtcgcg tcgtgaccgt gcgcgtcgac     180
ggcatgacct ttttgcgccc ggtggcggtc ggcgacgtcg tgtgctgcta cgccaactgc     240
gtgaagcgcg gcaatacgtc gataactatc aatatggaag tgtgggtcaa gaaagtgtcg     300
tctgagccca tcggccagcg ctacaaagcc accgaagcgc tgtttatcta cgtcgcggtg     360
gataatcagg gaaaaccgcg cgcactgccg actctgtga                            399

<210> SEQ ID NO 407
<211> LENGTH: 402
<212> TYPE: DNA
<213> ORGANISM: Cronobacter turicensis
<220> FEATURE:
<221> NAME/KEY: Gene
<222> LOCATION: (1)..(402)
<223> OTHER INFORMATION: yciA gene

<400> SEQUENCE: 407
atgacgacag agcaaaccac gcctcaaggt gaactggttt tacgtaccct ggcgatgccc      60
gccgatacca acgccaatgg cgatattttt ggcggctggc tgatggccca gatggacatt     120
ggcggcgcga tccttgccaa agagatagcc catgccgcg tggtgacggt acgcgttgac      180
ggcatgacgt tcctgcgccc ggtcgcggtt ggcgatgtgg tgtgctgtta tgcccgttgc     240
gtgaagcgcg gcaatacatc ggtgacgatt aatattgaag tgtgggtgaa gaaggtttct     300
tccgagccgc ttggccagcg ctaccgcgcg accgaggcgc tgttcattta tgttgcggtc     360
gatgacaacg gcaaaccgcg cccgctgccg cctgtggcgt ga                        402

<210> SEQ ID NO 408
<211> LENGTH: 402
<212> TYPE: DNA
<213> ORGANISM: Citrobacter freundii
<220> FEATURE:
<221> NAME/KEY: Gene
<222> LOCATION: (1)..(402)
<223> OTHER INFORMATION: D186_20262 gene

<400> SEQUENCE: 408
atgacaacaa cgaataacac tccccagggt gaactggttt tacgcactct ggccatgcct      60
gccgatacca acgcgaacgg tgatattttt ggcggctggc tgatgtcaca aatggatata     120
ggtggcgcga ttcaggccaa agagatcgca catggtcgtg tggtaactgt gcggggttgaa    180 ggaatgagct ttttgcgccc ggtcgccgta ggtgatgtag tgtgttgcta tgctcgctgt     240
gtgaaacgcg gacaacctc aatcagcatc aatattgaag tttgggtgaa gaaagtcgct     300
tctgaaccta ttggccagcg ttataaggcc accgaagctc tgtttatcta cgttgccgtt     360
gataaagacg ggaaaccgcg tccaatcccc acgttggcct ga                        402

<210> SEQ ID NO 409
```

```
<211> LENGTH: 393
<212> TYPE: DNA
<213> ORGANISM: Salmonella enterica
<220> FEATURE:
<221> NAME/KEY: MISC_FEATURE
<222> LOCATION: (1)..(393)
<223> OTHER INFORMATION: SeI_A1458

<400> SEQUENCE: 409
atggataata ctcctcaggg cgagctggtt ttacgtacat tggccatgcc tgccgatacc      60
aatgcgaacg gcgatatttt tggcggctgg ctgatgtcgc aaatggatat tggcggcgcg     120
atactggcca aagagatcgc gcacggtcgg gttgtaaccg tacgcgtgga aggaatgaca     180
tttctgcgcc ccgtcgcggt tggcgatgtc gtatgctgct acgcgcgctg cgttaaacgc     240
ggtacgacgt ctattagcat aaatattgaa gtctgggtga aaaaagtcgc gtcagaaccg     300
attgggcagc gctacaaggc caccgaggcg ctgtttattt atgttgccgt cgatccggac     360
ggtaaacctc gcccgctccc ggttcagggt taa                                  393

<210> SEQ ID NO 410
<211> LENGTH: 402
<212> TYPE: DNA
<213> ORGANISM: Shigella flexneri
<220> FEATURE:
<221> NAME/KEY: Gene
<222> LOCATION: (1)..(402)
<223> OTHER INFORMATION: 1235-66  SF123566_2028 gene

<400> SEQUENCE: 410
atgacaacaa cgaataacac cccccagggt gaactggttt tacgcactct ggccatgcct      60
gccgatacca atgctaacgg tgatattttt ggcggctggc tgatgtcaca gatggatatt     120
ggtggcgcta ttcaggccaa agagatcgca cacggtcgcg tggtgacggt gcgagttgaa     180
ggaatgagct ttttgcgccc ggttgccgtg ggtgatgtgg tctgttgcta cgcacgctgc     240
gtaaaacgcg ggacgacgtc aatcagcatt aatattgaag tctgggtgaa gaaagtcgct     300
tcggaaccta ttggccagcg ttacaaagcc actgaagccc tgtttatcta cgtcgctgta     360
gataaagacg gtaaaccccg tccgatacct aaacaggtct ga                        402
```